US008252917B2

(12) United States Patent
Mermod et al.

(10) Patent No.: US 8,252,917 B2
(45) Date of Patent: Aug. 28, 2012

(54) HIGH EFFICIENCY GENE TRANSFER AND EXPRESSION IN MAMMALIAN CELLS BY A MULTIPLE TRANSFECTION PROCEDURE OF MAR SEQUENCES

(75) Inventors: Nicolas Mermod, Buchillon (CH); Pierre Alain Girod, Lausanne (CH); Philipp Bucher, Lausanne (CH); Duc-Quang Nguyen, Saint Prex (CH); David Calabrese, Lausanne (CH); Damien Saugy, Lausanne (CH); Stefania Puttini, Lausanne (CH)

(73) Assignee: Selexis S.A., Plan-les-Ouates (CH)

( * ) Notice: Subject to any disclaimer, the term of this patent is extended or adjusted under 35 U.S.C. 154(b) by 569 days.

(21) Appl. No.: 10/595,495

(22) PCT Filed: Oct. 22, 2004

(86) PCT No.: PCT/EP2004/011974

§ 371 (c)(1),
(2), (4) Date: Apr. 24, 2006

(87) PCT Pub. No.: WO2005/040377

PCT Pub. Date: May 6, 2005

(65) Prior Publication Data

US 2007/0178469 A1 Aug. 2, 2007

Related U.S. Application Data

(60) Provisional application No. 60/513,574, filed on Oct. 24, 2003.

(30) Foreign Application Priority Data

Feb. 6, 2004 (EP) .................................... 04002722

(51) Int. Cl.
*C07H 21/04* (2006.01)
*C12N 15/63* (2006.01)
*C12N 15/85* (2006.01)
*C12N 15/09* (2006.01)

(52) U.S. Cl. .................... 536/24.1; 435/320.1; 435/325; 435/455

(58) Field of Classification Search ........................ None
See application file for complete search history.

(56) References Cited

U.S. PATENT DOCUMENTS

| | | | |
|---|---|---|---|
| 4,094,640 A | 6/1978 | Iwantscheff et al. | |
| 5,464,758 A | 11/1995 | Gossen et al. | |
| 5,610,053 A | 3/1997 | Chung et al. | |
| 5,773,695 A | 6/1998 | Thompson et al. | |
| 5,831,063 A | 11/1998 | Hughes-Jones | |
| 5,907,078 A | 5/1999 | Greenberg et al. | |
| 6,043,077 A | 3/2000 | Barber et al. | |
| 6,245,974 B1 * | 6/2001 | Michalowski et al. | 800/317.3 |
| 6,252,058 B1 | 6/2001 | Thompson | |
| 6,338,066 B1 | 1/2002 | Martin et al. | |
| 6,410,314 B1 | 6/2002 | Baiker et al. | |
| 6,426,446 B1 | 7/2002 | McElroy et al. | |
| 6,429,357 B1 | 8/2002 | McElroy et al. | |
| 6,437,217 B1 | 8/2002 | McElroy et al. | |
| 6,521,449 B1 | 2/2003 | Polack et al. | |
| 6,537,542 B1 | 3/2003 | Treco et al. | |
| 6,565,844 B1 | 5/2003 | Treco et al. | |
| 6,569,681 B1 | 5/2003 | Ivanov | |
| 6,573,429 B1 | 6/2003 | Shinmyo et al. | |
| 6,583,338 B2 | 6/2003 | McElroy et al. | |
| 6,596,514 B2 | 7/2003 | Morris et al. | |
| 6,635,806 B1 | 10/2003 | Kriz et al. | |
| 6,649,373 B2 | 11/2003 | Brough et al. | |
| 6,660,521 B2 | 12/2003 | Brough et al. | |
| 6,706,470 B2 | 3/2004 | Choo et al. | |
| 6,730,826 B2 | 5/2004 | Wagner et al. | |
| 6,747,189 B1 | 6/2004 | McElroy et al. | |
| 6,783,756 B2 | 8/2004 | Bujard et al. | |
| 6,821,775 B1 | 11/2004 | Kovesdi et al. | |
| 6,897,066 B1 | 5/2005 | Harrington | |
| 2002/0001579 A1 | 1/2002 | Hillenberg et al. | |
| 2002/0068362 A1 | 6/2002 | Murray et al. | |
| 2002/0073448 A1 | 6/2002 | Michalowski et al. | |
| 2002/0094967 A1 | 7/2002 | Antoniou et al. | |
| 2002/0098475 A1 | 7/2002 | Luo et al. | |
| 2002/0103148 A1 | 8/2002 | Agarwal et al. | |
| 2003/0018997 A1 | 1/2003 | Conkling et al. | |

(Continued)

FOREIGN PATENT DOCUMENTS

EP 0113551 B1 4/1988

(Continued)

OTHER PUBLICATIONS

Kries et al. A non-curved chicken lysozyme 5' matrix attachment site is 3' followed by a strongly curved DNA sequence. Nucleic Acids Research, vol. 18, No. 13, pp. 3881-3885, 1990.*

AL389920, *Homo sapiens* chromosome 1 clone RP5-852H15. Jul. 10, 2001. McLay, K.*

Gail Urlaub, et al., Deletion of the diploid dihydrofolate reductase locus from cultured mammalian cells, Cell, Jun. 1983, pp. 405-412, vol. 33, MIT, US.

Chao Chen and Lawrence A. Chasin, Cointegration of DNA Molecules Introduced into Mammalian Cells by Electroporation, Somatic Cell and Molecular Genetics, Jul. 1998, pp. 249-256, vol. 24, No. 4, Springer Netherlands, US.

(Continued)

*Primary Examiner* — Celine Qian

(74) *Attorney, Agent, or Firm* — Joyce von Natzmer; Agris & von Natzmer LLP

(57) ABSTRACT

The present invention relates to purified and isolated DNA sequences having protein production increasing activity and more specifically to the use of matrix attachment regions (MARs) for increasing protein production activity in a eukaryotic cell. Also disclosed is a method for the identification of said active regions, in particular MAR nucleotide sequences, and the use of these characterized active MAR sequences in a new multiple transfection method.

46 Claims, 15 Drawing Sheets

U.S. PATENT DOCUMENTS

| | | | |
|---|---|---|---|
| 2003/0032597 | A1 | 2/2003 | Sebestyen |
| 2003/0054548 | A1 | 3/2003 | Kaleko et al. |
| 2003/0082552 | A1 | 5/2003 | Wolffe et al. |
| 2003/0087342 | A1 | 5/2003 | Mermod et al. |
| 2003/0100077 | A1 | 5/2003 | Korte et al. |
| 2003/0140363 | A1 | 7/2003 | Rapp |
| 2003/0140364 | A1 | 7/2003 | Hichney et al. |
| 2003/0157715 | A1 | 8/2003 | Laemmli |
| 2003/0224477 | A1 | 12/2003 | Heartlein et al. |
| 2003/0228612 | A1 | 12/2003 | Kenward et al. |
| 2003/0232414 | A1 | 12/2003 | Moore |
| 2004/0016015 | A1 | 1/2004 | Nguyen et al. |
| 2004/0038394 | A1 | 2/2004 | Kim et al. |
| 2004/0072352 | A1 | 4/2004 | Kim et al. |
| 2004/0076954 | A1 | 4/2004 | Caldwell et al. |
| 2004/0077842 | A1 | 4/2004 | Himawan |
| 2004/0088764 | A1 | 5/2004 | Gleba et al. |
| 2004/0103454 | A1 | 5/2004 | Conkling et al. |
| 2004/0115776 | A1 | 6/2004 | Simesen et al. |
| 2004/0126883 | A1 | 7/2004 | Liu |
| 2004/0216189 | A1 | 10/2004 | Houmard et al. |
| 2004/0221330 | A1 | 11/2004 | Klimyuk et al. |
| 2004/0242512 | A1 | 12/2004 | Misawa et al. |
| 2005/0022262 | A1 | 1/2005 | Vance |
| 2005/0034187 | A1 | 2/2005 | Golovko et al. |
| 2005/0050581 | A1 | 3/2005 | Harvey et al. |
| 2005/0064467 | A1 | 3/2005 | Ivanova et al. |
| 2005/0129669 | A1 | 6/2005 | Treco et al. |
| 2005/0130267 | A1 | 6/2005 | Wolffe et al. |

FOREIGN PATENT DOCUMENTS

| | | | |
|---|---|---|---|
| EP | 0663921 | B1 | 9/1993 |
| EP | 1135512 | | 6/2000 |
| EP | 1471144 | | 10/2004 |
| FR | 2832423 | A1 | 5/2003 |
| WO | WO 97/27207 | A1 | 7/1997 |
| WO | 97/46687 | A1 | 12/1997 |
| WO | 00/05393 | B1 | 2/2000 |
| WO | WO00/05393 | B1 | 2/2000 |
| WO | WO 00/20950 | A1 | 4/2000 |
| WO | 00/32800 | A1 | 6/2000 |
| WO | WO0032800 | | 6/2000 |
| WO | WO00/53137 | A1 | 9/2000 |
| WO | 02/00262 | A2 | 1/2002 |
| WO | WO 02/00262 | A2 | 1/2002 |
| WO | 02/09507 | A1 | 2/2002 |
| WO | 02/068669 | A2 | 9/2002 |
| WO | 02074969 | A2 | 9/2002 |
| WO | WO 02/072138 | A1 | 9/2002 |
| WO | WO 02/077180 | A2 | 10/2002 |
| WO | WO02079447 | | 10/2002 |
| WO | WO 03/024199 | A2 | 3/2003 |
| WO | WO 03/043415 | A1 | 5/2003 |
| WO | WO 2004/053106 | A2 | 6/2004 |
| WO | 2004/055182 | A1 | 7/2004 |
| WO | WO 2004/070040 | A1 | 8/2004 |
| WO | 2004/094640 | A1 | 11/2004 |
| WO | WO 2004/106375 | A1 | 12/2004 |
| WO | WO 2005/021765 | A2 | 3/2005 |
| WO | 2005/040377 | A2 | 5/2005 |
| WO | WO 2005/040384 | A1 | 5/2005 |
| WO | 2008023247 | A2 | 2/2008 |

OTHER PUBLICATIONS

Bode, J. et al., Scaffold/Matrix-Attached Regions: Structural Properties Creating Transcriptionally Active Loci, International Review of Cytology, vol. 162A; p. 389-444 (1995).

Manju Agarwal, et al., Scaffold Attachment Region-Mediated Enhancement of Retroviral Vector Expression in Primary T Cells, Journal of Virology, May 1998, pp. 3720-3728, vol. 72, No. 5, American Society for Microbiology, US.

George C. Allen, et al., High-Level Transgene Expression in Plant Cells: Effects of a Strong Scaffold Attachment Region from Tobacco, The Plant Cell, May 1996, pp. 899-913, vol. 8, American Society of Plant Physiologists, US.

Adam C. Bell and Gary Felsenfeld, Stopped at the border: boundries and insulators, Current Opinion in Genetics & Development, 1999, p. 191-198, vol. 9, Elsevier Science Ltd., US.

Xin Bi and James R. Broach, UASrpg can function as a heterochromatin boundary element in yeast, Genes & Development, 1999, pp. 1089-1101, vol. 13, Cold Spring Harbor Laboratory Press, US.

Jurgen Bode, et al., Transcriptional Augmentation: Modulation of Gene Expression by Scaffold/Matrix-Attached Regions (S/MAR Elements), Critical ReviewsTM in Eukaryotic Gene Expression, 2000, pp. 73-90, vol. 10(1), Begell House, Inc., US.

Eliette Bonnefoy, et al., Specific Binding of High-Mobility-Group I (HMGI) Protein and Histone H1 to the Upstream AT-Rich Region of the Murine Beta Interferon Promoter: HMGI Protein Acts as a Potential Antirepressor of the Promoter, Molecular and Cellular Biology, Apr. 1999, pp. 2803-2816, vol. 19, No. 4, American Society for Microbiology, US.

Otmane Boussif, et al., A versatile vector for gene and oligonucleotide transfer into cellsin culture and in vivo: Polyethylenimine, Biochemistry, Aug. 1995, pp. 7297-7301, vol. 92, Proc. Natl. Acad. Sci. USA, US.

Joaquin Castilla, et al., Engineering passive immunity in transgenic mice secreting virus-neutralizing antibodies in milk, Nature Biotechnology, Apr. 1998, pp. 349-354, vol. 16, Nature Publishing Group, US.

J. Patrick Condreay, et al., Transient and stable gene expression in mammalian cells transduced with a recombinant baculovirus vector, Cell Biology, Jan. 1999, pp. 127-132, vol. 96, Proc. Natl. Acad. Sci. USA, US.

George W. Cox, et al., Molecular Cloning and Characterization of a Novel MouseMacrophage Gene That Encodes a Nuclear Protein ComprisingPolyglutamine Repeats and Interspersing Histidines, The Journal of Biological Chemistry, Oct. 11, 1996, pp. 25515-25523, vol. 271, No. 41, The American Society for Biochemistry and Molecular Biology, US.

Olivier Cuvier, et al., Identification of a Class of Chromatin Boundary Elements, Molecular and Cellular Biology, Dec. 1998, pp. 7478-7486, vol. 18, No. 12, American Society for Microbiology, US.

Database EMBL [Online] Feb. 11, 1995, "*G. gallus* lysozyme gene promoter" X84223 retrieved from EBI accession No. EM_VRT:X84223 Database accession No. X84223.

Database EMBL [Online] Jul. 16, 1990, "Chicken Lysozyme gene intrinsically curved segment of DNA" X52989 retrieved from EBI accession No. EM_VRT:X52989 Database accession No. X52989.

Database EMBL [Online] May 17, 2000, "Cloning vector pMAR luciferase reporter vector containing MAR insulator sequence". AJ277960 retrieved from EBI accession No. EM_SYN:AJ277960 Database accession No. AJ277960.

Database EMBL [Online] Jun. 14, 1996, *G. gallus* lysozyme gene 5' matrix attachment region (MAR) subfragment B-1-H1 X98408 retrieved from EBI accession No. EM_VRT:X98408 Database accession No. X98408.

Database EMBL [Online] Jan. 4, 2002, "Human DNA sequence from clone RP4-743D20 on chromosome 1 Contains novel gene and a CpG island." XP002322943 retrieved from EBI accession No. EM_HUM:AL663105.

Matthias Frisch, et al., In Silico Prediction of Scaffold/Matrix Attachment Regions in Large Genomic Sequences, Genome Research, 2001, pp. 349-354, vol. 12, Cold Harbor Laboratory Press, US.

Frank Grosveld, Activation by locus control regions?, Current Opinion in Gentics & Development, 1999, pp. 152-157, vol. 9, Elsevier Science Ltd., US.

Craig Hart and Ulrich Laemmli, Facilitation of chromatin dynamics by SARs, Current Opinion in Genetics & Development, 1998, pp. 519-525, vol. 8, Current Biology Limited, US.

Thomas Jenuwein, et al., Extension of chromatin accessibility by nuclear matrix attachment regions, Nature, Jan. 16, 1997, pp. 269-272, vol. 385, Nature Publishing Group, US.

Martin Jordan, 'et al., Transfecting mammalian cells: optimization of critical parameters affecting calcium-phosphate precipitate formation, Nucleic Acids Research, 1996, pp. 596-601, vol. 24, No. 4, Oxford University Press, UK.

Michael Kalos and R. E. K. Fournier, Molecular and Cellular Biology, Jan. 1995, pp. 198-207, vol. 15, No. 1, American Society for Microbiology, US.
Randal Kaufman and Phillip Sharp, Amplification and Expression of Sequences Cotransfected with a Modular Dihydrofolate Reductase Complementary DNA Gene, Journal of Molecular Biology, 1982, pp. 601-621, vol. 159, Academic Press Inc. (London) Ltd., UK.
Dagmar Klehr, et al., Scaffold-Attached Regions from the Human Interferon, i3 Domain Can Be Used to Enhance the Stable Expression of Genes under the Control of Various Promoters, Biochemistry, 1991, pp. 1264-1270, vol. 30, American Chemical Society, US.
Ted H.J. Kwaks, et al., Identification of anti-repressor elements that confer high and stable protein production in mammalian cells, Nature Biotechnology, May 2003, pp. 553-558, vol. 21, Nature Publishing Group, US.
Victor Levitsky, et al., Nucleosomal DNA property database, Bioinformatics, 1999, pp. 582-592, vol. 15, Nos. 7/8, Oxford University Press, UK.
Robert McKnight, et al., Martrix-attachment regions can impart position-independent regulation of a tissue-specific gene in transgenic mice, Genetics, Aug. 1992, pp. 6943-6947, vol. 89, Proc. Natl. Acad. Sci. USA, US.
Sylvia Miescher, et al., CHO expression of a novel human recombiant IgG1 anti-RhD antibody isolated by ohage display, British Journal of Haematology, 2000, pp. 157-166, vol. 111, Blackwell Science Ltd., UK.
Grant MacGregor and C. Thomas Caskey, Construction of plasmids that express *E. coli* b-galactosidase in mammalian cells, Nucleic Acids Research, 1989, p. 2365, vol. 17, No. 6, IRL Press, US.
Tobias Neff, et al., Stem Cell Gene Therapy, Position Effects and Chromatin Insulators, Hematopoietic Stem Cells, Stem Cells, 1997, pp. 265-271, vol. 15(suppl 1), AlphaMed Press, US.
Bejamin Ortiz, et al., Adjacent DNA elements dominantly restrict the ubiquitous activity of a novel chromatin-opening region to specific tissues, The EMBO Journal, 1997, pp. 5037-5045, vol. 16, No. 16, Oxford University Press, UK.
Loc Phi-Van, et al., The Chicken Lysozyme 5' Matrix Attachment Region Increases Transcription from a Heterologous Promoter in Heterologous Cells and Dampens Position Effects on the Expression of Transfected Genes, Molecular and Cellular Biology, May 1990, pp. 2302-2307, vol. 10, No. 5, American Society for Microbiology, US.
C. Piechaczek, et al., A vector based on the SV40 origin of replication and chromosomal S/MARs replicates episomally in CHO cells, Nucleic Acids Research, 1999, pp. 426-428, vol. 27, No. 2, Oxford University Press, UK.
Leonora Poljak, et al., SARs stimulate but do not confer position independent gene expression, Nucleic Acids Research, 1994, pp. 4386-4394, vol. 22, No. 21, Oxford University Press, UK.
Pierre Rollini, et al. Identification and characterization of nuclear matrix-attach,emt regions in the human serpin gene cluster at 14q32. 1, Nucleic Acids Research, 1999, pp. 3779-3791, vol. 27, No. 19, Oxford University Press, UK.
Gautam Singh, et al., Mathematical model to predict regions of chromatin attachment to the nuclear matrix, Nucleic Acids Research, 1997, pp. 1419-1425, vol. 25, No. 7, Oxford University Press, UK.
T. D. Southgate, et al., Transcriptional Targeting to Anterior Pituitary Lactotrophic Cells Using Recombinant Adenovirus Vectors in Vitro and in Vivo in Normal and Estrogen/Sulpiride-Induced Hyperplasic Anterior Pituitaries, Endocrinology, 2000, pp. 3493-3505, vol. 141, No. 9, The Endocrine Society, US.
Dale Talbot, et al., The 5' flanking region of the rat LAP (C/EBPf) gene can direct high-level, position-independent, copy numberdependent expression in multiple tissues in transgenic mice, Nucleic Acids Research, 1994, pp. 756-766, vol. 22, No. 5, Oxford University Press, US.
Masaaki Tatsuka, et al., Experimental Cell Research, 1988, pp. 154-162, vol. 178, Academic Press, Inc., SE.
Andor Udvary, Dividing the empire: boundary chromatin elements delimit the territory of enhancers, The EMBO Journal, 1999, pp. 1-8, vol. 18, No. 1.
Mark Walters, et al., The Chicken b-Globin 59HS4 Boundary Element Blocks Enhancer-Mediated Suppression of Silencing,Mark Walters, et al., The Chicken b-Globin 59HS4 Boundary Element Blocks Enhancer-Mediated Suppression of Silencing, Molecular and Cellular Biology, May 1999, pp. 3714-3726, vol. 19, No. 5, American Society for Microbiology, US Molecular and Cellular Biology, May 1999, pp. 3714-3726, vol. 19, No. 5, American Society for Microbiology, US.
Yaolin Wang, et al., Ligand-inducible and liver-specific target gene expression in transgenic mice, Nature Biotechnology, Mar. 1997, pp. 239-243, vol. 15, Nature Publishing Group, US.
Kevin Wells, et al., Codon optimization, genetic insulation, and an rtTA reporter improve performance of the tetracycline switch, Transgenic Research, 1999, pp. 371-381, vol. 8, Kluwer Academic Publishers, NL.
Monique Zahn-Zabal, et al., Development of stable cell lines for production or regulated expression using matrix attachment regions, Journal of Biotechnology, 2001, pp. 29-42, vol. 87, Elsiver Science Ltd., US.
Robert Pawliuk, et al., Retroviral vectors aimed at the gene therapy of human beta-golbin gene disorder, Annals New York Academy of Sciences, 1998, pp. 151-162, vol. 850, New York Academy of Sciences, US.
Martin Fussenegger, et al., Genetic optimization of recombinant glycoprotein production by mammalian cells, TIBTECH, Jan. 1999, pp. 35-42, vol. 17, Elsevier Science Ltd., US.
N. M. Greenberg, et al., The rat probasin gene promoter directs hormonally and developmentally regulated expression of a heterologous gene specifically to the prostate in transgenic mice, Molecular Endocrinology, 1994, pp. 230-239, vol. 8, No. 2, The Endocrine Society, US.
Cornelia M. Gorman and Bruce H. Howard, Expression of recombinant plasmids in mammalian cells is enhanced by sodium butyrate, Nucleic Acids Research, 1983, pp. 7631-7648, vol. 11, No. 21, IRL Press Limited, UK.
Markus O. Imhof, et al., A regulatory network for the efficient control of transgene expression, The Journal of Gene Medicine, 2000, pp. 107-116, vol. 2, John Wiley & Sons, Ltd., US.
Aribert Stief, et al. A nuclear DNA attachment element mediates elevated and position-independent gene activity, Nature, Sep. 28, 1989, pp. 343-345, vol. 341, Nature Publishing Group, US.
Girod Pierre-Alain et al: "Genome-wide prediction of matrix attachment regions that increase gene expression in mammalian cells" in Nature Methods, vol. 4, No. 9, Aug. 5, 2007, pp. 747-753.
Tianyun Wang et al: "Increased expression of transgene in stably transformed cells of Dunaliella salina by matrix attachment regions" in Applied Microbiology and Biotechnology, Springer-Verlag, BE, vol. 76, No. 3, Jul. 5, 2007, pp. 651-657.
Database EMBL, Jan. 12, 2006, Birren B. Nusbaum C. Lander E.: "Mus musculus chromosome 1, clone RP23-444A8" Database accession No. AC102666.
Database EMBL, May 16, 2004, Kruchowski S et al.: "The sequence of Mus musculus BAC clone RP23-388E14" Database accession No. AC134595.
Whitelaw C B A et al: "Matrix attachment region regulates basal beta-lactoglobulin transgene expression" in Gene, Elsevier, Amsterdam, NL, vol. 244, No. 1-2, Feb. 2000, pp. 73-80.
Girod Pierre-Alain et al: "Use of the chicken lysozyme 5' matrix attachment region to generate high producer CHO cell lines" in Biotechnology and Bioengineering, vol. 91, No. 1, Jul. 2005, pp. 1-11.
Gutierrez-Adan A et al: "Effect of Flanking Matrix Attachment Regions on the Expression of Microinjected Transgenes During Preimplantation Development of Mouse Embryos" in Transgenic Research, London, GB, vol. 9, No. 2, Apr. 2000, pp. 81-89.
Kim Jong-Mook et al: "Improved recombinant gene expression in CHO cells using matrix attachment regions" in Journal of Biotechnology, Elsevier Science Publishers, Amsterdam, NL, vol. 107, No. 2, Jan. 22, 2004, pp. 95-105.
Vain P et al: "Matrix Attachment Regions Increase Transgene Expression Levels and Stability in Transgenic Rice Plants and Their Progeny" in Plant Journal, Blackwell Scientific Publications, Oxford, GB, vol. 18, No. 3, 1999, pp. 233-242.

Liebich I et al: “Evaluation of sequence motifs found in scaffold/matrix-attached regions (S/MARs)” in Nucleic Acids Research, Oxford University Press, Surrey, GB, vol. 30, No. 15, Aug. 1, 2002, pp. 3433-3442.
Liebich Ines et al: “S/MARt DB: A database on scaffold/matrix attached regions” Nucleic Acids Research, vol. 30, No. 1, Jan. 1, 2002, pp. 372-374.
Bode Juergen et al: “Transcriptional augmentation: Modulation of gene expression by scaffold/matrix-attached regions (S/MAR elements)” in Critical Reviews in Eukaryotic Gene Expression, vol. 10, No. 1, 2000,pp. 73-90.
Kries et al: “A non-curved chicken lysyzyme matrix attachment site is 3' followed by a strongly curved DNA sequence” in Nucleic Acids Research, Oxford University Press, Surrey, GB, vol. 18, No. 13, Jul. 11, 1990, pp. 3881-3885.
Yamamura J et al: “Analysis of sequence-dependent curvature in matrix attachment regions” in FEBS Letters, Elsevier, Amsterdam, NL, vol. 489, No. 2-3, Feb. 2, 2001, pp. 166-170.
Boulikas Teni: “Nature of DNA sequences at the attachment regions of genes to the nuclear matrix” in Journal of Cellular Biochemistry, vol. 52, No. 1, 1993, pp. 14-22.
Singh G B et al: “Mathematical model to predict regions of chromatin attachment to the nuclear matrix” in Nucleic Acids Research, Oxford University Press, Surrey, GB, vol. 25, No. 7, 1997, pp. 1419-1425.
Frisch M et al: “In silico prediction of scaffold/matrix attachment regions in large genomic sequences” in Genome Research, Cold Spring Harbor Laboratory Press, Woodbury, NY, US, vol. 12, No. 2, Feb. 2002, pp. 349-354.
Bode J et al: “Scaffold/matrix-attached regions: Structural properties creating transcriptionally active loci” in International Review of Cytology, Academic Press, 1995, pp. 389-454.
Kwaks et al: “Employing epigenetics to augment the expression of therapeutic proteins in mammalian cells” in Trends in Biotechnology, Elsevier Publications, Cambridge, GB, vol. 24, No. 3, Mar. 2006, pp. 137-142.
Tatsuka et al, An Improved Method of Electroporation for Introducing Biologically Active Foreign Genes into Cultured Mammalian Cells, Exp Cell Res, 1988, vol. 178 pp. 154-162.
Southgate et al, Transcriptional Targeting to Anterior Pituitary Lactotrophic Cells Using Recombinant Adenovirus Vectors in Vitro and in Vivo in Normal and Estrogen/Sulpiride-Induced Hyperplasic Anterios Pituitaries, Endocr, 2000, vol. 141 pp. 3493-3505.
MacGregor, et al., “Construction of Plasmids that Express *E.Coli* B-Galactosidase in Mammalian Cells,” Nucleic Acids Research, vol. 17, No. 6, IRL Press, US, 1989 p. 2365.
Kiehr et al., “Scaffold-Attached Regions from the Human Interferon B Domain Can Be Used to Enhance the Stable Expression of Genes Under the Control of Various Promoters,” Biochemistry, vol. 30, 1991, pp. 1264-1270.
Roulet et al., “Evaluation of computer tools for the prediction of transcription factor binding sites on genomic DNA,” Bioinformation Systems, e.V., available at http://www.bioinfo.de/isb/1998010004/main.html, accessed Sep. 7, 2010.
Evans et al., “A comparative study of S/MAR prediction tools,” BMC Bioinformatics, vol. 8 (71), Mar. 2, 2007, pp. 1-29.
Zahn-Zabal et al., “Development of Stable Cell Lines for Production or Regulated Expression Using Matrix Attachment Regions,” in Journal of Biotechnology, vol. 87, 2001, pp. 29-42.
Frisch et al., “In Silico Prediction of Scaffold/Matrix Attachment Regions in Large Genomic Sequences,” in Genome Research, Cold Spring Harbor Laboratory Press, Woodbury, NY, vol. 12(2), Feb. 1, 2002, pp. 349-354.
Singh et al., “Mathematical Model to Predict Regions of Chromatin Attachment to the Nuclear Matrix,” in Nucleic Acid Research, vol. 25(7), 1997, pp. 1419-1425.
Levitsky et al., “Nucleosomal DNA Property Database,” in Bioinformatics, vol. 15(7/8), 1999, pp. 582-592.
Cox et al., “Molecular Cloning and Characterization of a Novel Mouse Macrophage Gene that Encodes a Nuclear Protein Comprising Polyglutamine Repeats and Interspersing Histidines,” in The Journal of Biological Chemistry, vol. 271(41), Oct. 11, 1996, pp. 25515-25523.
Database EMBL [online], “Human DNA Sequence from Clone RP11-329A14 on Chromosome 1 Contains the 5' end of the SPATA6 Gene for Spermatogenesis Associated 6, an Amyotrophic Lateral Sclerosis 2 (Juvenile) Chromosome Region, Candidate 2 (ALS2CR2) Pseudogene, a Ribosomal Protein L21 (RPL21) Pseudogene and a CpG Island,” XP002488536, May 26, 2000.
Kwaks et al., “Identification of Anti-Repressor Elements that Confer High and Stable Protein Production in Mammalian Cells,” in Nature Biotechnology, Nature Publishing Group, New York, NY, vol. 21(5), May 20, 2003, pp. 553-558.
Phi-Van & Staetling; The matrix attachment regions of the chicken lysozyme gene co-map with the boundaries of the chromatin domain, EMBO J.. 7, No. 3: 655-664 (1988).

* cited by examiner (A)

(B)

% TA dinucleotide vs Bent DNA

HIGH EFFICIENCY GENE TRANSFER AND EXPRESSION IN MAMMALIAN CELLS BY A MULTIPLE TRANSFECTION PROCEDURE OF MAR SEQUENCES

This is the U.S. national stage of International application PCT/EP2004/011974, filed Oct. 22, 2004 designating the United States and claiming the benefit of U.S. provisional application 60/513,574, filed Oct. 24, 2003 and priority to European application EP04002722.9, filed Feb. 6, 2004.

FIELD OF THE INVENTION

The present invention relates to purified and isolated DNA sequences having protein production increasing activity and more specifically to the use of matrix attachment regions (MARs) for increasing protein production activity in a eukaryotic cell. Also disclosed is a method for the identification of said active regions, in particular MAR nucleotide sequences, and the use of these characterized active MAR sequences in a new multiple transfection method.

BACKGROUND OF THE INVENTION

Nowadays, the model of loop domain organization of eukaryotic chromosomes is well accepted (Boulikas T, "Nature of DNA sequences at the attachment regions of genes to the nuclear matrix", *J. Cell Biochem.,* 52:14-22, 1993). According to this model chromatin is organized in loops that span 50-100 kb attached to the nuclear matrix, a proteinaceous network made up of RNPs and other nonhistone proteins (Bode J, Stengert-Iber M, Kay V, Schalke T and Dietz-Pfeilstetter A, *Crit. Rev. Euk. Gene Exp.,* 6:115-138, 1996).

The DNA regions attached to the nuclear matrix are termed SAR or MAR for respectively scaffold (during metaphase) or matrix (interphase) attachment regions (Hart C and Laemmli U (1998), "Facilitation of chromatin dynamics by SARs" *Curr Opin Genet Dev* 8, 519-525.)

As such, these regions may define boundaries of independent chromatin domains, such that only the encompassing cis-regulatory elements control the expression of the genes within the domain.

However, their ability to fully shield a chromosomal locus from nearby chromatin elements, and thus confer position-independent gene expression, has not been seen in stably transfected cells (Poljak L, Seum C, Mattioni T and Laemmli U. (1994) "SARs stimulate but do not confer position independent gene expression", *Nucleic Acids Res* 22, 4386-4394). On the other hand, MAR (or S/MAR) sequences have been shown to interact with enhancers to increase local chromatin accessibility (Jenuwein T, Forrester W, Fernandez-Herrero L, Laible G, Dull M, and Grosschedl R. (1997) "Extension of chromatin accessibility by nuclear matrix attachment regions" *Nature* 385, 269-272). Specifically, MAR elements can enhance expression of heterologous genes in cell culture lines (Kalos M and Fournier R (1995) "Position-independent transgene expression mediated by boundary elements from the apolipoprotein B chromatin domain" *Mol Cell Biol* 15, 198-207), transgenic mice (Castilla J, Pintado B, Sola, I, Sanchez-Morgado J, and Enjuanes L (1998) "Engineering passive immunity in transgenic mice secreting virus-neutralizing antibodies in milk" *Nat Biotechnol* 16, 349-354) and plants (Allen G, Hall G J, Michalowski S, Newman W, Spiker S, Weissinger A, and Thompson W (1996), "High-level transgene expression in plant cells: effects of a strong scaffold attachment region from tobacco" *Plant Cell* 8, 899-913). The utility of MAR sequences for developing improved vectors for gene therapy is also recognized (Agarwal M, Austin T, Morel F, Chen J, Bohnlein E, and Plavec I (1998), "Scaffold attachment region-mediated enhancement of retroviral vector expression in primary T cells" *J Virol* 72, 3720-3728).

Recently, it has been shown that chromatin-structure modifying sequences including MARs, as exemplified by the chicken lysozyme 5' MAR is able to significantly enhance reporter expression in pools of stable Chinese Hamster Ovary (CHO) cells (Zahn-Zabal M, et al., "Development of stable cell lines for production or regulated expression using matrix attachment regions" *J Biotechnol,* 2001, 87(1): p. 29-42). This property was used to increase the proportion of high-producing clones, thus reducing the number of clones that need to be screened. These benefits have been observed both for constructs with MARs flanking the transgene expression cassette, as well as when constructs are co-transfected with the MAR on a separate plasmid. However, expression levels upon co-transfection with MARs were not as high as those observed for a construct in which two MARs delimit the transgene expression unit. A third and preferable process was shown to be the transfection of transgenes with MARs both linked to the transgene and on a separate plasmid (Girod et al., submitted for publication). However, one persisting limitation of this technique is the quantity of DNA that can be transfected per cell. Many multiples transfection protocols have been developed in order to achieve a high transfection efficiency to characterize the function of genes of interest. The protocol applied by Yamamoto et al, 1999 ("High efficiency gene transfer by multiple transfection protocol", *Histochem. J.* 31(4), 241-243) leads to a transfection efficiency of about 80% after 5 transfections events, whereas the conventional transfection protocol only achieved a rate of <40%. While this technique may be useful when one wishes to increase the proportion of expressing cells, it does not lead to cells with a higher intrinsic productivity. Therefore, it cannot be used to generate high producer monoclonal cell lines. Hence, the previously described technique has two major drawbacks:

i) this technique does not generate a homogenous population of transfected cells, since it cannot favour the integration of further gene copy, nor does it direct the transgenes to favorable chromosomal loci, ii) the use of the same selectable marker in multiple transfection events does not permit the selection of doubly or triply transfected cells.

In patent application WO02/074969, the utility of MARs for the development of stable eukaryotic cell lines has also been demonstrated. However, this application does not disclose neither any conserved homology for MAR DNA element nor any technique for predicting the ability for a DNA sequence to be a MAR sequence.

In fact no clear-cut MAR consensus sequence has been found (Boulikas T, "Nature of DNA sequences at the attachment regions of genes to the nuclear matrix", *J. Cell Biochem.,* 52:14-22, 1993) but evolutionarily, the structure of these sequences seem to be functionally conserved in eukaryotic genomes, since animal MARs can bind to plant nuclear scaffolds and vice versa (Mielke C, Kohwi Y, Kohwi-Shigematsu T and Bode J, "Hierarchical binding of DNA fragments derived from scaffold-attached regions: correlation of properties in vitro and function in vivo", *Biochemistry,* 29:7475-7485, 1990).

The identification of MARs by biochemical studies is a long and unpredictable process; various results can be obtained depending on the assay (Razin S V, "Functional architecture of chromosomal DNA domains", *Crit Rev Eukaryot Gene Expr.,* 6:247-269, 1996). Considering the huge number of expected MARs in a eukaryotic genome and the amount of sequences issued from genome projects, a tool able to filter potential MARS in order to perform targeted experiments would be greatly useful.

Currently two different predictive tools for MARs are available via the Internet. The first one, MAR-Finder; Singh G B, Kramer J A and Krawetz S A, "Mathematical model to predict regions of chromatin attachment to the nuclear matrix", Nucleic Acid Research, 25:1419-1425, 1997) is based on set of patterns identified within several MARs and a statistical analysis of the co-occurrence of these patterns. MAR-Finder predictions are dependent of the sequence context, meaning that predicted MARs depend on the context of the submitted sequence. The other predictive software, SMARTest; Frisch M, Frech K, Klingenhoff A, Cartharius K, Liebich I and Werner T, "In silico prediction of scaffold/matrix attachment regions in large genomic sequences", Genome Research, 12:349-354, 2001), use weight-matrices derived from experimentally identified MARs. SMARTest is said to be suitable to perform large-scale analyses. But actually aside its relative poor specificity, the amount of hypothetical MARs rapidly gets huge when doing large scale analyses with it, and in having no way to increase its specificity to restrain the number of hypothetical MARs, SMARTest becomes almost useless to screen forpotent MARs form large DNA sequences.

Some other softwares, not available via the Internet, also exists; they are based as well on the frequency of MAR motifs (MRS criterion; Van Drunen C M et al., "A bipartite sequence element associated with matrix/scaffold attachment regions", *Nucleic Acids Res,* 27:2924-2930, 1999), (ChrClass; Glazko G V et al., "Comparative study and prediction of DNA fragments associated with various elements of the nuclear matrix", *Biochim. Biophys. Acta,* 1517:351-356, 2001) or based on the identification of sites of stress-induced DNA duplex (SIDD; Benham C and al., "Stress-induced duplex DNA destabilization in scaffold/matrix attachment regions", *J. Mol. Biol.,* 274:181-196, 1997). However, their suitability to analyze complete genome sequences remains unknown, and whether these tools may allow the identification of protein production-increasing sequences has not been reported.

Furthermore, due to the relatively poor specificity of these softwares (Frisch M, Frech K, Klingenhoff A, Cartharius K, Liebich I and Werner T, "In silico prediction of scaffold/matrix attachment regions in large genomic sequences", *Genome Research,* 12:349-354, 2001), the amount of hypothetical MARs identified in genomes rapidly gets unmanageable when doing large scale analyses, especially if most of these have no or poor activity in practice. Thus, having no way to increase prediction specificity to restrain the number of hypothetical MARs, many of the available programs become almost useless to identify potent genetic elements in view of efficiently increasing recombinant protein production.

Since all the above available predictive methods have some drawbacks that prevent large-scale analyses of genomes to identify reliably novel and potent MARs, the object of this invention is to 1) understand the functional features of MARs that allow improved recombinant protein expression; 2) get a new Bioinformatic tool compiling MAR structural features as a prediction of function, in order to 3) perform large scale analyses of genomes to identify novel and more potent MARs, and, finally 4) to demonstrate improved efficiency to increase the production of recombinant proteins from eukaryotic cells or organisms when using the newly identified MAR sequences.

SUMMARY OF THE INVENTION

This object has been achieved by providing an improved and reliable method for the identification of DNA sequences having protein production increasing activity, in particular MAR nucleotide sequences, and the use of these characterized active MAR sequences in a new multiple transfection method to increase the production of recombinant proteins in eukaryotic cells.

BRIEF DESCRIPTION OF THE FIGURES

FIG. 8 (B) represents a Map of locations for various DNA sequence motifs within the cLysMAR. Vertical lines represent the position of the computer-predicted sites or sequence motifs along the 3034 base pairs of the cLysMAR and its active regions, as presented in FIG. 5. The putative transcription factor sites, (MEF2 05, Oct-1, USF-02, GATA, NFAT) for activators and (CDP, SATB1, CTCF, ARBP/MeCP2) for repressors of transcription, were identified using MatInspector (Genomatix), and CpG islands were identified with CPGPLOT. Motifs previously associated with MAR elements are labelled in black and include CpG dinucleotides and CpG islands, unwinding motifs (AATATATT and MTATT), poly As and Ts, poly Gs and Cs, *Drosophila* topoisomerase II binding sites (GTNWAYATTNATTNATNNR (SEQ ID NO: 242)) which had identity to the 6 bp core and High mobility group I (HMG-I/Y) protein binding sites. Other structural motifs include nucleosome-binding and nucleosome disfavouring sites and a motif thought to relieve the superhelical strand of DNA. FIG. 8(A) represents the comparison of the ability of portions of the cLysMAR to activate transcription with MAR prediction score profiles with MarFinder. The top diagram shows the MAR fragment activity as in FIG. 5, while the middle and bottom curves show MARFinder-predicted potential for MAR activity and for bent DNA structures respectively.

FIG. 9(A), represents the DNA melting temperature, double helix bending, major groove depth and minor groove width profiles of the 5'-MAR and were determined using the algorithms of Levitsky et al (Levitsky V G, Ponomarenko M P, Ponomarenko J V, Frolov A S, Kolchanov N A "Nucleosomal DNA property database", *Bioinformatics,* 15; 582592, 1999). The most active B, K and F fragments depicted at the top are as shown as in FIG. 1. FIG. 9(B), represents the enlargement of the data presented in panel A to display the F fragment map aligned with the tracings corresponding to the melting temperature (top curve) and DNA bending (bottom curve). The position of the most active FIB fragment and protein binding site for specific transcription factors are as indicated.

DETAILED DESCRIPTION OF THE INVENTION

Figure 1:
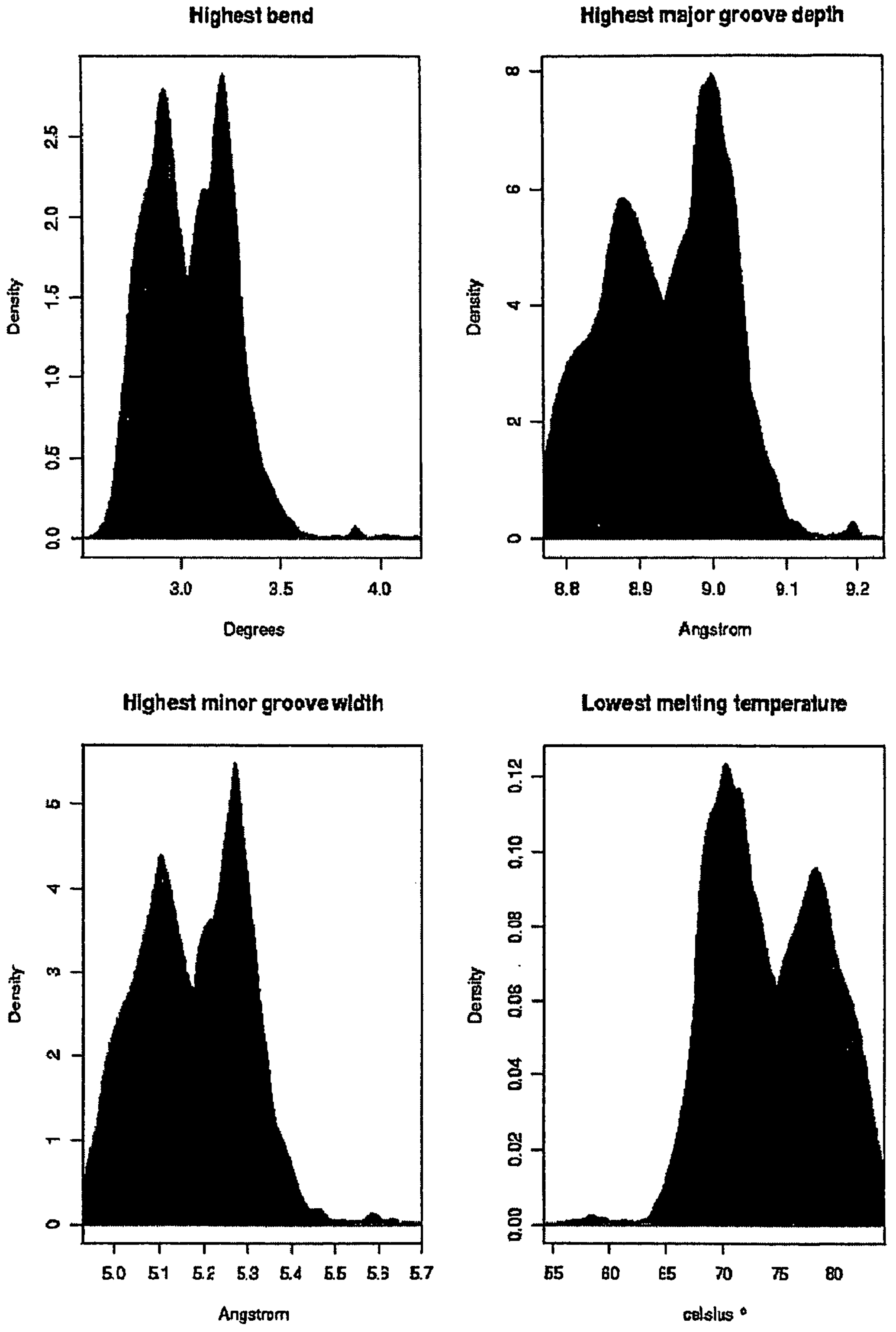
FIG. 1 shows the distribution plots of MARs and non-MARs sequences. Histograms are density plots (relative frequency divided by the bin width) relative to the score of the observed parameter. The density histogram for human MARs in the SMARt DB database is shown in black, while the density histogram for the human chromosome 22 are in grey.

The present invention relates to a purified and isolated DNA sequence having protein production increasing activity characterized in that said DNA sequence comprises at least one bent DNA element, and at least one binding site for a DNA binding protein.

Certain sequences of DNA are known to form a relatively "static curve", where the DNA follows a particular 3-dimensional path. Thus, instead of just being in the normal B-DNA conformation ("straight"), the piece of DNA can form a flat, planar curve also defined as bent DNA (Marini, et al., 1982 "Bent helical structure in kinetoplast DNA", *Proc. Natl. Acad. Sci. USA,* 79: 7664-7664).

Surprisingly, Applicants have shown that the bent DNA element of a purified and isolated DNA sequence having protein production increasing activity of the present invention usually contains at least 10% of dinucleotide TA, and/or at least 12% of dinucleotide AT on a stretch of 100 contiguous base pairs. Preferably, the bent DNA element contains at least 33% of dinucleotide TA, and/or at least 33% of dinucleotide AT on a stretch of 100 contiguous base pairs. These data have been obtained by the method described further.

According to the present invention, the purified and isolated DNA sequence usually comprises a MAR nucleotide sequence selected from the group comprising the sequences SEQ ID Nos 1 to 27 or a cLysMAR element or a fragment thereof. Preferably, the purified and isolated DNA sequence is a MAR nucleotide sequence selected from the group comprising the sequences SEQ ID Nos 1 to 27, more preferably the sequences SEQ ID Nos 24 to 27.

Encompassed by the present invention are as well complementary sequences of the above-mentioned sequences SEQ ID Nos 1 to 27 and the cLysMAR element or fragment, which can be produced by using PCR or other means.

An "element" is a conserved nucleotide sequences that bears common functional properties (i.e. binding sites for transcription factors) or structural (i.e. bent DNA sequence) features.

A part of sequences SEQ ID Nos 1 to 27 and the cLysMAR element or fragment refers to sequences sharing at least 70% nucleotides in length with the respective sequence of the SEQ ID Nos 1 to 27. These sequences can be used as long as they exhibit the same properties as the native sequence from which they derive. Preferably these sequences share more than 80%, in particular more than 90% nucleotides in length with the respective sequence of the SEQ ID Nos 1 to 27.

The present invention also includes variants of the aforementioned sequences SEQ ID Nos 1 to 27 and the cLysMAR element or fragment, that is nucleotide sequences that vary from the reference sequence by conservative nucleotide substitutions, whereby one or more nucleotides are substituted by another with same characteristics.

The sequences SEQ ID Nos 1 to 23 have been identified by scanning human chromosome 1 and 2 using SMAR SCAN, showing that the identification of novel MAR sequences is feasible using the tools reported thereafter whereas SEQ ID No 24 to 27 have been identified by scanning the complete human genome using the combined SMAR SCAN method.

Figure 3:
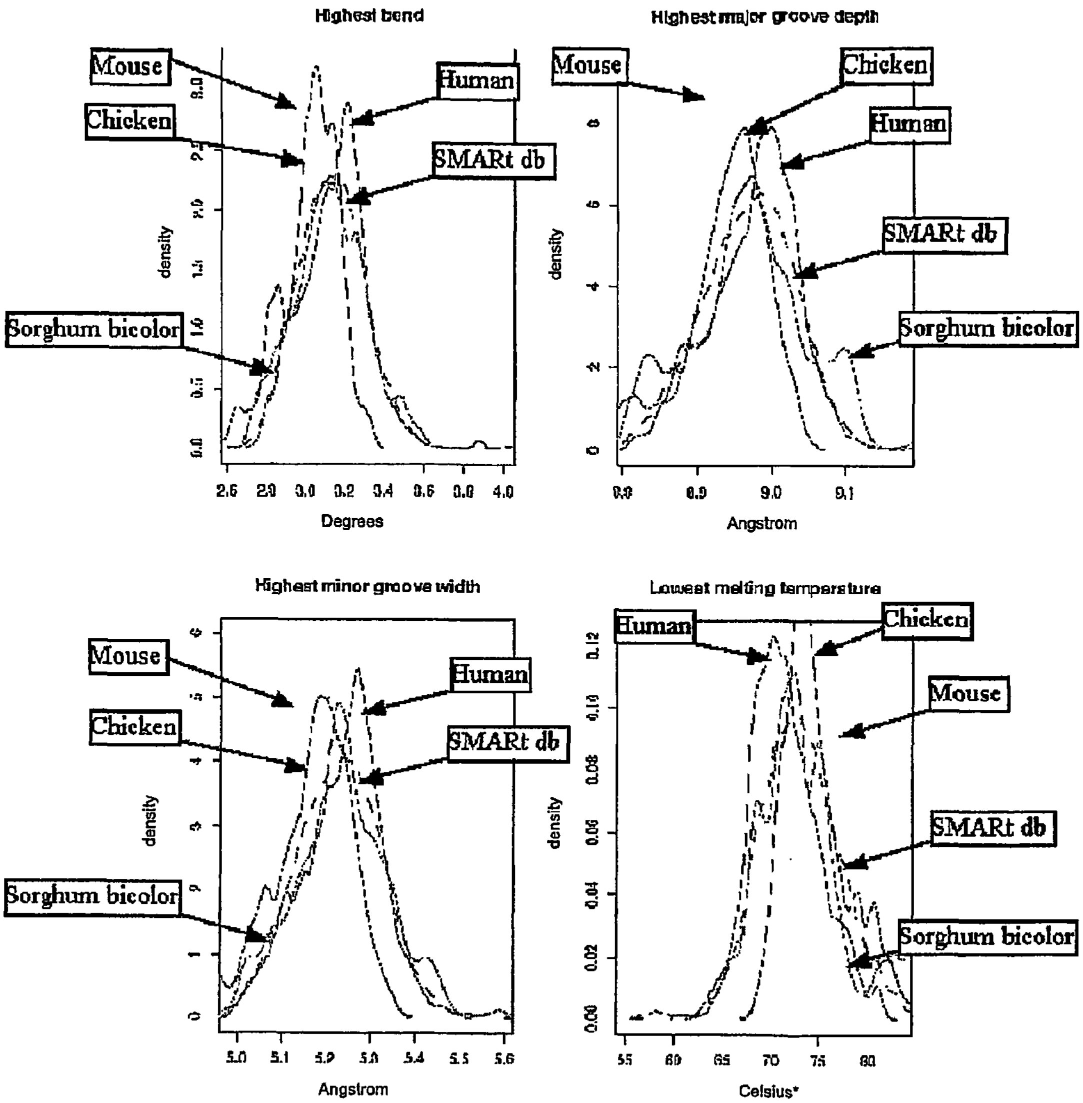
FIG. 3 shows the distribution plots of MAR sequences by organism. MAR sequences from SMARt DB of other organisms were retrieved and analyzed. The MAR sequences density distributions for the mouse, the chicken, the sorghum bicolor and the human are plotted jointly.
Figure 8:
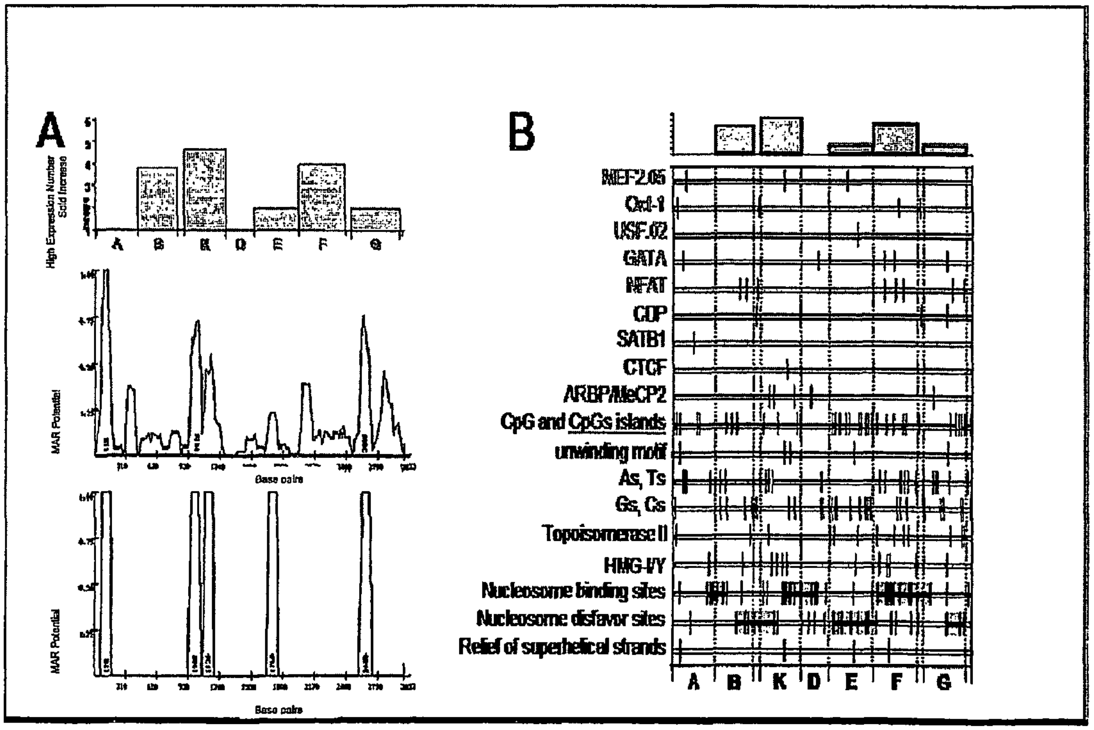
FIG. 8 shows a map of locations for various DNA sequence motifs within the cLysMAR.

In a first step, the complete chromosome 1 and 2 were screened to identify bent DNA element as region corresponding to the highest bent, major groove depth, minor groove width and lowest melting temperature as shown in FIG. 3. In a second step, this collection of sequence was scanned for binding sites of regulatory proteins such as SATB1, GATA, etc. as shown in the FIG. 8B) yielding sequences SEQ ID 1-23. Furthermore, sequences 21-23 were further shown to be located next to known gene from the Human Genome Data Base.

With regard to SEQ ID No 24 to 27 these sequences have been yielded by scanning the human genome according to the combined method and were selected as examples among 1757 MAR elements so detected.

Molecular chimera of MAR sequences are also considered in the present invention. By molecular chimera is intended a nucleotide sequence that may include a functional portion of a MAR element and that will be obtained by molecular biology methods known by those skilled in the art.

Particular combinations of MAR elements or fragments or sub-portions thereof are also considered in the present invention. These fragments can be prepared by a variety of methods known in the art. These methods include, but are not limited to, digestion with restriction enzymes and recovery of the fragments, chemical synthesis or polymerase chain reactions (PCR).

Therefore, particular combinations of elements or fragments of the sequences SEQ ID Nos 1 to 27 and cLysMAR elements or fragments are also envisioned in the present invention, depending on the functional results to be obtained. Elements of the cLysMAR are e.g. the B, K and F regions as described in WO 02/074969, the disclosure of which is hereby incorporated herein by reference, in its entirety. The preferred elements of the cLysMAR used in the present invention are the B, K and F regions. Only one element might be used or multiple copies of the same or distinct elements (multimerized elements) might be used (see FIG. 8 A)).

By fragment is intended a portion of the respective nucleotide sequence. Fragments of a MAR nucleotide sequence may retain biological activity and hence bind to purified nuclear matrices and/or alter the expression patterns of coding sequences operably linked to a promoter. Fragments of a MAR nucleotide sequence may range from at least about 100 to 1000 bp, preferably from about 200 to 700 bp, more preferably from about 300 to 500 bp nucleotides. Also envisioned are any combinations of fragments, which have the same number of nucleotides present in a synthetic MAR sequence consisting of natural MAR element and/or fragments. The fragments are preferably assembled by linker sequences. Preferred linkers are BglII-BamHI linker.

"Protein production increasing activity" refers to an activity of the purified and isolated DNA sequence defined as follows: after having been introduced under suitable conditions into a eukaryotic host cell, the sequence is capable of increasing protein production levels in cell culture as compared to a culture of cell transfected without said DNA sequence. Usually the increase is 1.5 to 10 fold, preferably 4 to 10 fold. This corresponds to a production rate or a specific cellular productivity of at least 10 pg per cell per day (see Example 11 and FIG. 13).

As used herein, the following definitions are supplied in order to facilitate the understanding of this invention.

"Chromatin" is the protein and nucleic acid material constituting the chromosomes of a eukaryotic cell, and refers to DNA, RNA and associated proteins.

A "chromatin element" means a nucleic acid sequence on a chromosome having the property to modify the chromatine structure when integrated into that chromosome.

"Cis" refers to the placement of two or more elements (such as chromatin elements) on the same nucleic acid molecule (such as the same vector, plasmid or chromosome).

"Trans" refers to the placement of two or more elements (such as chromatin elements) on two or more different nucleic acid molecules (such as on two vectors or two chromosomes).

Chromatin modifying elements that are potentially capable of overcoming position effects, and hence are of interest for the development of stable cell lines, include boundary elements (BEs), matrix attachment regions (MARs), locus control regions (LCRs), and universal chromatin opening elements (UCOEs).

Boundary elements ("BEs"), or insulator elements, define boundaries in chromatin in many cases (Bell A and Felsenfeld G. 1999; "Stopped at the border: boundaries and insulators, *Curr Opin Genet Dev* 9, 191-198) and may play a role in defining a transcriptional domain in vivo. BEs lack intrinsic promoter/enhancer activity, but rather are thought to protect genes from the transcriptional influence of regulatory elements in the surrounding chromatin. The enhancer-block assay is commonly used to identify insulator elements. In this assay, the chromatin element is placed between an enhancer and a promoter, and enhancer-activated transcription is measured. Boundary elements have been shown to be able to protect stably transfected reporter genes against position effects in *Drosophila*, yeast and in mammalian cells. They have also been shown to increase the proportion of transgenic mice with inducible transgene expression.

Locus control regions ("LCRs") are cis-regulatory elements required for the initial chromatin activation of a locus and subsequent gene transcription in their native locations (Grosveld, F. 1999, "Activation by locus control regions?" *Curr Opin Genet Dev* 9, 152-157). The activating function of LCRs also allows the expression of a coupled transgene in the appropriate tissue in transgenic mice, irrespective of the site of integration in the host genome. While LCRs generally confer tissue-specific levels of expression on linked genes, efficient expression in nearly all tissues in transgenic mice has been reported for a truncated human T-cell receptor LCR and a rat LAP LCR. The most extensively characterized LCR is that of the globin locus. Its use in vectors for the gene therapy of sickle cell disease and (3-thalassemias is currently being evaluated.

"MARs", according to a well-accepted model, may mediate the anchorage of specific DNA sequence to the nuclear matrix, generating chromatin loop domains that extend outwards from the heterochromatin cores. While MARs do not contain any obvious consensus or recognizable sequence, their most consistent feature appears to be an overall high A/T content, and C bases predominating on one strand (Bode J, Schlake T, RiosRamirez M, Mielke C, Stengart M, Kay V and KlehrWirth D, "Scaffold/matrix-attached regions: structural properties creating transcriptionally active loci", Structural and Functional Organization of the Nuclear Matrix: International Review of Citology, 162A:389453, 1995). These regions have a propensity to form bent secondary structures that may be prone to strand separation. They are often referred to as base-unpairing regions (BURs), and they contain a core-unwinding element (CUE) that might represent the nucleation point of strand separation (Benham C and al., Stress induced duplex DNA destabilization in scaffold/matrix attachment regions, J. MoL BioL, 274:181-196, 1997). Several simple AT-rich sequence motifs have often been found within MAR sequences, but for the most part, their functional importance and potential mode of action remain unclear. These include the A-box (AATAAAYAAA (SEQ ID NO: 243)), the T-box (TTWTWTTWTT (SEQ ID NO: 244)), DNA unwinding motifs (AATATATT, AATATT), SATB1 binding sites (H-box, A/T/C25) and consensus Topoisomerase II sites for vertebrates (RNYNNCNNGYNGKTNYNY(SEQ ID NO: 245)) or *Drosophila* (GTNWAYATTNATNNR (SEQ ID NO: 246)).

Ubiquitous chromatin opening elements ("UCOEs", also known as "ubiquitously-acting chromatin opening elements") have been reported in WO 00/05393.

An "enhancer" is a nucleotide sequence that acts to potentiate the transcription of genes independent of the identity of the gene, the position of the sequence in relation to the gene, or the orientation of the sequence. The vectors of the present invention optionally include enhancers.

A "gene" is a deoxyribonucleotide (DNA) sequence coding for a given mature protein. As used herein, the term "gene" shall not include untranslated flanking regions such as RNA transcription initiation signals, polyadenylation addition sites, promoters or enhancers.

A "product gene" is a gene that encodes a protein product having desirable characteristics such as diagnostic or therapeutic utility. A product gene includes, e.g., structural genes and regulatory genes.

A "structural gene" refers to a gene that encodes a structural protein. Examples of structural genes include but are not limited to, cytoskeletal proteins, extracellular matrix proteins, enzymes, nuclear pore proteins and nuclear scaffold proteins, ion channels and transporters, contractile proteins, and chaperones. Preferred structural genes encode for antibodies or antibody fragments.

A "regulatory gene" refers to a gene that encodes a regulatory protein. Examples of regulatory proteins include, but are not limited to, transcription factors, hormones, growth factors, cytokines, signal transduction molecules, oncogenes, proto-oncogenes, transmembrane receptors, and protein kinases.

"Orientation" refers to the order of nucleotides in a given DNA sequence. For example, an inverted orientation of a DNA sequence is one in which the 5' to 3' order of the sequence in relation to another sequence is reversed when compared to a point of reference in the DNA from which the sequence was obtained. Such reference points can include the direction of transcription of other specified DNA sequences in the source DNA and/or the origin of replication of replicable vectors containing the sequence.

"Eukaryotic cell" refers to any mammalian or non-mammalian cell from a eukaryotic organism. By way of non-limiting example, any eukaryotic cell that is capable of being maintained under cell culture conditions and subsequently transfected would be included in this invention. Especially preferable cell types include, e.g., stem cells, embryonic stem cells, Chinese hamster ovary cells (CHO), COS, BHK21, NIH3T3, HeLa, C2C12, cancer cells, and primary differentiated or undifferentiated cells. Other suitable host cells are known to those skilled in the art.

The terms "host cell" and "recombinant host cell" are used interchangeably herein to indicate a eukaryotic cell into which one or more vectors of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The terms "introducing a purified DNA into a eukaryotic host cell" or "transfection" denote any process wherein an extracellular DNA, with or without accompanying material, enters a host cell. The term "cell transfected" or "transfected cell" means the cell into which the extracellular DNA has been introduced and thus harbours the extracellular DNA. The DNA might be introduced into the cell so that the nucleic acid is replicable either as a chromosomal integrant or as an extra chromosomal element.

"Promoter" as used herein refers to a nucleic acid sequence that regulates expression of a gene.

"Co-transfection" means the process of transfecting a eukaryotic cell with more than one exogenous gene, or vector, or plasmid, foreign to the cell, one of which may confer a selectable phenotype on the cell.

The purified and isolated DNA sequence having protein production increasing activity also comprises, besides one or more bent DNA element, at least one binding site for a DNA binding protein.

Usually the DNA binding protein is a transcription factor. Examples of transcription factors are the group comprising the polyQpolyP domain proteins.

Another example of a transcription factor is a transcription factor selected from the group comprising SATB1, NMP4, MEF2, S8, DLX1, FREAC7, BRN2, GATA 1/3, TATA, Bright, MSX, AP1, C/EBP, CREBP1, FOX, Freac7, HFH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or a combination of two or more of these transcription factors are preferred. Most preferred are SATB1, NMP4, MEF2 and polyQpolyP domain proteins.

SATB1, NMP4 and MEF2, for example, are known to regulate the development and/or tissue-specific gene expression in mammals. These transcription factors have the capacity to alter DNA geometry, and reciprocally, binding to DNA as an allosteric ligand modifies their structure. Recently, SATB1 was found to form a cage-like structure circumscribing heterochromatin (Cai S, Han H J, and Kohwi-Shigematsu T, "Tissue-specific nuclear architecture and gene expression regulated by SATB1 " *Nat Genet,* 2003. 34(1): p. 42-51).

Yet another object of the present invention is to provide a purified and isolated cLysMAR element and/or fragment, a sequence complementary thereof, a part thereof sharing at least 70% nucleotides in length, a molecular chimera thereof, a combination thereof and variants.

More preferably, the cLysMAR element and/or fragment are consisting of at least one nucleotide sequence selected from the B, K and F regions.

A further object of the present invention is to provide a synthetic MAR sequence comprising natural MAR element and/or fragments assembled between linker sequences.

Preferably, the synthetic MAR sequence comprises a cLys-MAR element and/or fragment a sequence complementary thereof, a part thereof sharing at least 70% nucleotides in length, a molecular chimera thereof, a combination thereof and variants. Also preferably, linker sequences are BglII-BamHI linker.

An other aspect of the invention is to provide a method for identifying a MAR sequence using a Bioinformatic tool comprising the computing of values of one or more DNA sequence features corresponding to DNA bending, major groove depth and minor groove width potentials and melting temperature. Preferably, the identification of one or more DNA sequence features further comprises a further DNA sequence feature corresponding to binding sites for DNA binding proteins, which is also computed with this method.

Preferably, profiles or weight-matrices of said bioinformatic tool are based on dinucleotide recognition.

The bioinformatic tool used for the present method is preferably, SMAR SCAN, which contains algorithms developed by Gene Express and based on Levitsky et al., 1999. These algorithms recognise profiles, based on dinucleotides weight-matrices, to compute the theoretical values for conformational and physicochemical properties of DNA.

Preferably, SMAR SCAN uses the four theoretical criteria also designated as DNA sequence features corresponding to DNA bending, major groove depth and minor groove width potentials, melting temperature in all possible combination, using scanning windows of variable size (see FIG. 3). For each function used, a cut-off value has to be set. The program returns a hit every time the computed score of a given region is above the set cut-off value for all of the chosen criteria. Two data output modes are available to handle the hits, the first (called "profile-like") simply returns all hit positions on the query sequence and their corresponding values for the different criteria chosen. The second mode (called "contiguous hits") returns only the positions of several contiguous hits and their corresponding sequence. For this mode, the minimum number of contiguous hits is another cut-off value that can be set, again with a tunable window size. This second mode is the default mode of SMAR SCAN. Indeed, from a semantic point of view, a hit is considered as a core-unwinding element (CUE), and a cluster of CUEs accompanied by clusters of binding sites for relevant proteins is considered as a MAR. Thus, SMAR SCAN considers only several contiguous hits as a potential MAR.

To tune the default cut-off values for the four theoretical structural criteria, experimentally validated MARs from SMARt DB were used. All the human MAR sequences from the database were retrieved and analyzed with SMAR SCAN using the "profile-like" mode with the four criteria and with no set cut-off value. This allowed the setting of each function for every position of the sequences. The distribution for each criterion was then computed according to these data (see FIGS. 1 and 3).

The default cut-off values of SMAR SCAN for the bend, the major groove depth and the minor groove width were set at the average of the 75th quantile and the median. For the melting temperature, the default cut-off value should be set at the 75th quantile. The minimum length for the "contiguous-hits" mode should be set to 300 because it is assumed to be the minimum length of a MAR (see FIGS. 8 and 9). However, one skilled in the art would be able to determine the cut-off values for the above-mentioned criteria for a given organism with minimal experimentation.

Preferably, DNA bending values are comprised between 3 to 5° (radial degree). Most preferably they are situated between 3.8 to 4.4°, corresponding to the smallest peak of FIG. 1.

Preferably the major groove depth values are comprised between 8.9 to 9.3 Å (Angström) and minor groove width values between 5.2 to 5.8 Å. Most preferably the major groove depth values are comprised between 9.0 to 9.2 Å and minor groove width values between 5.4 to 5.7 Å.

Preferably the melting temperature is comprised between 55 to 75° C. (Celsius degree). Most preferably, the melting temperature is comprised between 55 to 62° C.

The DNA binding protein of which values can be computed by the method is usually a transcription factor preferably a polyQpolyP domain or a transcription factor selected from the group comprising SATB1, NMP4, MEF2, S8, DLX1, FREAC7, BRN2, GATA 1/3, TATA, Bright, MSX, AP1, C/EBP, CREBP1, FOX, Freac7, HFH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or a combination of two or more of these transcription factors.

However, one skilled in the art would be able to determine other kinds of transcription factors in order to carry out the method according to the present invention.

In case SMAR SCAN is envisaged to perform, for example, large scale analysis, then, preferably, the above-mentioned method further comprises at least one filter predicting DNA binding sites for DNA transcription factors in order to reduce the computation.

The principle of this method combines SMAR SCAN to compute the structural features as described above and a filter, such as for example, the pfsearch, (from the pftools package as described in Bucher P, Karplus K, Moeri N, and Hofmann K, "A flexible search technique based on generalized profiles", *Computers and Chemistry,* 20:324, 1996) to predict the binding of some transcription factors.

Examples of filters comprise, but are not limited to, pfsearch, MatInspector, RMatch Professional and TRANSFAC Professional This combined method uses the structural features of SMAR SCAN and the predicted binding of specific transcription factors of the filter that can be applied sequentially in any order to select MARs, therefore, depending on the filter is applied at the beginning or at the end of the method.

The first level selects sequences out of the primary input sequence and the second level, consisting in the filter, may be used to restrain among the selected sequences those which satisfy the criteria used by the filter.

In this combined method the filter detects clusters of DNA binding sites using profiles or weightmatrices from, for example, MatInspector (Quandt K, Frech K, Karas H, Wingender E, Werner T, "MatInd and MatInspector New fast and versatile tools for detection of consensus matches in nucleotide sequence data", *Nucleic Acids Research,* 23, 48784884, 1995.). The filter can also detect densities of clusters of DNA binding sites.

The combined method is actually a "wrapper" written in Perl for SMAR SCAN and, in case the pfsearch is used as a filter, from the pftools. The combined method performs a twolevel processing using at each level one of these tools (SMAR SCAN or filter) as a potential "filter", each filter being optional and possible to be used to compute the predicted features without doing any filtering.

If SMAR SCAN is used in the first level to filter subsequences, it has to be used with the "all the contiguous hits" mode in order to return sequences. If the pfsearch is used in the first level as first filter, it has to be used with only one profile and a distance in nucleotide needs to be provided. This distance is used to group together pfsearch hits that are located at a distance inferior to the distance provided in order to return sequences; The combined method launches pfsearch, parses its output and returns sequences corresponding to pfsearch hits that are grouped together according to the distance provided. Then whatever the tool used in the first level, the length of the subsequences thus selected can be systematically extended at both ends according to a parameter called "hits extension".

Figure 20:
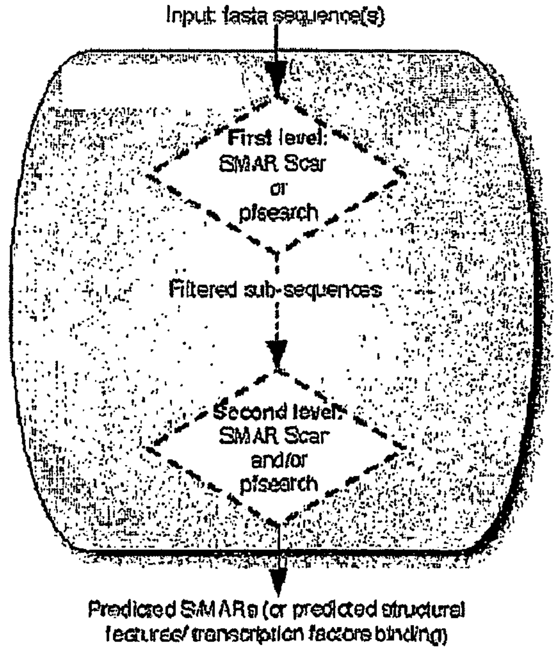
FIG. 20 depicts the effect of the induction of hematocrit in mice injected by MAR-network.

The second and optional level can be used to filter out sequences (already filtered sequences or unfiltered input sequences) or to get the results of SMAR SCAN and/or pfsearch without doing any filtering on these sequences. If the second level of combined method is used to filter, for each criteria considered cutoff values (hit per nucleotide) need to be provided to filter out those sequences (see FIG. 20).

Another concern of the present invention is also to provide a method for identifying a MAR sequence comprising at least one filter detecting clusters of DNA binding sites using profiles or weightmatrices. Preferably, this method comprises two levels of filters and in this case, SMAR SCAN is totally absent from said method. Usually, the two levels consist in pfsearch.

Also embraced by the present invention is a purified and isolated MAR DNA sequence identifiable according to the method for identifying a MAR sequence using the described bioinformatic tool, the combined method or the method comprising at least one filter.

Analysis by the combined method of the whole human genome yielded a total of 1757 putative MARs representing a total of 1 065 305 base paires. In order to reduce the number of results, a dinucleotide analysis was performed on these 1757 MARs, computing each of the 16 possible dinucleotide percentage for each sequence considering both strands in the 5' to 3' direction.

Surprisingly, Applicants have shown that all of the "super" MARs detected with the combined method contain at least 10% of dinucleotide TA on a stretch of 100 contiguous base pairs. Preferably, these sequences contain at least 33% of dinucleotide TA on a stretch of 100 contiguous base pairs.

Applicants have also shown that these same sequences further contain at least 12% of dinucleotide AT on a stretch of 100 contiguous base pairs. Preferably, they contain at least 33% of dinucleotide AT on a stretch of 100 contiguous base pairs.

An other aspect of the invention is to provide a purified and isolated MAR DNA sequence of any of the preceding described MARs, comprising a sequence selected from the sequences SEQ ID Nos 1 to 27, a sequence complementary thereof, a part thereof sharing at least 70% nucleotides in length, a molecular chimera thereof, a combination thereof and variants.

Preferably, said purified and isolated MAR DNA sequence comprises a sequence selected from the sequences SEQ ID Nos 24 to 27, a sequence complementary thereof, a part thereof sharing at least 70% nucleotides in length, a molecular chimera thereof, a combination thereof and variants. These sequences 24 to 27 correspond to those detected by the combined method and show a higher protein production increasing activity over sequences 1 to 23.

The present invention also encompasses the use of a purified and isolated DNA sequence comprising a first isolated matrix attachment region (MAR) nucleotide sequence which is a MAR nucleotide sequence selected from the group comprising

- a purified and isolated DNA sequence having protein production increasing activity,
- a purified and isolated MAR DNA sequence identifiable according to the method for identifying a MAR sequence using the described bioinformatic tool, the combined method or the method comprising at least one filter,
- the sequences SEQ ID Nos 1 to 27,
- a purified and isolated cLysMAR element and/or fragment,
- a synthetic MAR sequence comprising natural MAR element and/or fragments assembled between linker sequences, a sequence complementary thereof, a part thereof sharing at least 70% nucleotides in length, a molecular chimera thereof, a combination thereof and variants or a MAR nucleotide sequence of a cLysMAR element and/or fragment, a sequence complementary thereof, a part thereof sharing at least 70% nucleotides in length, a molecular chimera thereof, a combination thereof and variants for increasing protein production activity in a eukaryotic host cell.

Said purified and isolated DNA sequence usually further comprises one or more regulatory sequences, as known in the art e.g. a promoter and/or an enhancer, polyadenylation sites and splice junctions usually employed for the expression of the protein or may optionally encode a selectable marker. Preferably said purified and isolated DNA sequence comprises a promoter which is operably linked to a gene of interest.

The DNA sequences of this invention can be isolated according to standard PCR protocols and methods well known in the art.

Promoters which can be used provided that such promoters are compatible with the host cell are, for example, promoters obtained from the genomes of viruses such as polyoma virus, adenovirus (such as Adenovirus 2), papilloma virus (such as bovine papilloma virus), avian sarcoma virus, cytomegalovirus (such as murine or human cytomegalovirus immediate early promoter), a retrovirus, hepatitis-B virus, and Simian Virus 40 (such as SV 40 early and late promoters) or promoters obtained from heterologous mammalian promoters, such as the actin promoter or an immunoglobulin promoter or heat shock promoters. Such regulatory sequences direct constitutive expression.

Furthermore, the purified and isolated DNA sequence might further comprise regulatory sequences which are capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33:741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application No. 264,166).

Developmentally-regulated promoters are also encompassed. Examples of such promoters include, e.g., the murine hox promoters (Kessel and Gruss, 1990. Science 249: 374-379) and thea-fetoprotein promoter (Campes and Tilghman, 1989. Genes Dev. 3: 537-546).

Regulatable gene expression promoters are well known in the art, and include, by way of non-limiting example, any promoter that modulates expression of a gene encoding a desired protein by binding an exogenous molecule, such as the CRE/LOX system, the TET system, the doxycycline system, the NFkappaB/UV light system, the Leu3p/isopropylmalate system, and the GLVPc/GAL4 system (See e.g., Sauer, 1998, Methods 14 (4): 381-92; Lewandoski, 2001, Nat. Rev. Genet 2 (10): 743-55; Legrand-Poels et al., 1998, J. Photochem. Photobiol. B. 45: 18; Guo et al., 1996, FEBS Lett. 390 (2): 191-5; Wang et al., PNAS USA, 1999, 96 (15): 84838).

However, one skilled in the art would be able to determine other kinds of promoters that are suitable in carrying out the present invention.

Enhancers can be optionally included in the purified DNA sequence of the invention then belonging to the regulatory sequence, e.g. the promoter.

The "gene of interest" or "transgene" preferably encodes a protein (structural or regulatory protein). As used herein "protein" refers generally to peptides and polypeptides having more than about ten amino acids. The proteins may be "homologous" to the host (i.e., endogenous to the host cell being utilized), or "heterologous," (i.e., foreign to the host cell being utilized), such as a human protein produced by yeast. The protein may be produced as an insoluble aggregate or as a soluble protein in the periplasmic space or cytoplasm of the cell, or in the extracellular medium. Examples of proteins include hormones such as growth hormone or erythropoietin (EPO), growth factors such as epidermal growth factor, analgesic substances like enkephalin, enzymes like chymotrypsin, receptors to hormones or growth factors, antibodies and include as well proteins usually used as a visualizing marker e.g. green fluorescent protein.

Preferably the purified DNA sequence further comprises at least a second isolated matrix attachment region (MAR) nucleotide sequence selected from the group comprising

- a purified and isolated DNA sequence having protein production increasing activity,
- a purified and isolated MAR DNA sequence identifiable according to the method for identifying a MAR sequence using the described bioinformatic tool, the combined method or the method comprising at least one filter,
- the sequences SEQ ID Nos 1 to 27,
- a purified and isolated cLysMAR element and/or fragment,
- a synthetic MAR sequence comprising natural MAR element and/or fragments assembled between linker sequences, a sequence complementary thereof, a part thereof sharing at least 70% nucleotides in length, a molecular chimera thereof, a combination thereof and variants. The isolated matrix attachment region (MAR) nucleotide sequence might be identical or different. Alternatively, a first and a second identical MAR nucleotide sequence are used.

Preferably, the MAR nucleotide sequences are located at both the 5' and the 3' ends of the sequence containing the promoter and the gene of interest. But the invention also envisions the fact that said first and or at least second MAR nucleotide sequences are located on a sequence distinct from the one containing the promoter and the gene of interest.

Embraced by the scope of the present invention is also the purified and isolated DNA sequence comprising a first isolated matrix attachment region (MAR) nucleotide sequence which is a MAR nucleotide sequence selected from the group comprising

- a purified and isolated DNA sequence having protein production increasing activity,
- a purified and isolated MAR DNA sequence identifiable according to the method for identifying a MAR sequence using the described bioinformatic tool, the combined method or the method comprising at least one filter,
- the sequences SEQ ID Nos 1 to 27,
- a purified and isolated cLysMAR element and/or fragment,
- a synthetic MAR sequence comprising natural MAR element and/or fragments assembled between linker sequences, a sequence complementary thereof, a part thereof sharing at least 70% nucleotides in length, a molecular chimera thereof, a combination thereof and variants that can be used for increasing protein production activity in a eukaryotic host cell by introducing the purified and isolated DNA sequence into a eukaryotic host cell according to well known protocols. Usually applied methods for introducing DNA into eukaryotic host cells applied are e.g. direct introduction of cloned DNA by microinjection or microparticle bombardment; electrotransfer; use of viral vectors; encapsulation within a carrier system; and use of transfecting reagents such as calcium phosphate, diethylaminoethyl (DEAE)-dextran or commercial transfection systems like the Lipofect-AMINE 2000 (Invitrogen). Preferably, the transfection method used to introduce the purified DNA sequence into a eukaryotic host cell is the method for transfecting a eukaryotic cell as described below.

The purified and isolated DNA sequence can be used in the form of a circular vector. Preferably, the purified and isolated DNA sequence is used in the form of a linear DNA sequence as vector.

As used herein, "plasmid" and "vector" are used interchangeably, as the plasmid is the most commonly used vector form. However, the invention is intended to include such other forms of expression vectors, including, but not limited to, viral vectors (e.g., replication defective retroviruses, adenoviruses and adeno-associated viruses), which serve equivalent functions.

The present invention further encompasses a method for transfecting a eukaryotic host cell, said method comprising a) introducing into said eukaryotic host cell at least one purified DNA sequence comprising at least one DNA sequence of interest and/or at least one purified and isolated DNA sequence comprising a MAR nucleotide sequence or other chromatin modifying elements, b) subjecting within a defined time said transfected eukaryotic host cell to at least one additional transfection step with at least one purified DNA sequence comprising at least one DNA sequence of interest and/or with at least one purified and isolated DNA sequence comprising a MAR nucleotide sequence or other chromatin modifying elements c) selecting said transfected eukaryotic host cell.

Preferably at least two up to four transfecting steps are applied in step b).

In order to select the successful transfected cells, a gene that encodes a selectable marker (e.g., resistance to antibiotics) is generally introduced into the host cells along with the gene of interest. The gene that encodes a selectable marker might be located on the purified DNA sequence comprising at least one DNA sequence of interest and/or at least one purified and isolated DNA sequence consisting of a MAR nucleotide sequence or other chromatin modifying elements or might optionally be co-introduced in separate form e.g. on a plasmid. Various selectable markers include those that confer resistance to drugs, such as G418, hygromycin and methotrexate. The amount of the drug can be adapted as desired in order to increase productivity Usually, one or more selectable markers are used. Preferably, the selectable markers used in each distinct transfection steps are different. This allows selecting the transformed cells that are "multi-transformed" by using for example two different antibiotic selections.

Any eukaryotic host cell capable of protein production and lacking a cell wall can be used in the methods of the invention. Examples of useful mammalian host cell lines include human cells such as human embryonic kidney line (293 or 293 cells subcloned for growth in suspension culture, Graham et al., J. Gen Virol 36, 59 (1977)), human cervical carcinoma cells (HELA, ATCC CCL 2), human lung cells (W138, ATCC CCL 75), human liver cells (Hep G2, HB 8065); rodent cells such as baby hamster kidney cells (BHK, ATCC CCL 10), Chinese hamster ovary cells/-DHFR (CHO, Urlaub and Chasin, *Proc. Nati. Acad. Sci. USA,* 77, 4216 (1980)), mouse sertoli cells (TM4, Mather, *Biol. Reprod* 23, 243-251 (1980)), mouse mammary tumor (MMT 060562, ATCC CCL51); and cells from other mammals such as monkey kidney CV1 line transformed by SV40 (COS-7, ATCC CRL 1651); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); myeloma (e.g. NS0)/hybridoma cells.

Preferably, the selected transfected eukaryotic host cells are high protein producer cells with a production rate of at least 10 pg per cell per day.

Most preferred for uses herein are mammalian cells, more preferred are CHO cells.

The DNA sequence of interest of the purified and isolated DNA sequence is usually a gene of interest preferably encoding a protein operably linked to a promoter as described above. The purified and isolated DNA sequence comprising at least one DNA sequence of interest might comprise additionally to the DNA sequence of interest MAR nucleotide sequence or other chromatin modifying elements.

Purified and isolated DNA sequence comprising a MAR nucleotide sequence are for example selected from the group comprising the sequences SEQ ID Nos 1 to 27 and/or particular elements of the cLysMAR e.g. the B, K and F regions as well as fragment and elements and combinations thereof as described above. Other chromatin modifying elements are for example boundary elements (BEs), locus control regions (LCRs), and universal chromatin opening elements (UCOEs) (see Zahn-Zabal et al. already cited). An example of multiple transfections of host cells is shown in Example 12 (Table 3). The first transfecting step (primary transfection) is carried out with the gene of interest (SV40EGFP) alone, with a MAR nucleotide sequence (MAR) alone or with the gene of interest and a MAR nucleotide sequence (MAR-SV40EGFP). The second transfecting step (secondary transfection) is carried out with the gene of interest (SV40EGFP) alone, with a MAR nucleotide sequence (MAR) alone or with the gene of interest and a MAR nucleotide sequence (MAR-SV40EGFP), in all possible combinations resulting from the first transfecting step.

Preferably the eukaryotic host cell is transfected by:

a) introducing a purified DNA sequence comprising one DNA sequence of interest and additionally a MAR nucleotide sequence,
b) subjecting within a defined time said transfected eukaryotic host cell to at least one additional transfection step with the same purified DNA sequence comprising one DNA sequence of interest and additionally a MAR nucleotide sequence of step a).

Also preferably, the MAR nucleotide sequence of the of the purified and isolated DNA sequence is selected form the group comprising

- a purified and isolated DNA sequence having protein production increasing activity,
- a purified and isolated MAR DNA sequence identifiable according to the method for identifying a MAR sequence using the described bioinformatic tool, the combined method or the method comprising at least one filter,
- the sequences SEQ ID Nos 1 to 27,
- a purified and isolated cLysMAR element and/or fragment,
- a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Surprisingly, a synergy between the first and second transfection has been observed. A particular synergy has been observed when MAR elements are present at one or both of the transfection steps. Multiple transfections of the cells with pMAR alone or in combination with various expression plasmids, using the method described above have been carried out. For example, Table 3 shows that transfecting the cells twice with the pMAR-SV40EGFP plasmid gave the highest expression of GFP and the highest degree of enhancement of all conditions (4.3 fold). In contrast, transfecting twice the vector without MAR gave little or no enhancement, 2.8-fold, instead of the expected two-fold increase. This proves that the presence of MAR elements at each transfection step is of particular interest to achieve the maximal protein synthesis.

As a particular example of the transfection method, said purified DNA sequence comprising at least one DNA sequence of interest can be introduced in form of multiple unlinked plasmids, comprising a gene of interest operably linked to a promoter, a selectable marker gene, and/or protein production increasing elements such as MAR sequences.

The ratio of the first and subsequent DNA sequences may be adapted as required for the use of specific cell types, and is routine experimentation to one ordinary skilled in the art.

The defined time for additional transformations of the primary transformed cells is tightly dependent on the cell cycle and on its duration. Usually the defined time corresponds to intervals related to the cell division cycle.

Therefore this precise timing may be adapted as required for the use of specific cell types, and is routine experimentation to one ordinary skilled in the art.

Preferably the defined time is the moment the host cell just has entered into the same phase of a second or a further cell division cycle, preferably the second cycle.

This time is usually situated between 6 h and 48 h, preferably between 20 h and 24 h after the previous transfecting event.

Also encompassed by the present invention is a method for transfecting a eukaryotic host cell, said method comprising co-transfecting into said eukaryotic host cell at least one first purified and isolated DNA sequence comprising at least one DNA sequence of interest, and a second purified DNA comprising at least one MAR nucleotide selected from the group comprising:

a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Said first purified and isolated DNA sequence can also comprise at least one MAR nucleotide as described above.

Also envisioned is a process for the production of a protein wherein a eukaryotic host cell is transfected according to the transfection methods as defined in the present invention and is cultured in a culture medium under conditions suitable for expression of the protein. Said protein is finally recovered according to any recovering process known to the skilled in the art.

Given as an example, the following process for protein production might be used.

The eukaryotic host cell transfected with the transfection method of the present invention is used in a process for the production of a protein by culturing said cell under conditions suitable for expression of said protein and recovering said protein. Suitable culture conditions are those conventionally used for in vitro cultivation of eukaryotic cells as described e.g. in WO 96/39488. The protein can be isolated from the cell culture by conventional separation techniques such as e.g. fractionation on immunoaffinity or ion-exchange columns; precipitation; reverse phase HPLC; chromatography; chromatofocusing; SDS-PAGE; gel filtration. One skilled in the art will appreciate that purification methods suitable for the polypeptide of interest may require modification to account for changes in the character of the polypeptide upon expression in recombinant cell culture.

The proteins that are produced according to this invention can be tested for functionality by a variety of methods. For example, the presence of antigenic epitopes and ability of the proteins to bind ligands can be determined by Western blot assays, fluorescence cell sorting assays, immunoprecipitation, immunochemical assays and/or competitive binding assays, as well as any other assay which measures specific binding activity.

The proteins of this invention can be used in a number of practical applications including, but not limited to:

1. Immunization with recombinant host protein antigen as a viral/pathogen antagonist.
2. Production of membrane proteins for diagnostic or screening assays.
3. Production of membrane proteins for biochemical studies.
4. Production of membrane protein for structural studies.
5. Antigen production for generation of antibodies for immuno-histochemical mapping, including mapping of orphan receptors and ion channels.

Also provided by the present invention is a eukaryotic host cell transfected according to any of the preceding transfection methods. Preferably, the eukaryotic host cell is a mammalian host cell line.

As already described, example of useful mammalian host cell lines include human cells such as human embryonic kidney line (293 or 293 cells subcloned for growth in suspension culture, Graham et al., J. Gen Virol 36, 59 (1977)), human cervical carcinoma cells (HELA, ATCC CCL 2), human lung cells (W138, ATCC CCL 75), human liver cells (Hep G2, HB 8065); rodent cells such as baby hamster kidney cells (BHK, ATCC CCL 10), Chinese hamster ovary cells/-DHFR (CHO, Urlaub and Chasin, *Proc. Natl. Acad. Sci. USA,* 77, 4216 (1980)), mouse sertoli cells (TM4, Mather, *Biol. Reprod* 23, 243-251 (1980)), mouse mammary tumor (MMT 060562, ATCC CCL51); and cells from other mammals such as monkey kidney CV1 line transformed by SV4O (COS-7, ATCC CRL 1651); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); myeloma (e.g. NS0)/hybridoma cells.

Most preferred for uses herein are CHO cells.

The present invention also provides for a cell transfection mixture or Kit comprising at least one purified and isolated DNA sequence according to the invention.

The invention further comprises a transgenic organism wherein at least some of its cells have stably incorporated at least one DNA sequence of a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants. Preferably, some of the cells of the transgenic organisms have been transfected according the methods described herein.

Also envisioned in the present invention is a transgenic organism wherein its genome has stably incorporated at least one DNA sequence of a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Transgenic eukaryotic organisms which can be useful for the present invention are for example selected form the group comprising mammals (mouse, human, monkey etc) and in particular laboratory animals such as rodents in general, insects (*drosophila*, etc), fishes (zebra fish, etc.), amphibians (frogs, newt, etc. . . . ) and other simpler organisms such as *c. elegans*, yeast, etc. . . .

Yet another object of the present invention is to provide a computer readable medium comprising computer-executable instructions for performing the method for identifying a MAR sequence as described in the present invention.

The foregoing description will be more fully understood with reference to the following Examples. Such Examples, are, however, exemplary of methods of practising the present invention and are not intended to limit the scope of the invention.

EXAMPLES

Example 1

SMAR SCAN and MAR Sequences

A first rough evaluation of SMAR SCAN was done by analyzing experimentally defined human MARs and non-MAR sequences. As MAR sequences, the previous results from the analysis of human MARs from SMARt Db were used to plot a density histogram for each criterion as shown in FIG. 1. Similarly, non-MAR sequences were also analyzed and plotted. As non-MAR sequences, all Ref-Seq-contigs from the chromosome 22 were used, considering that this latter was big enough to contain a negligible part of MAR sequences regarding the part of non-MAR sequences.

The density distributions shown in FIG. 1 are all skewed with a long tail. For the highest bend, the highest major groove depth and the highest minor groove width, the distributions are right skewed. For the lowest melting temperature, the distributions are left-skewed which is natural given the inverse correspondence of this criterion regarding the three others. For the MAR sequences, biphasic distributions with a second weak peak, are actually apparent. And between MAR and non-MAR sequences distributions, a clear shift is also visible in each plot.

Among all human MAR sequences used, in average only about 70% of them have a value greater than the 75th quantile of human MARs distribution, this for the four different criteria. Similarly concerning the second weak peak of each human MARs distribution, only 15% of the human MAR sequences are responsible of these outlying values. Among these 15% of human MAR sequences, most are very well documented MARs, used to insulate transgene from position effects, such as the interferon locus MAR, the beta-globin locus MAR (Ramezani A, Hawley T S, Hawley R G, "Performance- and safety-enhanced lentiviral vectors containing the human interferon-beta scaffold attachment region and the chicken beta-globin insulator", *Blood,* 101:4717-4724, 2003), or the apolipoprotein MAR (Namciu, S, Blochinger K B, Fournier R E K, "Human matrix attachment regions insulate transgene expression from chromosomal position effects in *Drosophila* melanogaster", *Mol. Cell. Biol.,* 18:2382-2391, 1998).

Figure 2:
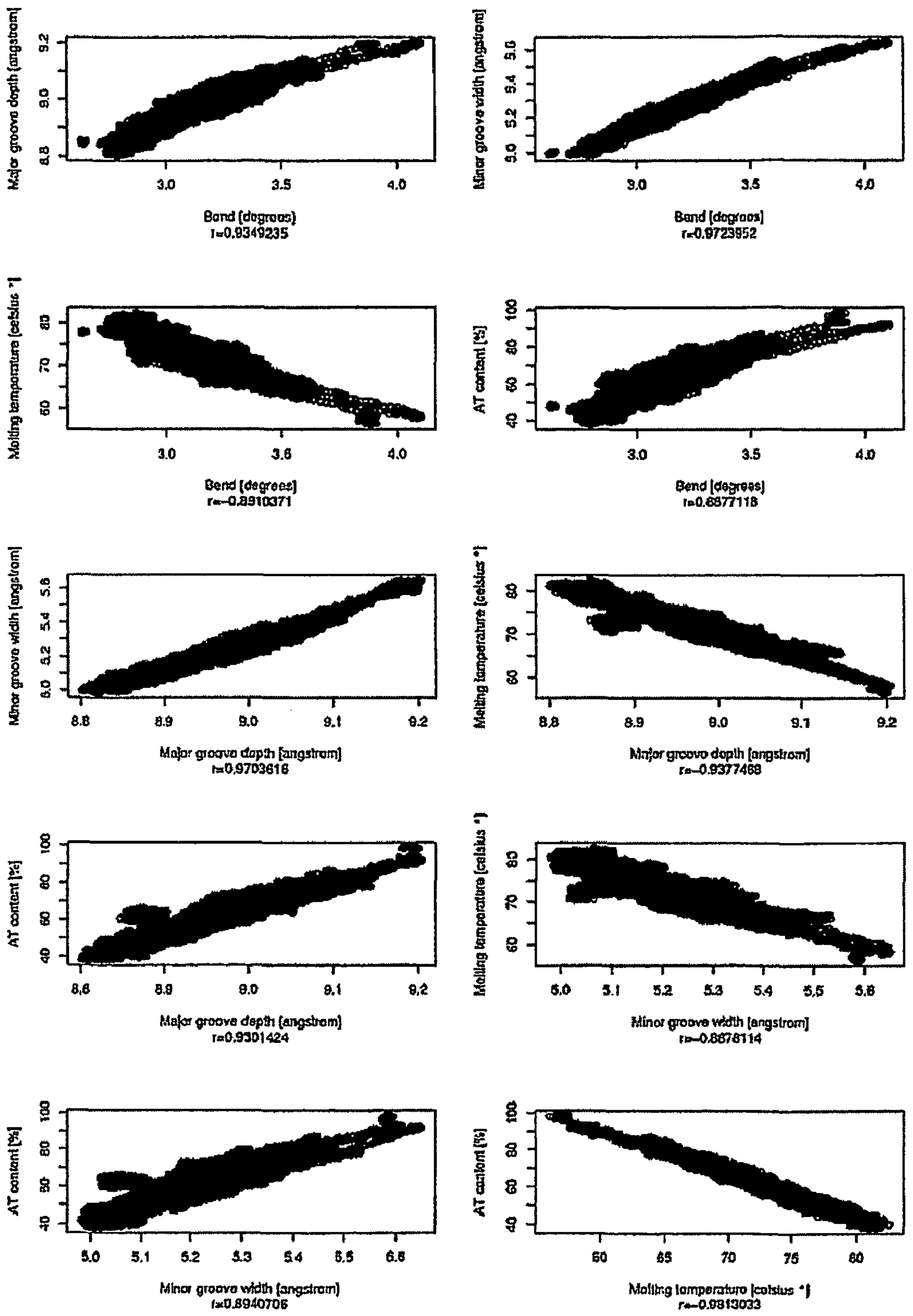
FIG. 2 shows Scatterplots of the four different criteria used by SMAR SCAN and the AT-content with human MARs from SMARt DB.

Always with the same data, human MAR sequences were also used to determine the association between the four theoretical structural properties computed and the AT-content. FIG. 2 represents the scatterplot and the corresponding correlation coefficient r for every pair of criteria.

Example 2

Distribution Plots of MAR Sequences by Organism

MAR sequences from SMARt DB of other organisms were also retrieved and analyzed similarly as explained previously. The MAR sequences density distributions for the mouse, the chicken, the sorghum bicolor and the human are plotted jointly in FIG. 3.

Example 3

MAR Prediction of the Whole Chromosome 22

All RefSeq contigs from the chromosome 22 were analyzed by SMAR SCAN using the default settings this time. The result is that SMAR SCAN predicted a total of 803 MARs, their average length being 446 bp, which means an average of one MAR predicted per 42 777 bp. The total length of the predicted MARs corresponds to 1% of the chromosome 22 length. The AT-content of the predicted regions ranged from 65.1% to 93.3%; the average AT-content of all these regions being 73.5%. Thus, predicted MARs were AT-rich, whereas chromosome 22 is not AT-rich (52.1% AT).

SMARTest was also used to analyze the whole chromosome 22 and obtained 1387 MAR candidates, their average length being 494 bp representing an average of one MAR predicted per 24 765 bp. The total length of the predicted MARs corresponds to 2% of the chromosome 22. Between all MARs predicted by the two softwares, 154 predicted MARs are found by both programs, which represents respectively 19% and 11% of SMAR SCAN and SMARTest predicted MARs. Given predicted MARs mean length for SMAR SCAN and SMARTest, the probability to have by chance an overlapping between SMAR SCAN and SMARTest predictions is 0.0027% per prediction.

Figure 4:
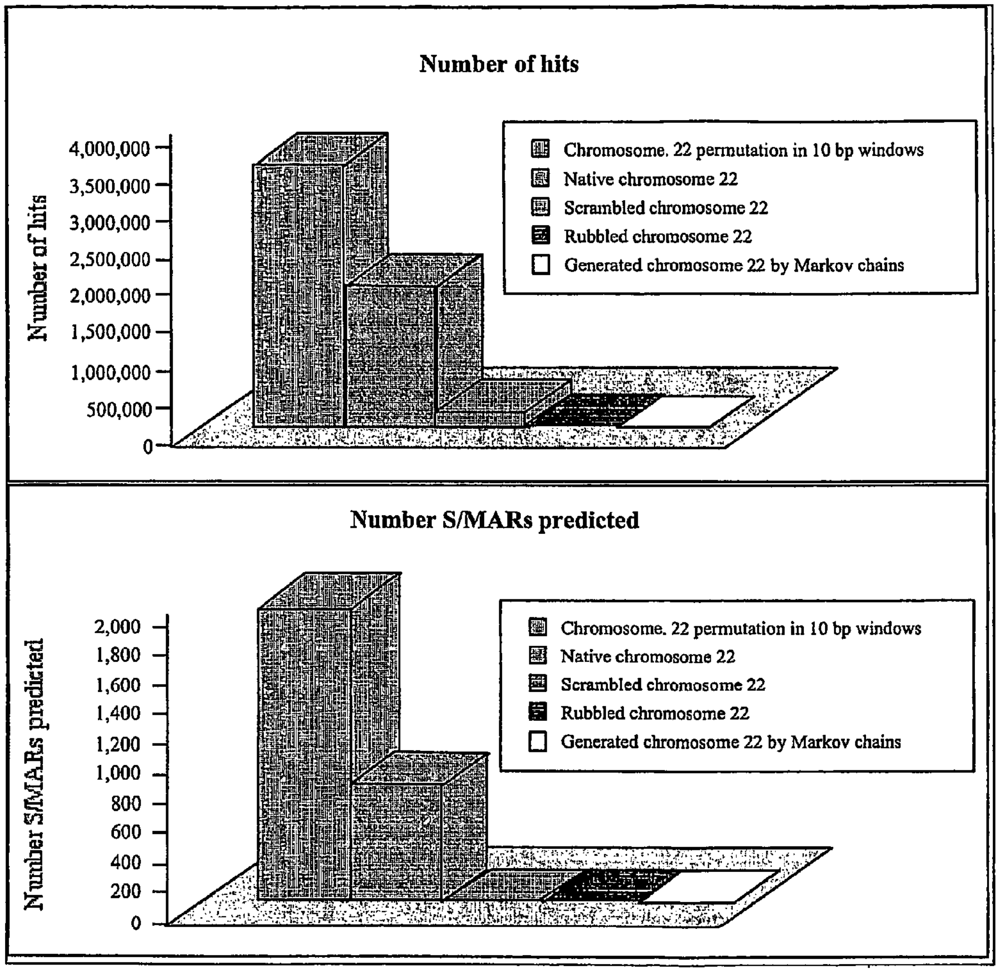
FIG. 4 shows SMAR SCAN predictions on human chromosome 22 and on shuffled chromosome 22. Top plot: Average number of hits obtained by SMAR SCAN with five: rubbled, scrambled, shuffled within nonoverlapping windows of 10 bp, order 1 Markov chains model and with the native chromosome 22. Bottom plot: Average number of MARs predicted by SMAR SCAN in five: rubbled, scrambled, shuffled within nonoverlapping windows of 10 bp, order 1 Markov chains model and with the native chromosome 22.

To evaluate the specificity of SMAR SCAN predictions, SMAR SCAN analyses were performed on randomly shuffled sequences of the chromosome 22 (FIG. 4). Shuffled sequences were generated using 4 different methods: by a segmentation of the chromosome 22 into nonoverlapping windows of 10 bp and by separately shuffling the nucleotides in each window; by "scrambling" which means a permutation of all nucleotides of the chromosome; by "rubbling" which means a segmentation of the chromosome in fragments of 10 bp and a random assembling of these fragments and finally by order 1 Markov chains, the different states being the all the different DNA dinucleotides and the transition probabilities between these states being based on the chromosome 22 scan. For each shuffling method, five shuffled chromosome 22 were generated and analyzed by SMAR SCAN using the default settings. Concerning the number hits, an average of 3 519 170 hits (sd: 18 353) was found for the permutated chromosome 22 within nonoverlapping windows of 10 bp, 171 936.4 hits (sd: 2 859.04) for the scrambled sequences and 24 708.2 hits (sd: 1 191.59) for the rubbled chromosome 22 and 2 282 hits in average (sd: 334.7) for the chromosomes generated according to order 1 Markov chains models of the chromosome 22, which respectively represents 185% (sd: 0.5% of the mean), 9% (sd: 1.5%), 1% (sd: 5%) and 0.1% (sd: 15%) of the number of hits found with the native chromosome 22. For the number of MARs predicted, which thus means contiguous hits of length greater than 300, 1 997 MARs were predicted with the shuffled chromosome 22 within windows of 10 bp (sd: 31.2), only 2.4 MARs candidates were found in scrambled sequences (sd: 0.96) and none for the rubbled and for the sequences generated according to Markov chains model, which respectively represents 249% and less than 0.3% of the number of predicted MARs found with the native chromosome 22. These data provide indications that SMAR SCAN detects specific DNA elements which organization is lost when the DNA sequences are shuffled.

Example 4

Figure 9:
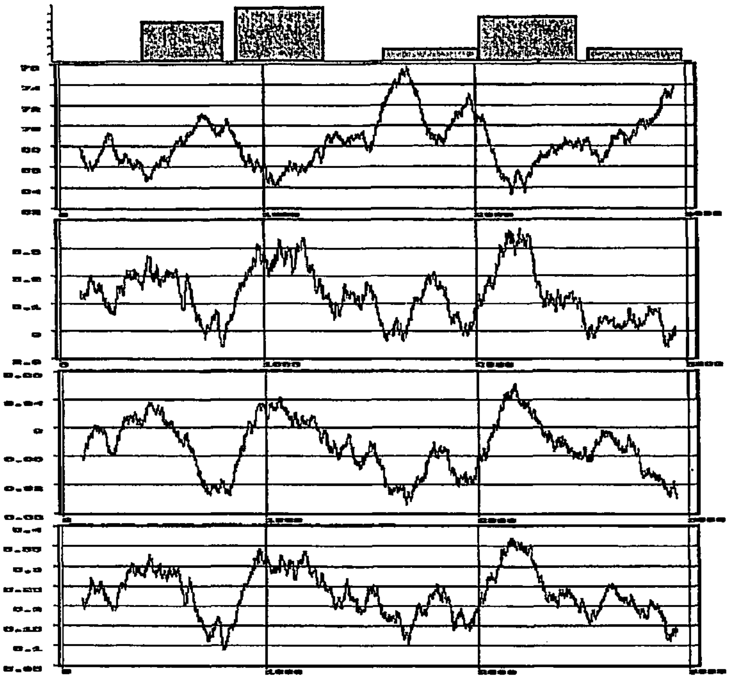
FIG. 9 shows the correlation of DNA physico-chemical properties with MAR activity.
Figure 9:
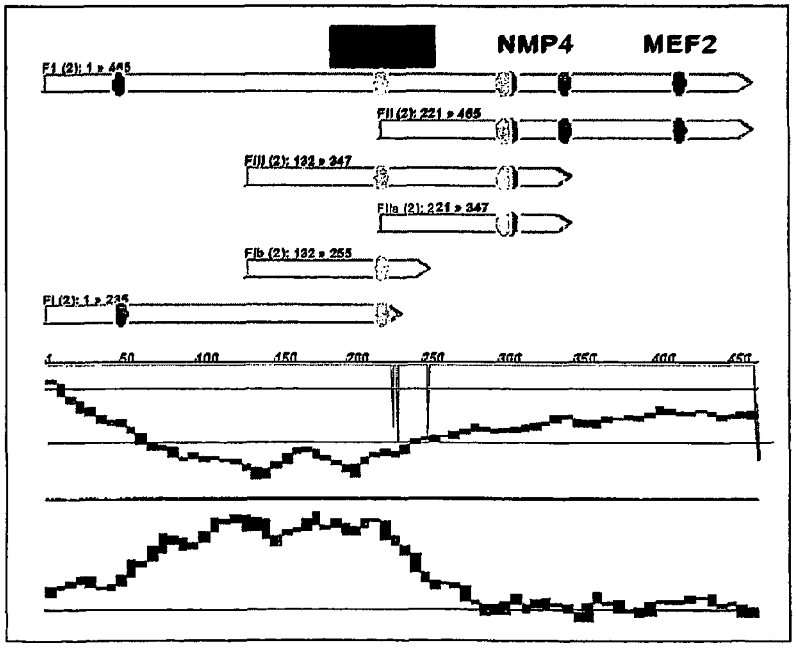

Analysis of Known Matrix Attachment Regions in the Interferon Locus with SMAR SCAN The relevance of MAR prediction by SMAR SCAN was investigated by analyzing the recently published MAR regions of the human interferon gene cluster on the short arm of chromosome 9 (9p22). Goetze et al. (already cited) reported an exhaustive analysis of the WP18A10A7 locus to analyze the suspected correlation between BURs (termed in this case stress-induced duplex destabilization or SIDD) and in vitro binding to the nuclear matrix (FIG. 9, lower part). Three of the SIDD peaks were in agreement with the in vitro binding assay, while others did not match matrix attachment sites. Inspection of the interferon locus with SMAR SCAN (FIG. 9, top part) indicated that three majors peaks accompanied by clusters of SATB1, NMP4 and MEF2 regulators binding sites correlated well with the active MARs. Therefore, we conclude that the occurrence of predicted CUEs and binding sites for these transcription factors is not restricted to the cLysMAR but may be a general property of all MARs. These results also imply that the SMAR SCAN program efficiently detects MAR elements from genomic sequences.

Example 5

Accuracy of SMAR SCAN Prediction and Comparison with Other Predictive Tools

The accuracy of SMAR Scan® was evaluated using six genomic sequences for which experimentally determined MARs have been mapped. In order to perform a comparison with other predictive tools, the sequences analyzed are the same with the sequences previously used to compare MAR-Finder and SMARTest. These genomic sequences are three plant and three human sequences (Table 1) totalizing 310 151 bp and 37 experimentally defined MARs. The results for SMARTest and MAR-Finder in Table 1 come from a previous comparison (Frisch M, Frech K, Klingenhoff A, Cartharius K, Liebich I and Werner T, In silico pre-diction of scaffold/matrix attachment regions in large genomic sequences, *Genome Research,* 12:349-354, 2001.).

MAR-Finder has been used with the default parameters excepted for the threshold that has been set to 0.4 and for the analysis of the protamine locus, the AT-richness rule has been excluded (to detect the non AT-rich MARs as was done for the protamine locus).

TABLE 1

Evaluation of SMAR SCAN accuracy

| Sequence, description and reference | Length (kb) | Experimentally defined MARs positions (kb) | SMARTest prediction positions (kb) | MAR-Finder prediction positions (kb) | SMAR Scan prediction positions (kb) |
|---|---|---|---|---|---|
| *Oryza Sativa* putative | 30.034 | 0.0-1.2 | – | – | – |
| ADP-glucose pyro- | | 5.4-7.4 | **6.5-7.0** | – | – |
| phosphorylase subunit | | | 15.2-15.7 | 15.7-15.9 | 15.6-16 |
| SH2 and putative | | | 16.2-16.6 | – | – |
| NADPH dependant | | 17.3-18.5 | **17.6-18.3** | **17.5-18.4** | **17.6-18.2** |
| reductase A1 genes | | 20.0-23.1 | **19.6-20.1** | **19.8-20.4** | **21.6-22** |
| (U70541). [4] | | | **20.7-21.3** | 21.3-21.5 | – |
| | | | 23.6-23.9 | 23.9-24.2 | 23.4-23.8 |
| | | | 25.0-25.4 | 24.7-25.1 | – |
| | | | 27.5-27.9 | — | – |
| *Sorghum bicolor* ADP- | 42.446 | 0.0-1.5 | – | – | – |
| glucose pyropho- | | 7.1-9.7 | – | – | **7.4-7.7** |
| phorylase subunit SH2, | | | 21.3-21.9 | – | 21.5-21.8 |
| NADPH-dependant | | 22.4-24.7 | **22.9-24.0** | 23.2-24.2 | **22.9-23.2** |
| reducatse A1-b genes | | | – | – | **23.6-24.0** |
| (AF010283). [4] | | | 27.3-27.6 | 26.9-27.5 | 27.3-27.6 |
| | | 32.5-33.7 | – | – | **33.4-33.9** |
| | | 41.6-42.3 | – | – | – |
| *Sorghum bicolor* BAC | 78.195 | ~0.9 | – | – | – |
| clone 110K5 | | ~5.8 | – | – | – |
| (AF124045), [37] | | ~6.3 | – | – | – |
| | | ~9.3 | – | – | – |
| | | ~15.0 | 15.1-15.8 | – | – |
| | | ~18.5 | – | – | – |
| | | ~21.9 | **21.7-22.0** | – | **21.4-21.9** |
| | | ~23.3 | – | – | – |
| | | ~25.6 | – | – | – |
| | | ~29.1 | – | – | **29.2-29.5** |
| | | ~34.6 | – | – | – |
| | | | – | – | 39.0-40.0 |
| | | ~44.1 | **44.1-44.5** | – | |
| | | ~48.5 | **47.9-49.5** | **47.9-49.4** | **48.1-48.6** |
| | | | – | – | **48.8-49.3** |
| | | ~57.9 | – | – | – |
| | | ~62.9 | **63.1-63.7** | – | – |
| | | ~67.1 | – | – | – |
| | | ~69.3 | – | – | – |
| | | ~73.7 | **74.3.74.7** | – | **74.3-74.6** |
| Human alpha-1-entitry- | 30.461 | 2.6-6.3 | **5.5-6.0** | **3.0-3.2** | **5.4-5.8** |
| sin and corticosteroid | | | – | **5.1-6.0** | – |
| binding globulin | | 22.0-30.4 | **25.7-26.2** | **24.9-25.3** | **25.8-26.4** |

TABLE 1-continued

Evaluation of SMAR SCAN accuracy

| Sequence, description and reference | Length (kb) | Experimentally defined MARs positions (kb) | SMARTest prediction positions (kb) | MAR-Finder prediction positions (kb) | SMAR Scan prediction positions (kb) |
|---|---|---|---|---|---|
| intergenic region | | | **27.5-27.8** | **25.5-25.8** | |
| (AF156545), [35] | | | – | **26.2-26.4** | – |
| | | | – | **27.5-28.2** | – |
| Human protamine locus | 53.080 | 8.8-9.7 | – | **8.0-8.9*** | – |
| (U15422). [24] | | 32.6-33.6 | – | **33.9-34.8*** | – |
| | | 37.2-39.4 | – | **33.9-34.8*** | – |
| | | 51.8-53.0 | – | –* | – |
| Human beta-globin | 75.955 | 1.5-3.0 | – | – | **2.3-2.6** |
| locus | | 15.6-19.0 | **18.0-18.4** | **15.5-16.0** | **15.3-15.6** |
| (U01317), [21] | | | – | **18.0-18.4** | – |
| | | | 34.4-34.9 | – | – |
| | | 44.7-52.7 | – | **50.6-50.8** | – |
| | | | 56.6-57.1 | 56.5-57.2 | – |
| | | 60.0-70.0 | 59.8-60.3 | **58.1-58.5** | **62.8-63.1** |
| | | | 65.6-66.0 | **63.0-63.6** | – |
| | | | **67.6-67.9** | **68.7-69.3** | **66.3-66.7** |
| | | | **68.8-69.1** | – | – |
| Sum (kb) | 310.151 | at least 56.1 | 14.5 | 13.8 | 9.5 |
| Total numbers: | | 37 | 28 | 25 | 22 |
| Average kb/predicted MAR | | | 11.076 | 12.406 | 14.097 |
| True positives [number of experimentally defined MAR found] | | | 19[14] | 20[12] | 17[14] |
| False positives | | | 9 | 5 | 5 |
| False negatives | | | 23 | 25 | 23 |
| Specificity | | | 19/28 = 68% | 20/25 = 80% | 17/22 = 77% |
| Sensitivity | | | 14/37 = 38% | 12/37 = 32% | 14/37 = 38% |

Table 1: Evaluation of SMAR SCAN Accuracy

Six different genomic sequences, three plant and three human sequences, for which experimentally defined MARs are known, were analyzed with MAR-Finder, SMARTest and SMAR SCAN. True positive matches are printed in bold, minus (–) indicates false negative matches. Some of the longer experimentally defined MARs contained more than one in silico prediction, each of them was counted as true positive match. Therefore, the number of true in silico predictions is higher than the number of experimentally defined MARs found. Specificity is defined as the ratio of true positive predictions, whereas sensitivity is defined as the ratio of experimentally defined MARs found. * AT-rich rule excluded using MAR-Finder.

SMARTest predicted 28 regions as MARs, 19 (true positives) of these correlate with experimentally defined MARs (specificity: 68%) whereas 9 (32%) are located in non-MARs (false positives). As some of the longest experimentally determined MARs contains more than one in silico prediction, the 19 true positives correspond actually to 14 different experimentally defined MARs (sensitivity: 38%). MARFinder predicted 25 regions as MARs, 20 (specificity: 80%) of these correlate with experimentally defined MARs corresponding to 12 different experimentally defined MARs (sensitivity: 32%). SMAR SCAN predicted 22 regions, 17 being true positives (specificity: 77%) matching 14 different experimentally defined MARs (sensitivity: 38%).

As another example, the same analysis has been applied to human chromosomes 1 and 2 and lead to the determination of 23 MARs sequences (SEQ ID NO 1 to 23). These sequences are listed in Annex 1 in ST25 format.

Example 6

Analyses of the Whole Genome Using the Combined Method (SMAR SCAN-pfsearch)

In order to test the potential correlation between the structural features computed by SMAR SCAN and the S/MAR functional activity, the whole human genome has been analyzed with the combined method with very stringent parameters, in order to get sequences with the highest values for the theoretical structural features computed, which are called "super" S/MARs below. This was done with the hope to obtain predicted MAR elements with a very potential to increase transgene expression and recombinant protein production. The putative S/MARs hence harvested were first analyzed from the bioinformatics perpective in an attempt to characterize and classify them.

6.1 S/MARs Predicted From the Analysis of the Whole Human Genome

As whole human genome sequence, all human RefSeq (National Center for Biotechnology Information, The NCBI handbook [Internet]. Bethesda (MD): National Library of Medicine (US), October. Chapter 17, The Reference Sequence (RefSeq) Project, 2002 contigs (release 5) were used and analyzed with the combined method, using SMAR SCAN as filter in the first level processing, employing default settings except for the highest bend cutoff value, whereas a stringent threshold of 4.0 degrees (instead of 3.202 degrees) has been used for the DNA bending criterion.

In the second level processing, predicted transcription factors binding have been sought in the sequences selected from the previous step without doing any filtering on these sequences.

The analysis by the combined method of the whole human genome came up with a total of 1757 putative "super" S/MARs representing a total of 1 065 305 bp (0.35% of the whole human genome). Table 2 shows for each chromosome: its size, its number of genes, its number of S/MARs predicted, its S/MARs density per gene and its kb per S/MAR. This table shows that there are very various gene densities per S/MAR predicted for the different chromosomes (standard deviation represents more than 50% of the mean of the density of genes per S/MAR predicted and the fold difference between the higher and the lower density of genes per S/MAR is 6.5). Table 2 also shows that the kb per S/MAR varies less that the density of genes per S/MAR (standard deviation represents 25% of the mean of kb per S/MAR and the fold difference between the higher and the lower kb per S/MAR is 3.2).

TABLE 2

Number of S/MARs predicted per chromosome.

| Chromosome | Number of genes per chromosome | Size of the chromosome (millions bp) | Number of S/MARs predicted | Density of genes per S/MAR | Kb per S/MAR |
|---|---|---|---|---|---|
| 1 | 2544 | 230 | 85 | 29.9 | 2705 |
| 2 | 1772 | 241 | 143 | 12.3 | 1685 |
| 3 | 1406 | 198 | 101 | 13.9 | 1960 |
| 4 | 1036 | 190 | 118 | 8.7 | 1610 |
| 5 | 1233 | 180 | 116 | 10.6 | 1551 |
| 6 | 1247 | 170 | 94 | 13.2 | 1808 |
| 7 | 1383 | 160 | 179 | 7.7 | 1754 |
| 8 | 942 | 145 | 77 | 12.2 | 1883 |
| 9 | 1100 | 119 | 48 | 22.9 | 2479 |
| 10 | 1003 | 133 | 71 | 14.1 | 1873 |
| 11 | 1692 | 132 | 67 | 25.2 | 1970 |
| 12 | 1278 | 131 | 78 | 16.3 | 1679 |
| 13 | 506 | 97 | 70 | 7.2 | 1385 |
| 14 | 1168 | 88 | 36 | 32.4 | 2444 |
| 15 | 895 | 83 | 35 | 25.5 | 2371 |
| 16 | 1107 | 81 | 41 | 27 | 1975 |
| 17 | 1421 | 80 | 37 | 38.4 | 2162 |
| 18 | 396 | 75 | 51 | 7.7 | 1470 |
| 19 | 1621 | 56 | 36 | 45.02 | 1555 |
| 20 | 724 | 60 | 28 | 25.8 | 2142 |
| 21 | 355 | 34 | 18 | 19.7 | 1888 |
| 22 | 707 | 34 | 28 | 25.2 | 1214 |
| X | 1168 | 154 | 170 | 6.8 | 905 |
| Y | 251 | 25 | 30 | 8.3 | 833 |
| Sum | 26955 | 3050 | 1757 | 457 | 43312 |
| Mean | 1123 | 127 | 73 | 19 | 1804 |
| Sd | 510 | 72.8 | 45 | 10 | 462 |

The number of genes per chromosome corresponds to the NCBI human genome statistics (Build 34 Version 3) (National Center for Biotechnology Information, The NCBI handbook [Internet]. Bethesda (MD): National Library of Medicine (US), Oct. Chapter 17, The reference Sequence (RefSeq) Project, 2002 (Available from http://www.ncbi.nih.gov/entrez/query.fcgi?db=Books) based on GenBank annotations.

Chromosome sizes are the sum of the corresponding human RefSeq (National Center for Biotechnology Information, The NCBI handbook [Internet]. Bethesda (MD): National Library of Medicine (US), Oct. Chapter 17, The reference Sequence (RefSeq) Project, 2002 (Available from http://www.ncbi.nih.gov/entrez/query.fcgi?db=Books) (release 5) contig lengths 6.2 Bioinformatics Analysis of "Super" MARS for Transcription Factor Binding Sites The 1757 predicted "super" S/MARs sequences obtained previously by SMAR SCAN were then analyzed for potential transcription factors binding sites. This has been achieved using RMatch™ Professional (Kel A E, Gossling E, Reuter I, Cheremushkin E, KelMargoulis O V, Wingender E, MATCH: A tool for searching transcription factor binding sites in DNA sequences, *Nucleic Acids Res.* 31(13):35769, 2003), a weight matrix based tool based on TRANSFAC (Wingender E, Chen X, Fricke E, Geffers R, Hehl R, Liebich I, Krull M, Matys V, Michael H, Ohnhauser R, Pruss M, Schacherer F, Thiele S, Urbach S, The TRANSFAC system on gene expression regulation, *Nucleic Acids Research,* 29(1):2813, 2001). Match™ 2.0 Professional has been used with most of the default settings Match™ analysis was based on TRANSFAC Professional, release 8.2 (20040630). The sums of all transcription factors binding prediction on the 1757 sequences analyzed according to Match™ are in Table 3. Based on this table, only the transcription factors totalizing at least 20 hits over the 1757 sequences analyzed were considered for further analyses.

Hereafter are some of the human transcription factors that are the most often predicted to bind on the 1757 putative S/MAR sequences and their Match description: Cdc5 (cell division control protein 5) a transcriptional regulator/repressor, Nkx3A a homeodomain protein regulated by androgen, POU1F1 (pituitary specific positive transcription factor 1) which is specific to the pituitary and stimulates cells proliferation. Thus, in addition to SATB1, NMP4 and MEF2, other transcription factors can participate in the activity of MARs.

TABLE 3 is a summary of all transcription factors binding prediction (totalizing 20 hits or more) on the 1757 sequences analyzed.

| | | | | | | | |
|---|---|---|---|---|---|---|---|
| AP1 | 1 | AR | 2 | Bach2 | 1 | Brn2 | 1 |
| C/EBP | 20 | C/EBPgamma | 5 | CDP CR3 | 1 | COMP1 | 2 |
| CREBP1 | 34 | Cdc5 | 858 | Cdx2 | 35 | Evil | 472 |
| FOX | 78 | FOXD3 | 79 | FOXJ2 | 244 | FOXP3 | 29 |
| Freac7 | 272 | GATA1 | 2 | GATA3 | 142 | GATA4 | 125 |
| HFH1 | 12 | HFH3 | 1 | HLF | 275 | HNF1 | 337 |
| HNF3alpha | 23 | HNF3beta | 71 | HP1 | 2 | Lhx3 | 22 |
| MEF2 | 114 | MRF2 | 57 | Myc | 18 | NKX3A | 849 |
| Nkx25 | 2 | Oct1 | 191 | PBX | 5 | POU1F1 | 483 |
| POU3F2 | 11 | POU6F1 | 29 | Pax3 | 3 | Pax6 | 20 |
| Pit1 | 505 | SRF | 8 | TEF | 2852 | TFIIA | 14 |
| TTF1 | 1 | V$MTATA_B | 4 | VBP | 53 | Vmw65 | 1 |
| XFD1 | 65 | XFD2 | 418 | XFD3 | 2 | | |

6.3 Bioinformatics Analysis of Predicted "Super" MARs for Dinucleotide Frequencies Various computer analysis were performed in order to easily identify "super" S/MAR sequences using an explicit criterion that could be identified without computing. Among those, a di-nucleotide analysis was performed on the 1757 superMARs, computing each of the 16 possible dinucleotide percentage for each sequence considering both strands in the 5'>3' direction.

A summary (min., max., median, mean, 25th percentile and 75th percentile) as well as the histograms of each dinucleotide percentage over the 1757 S/MAR sequences are respectively presented in Table 4. A similar analysis was performed on randomly selected sequences from the human genome, representing randomly selected non-S/MAR sequences (which might however contain some MARs). Table 5 represents respectively a summary of the dinucleotide content analysis for these sequences.

TABLE 4

Dinucleotide percentages over the 1757 S/MAR sequences

| | AA % | AC % | AG % | AT % |
|---|---|---|---|---|
| Minimum | 0.000 | 0.0000 | 0.0000 | 18.50 |
| 25th percentile | 4.234 | 0.9372 | 0.1408 | 32.11 |
| Median | 7.843 | 2.2408 | 0.4777 | 34.68 |
| Mean | 7.184 | 3.2117 | 1.0865 | 34.32 |
| 75th percentile | 10.110 | 4.7718 | 1.5096 | 36.94 |
| Maximum | 17.290 | 12.9479 | 8.1230 | 50.00 |

| | CA % | CC % | CG % | CT % |
|---|---|---|---|---|
| Minimum | 0.0000 | 0.00000 | 0.0000 | 0.0000 |
| 25th percentile | 0.9695 | 0.00000 | 0.0000 | 0.1408 |
| Median | 1.9776 | 0.00000 | 0.0000 | 0.4777 |
| Mean | 2.6977 | 0.14123 | 0.2709 | 1.0865 |
| 75th percentile | 3.7543 | 0.09422 | 0.1256 | 1.5096 |
| Maximum | 10.4061 | 4.24837 | 7.4410 | 8.1230 |

| | GA % | GC % | GG % | GT % |
|---|---|---|---|---|
| Minimum | 0.00000 | 0.0000 | 0.00000 | 0.0000 |
| 25th percentile | 0.08696 | 0.0000 | 0.00000 | 0.9372 |
| Median | 0.32616 | 0.0000 | 0.00000 | 2.2408 |
| Mean | 0.63347 | 0.2104 | 0.14123 | 3.2117 |
| 75th percentile | 0.83333 | 0.1914 | 0.09422 | 4.7718 |
| Maximum | 5.77889 | 9.8795 | 4.24837 | 12.9479 |

TABLE 4-continued

Dinucleotide percentages over the 1757 S/MAR sequences

| | TA % | TC % | TG % | TT % |
|---|---|---|---|---|
| Minimum | 28.63 | 0.00000 | 0.0000 | 0.000 |
| 25th percentile | 33.48 | 0.08696 | 0.9695 | 4.234 |
| Median | 35.22 | 0.32616 | 1.9776 | 7.843 |
| Mean | 35.29 | 0.63347 | 2.6977 | 7.184 |
| 75th percentile | 37.14 | 0.83333 | 3.7543 | 10.110 |
| Maximum | 50.00 | 5.77889 | 10.4061 | 17.290 |

Considering the results of the predicted S/MAR elements and of the nonS/MAR sequences in the summary tables, noticeable differences can be noticed in the AT et TA dinucleotide contents between these two groups of sequences. AT and TA represent respectively at least 18.5% and 28.6% of the dinucleotide content of the predicted S/MAR sequences, whereas the minimum percentages for the same dinucleotides in nonS/MAR sequences are respectively 0.3% and 0%. Similarly, the maximum CC and GG content in S/MAR sequences is 4.2%, whereas in nonS/MAR sequences the percentages for these two dinucleotides can amount up to 20.8%.

Figure 17:
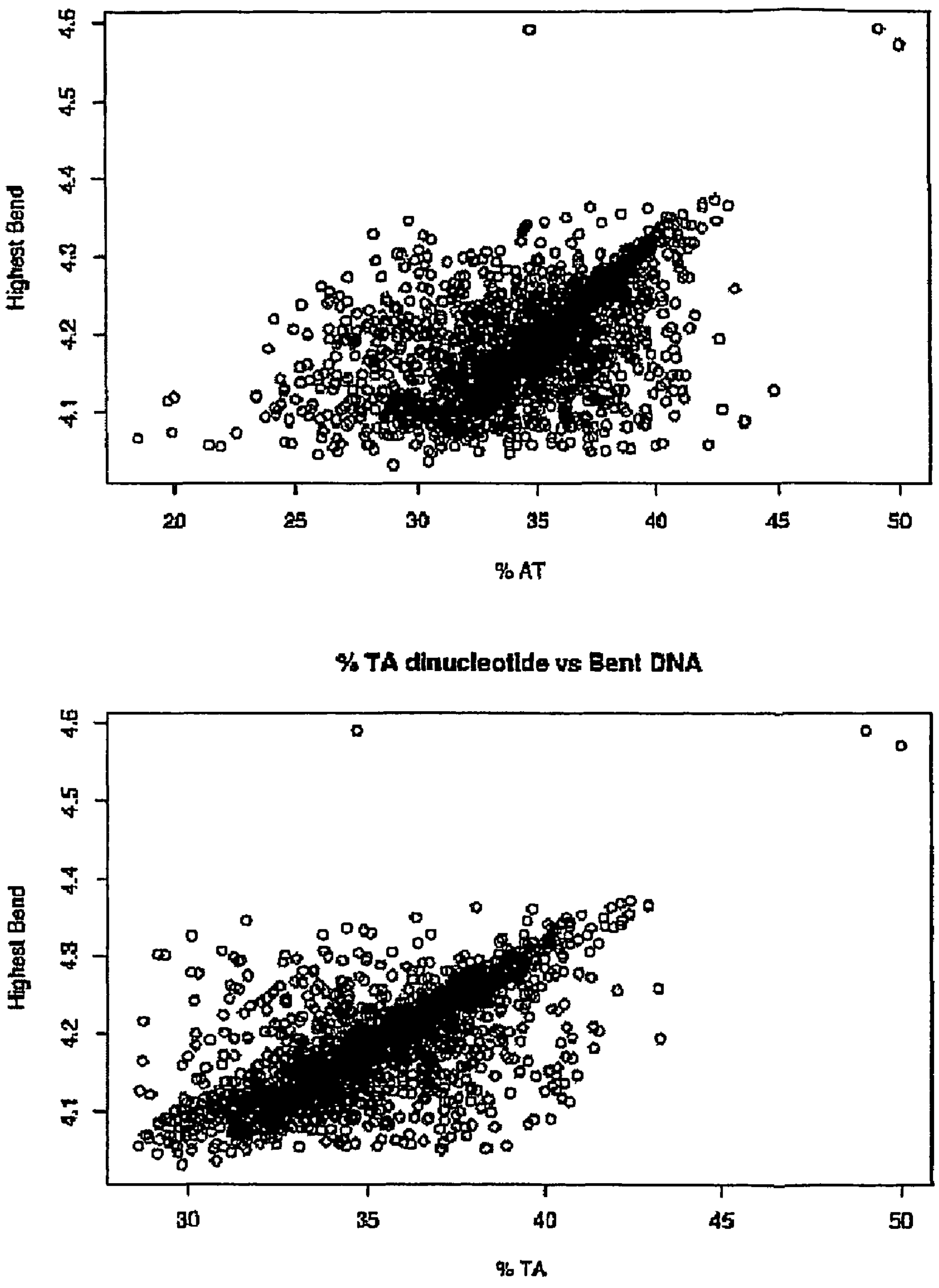
FIG. 17 represents the scatterplot for the 1757 S/MAR sequences of the AT (top) and TA (bottom) dinucleotide percentages versus the predicted DNA bending as computed by SMAR SCAN.
Figure 18:
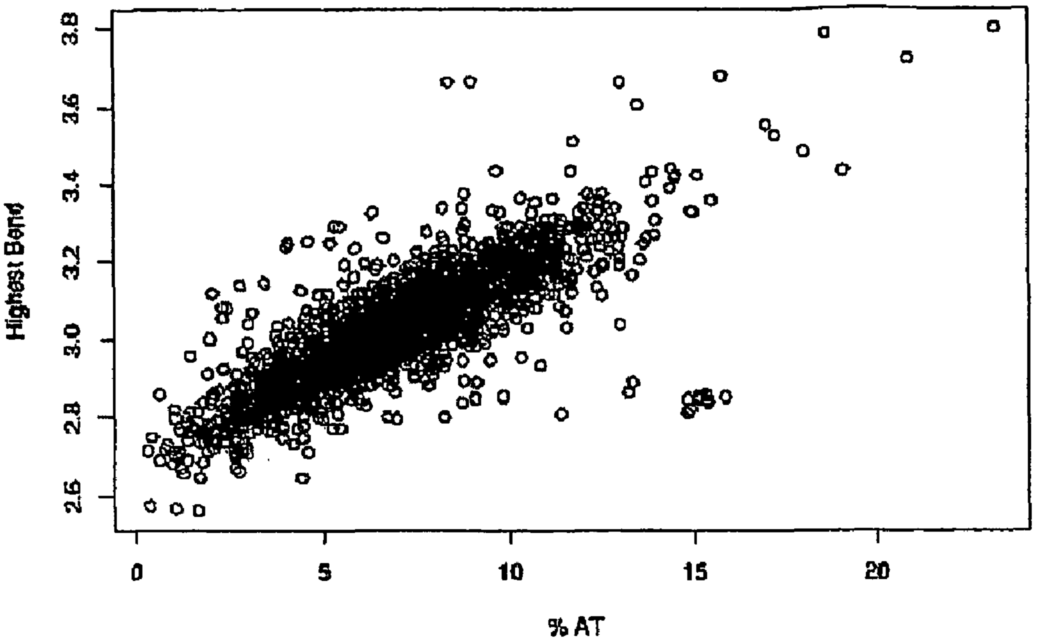
FIG. 18 represents the dinucleotide percentage distribution plots over the 1757 non-S/MARs sequences.
Figure 18:
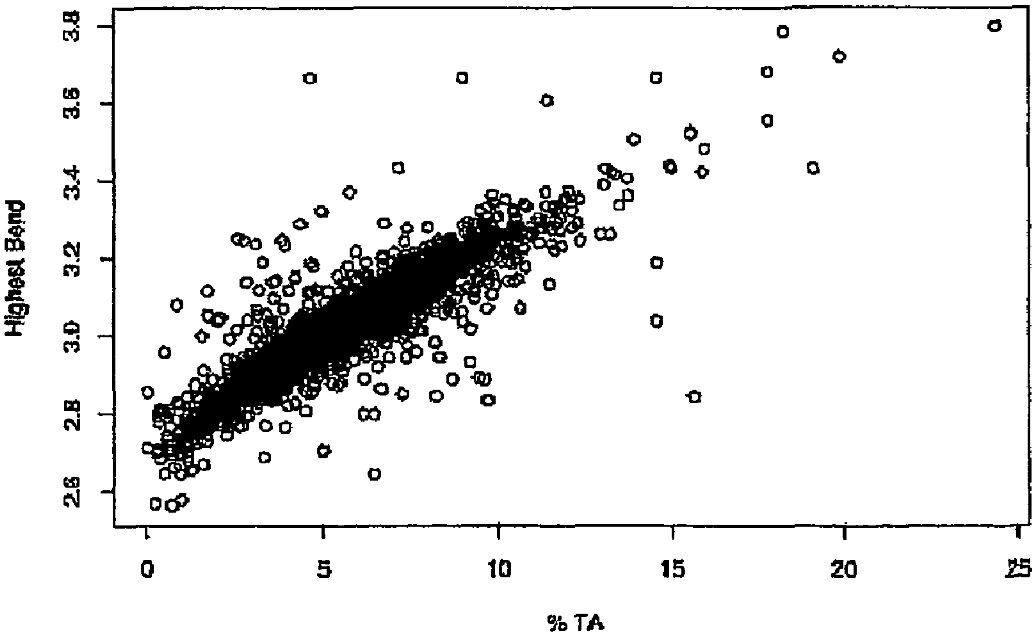

The correlation between AT and TA dinucleotide percentages and the DNA highest bend as computed by SMAR SCAN is depicted in FIG. 17 for the predicted S/MAR sequences and in FIG. 18 for the nonS/MAR sequences. The different scatterplots of these figures show that the TA percentage correlates well with the predicted DNA bend as predicted by SMAR SCAN.

TABLE 5

Dinucleotide percentages over the 1757 nonS/MAR sequences summary

| | AA % | AC % | AG % | AT % |
|---|---|---|---|---|
| Minimum | 0.000 | 1.735 | 1.512 | 0.3257 |
| 25th percentile | 7.096 | 4.586 | 6.466 | 5.1033 |
| Median | 9.106 | 5.016 | 7.279 | 6.8695 |
| Mean | 8.976 | 5.054 | 7.184 | 7.0108 |
| 75th percentile | 10.939 | 5.494 | 7.969 | 8.7913 |
| Maximum | 17.922 | 13.816 | 12.232 | 23.1788 |

| | CA % | CC % | CG % | CT % |
|---|---|---|---|---|
| Minimum | 3.571 | 0.8278 | 0.0000 | 1.512 |
| 25th percentile | 6.765 | 4.1077 | 0.4727 | 6.466 |

TABLE 5-continued

| Dinucleotide percentages over the 1757 nonS/MAR sequences summary | | | | |
|---|---|---|---|---|
| Median | 7.410 | 5.5556 | 0.8439 | 7.279 |
| Mean | 7.411 | 5.9088 | 1.2707 | 7.184 |
| 75th percentile | 8.010 | 7.2460 | 1.5760 | 7.969 |
| Maximum | 15.714 | 20.8415 | 12.6074 | 12.232 |
| | GA % | GC % | GG % | GT % |
| Minimum | 1.319 | 0.4967 | 0.8278 | 1.735 |
| 25th percentile | 5.495 | 3.2615 | 4.1077 | 4.586 |
| Median | 6.032 | 4.4092 | 5.5556 | 5.016 |
| Mean | 6.065 | 4.7468 | 5.9088 | 5.054 |
| 75th percentile | 6.602 | 5.8824 | 7.2460 | 5.494 |
| Maximum | 10.423 | 16.0000 | 20.8415 | 13.816 |
| | TA % | TC % | TG % | TT % |
| Minimum | 0.000 | 1.319 | 3.571 | 0.000 |
| 25th percentile | 3.876 | 5.495 | 6.765 | 7.096 |
| Median | 5.625 | 6.032 | 7.410 | 9.106 |
| Mean | 5.774 | 6.065 | 7.411 | 8.976 |
| 75th percentile | 7.464 | 6.602 | 8.010 | 10.939 |
| Maximum | 24.338 | 10.423 | 15.714 | 17.922 |

Four of the novel super MARs were randomly picked and analyzed for AT and TA dinucleotide content, and compared with the previously known chicken lysMAR, considering windows of 100 base pairs (Table 6).

Surprisingly, Applicants have shown that all of the super MARs have AT dinucleotide frequencies greater then 12%, and TA dinucleotides greater than 10% of the total dinucleotides analysed in a window of 100base pairs of DNA. The most efficient MARs display values around 34% of the two dinucleotide pairs.

TABLE 6

| Summary of % AT and TA dinucleotide frequencies of experimentally verified MARs | | | |
|---|---|---|---|
| CLysMAR (average of CUEs) | AT %: 12.03 | TA %: 10.29 | |
| P1_68 | AT %: 33.78 | TA %: 33.93 | SEQ ID No. 25 |
| P1_6 | AT %: 34.67 | TA %: 34.38 | SEQ ID No. 24 |
| P1_42 | AT %: 35.65 | TA %: 35.52 | SEQ ID No. 26 |
| Mean value for all human "super"MARs | AT %: 34.32 | TA %: 35.29 | |
| Mean value for all human non-MARs | AT %: 7.01 | TA %: 5.77 | |

6.4 Analysis of Orthologous Intergenic Regions of Human and Mouse Genomes

In order to get an insight on S/MAR evolution, orthologous intergenic regions of human and mouse genomes have been analysed with SMAR SCAN. The data set used is composed of 87 pairs of complete orthologous intergenic regions from the human and mouse genomes (Shabalina S A, Ogurtsov A Y, Kondrashov V A, Kondrashov A S, Selective constraint in intergenic regions of human and mouse genomes, *Trends Genet,* 17(7):3736, 2001) (average length ~12 000 bp) located on 12 human and on 12 mouse chromosomes, the synteny of these sequences was confirmed by pairwise sequence alignment and consideration of the annotations of the flanking genes (experimental or predicted).

Analysis of the 87 human and mouse orthologous intergenic sequences have been analysed with SMAR SCAN using its default settings. Analysis of the human sequences yielded a total of 12 S/MARs predicted (representing a total length of 4 750 bp), located on 5 different intergenic sequences.

Among the three human intergenic sequences predicted to contain a "super" S/MAR using SMAR SCAN stringent settings, one of the corresponding mouse orthologous intergenic sequence is also predicted to contain a S/MAR (human EMBL ID: Z96050, position 28 010 to 76 951 othologous to mouse EMBL ID: AC015932, positions 59 884 to 89 963). When a local alignement of these two orthologous intergenic sequences is performed, the best local alignement of these two big regions correspond to the regions predicted by SMAR SCAN to be S/MAR element. A manual search for the mouse orthologs of the two other human intergenic sequences predicted to contain a "super" S/MAR was performed using the Ensembl Genome Browser. The mouse orthologous intergenic sequences of these two human sequences were retrieved using Ensembl orthologue predictions (based on gene names), searching the orthologous mouse genes for the pairs of human genes flanking these intergenic regions.

Because SMAR SCAN has been tuned for human sequences and consequently yields little "super"MARs with mouse genomic sequences, its default cutoff values were slightly relaxed for the minimum size of contiguous hits to be considered as S/MAR (using 200 bp instead of 300 bp). Analysis by SMAR SCAN of these mouse sequences predicted several S/MARs having high values for the different computed structural features. This finding suggests that the human MAR elements are conserved across species.

Example 7

Dissection of the Chicken Lysozyme Gene 5'-MAR

The 3000 base pair 5'-MAR was dissected into smaller fragments that were monitored for effect on transgene expression in Chinese hamster ovary (CHO) cells. To do so, seven fragments of ~400 bp were generated by polymerase chain reaction (PCR). These PCR-amplified fragments were contiguous and cover the entire MAR sequence when placed end-to-end. Four copies of each of these fragments were ligated in a head-to-tail orientation, to obtain a length corresponding to approximately half of that of the natural MAR. The tetramers were inserted upstream of the SV40 promoter in pGEGFPControl, a modified version of the pGL3Control vector (Promega). The plasmid pGEGFPControl was created by exchanging the luciferase gene of pGL3Control for the EGFP gene from pEGFP-N1 (Clontech). The 5'-MAR-fragment-containing plasmids thus created were co-transfected with the resistance plasmid pSVneo in CHO-DG44 cells using LipofectAmine 2000 (Invitrogen) as transfection reagent, as performed previously (Zahn-Zabal, M., et al., "Development of stable cell lines for production or regulated expression using matrix attachment regions" *J Biotechnol,* 2001. 87(1): p. 29-42.). After selection of the antibiotic (G-418) resistant cells, polyclonal cell populations were analyzed by FACS for EGFP fluorescence.

Figure 5:
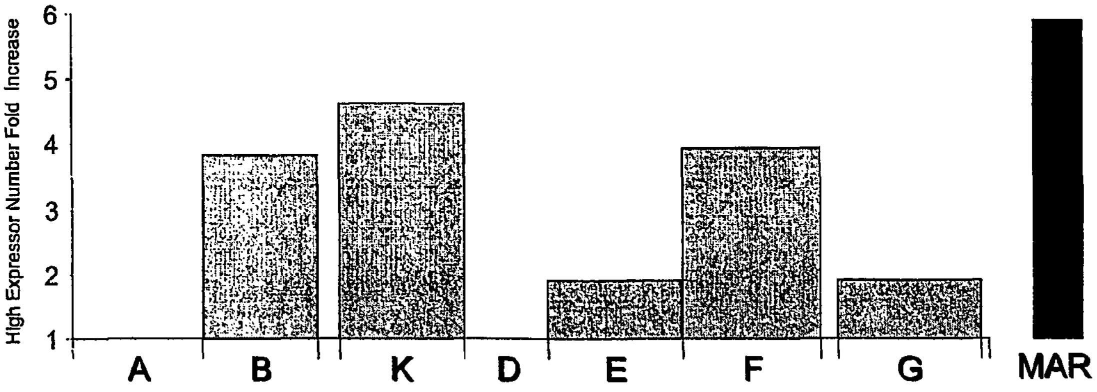
FIG. 5 shows the dissection of the ability of the chicken lysozyme gene 5'-MAR to stimulate transgene expression in CHO-DG44 cells. Fragments B, K and F show the highest ability to stimulate transgene expression. The indicated relative strength of the elements was based on the number of high-expressor cells.

Transgene expression was expressed at the percentile of high expressor cells, defined as the cells which fluorescence levels are at least 4 orders of magnitude higher than the average fluorescence of cells transfected with the pGEGFP-Control vector without MAR. FIG. 5 shows that multimerized fragments B, K and F enhance transgene expression, despite their shorter size as compared to the original MAR sequence. In contrast, other fragments are poorly active or fully inactive.

Example 8

Specificity of B, K and F Regions in the MAR Context

Figure 6:
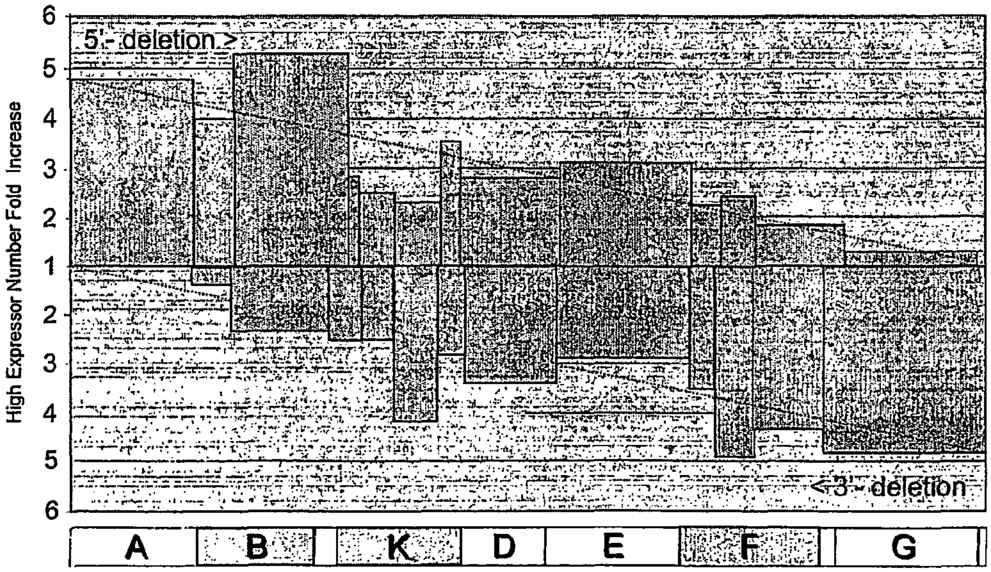
FIG. 6 shows the effect of serial-deletions of the 5'-end (upper part) and the 3'-end (lower part) of the 5'-MAR on the loss of ability to stimulate transgene expression. The transition from increased to decreased activity coincide with B-, K- and F-fragments.

The 5'-MAR was serially deleted from the 5'-end (FIG. 6, upper part) or the 3'-end (FIG. 6, lower part), respectively. The effect of the truncated elements was monitored in an assay similar to that described in the previous section. FIG. 6 shows that the loss of ability to stimulate transgene expression in CHO cells was not evenly distributed.

In this deletion study, the loss of MAR activity coincided with discrete regions of transition which overlap with the 5'-MAR B-, K- and F-fragment, respectively. In 5' deletions, activity was mostly lost when fragment K and F were removed. 3' deletions that removed the F and b elements had the most pronounced effects. In contrast, flanking regions A, D, E and G that have little or no ability to stimulate transgene expression on their own (FIG. 5), correspondingly did not contribute to the MAR activity in the 5'- and 3'-end deletion studies (FIG. 6).

Example 9

Structure of the F Element

Figure 7:
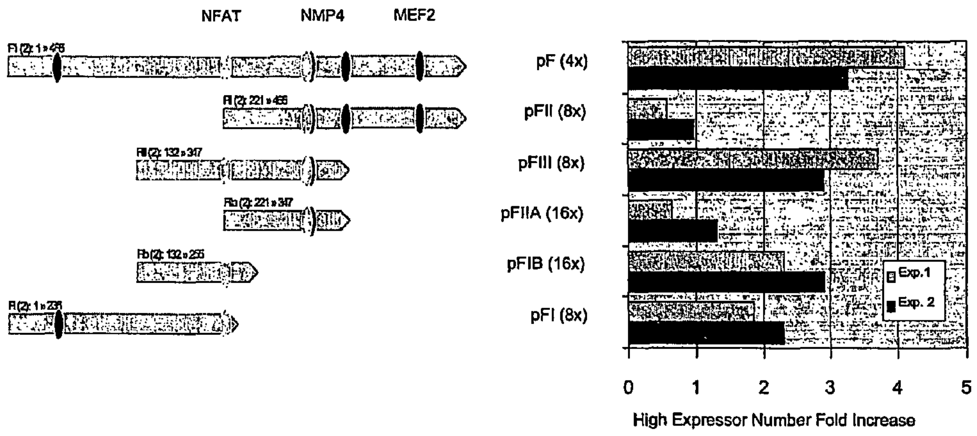
FIG. 7 shows that portions of the F fragment significantly stimulate transgene expression. The F fragment regions indicated by the light grey arrow were multimerized, inserted in pGEGFP Control and transfected in CHO cells. The element that displays the highest activity is located in the central part of the element and corresponds to fragment FIII (black bar labelled minimal MAR). In addition, an enhancer activity is located in the 3'-flanking part of the FIII fragment (dark grey bar labelled MAR enhancer).

The 465 bp F fragment was further dissected into smaller sub-fragments of 234, 243, 213 bp and 122, 125 and 121 bp, respectively. Fragments of the former group were octamerized (8 copies) in a head-to-tail orientation, while those of the latter group were similarly hexa-decamerized (16 copies), to maintain a constant length of MAR sequence. These elements were cloned in pGEGFPControl vector and their effects were assayed in CHO cells as described previously. Interestingly, fragment FIII retained most of the activity of the full-length F fragment whereas fragment FIII, which contains the right-hand side part of fragment FIII, lost all the ability to stimulate transgene expression (FIG. 7). This points to an active region comprised between nt 132 and nt 221 in the FIB fragment. Consistently, multiple copies of fragments FI and FIB, which encompass this region, displayed similar activity. FIIA on its own has no activity. However, when added to FIB, resulting in FIII, it enhances the activity of the former. Therefore FIIA appears to contain an auxiliary sequence that has little activity on its own, but that strengthens the activity of the minimal domain located in FIB.

Analysis of the distribution of individual motifs within the lysozyme gene 5'-MAR is shown in FIG. 8A, along with some additional motifs that we added to the analysis. Most of these motifs were found to be dispersed throughout the MAR element, and not specifically associated with the active portions. For instance, the binding sites of transcription factors and other motifs that have been associated with MARs were not preferentially localized in the active regions. It has also been proposed that active MAR sequences may consist of combination of distinct motifs. Several computer programs (MAR Finder, SMARTest, SIDD duplex stability) have been reported to identify MARs as regions of DNA that associate with the DNA matrix. They are usually based on algorithms that utilizes a predefined series of sequence-specific patterns that have previously been suggested as containing MAR activity, as exemplified by MAR Finder, now known as MAR Wiz. The output of these programs did not correlate well with the transcriptionally active portions of the cLysMAR. For instance, peaks of activity obtained with MAR Finder did not clearly match active MAR sub-portion, as for instance the B fragment is quite active in vivo but scores negative with MAR Finder (FIG. 8B, compare the top and middle panels). Bent DNA structures, as predicted by this program, did not correlate well either with activity (FIG. 8B, compare the top and bottom panels). Similar results were obtained with the other available programs (data not shown).

The motifs identified by available MAR prediction computer methods are therefore unlikely to be the main determinants of the ability of the cLysMAR to increase gene expression. Therefore, a number of other computer tools were tested. Surprisingly, predicted nucleosome binding sequences and nucleosome disfavouring sequences were found to be arranged in repetitively interspersed clusters over the MAR, with the nucleosome favouring sites overlapping the active B, K and F regions. Nucleosome positioning sequences were proposed to consist of DNA stretches that can easily wrap around the nucleosomal histones, and they had not been previously associated with MAR sequences.

Nucleosome-favouring sequences may be modelled by a collection of DNA features that include moderately repeated sequences and other physico-chemical parameters that may allow the correct phasing and orientation of the DNA over the curved histone surface. Identification of many of these DNA properties may be computerized, and up to 38 different such properties have been used to predict potential nucleosome positions. Therefore, we set up to determine if specific components of nucleosome prediction programs might correlate with MAR activity, with the objective to construct a tool allowing the identification of novel and possibly more potent MARs from genomic sequences.

To determine whether any aspects of DNA primary sequence might distinguish the active B, K and F regions from the surrounding MAR sequence, we analyzed the 5'-MAR with MAR Scan® SCAN. Of the 38 nucleosomal array prediction tools, three were found to correlate with the location of the active MAR sub-domains (FIG. 9A). Location of the MAR B, K and F regions coincides with maxima for DNA bending, major groove depth and minor groove width. A weaker correlation was also noted with minima of the DNA melting temperature, as determined by the GC content. Refined mapping over the MAR F fragment indicated that the melting temperature valley and DNA bending summit indeed correspond the FIB sub-fragment that contains the MAR minimal domain (FIG. 9B). Thus active MAR portions may correspond to regions predicted as curved DNA regions by this program, and we will refer to these regions as CUE-B, CUE-K and CUE-F in the text below. Nevertheless, whether these regions correspond to actual bent DNA and base-pair unwinding regions is unknown, as they do not correspond to bent DNA as predicted by MAR Wiz (FIG. 9B).

Example 10

Imprints of Other Regulatory Elements in the F Fragment

Nucleosome positioning features may be considered as one of the many specific chromatin codes contained in genomic DNA. Although this particular code may contribute to the activity of the F region, it is unlikely to determine MAR activity alone, as the 3' part of the F region enhanced activity of the minimal MAR domain contained in the FIB portion. Using the MatInspector program (Genomatix), we searched for transcription factor binding sites with scores higher than 0.92 and found DNA binding sequences for the NMP4 and MEF2 proteins in the 3' part of the F fragment (FIG. 8B).

Figure 10:
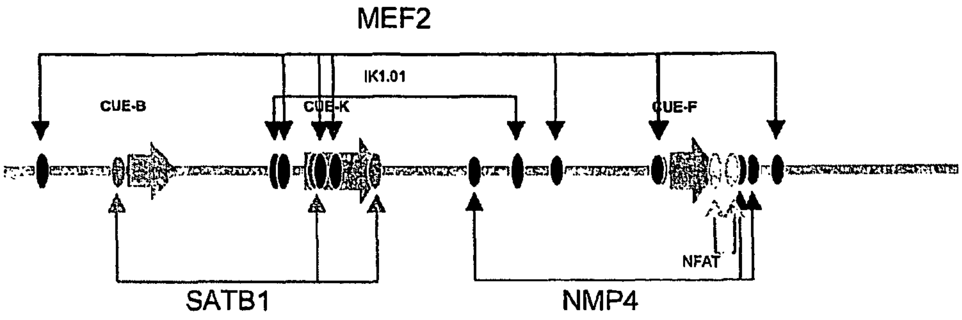
FIG. 10 shows the distribution of putative transcription factor binding sites within the 5'-cLysMAR. Large arrows indicate the position of the CUE elements as identified with SMAR SCAN.

To determine whether any of these transcription factor-binding sites might localize close to the B and K active regions, the entire 5'-MAR sequence was analyzed for binding by NMP4 and MEF2 and proteins reported to bind to single-stranded or double-stranded form of BURs. Among those, SATB1 (special AT-rich binding protein 1) belongs to a class of DNA-binding transcription factor that can either activate or repress the expression of nearby genes. This study indicated that specific proteins such as SATB1, NMP4 (nuclear matrix protein 4) and MEF2 (myogenic enhancer factor 2), have a specific distribution and form a framework around the minimal MAR domains of cLysMAR (FIG. 10). The occurrence of several of these NMP4 and SATB1 binding sites has been confirmed experimentally by the EMSA analysis of purified recombinant proteins (data not shown).

Example 11

Construction of Artificial MARs by Combining Defined Genetic Elements

Figure 11:
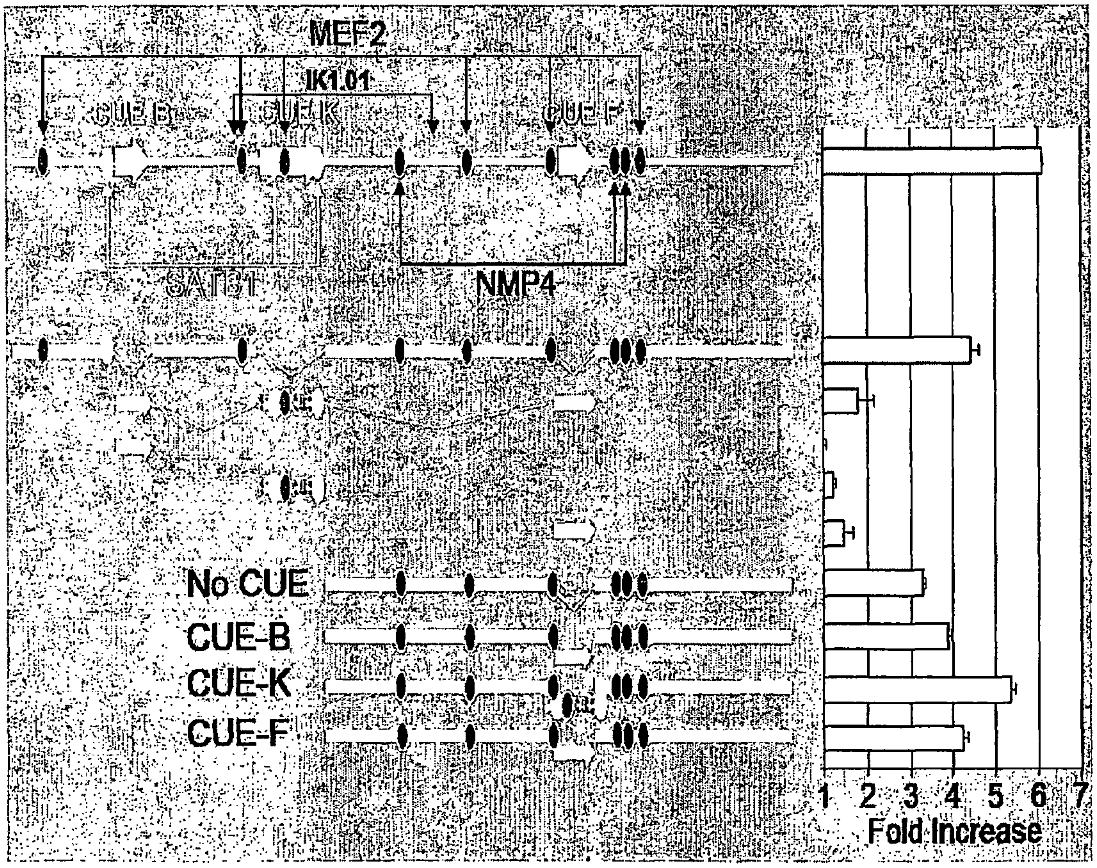
FIG. 11 shows the scheme of assembly of various portions of the MAR. The indicated portions of the cLysMAR were amplified by PCR, introducing BglII-BamHI linker elements at each extremity, and assembled to generate the depicted composite elements. For instance, the top construct consists of the assembly of all CUE and flanking sequences at their original location except that BglI-BamHII linker sequences separate each element.

To further assess the relative roles of the various MAR components, the cLysMAR was deleted of all three CUE regions (FIG. 11, middle part), which resulted in the loss of part of its activity when compared to the complete MAR sequence similarly assembled from all of its components as a control (FIG. 11, top part). Consistently, one copy of each CUE alone, or one copy of each of the three CUEs assembled head-to-tail, had little activity in the absence of the flanking sequences. These results strengthen the conclusion that optimal transcriptional activity requires the combination of CUEs with of flanking sequences. Interestingly, the complete MAR sequence generated from each of its components, but containing also BglII-BamHI linker sequences (AGATCC) used to assemble each DNA fragment, displayed high transcriptional activity (6 fold activation) as compared to the 4.8 fold noted for the original MAR element in this series of assays (see FIG. 5).

We next investigated whether the potentially curved DNA regions may also be active in an environment different from that found in their natural MAR context. Therefore, we set up to swap the CUE-F, CUE-B and CUE-K elements, keeping the flanking sequences unchanged. The sequences flanking the CUE-F element were amplified by PCR and assembled to bracket the various CUEs, keeping their original orientation and distance, or without a CUE. These engineered ~1.8 kb MARs were then assayed for their ability to enhance transgene expression as above. All three CUE were active in this context, and therefore there action is not restricted to one given set of flanking sequences. Interestingly, the CUE-K element was even more active than CUE-F when inserted between the CUE-F flanking sequences, and the former composite construct exhibited an activity as high as that observed for the complete natural MAR (4.8 fold activation). What distinguishes the CUE-K element from CUE-F and CUE-B is the presence of overlapping binding sites for the MEF-2 and SatB1 proteins, in addition to its CUE feature. Therefore, fusing CUE-B with CUE-F-flanking domain results in a higher density of all three binding sites, which is likely explanation to the increased activity.

These results indicate that assemblies of CUEs with sequences containing binding sites for proteins such as NMP4, MEF-2, SatB1, and/or polyPpolyQ proteins constitute potent artificial MAR sequences.

Example 12

Expression Vectors

Figure 12:
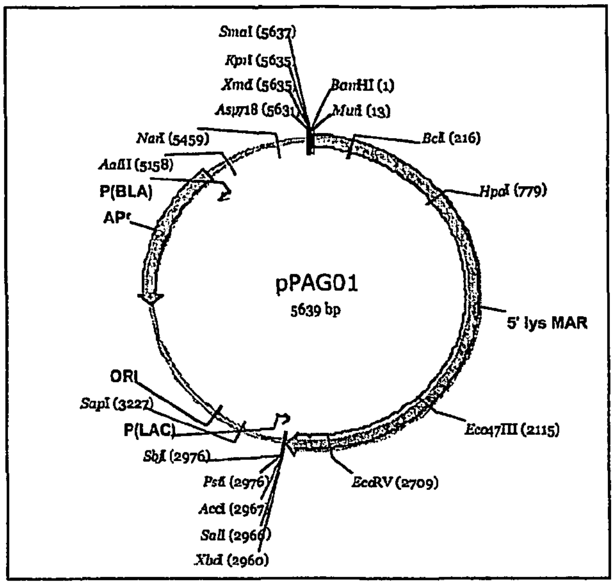
FIG. 12 represents the plasmid maps.
Figure 12:
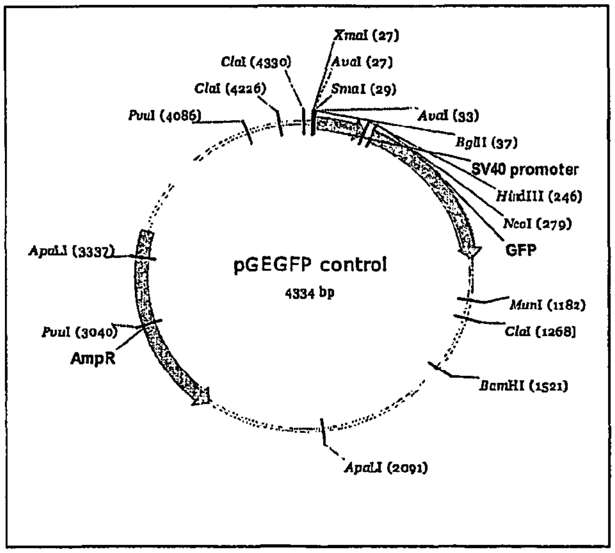
Figure 12:
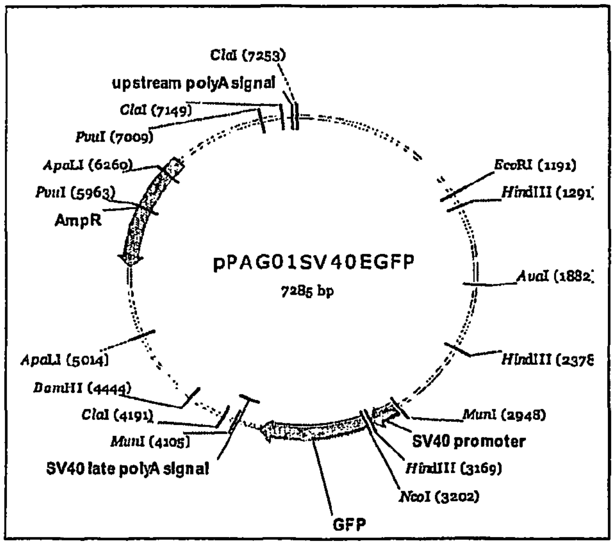

Three expression vectors according to the present invention are represented on FIG. 12.

Plasmid pPAG01 is a 5640 bp pUC19 derivative. It contains a 2960 bp chicken DNA fragment cloned in BamH1 and Xbal restriction sites. The insert comes from the border of the 5'-end of the chicken lyzozyme locus and has a high A/T-content.

Plasmid pGEGFP (also named pSV40EGFP) control is a derivative of the pGL3-control vector (Promega) in which the luciferase gene sequence has been replaced by the EGFP gene sequence form the pEGFP-N1 vector (Clontech). The size of pGEGFP plasmid is 4334 bp.

Plasmid pUbCEGFP control is a derivative of the pGL3 with an Ubiquitin promoter.

Plasmid pPAG01GFP (also named pMAR-SV40EGFP) is a derivative of pGEGFP with the 5'-Lys MAR element cloned in the MCS located just upstream of the SV40 promoter. The size of the pPAG01EGF plasmid is 7285 bp.

Example 13

Effect of the Additional Transfection of Primary Transfectant Cells on Transgene Expression One day before transfection, cells were plated in a 24-well plate, in growth medium at a density of $1.35\times10^5$ cells/well for CHO-DG44 cells. 16 hours post-inoculum, cells were transfected when they reached 30-40% confluence, using Lipofect-AMINE 2000 (hereinafter LF2000), according to the manufacturer's instructions (Invitrogen). Twenty-seven microliters of serum free medium (Opti-MEM; Invitrogen) containing 1.4 μl of LF2000 were mixed with 27 μl of Opti-MEM containing 830 ng of linear plasmid DNA. The antibiotic selection plasmid (pSVneo) amounted to one tenth of the reporter plasmid bearing the GFP transgene. The mix was incubated at room temperature for 20 min, to allow the DNA-LF2000 complexes to form. The mixture was diluted with 300 μl of Opti-MEM and poured into previously emptied cell-containing wells. Following 3 hours incubation of the cells with the DNA mix at 37° C. in a $CO_2$ incubator, one ml of DMEM-based medium was added to each well. The cells were further incubated for 24 hours in a $CO_2$ incubator at 37° C. The cells were then transfected a second time according to the method described above, except that the resistance plasmid carried another resistance gene (pSVpuro). Twenty-four hours after the second transfection, cells were passaged and expanded into a T-75 flask containing selection medium supplemented with 500 μg/ml G-418 and 5 μg/ml puromycin. After a two week selection period, stably transfected cells were cultured in 6-well plates. Alternatively, the cell population was transfected again using the same method, but pTKhygro (Clontech) and pSVdhfr as resistance plasmids. The expression of GFP was analysed with Fluorescence-activated cell sorter (FACS) and with a Fluoroscan.

Figure 13:
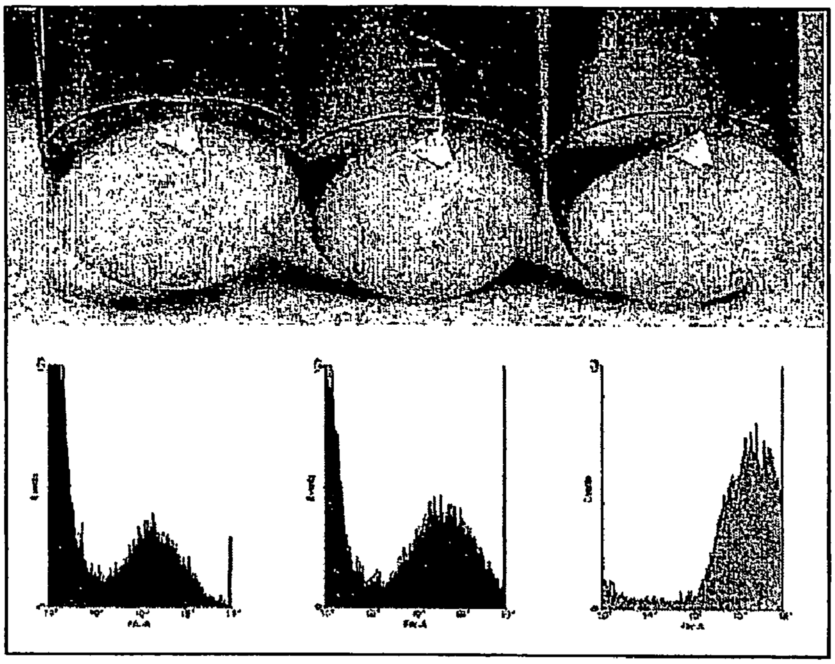
FIG. 13 shows the effect of re-transfecting primary transfectants on GFP expression. Cells (CHO-DG44) were co-transfected with pSV40EGFP (left tube) or pMAR-SV40EGFP (central tube) and pSVneo as resistance plasmid. Cells transfected with pMAR-SV40EGFP were re-transfected 24 hours later with the same plasmid and a different selection plasmid, pSVpuro (right tube). After two weeks selection, the phenotype of the stably transfected cell population was analysed by FACS.

FIG. 13 shows that the phenotype of the twice-transfected cells (hereafter called secondary transfectants) not only was strongly coloured, such that special bulb and filter were not required to visualize the green color from the GFP protein, but also contained a majority of producing cells (bottom right-hand side FACS histogram) as compared to the parental population (central histogram). This level of fluorescence corresponds to specific cellular productivities of at least 10 pg per cell per day. Indeed, cells transfected only one time (primary transfectants) that did not express the marker protein were almost totally absent from the cell population after re-transfection. Bars below $10^1$ units of GFP fluorescence amounted 30% in the central histogram and less than 5% in the right histogram. This suggested that additional cells had been transfected and successfully expressed GFP.

Strikingly, the amount of fluorescence exhibited by re-transfected cells suggested that the subpopulation of cells having incorporated DNA twice expressed much more GFP than the expected two-fold increase. Indeed, the results shown in Table 2 indicate that the secondary transfectants exhibited, on average, more than the two-fold increase of GFP expected if two sets of sequences, one at each successive transfection, would have been integrated independently and with similar efficiencies. Interestingly, this was not dependent on the promoter sequence driving the reporter gene as both viral and cellular promoter-containing vectors gave a similar GFP enhancement (compare lane 1 and 2). However, the effect was particularly marked for the MAR-containing vector as compared to plasmids without MAR-(lane 3), where the two consecutive transfections resulted in a 5.3 and 4.6 fold increase in expression, in two distinct experiments.

TABLE 7

Effect of re-transfecting primary transfectants at 24 hours interval on GFP expression.

| Type of plasmids | Primary transfection | Secondary transfection | EGFP fluorescence Fold increase |
|---|---|---|---|
| pUbCEGFP | 4,992 | 14,334 | 2.8 |
| pSV40EGFP | 4,324 | 12,237 | 2.8 |
| pMAR-SV40EGFP | 6,996 | 36,748 | **5.3** |
| pUbCEGFP | 6,452 | 15,794 | 2.5 |
| pSV40EGFP | 4,433 | 11,735 | 2.6 |
| pMAR-SV40EGFP | 8,116 | 37,475 | **4.6** |

Two independent experiments are shown.
The resistance plasmid pSVneo was co-transfected with various GFP expression vectors. One day post-transfection, cells were re-transfected with the same plasmids with the difference that the resistance plasmid was changed for pSVpuro.
Cells carrying both resistance genes were selected on 500 μg/ml G-418 and 5 μg/ml puromycin and the expression of the reporter gene marker was quantified by Fluoroscan.
The fold increases correspond to the ratio of fluorescence obtained from two consecutive transfections as compared to the sum of fluorescence obtained from the corresponding independent transfections.
The fold increases that were judged significantly higher are shown in bold, and correspond to fluorescence values that are consistently over 2-fold higher than the addition of those obtained from the independent transfections.

The increase in the level of GFP expression in multiply tranfected cells was not expected from current knowledge, and this effect had not been observed previously.

Taken together, the data presented here support the idea that the plasmid sequences that primarily integrated into the host genome would facilitate integration of other plasmids by homologous recombination with the second incoming set of plasmid molecules. Plasmid recombination events occur within a 1-h interval after the plasmid DNA has reached the nucleus and the frequency of homologous recombination between co-injected plasmid molecules in cultured mammalian cells has been shown to be extremely high, approaching unity (Folger, K. R., K. Thomas, and M. R. Capecchi, Nonreciprocal exchanges of information between DNA duplexes coinjected into mammalian cell nuclei. Mol Cell Biol, 1985. 5(1): p. 59-69], explaining the integration of multiple plasmid copies. However, homologous recombination between newly introduced DNA and its chromosomal homolog normally occurs very rarely, at a frequency of 1 in $10^3$ cells receiving DNA to the most [Thomas, K. R., K. R. Folger, and M. R. Capecchi, High frequency targeting of genes to specific sites in the mammalian genome. Cell, 1986. 44(3): p. 419-28.]. Thus, the results might indicate that the MAR element surprisingly acts to promote such recombination events. MARs would not only modify the organization of genes in vivo, and possibly also allow DNA replication in conjunction with viral DNA sequences, but they may also act as DNA recombination signals.

Example 14

MARs Mediate the Unexpectedly High Levels of Expression in Multiply Transfected Cells If MAR-driven recombination events were to occur in the multiple transfections process, we expect that the synergy between the primary and secondary plasmid DNA would be affected by the presence of MAR elements at one or both of the transfection steps. We examined this possibility by multiply transfections of the cells with pMAR alone or in combination with various expression plasmids, using the method described previously. Table 3 shows that transfecting the cells twice with the pMAR-SV40EGFP plasmid gave the highest expression of GFP and the highest degree of enhancement of all conditions (4.3 fold). In contrast, transfecting twice the vector without MAR gave little or no enhancement, 2.8-fold, instead of the expected two-fold increase. We conclude that the presence of MAR elements at each transfection step is necessary to achieve the maximal protein synthesis.

TABLE 8

| Primary transfection | | Secondary transfection | | |
|---|---|---|---|---|
| Type of plasmid | EGFP-fluorescence | Type of plasmid | EGFP-fluorescence | Fold increase |
| pMAR | 0 | pMAR | 0 | 0 |
| | | pSV40EGFP | 15,437 | **2.3-2.5** |
| | | pMAR-SV40EGFP | 30,488 | **2.6-2.7** |
| pMAR-SV40EGFP | 11,278 | pMAR-SV40EGFP | 47,027 | **4.3-5.3** |
| | | pMAR | 12,319 | 1.0-1.1 |
| pSV40EGFP | 6,114 | pSV40EGFP | 17,200 | 2.8 |
| | | pMAR | 11,169 | 1.8-2.3 |

Interestingly, when cells were first transfected with pMAR alone, and then re-transfected with pSV40EGFP or pMAR-SV40EGFP, the GFP levels were more than doubled as compared to those resulting from the single transfection of the later plasmids (2.5 and 2.7 fold respectively, instead of the expected 1-fold). This indicates that the prior transfection of the MAR can increase the expression of the plasmid used in the second transfection procedure. Because MARs act only locally on chromatin structure and gene expression, this implies that the two types of DNA may have integrated at a similar chromosomal locus. In contrast, transfecting the GFP expression vectors alone, followed by the MAR element in the second step, yielded little or no improvement of the GFP levels. This indicates that the order of plasmid transfection is important, and that the first transfection event should contain a MAR element to allow significantly higher levels of transgene expression.

If MAR elements favoured the homologous recombination of the plasmids remaining in episomal forms from the first and second transfection procedures, followed by their co-integration at one chromosomal locus, one would expect that the order of plasmid transfection would not affect GFP levels. However, the above findings indicate that it is more favourable to transfect the MAR element in the first rather than in the second transfection event. This suggests the following molecular mechanism: during the first transfection procedure, the MAR elements may concatemerize and integrate, at least in part, in the cellular chromosome. This integrated MAR DNA may in turn favour the further integration of more plasmids, during the second transfection procedure, at the same or at a nearby chromosomal locus.

Example 15

MARs as Long Term DNA Transfer Facilitators

If integrated MARs mediated a persistent recombination-permissive chromosomal structure, one would expect high levels of expression even if the second transfection was performed long after the first one, at a time when most of the transiently introduced episomal DNA has been eliminated. To address this possibility, the cells from Table 3, selected for antibiotic resistance for three weeks, were transfected again once or twice and selected for the incorporation of additional DNA resistance markers. The tertiary, or the tertiary and quaternary transfection cycles, were performed with combinations of pMAR or pMAR-SV40EGFP, and analyzed for GFP expression as before.

TABLE 9

Table 9. MARs act as facilitator of DNA integration.

| Type of plasmid | EGFP-fluorescence | Fold increase |
|---|---|---|
| Tertiary transfection | | |
| pMAR | 18368 | **2.2** |
| pMAR-SV40EGFP | 16544 | 2.0 |
| Quaternary transfection | | |
| pMAR | 43,186 | **2.4** |
| pMAR-SV40EGFP | 140,000 | **7.6** |
| pMAR-SV40EGFP | 91,000 | **5.5** |
| pMAR | 33,814 | **2.0** |

The pMAR-SV40EGFP/pMAR-SV40EGFP secondary transfectants were used in a third cycle of transfection at the end of the selection process. The tertiary transfection was accomplished with pMAR or pMAR-SV40EGFP, and pTKhygro as selection plasmid, to give tertiary transfectants. After 24 hours, cells were transfected again with either plasmid and pSVdhfr, resulting in the quaternary transfectants which were selected in growth medium containing 500 μg/ml G-418 and 5 μg/ml puromycin, 300 μg/ml hygromycin B and 5 μM methotrexate. The secondary transfectants initially exhibited a GFP fluorescence of 8300. The fold increases correspond to the ratio of fluorescence obtained from two consecutive transfections as compared to the sum of fluorescence obtained from the corresponding independent transfections. The fold increases that were judged significantly higher are shown in bold, and correspond to fluorescence values that are 2-fold higher than the addition of those obtained from the independent transfections.

These results show that loading more copies of pMAR or pMAR-SV40EGFP resulted in similar 2-fold enhancements of total cell fluorescence. Loading even more of the MAR in the quaternary transfection further enhanced this activity by another 2.4-fold. This is consistent with our hypothesis that newly introduced MAR sequences may integrate at the chromosomal transgene locus by homologous recombination and thereby further increase transgene expression.

Figure 14:
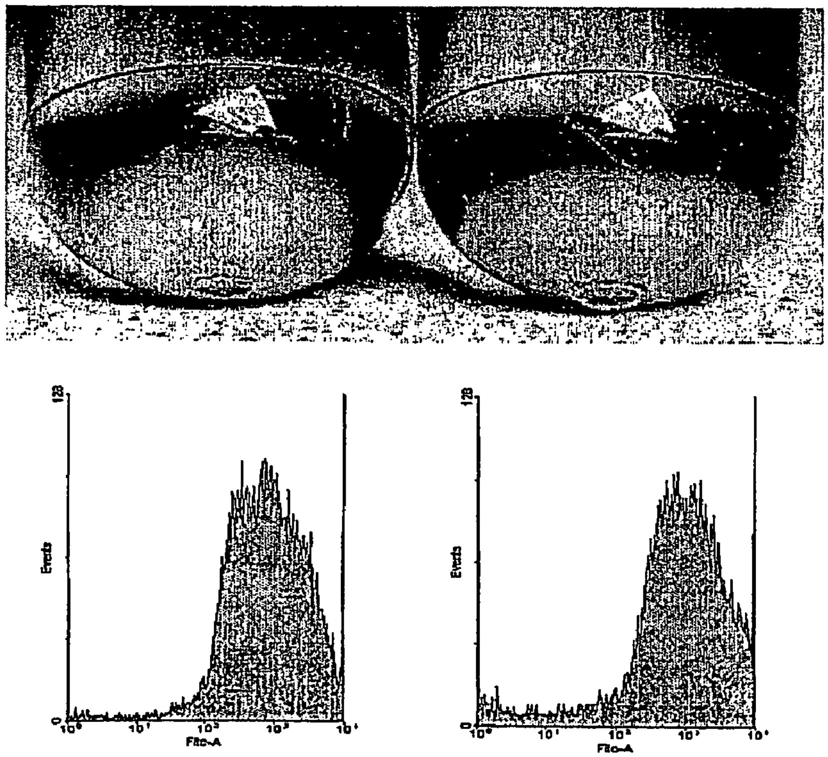
FIG. 14 shows the effect of multiple load of MAR-containing plasmid. The pMAR-SV40EGFP/pMAR-SV40EGFP secondary transfectants were used in a third cycle of transfection at the end of the selection process. The tertiary transfection was accomplished with pMAR or pMAR-SV40EGFP to give tertiary transfectants. After 24 hours, cells were transfected again with either plasmid, resulting in the quaternary transfectants (see Table 4).
Figure 15:
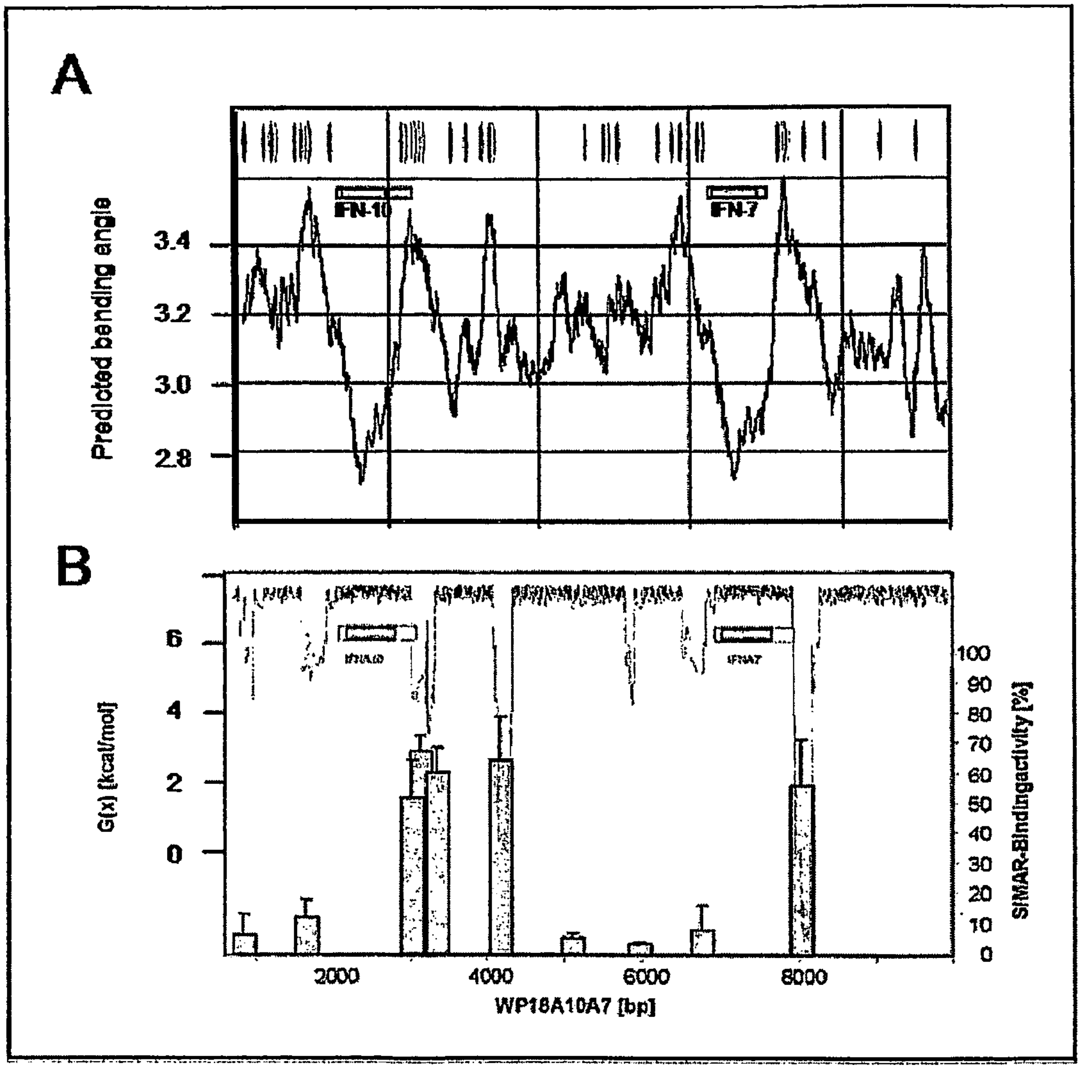
FIG. 15 shows comparative performance of SMAR prediction algorithms exemplified by region WP18A10A7. (A) SMAR SCAN analysis was performed with default settings. (B) SIDD analysis (top curve and left-hand side scale), and the attachment of several DNA fragments to the nuclear matrix in vitro (bar-graph, right-hand side scale) was taken from Goetze et al (Goetze S, Gluch A, Benham C, Bode J, "Computational and in vitro analysis of destabilized DNA regions in the interferon gene cluster: potential of predicting functional gene domains." *Biochemistry,* 42:154-166, 2003).

When the cells were transfected a third and fourth time with the pMAR-SV40EGFP plasmid, GFP activity further increased, once again to levels not expected from the addition of the fluorescence levels obtained from independent transfections. GFP expression reached levels that resulted in cells visibly glowing green in day light (FIG. 14). These results further indicate that the efficiency of the quaternary transfection was much higher than that expected from the efficacy of the third DNA transfer, indicating that proper timing between transfections is crucial to obtain the optimal gene expression increase, one day being preferred over a three weeks period. We believe that MAR elements favour secondary integration events in increasing recombination frequency at their site of chromosomal integration by relaxing closed chromatin structure, as they mediate a local increase of histone acetylation (Yasui, D., et al., SATB1 targets chromatin remodelling to regulate genes over long distances. *Nature,* 2002. 419(6907): p. 641-5.]. Alternatively, or concomitantly, MARs potentially relocate nearby genes to subnuclear locations thought to be enriched in trans-acting factors, including proteins that can participate in recombination events such as topoisomerases. This can result in a locus in which the MAR sequences can bracket the pSV40EGFP repeats, efficiently shielding the transgenes from chromatin-mediated silencing effects.

Example 16

Figure 19:
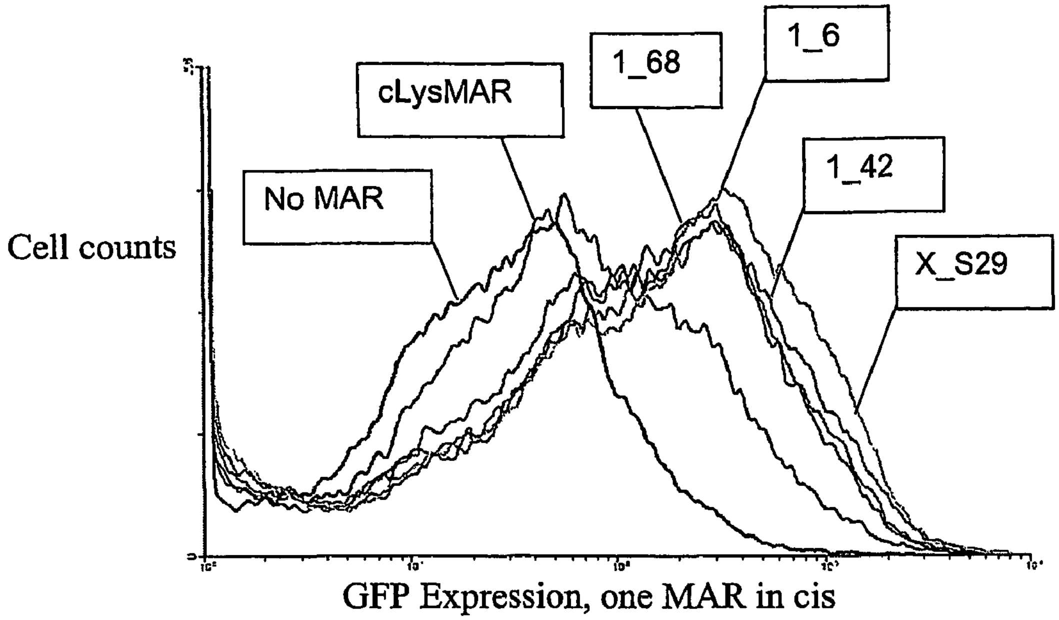
FIG. 19 shows the effect of various S/MAR elements on the production of recombinant green fluorescent protein (GFP). Populations of CHO cells transfected with a GFP expression vector containing or a MAR element, as indicated, were analyzed by a fluorescence-activated cell sorter (FACS®), and typical profiles are shown. The profiles display the cell number counts as a function of the GFP fluorescence levels.

Use of MARs Identified with SMAR SCAN II to Increase the Expression of a Recombinant Protein Four MAR elements were randomly selected from the sequences obtained from the analysis of the complete human genome sequence with SMAR SCAN or the combined method. These are termed 1_6, 1_42, 1_68, (where the first number represents the chromosome from which the sequence originates, and the second number is specific to the predicted MAR along this chromosome) and X_S29, a “super” MAR identified on chromosome X. These predicted MARs were inserted into the pGEGFPControl vector upstream of the SV40 promoter and enhancer driving the expression of the green fluorescent protein and these plasmids were transfected into cultured CHO cells, as described previously (Zahn-Zabal, M., et al., *Development of stable cell lines for production or regulated expression using matrix attachment regions*. J Biotechnol, 2001. 87(1): p. 29-42). Expression of the transgene was then analyzed in the total population of stably transfected cells using a fluorescent cell sorter (FACS) machine. As can be seen from FIG. 19, all of these newly identified MARs increased the expression of the transgene significantly above the expression driven by the chicken lysosyme MAR, the “super” MAR X_S29 being the most potent of all of the newly identified MARs.

Example 17

Effect on Hematocrit of in vivo Expression of mEpo by Electrotransfer of Network System with and without Human MAR (1-68)

The therapeutic gene encodes EPO (erythropoietin), an hormone used for the treatment of anemia. The EPO gene is placed under the control of a doxycycline inducible promoter, in a gene switch system described previously called below the Network system (Imhof, M. O., Chatellard, P., and Mermod, N. (2000). A regulatory network for efficient control of transgene expression. J. Gene. Med. 2, 107-116.). The EPO and regulatory genes are then injected in the muscle of mice using an in vivo electroporation procedure termed the electrotransfer, so that the genes are transferred to the nuclei of the muscle fibers. When the doxycycline antibiotic is added to the drinking water of the mice, this compound is expected to induce the expression of EPO, which will lead to the elevation of the hematocrit level, due to the increase in red blood cell counts mediated by the high levels of circulating EPO. Thus, if the MAR improved expression of EPO, higher levels of hematocrit would be expected.

In vivo experiments were carried out on 5 week-old C57BL6 female mice (Iffa Credo-Charles River, France). 30 μg of plasmid DNA in normal saline solution was delivered by trans-cutaneous injections in the tibialis anterior muscle. All injections were carried out under Ketaminol (75 mg/kg) and Narcoxyl (10 mg/kg) anesthesia. Following the intramuscular injection of DNA, an electrical field was applied to the muscle. A voltage of 200 V/cm was applied in 8 ms pulses at 1 Hz (Bettan M, Darteil R, Caillaud J M, Soubrier F, Delaere P, Branelec D, Mahfoudi A, Duverger N, Scherman D. 2000. "High-level protein secretion into blood circulation after electric pulse-mediated gene transfer into skeletal muscle". *Mol Ther.* 2: 204-10).

16 mice were injected by the Network system expressing EPO without the 1_68 MAR and 16 other mice were injected with the Network system incorporating the MAR in 5' of the promoter/enhancer sequences driving the expression of the activator and EPO genes. In each group, half of the mice were submitted to doxycycline in drinking water from the beginning of the experiment (day 0—the day of electrotransfer) and in the other half, doxycycline was put in drinking water starting at day 21.

Blood samples were collected using heparinated capillaries by retro-orbital punction at different times after the injection of plasmids. Capillaries were centrifugated 10 minutes at 5000 rpm at room temperature and the volumetric fraction of blood cells is assessed in comparison to the total blood volume and expressed as a percentile, determining the hematocrit level.

Figure 16:
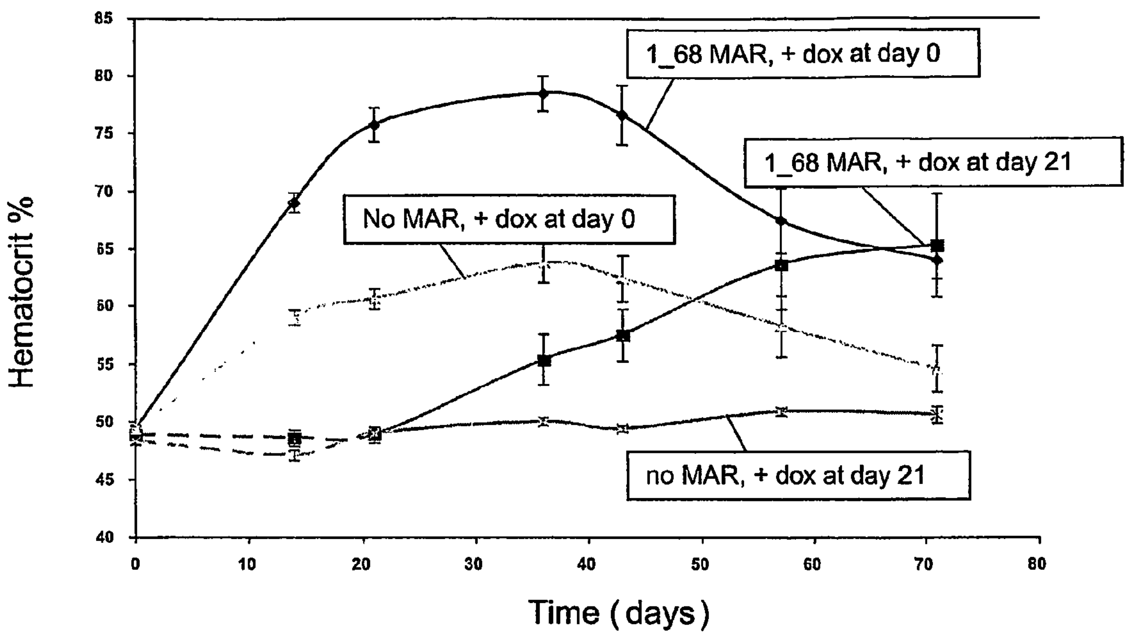
FIG. 16 represents the results of a a gene therapy-like protocol using MARs. The group of mice injected by MAR-network, induced from the beginning of the experiment, display a better induction of the hematocrit in comparison of mice injected by original network without MAR. After 2 months, hematocrits in "MAR-containing group" is still at values higher (65%) than normal hematocrit levels (45-55%).

As can be deduced from FIG. 16 The group of mice injected by MAR-network, induced from the beginning of the experiment, display a better induction of the hematocrit in comparison of mice injected by original network without MAR. After 2 months, haematocrits in "MAR-containing group" is still at values higher (65%) than normal hematocrit levels (45-55%).

More importantly, late induction (day 21) is possible only in presence of MAR but not from mice where the Network was injected without the MAR. Thus the MAR likely protects the transgenes from silencing and allows induction of its expression even after prolong period in non-inducing conditions.

Overall, the MAR element is able to increase the expression of the therapeutic gene as detected from its increased physiological effect on the hematocrit.

What is claimed is:

1. A purified and isolated DNA sequence comprising:

a) at least one bent DNA element comprising at least 33% of the dinucleotide TA and/or at least 33% of the dinucleotide AT on a stretch of 100 contiguous base pairs, b) at least one binding site for a DNA binding protein, wherein said purified and isolated DNA sequence is a MAR nucleotide sequence with sequence ID NO: 25, or a sequence complementary to sequence ID NO: 25, or a sequence having at least 90% identity with said SEQ ID NO: 25.

2. The purified and isolated DNA sequence of claim 1, wherein said bent DNA element comprises at least five contiguous AT or TA dinucleotides.

3. The purified and isolated DNA sequence of claim 2, wherein said bent DNA element comprises at least 10 contiguous AT or TA dinucleotides.

4. The purified and isolated DNA sequence of claim 1, wherein said DNA binding protein is a transcription factor.

5. The purified and isolated DNA sequence of claim 4, wherein the transcription factor is a polyQpolyP domain protein.

6. The purified and isolated DNA sequence of claim 1, wherein the purified and isolated DNA sequence has a melting temperature of between 55 and 75° and a DNA bending value of more than 4 radial degrees and wherein said binding protein is a transcription factor.

7. The purified and isolated DNA sequence of claim 1, wherein said purified and isolated DNA sequence has protein production increasing activity.

8. The purified and isolated DNA sequence of claim 7, wherein said bent DNA element comprises at least five contiguous AT or TA dinucleotides.

9. The purified and isolated DNA sequence of claim 8, wherein said transcription factor is selected from the group consisting of: SATB1, NMP4, MEF2, S8, DLX1, FREAC7, BRN2, GATA 1/3, TATA, Bright, MSX, AP1, C/EBP, CREBP1, FOX, Freac7, HGH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or Vmw65 and a combination of two or more of said transcription factors.

10. The purified and isolated DNA sequence of claim 6, having a melting temperature of between 55 and 62°.

11. A vector comprising a first purified and isolated DNA sequence according to claim 1 and a gene of interest.

12. The vector of claim 11, wherein said vector further comprises a second purified and isolated DNA sequence comprising at least one bent DNA element and at least one binding site for a DNA binding protein.

13. The vector of claim 12, wherein said purified and isolated DNA sequences are 5' and 3' to said gene of interest.

14. The vector of claim 12, wherein said vector further comprises one or more regulatory sequences.

15. The vector of claim 14, wherein said regulatory sequence comprises a promoter that is operably linked to said gene of interest.

16. The vector of claim 14, wherein said regulatory sequence comprises an enhancer sequence.

17. The vector of claim 11, wherein said first purified and isolated DNA sequence has a melting temperature of between 55 and 75° and a DNA bending value of more than 4 radial degrees and wherein said binding protein is a transcription factor.

18. The vector of claim 12, wherein said second purified and isolated DNA sequence comprises at least 10% of the dinucleotide TA and/or at least 12% of the dinucleotide AT on a stretch of 100 contiguous base pairs.

19. The vector of claim 12, wherein said second purified and isolated DNA sequence is a MAR nucleotide sequence with sequence ID NO: 25, or a sequence complementary to sequence ID NO: 25, or a sequence having at least 90% identity with said SEQ ID NO: 25.

20. The vector of claim 11, wherein said gene of interest is a structural gene.

21. The vector of claim 20, wherein said structural gene encodes an antibody or fragment thereof.

22. The vector of claim 11, wherein said bent DNA element comprises at least five contiguous AT or TA nucleotides and wherein said binding protein is a transcription factor and has a DNA bending value of more than 4 radial degrees.

23. The vector of claim 11, wherein said first purified and isolated DNA sequence is SEQ ID No: 25 or a sequence complementary thereof.

24. The vector of claim 11, wherein said isolated and purified DNA has a DNA bending value of more than 4 radial degrees.

25. The vector of claim 19, wherein said second purified and isolated DNA sequence has a melting temperature of between 55 and 75° and a DNA bending value of more than 4 radial degrees.

26. The vector of claim 15, wherein said first DNA sequence and said second DNA sequence are located on a sequence distinct from the one containing a promoter and said gene of interest.

27. A vector comprising a first purified and isolated DNA sequence according to claim 7 and a gene of interest.

28. The vector of claim 27, wherein said vector further comprises a second purified and isolated DNA sequence comprising at least one bent DNA element and at least one binding site for a DNA binding protein.

29. A eukaryotic host cell transfected with at least one vector comprising at least one purified DNA sequence comprising:

a) at least one bent DNA element comprising at least 33% of the dinucleotide TA and/or at least 33% of the dinucleotide AT on a stretch of 100 contiguous base pairs, b) at least one binding site for a DNA binding protein, wherein said purified DNA sequence is a MAR nucleotide sequence with sequence ID NO: 25, or a sequence complementary to sequence ID NO: 25, or a sequence having at least 90% identity with said SEQ ID NO: 25.

30. The host cell of claim 29, further comprising at least one DNA sequence of interest.

31. The host cell of claim 30, wherein said at least one DNA sequence of interest comprises a structural gene.

32. The host cell of claim 31, wherein said at least one purified DNA sequence and said at least one DNA sequence of interest are on the same vector.

33. The host cell of claim 31, wherein said at least one purified DNA sequence and said at least one DNA sequence of interest are on separate vectors.

34. The host cell of claim 29, wherein said at least one purified DNA sequence has a melting temperature of between 55 and 75° and a DNA bending value of more than 4 radial degrees and wherein said binding protein is a transcription factor.

35. The host cell of claim 29, wherein said at least one purified and isolated DNA sequence is SEQ ID No: 25, a sequence complementary thereof, a sequence having at least 90% identity with said SEQ ID NO: 25, and wherein said binding protein is a transcription factor.

36. The host cell according to claim 29, wherein the host cell is a high recombinant protein producing cell with a production rate of at least 10 pg per cell per day.

37. A purified and isolated DNA sequence, wherein said DNA sequence comprises a) at least one bent DNA element, b) and at least one binding site for a DNA binding protein, and wherein said DNA sequence is a MAR nucleotide with SEQ ID NO: 25, or a sequence complementary thereof, or a sequence having at least 90% identity with said sequence.

38. A synthetic MAR sequence comprising natural human MAR elements and/or fragments thereof assembled between linker sequences, wherein the MAR sequence is sequence ID NO: 25, or a sequence complementary to sequence ID NO: 25, or a sequence having at least 90% identity with said SEQ ID NO: 25.

39. A synthetic MAR sequence comprising natural human MAR elements and/or fragments thereof assembled between linker sequences, wherein the human MAR sequence comprises SEQ ID NO: 25, a sequence complementary thereof, or a sequence having at least 90% identity with said SEQ ID NO: 25, wherein said sequence comprises at least 33% of dinucleotide TA and/or at least 33% of dinucleotide AT on a stretch of 100 continuous base pairs and a transcription factor binding site.

40. The synthetic MAR sequence of claim 39, wherein the linker sequences are BglII-BamHI linkers.

41. A cell transfection mixture or kit comprising at least one purified and isolated DNA sequence according to claim 1.

42. A method for transfecting a eukaryotic host cell, said method comprising a) introducing into said eukaryotic host cell at least one first purified and isolated DNA sequence according to claim 1, b) subjecting said transfected eukaryotic host cell to at least one additional transfection step with at least one second purified DNA sequence of interest, and c) selecting said transfected eukaryotic host cell.

43. The method of claim 42, wherein said DNA sequence of interest is a gene of interest coding for a protein operably linked to a promoter.

44. The method of claim 42, wherein said second purified and isolated DNA sequence is a MAR nucleotide sequence with sequence ID NO: 25, or a sequence complementary to sequence ID NO: 25, or a sequence having at least 90% identity with said SEQ ID NO: 25.

45. A method for transfecting a eukaryotic host cell, said method comprising co-transfecting into said eukaryotic host cell at least one first purified and isolated DNA sequence comprising at least one DNA sequence of interest, and a second purified and isolated DNA comprising at least one purified and isolated DNA sequence of claim 1.

46. The method of claim 42, wherein said at least one additional transfection step is performed between 6 hours and 48 hours after the introduction of said first purified and isolated DNA sequence.

* * * * *

SEQUENCE LISTING

```
<160> NUMBER OF SEQ ID NOS: 246

<210> SEQ ID NO 1
<211> LENGTH: 320
<212> TYPE: DNA
<213> ORGANISM: Homo sapiens
<220> FEATURE:
<221> NAME/KEY: misc_binding
<222> LOCATION: (1)..(320)
<223> OTHER INFORMATION: MAR of human chromosome 1, nt from 36686 to
      37008
<220> FEATURE:
<221> NAME/KEY: misc_binding
<222> LOCATION: (1)..(320)
<223> OTHER INFORMATION: MAR of human chromosome 1, genomic contig;
      36686 to 37008

<400> SEQUENCE: 1

ttatattatg ttgttatata tattatatta tgttattaga ttatattatg ttgttatatt     60

atataataat attatattat atattatata ttatattata taatatataa taatattata    120

taattatata ttacattata taatatataa taatattata taattatata ttacattata    180

taatatataa taatattata taataatata taattatata atatataata atattatata    240

atattatata atattatata atatataaat atataataat atatattata ttatataata    300

gtatataata ttatataata                                                320


<210> SEQ ID NO 2
<211> LENGTH: 709
<212> TYPE: DNA
<213> ORGANISM: Homo sapiens
<220> FEATURE:
<221> NAME/KEY: misc_binding
<222> LOCATION: (1)..(709)
<223> OTHER INFORMATION: MAR of human chromosome 1, nt from 142276 to
      142984
```

<220> FEATURE:
<221> NAME/KEY: misc_binding
<222> LOCATION: (1)..(709)
<223> OTHER INFORMATION: MAR of human chromosome 1, genomic contig; 142276 to 142984

<400> SEQUENCE: 2

```
tacaatatat tttctattat atatattttg tattatatat aatatacaat atattttcta     60

ttatatataa tatattttgt attatatata ttacaatata ttttgtatta tataatatat    120

aatacaatat ataatatatt gtattatata ttatataata caatatatta tatattgtat    180

tatatattat atataatact atataatata ttgtattata tattatatat aatactatat    240

aatatatttt attatatatt atatataata caatatataa tatattgtat tataatacaa    300

tgtattataa tgtattatat tgtattatat attatatata atacaatata taataatata    360

ttataatata taataataat ataatataat aataatatat attgtattat atattatata    420

atacaatata taatatattg tattatatat attttattac atataatata taatacatta    480

tataatatat tttgtattat atataatata ttttattatg tattatagat aatatatttt    540

attatatatt atatataata caatatataa tatattttgt attgtatata atatataata    600

caatatataa tatattgtat tatatataat attaatatat tttgtattat atatttatat    660

tttatattat aattatgttt tgcattatat atttcatatt atatatacc               709
```

<210> SEQ ID NO 3
<211> LENGTH: 409
<212> TYPE: DNA
<213> ORGANISM: Homo sapiens
<220> FEATURE:
<221> NAME/KEY: misc_binding
<222> LOCATION: (1)..(409)
<223> OTHER INFORMATION: MAR of human chromosome 1, nt from 1368659 to 1369067
<220> FEATURE:
<221> NAME/KEY: misc_binding
<222> LOCATION: (1)..(409)
<223> OTHER INFORMATION: MAR of human chromosome 1, genomic contig; 1368659 to 1369067

<400> SEQUENCE: 3

```
tacacataaa tacatatgca tatatattat gtatatatac ataaatacat atgcatatac     60

attatgtata tatacataaa tacatatgca tatacattat gtatatatac ataaatacat    120

atgcatatac attatgtata tatacataaa tacatatgca tatacattat gtatatatac    180

ataaatacat atgcatatac attatgtata tatacataaa tacatatgca tatacattat    240

gtatatatac ataaatacat atgcatatat tatatacata aattatatta tatacataat    300

acatatacat atattatgtg tatatataca taaatacata tacatatatt atgtgtatat    360

atacatgata catatacata tattatgtat atatatacat aaatacata               409
```

<210> SEQ ID NO 4
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of human chromosome 1, genomic contig; 2839089 to 2839482

<400> SEQUENCE: 4

```
tatgtatata tacacacata tgtatatata cacacatatg tatatacgta tatatgtata     60

tatacacaca tatgtatata cgtatatatg tatatataca cacatatgta tatacgtata    120
```

tatgtatata tacacacata tgtatatacg tatatatgta tatatacaca catatgtata 180
tatgtatata tacacacata tgtatatacg tatatatgta tatatacaca catgtgtata 240
tatatataca catatgtata tatgtatata tacacacata tgtatatatg tgtatgtata 300
tatacacaca tatgtatata tacacatata tatgtatata tacacacata cttatatata 360
cacatatata tgtatatata cacatatgta taca 394

<210> SEQ ID NO 5
<211> LENGTH: 832
<212> TYPE: DNA
<213> ORGANISM: Homo sapiens
<220> FEATURE:
<221> NAME/KEY: misc_binding
<222> LOCATION: (1)..(832)
<223> OTHER INFORMATION: MAR of human chromosome 1, genomic contig; 1452269 to 1453100

<400> SEQUENCE: 5
tatattacta tatatacaat atacatatta ctatatatac catgtattac tatatatatc 60
tactatatat attactatat atacaaaata tatattacta tatatacaat atacatatta 120
ctatatatac catatattac tatatatatc tactatatat attactatat atacaaaata 180
tatattacta tatatactat atattactgt atatacaata tatattacta tatatatact 240
atatattact atatatacac tatatattac tatatataca caatatatat attactatat 300
atacacaatg tatataacta tatatacaat atatattact atatatacta tatatattac 360
tatacatact atatattact ctatatatac aatatatata ttacaatata tactacatat 420
tactacatat actttatata ttactatata tactatatat tactgtatat acaatatata 480
ttactaaata tacacaatat atattactat atatacacaa tatatatatt actatatata 540
cacattatat atgactatat atacacacta tatatattac tatatataca caatatataa 600
ctatatatac acagtataca tattactata tatacacaat atatatatta ctatatatac 660
actatatatt actatatata cacaatatat attactctat gtatacacta tatatattac 720
tatatataca gaatatatat aactatatat acactatatt actatatata ctatatatta 780
ctatatgtac tatatatatt actatatata ctatatatta ctatatatac ac 832

<210> SEQ ID NO 6
<211> LENGTH: 350
<212> TYPE: DNA
<213> ORGANISM: Homo sapiens
<220> FEATURE:
<221> NAME/KEY: misc_binding
<222> LOCATION: (1)..(350)
<223> OTHER INFORMATION: MAR of human chromosome 1, genomic contig; 831495 to 831844

<400> SEQUENCE: 6
aatatataat atataaatat taatatgtat tatataatat atattaatat attatattat 60
attactatat aaataatatt aatatattat attaaaatat taataaatat atcatattaa 120
atattatatt aattaaatat taataaatat attatattaa tatatttata tattaaacct 180
ataacatatg catatactta tttatatata acatgcatgt acttatttat atatacaata 240
tatatttata tattatataa tatattatat gtatttatat attatatatc atatattata 300
tgtatttata tattatatat catataatat atatatttat attatatata 350

<210> SEQ ID NO 7
<211> LENGTH: 386

-continued

<212> TYPE: DNA
<213> ORGANISM: Homo sapiens
<220> FEATURE:
<221> NAME/KEY: misc_binding
<222> LOCATION: (1)..(386)
<223> OTHER INFORMATION: MAR of human chromosome 1, genomic contig; 1447225 to 1447610

<400> SEQUENCE: 7
acatttaatt taattatata ctgctatata taattaaatc tatatatcta tataacttat 60
aatttatttt aatttaatta tatatactat atagttatat atacatatat gtaattatat 120
atagtataat tatagtatat atgtatatat aatgtaagta aatatatagt atatatttat 180
atatactata tatttataca tatgtcttta tatatactaa tatatataca catatgtaat 240
atgtacatat ggcatatatt ttatagtgta tatatacata tatgtaatat atatagtaat 300
atgtaaatat atagtacata tttaattata tggtaatata tacacatata tgtaatatgt 360
gtattatagt acatatttta tagtat 386

<210> SEQ ID NO 8
<211> LENGTH: 585
<212> TYPE: DNA
<213> ORGANISM: Homo sapiens
<220> FEATURE:
<221> NAME/KEY: misc_binding
<222> LOCATION: (1)..(585)
<223> OTHER INFORMATION: MAR of human chromosome 1, genomic contig; 4955365 to 4955949

<400> SEQUENCE: 8
atacacacat atacacatat gtacgtatat atactatata tacacacata tacacatatg 60
tacgtatata tactatatat acacacatat acacatatgt acgtatatat actatatata 120
cacacatata cacatatgta cgtatatata ctatatatac acacatatac acatatgtac 180
gtatatatac tatatataca cacatataca catatgtacg tatatattat atatacacac 240
atatacacat atgtacgtat atatactata tatacacaca tatacacata tgtacgtata 300
tatactatat atacacacat atacacatat gtacgtatat atactatata tacacacata 360
tacacatatg tacgtatata tactatatat acacacatat acacatatgt acgtatatat 420
actatatata cacacatata cacatatgta cgtatatata ctatatatac acacatatac 480
acatatgtac gtatatatac tatatataca cacatataca catatgtacg tatatatact 540
atatataccc atacacatac gtatatacgt acatatatat acgta 585

<210> SEQ ID NO 9
<211> LENGTH: 772
<212> TYPE: DNA
<213> ORGANISM: Homo sapiens
<220> FEATURE:
<221> NAME/KEY: misc_binding
<222> LOCATION: (1)..(772)
<223> OTHER INFORMATION: MAR of human chromosome 1, genomic contig; 5971862 to 5972633

<400> SEQUENCE: 9
agtaaacata tatatagtaa atatatatag tgtatatata gtaaatatat atagtgcata 60
tatatagtgc atatatatag tgtatatata gtaaatatat agtgtatata tatagtaaat 120
atatatagtg tatatatagt aaatatatat agtaaatata tatatactat atatagtaaa 180
tatatatata ctatatatag taaatatata tatagtatat atatagtaaa tatatatata 240
gtatatatat agtaaatata tatatagtat atatatagta aatatatata tagtatatat 300

```
agtaaatata tatagtatat atatagtaaa tatatatata gtatatatat agtaaatata    360

tatatagtat atatatagta aatatatata tagtatatat atagtaaata tatatagtat    420

atatatagta aatatatata gtatatatat agtaaatata tatagtatat atatagtaaa    480

tatatataca ctgtatatat atagtaaata tatatacact gtatatatat agtaaatata    540

tatacactgt atatatatag taaatatata tacactgtat atatatagta aatatatata    600

cactgtatat acatagtaaa tatatataca ctgtatatac atagtaaata tatatacact    660

gtatatacat agtaaatata tatacactgt atatacatag taaatatata tacagtgtat    720

atacatagta aatatatata cagtgtatat acatagtaaa tatatataca gt            772


<210> SEQ ID NO 10
<211> LENGTH: 304
<212> TYPE: DNA
<213> ORGANISM: Homo sapiens
<220> FEATURE:
<221> NAME/KEY: misc_binding
<222> LOCATION: (1)..(304)
<223> OTHER INFORMATION: MAR of human chromosome 1, genomic contig;
      6221897 to 6222200

<400> SEQUENCE: 10

atatataata tatataatta tattatatat aatatataat atatataatt atattatata     60

ttatatataa tatattatat attatatata taatatatat tatatattaa atatatatta    120

tatatataat atatattata tattaaatat atattatata tataatatat attatatata    180

atatatataa tatatattat atatatatta tatattatat atatatatta tatatatata    240

atatatataa tatatattat atataatata tattatatat atataatata tataatatat    300

atta                                                                 304


<210> SEQ ID NO 11
<211> LENGTH: 311
<212> TYPE: DNA
<213> ORGANISM: Homo sapiens
<220> FEATURE:
<221> NAME/KEY: misc_binding
<222> LOCATION: (1)..(311)
<223> OTHER INFORMATION: MAR of human chromosome 1, genomic contig;
      9418531 to 9418841

<400> SEQUENCE: 11

tatatataat atttatatat aatattcatg tatttatata taaatattta tatatttata     60

tataaatatt tatatattta tatataaata tttatatatt tatatataat atttatacat    120

tatatataat atttatatat tatatataat atttatatat aatatttata tattatatat    180

aatatttata tatttatatg tataatatat attttatata tgtatgtata atatatattt    240

tatatatgta tgtataatat attttatata tgtatgtata atatattatt atatataata    300

tataatttat a                                                         311


<210> SEQ ID NO 12
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of human chromosome 1, genomic contig;
      15088789 to 15089090

<400> SEQUENCE: 12

atataatata tatattatat atataaatat atataaatat ataacatata tattatatat     60
```

-continued

```
aaatatatat aaatatataa catatatatt atatatataa atatatataa atatataaca    120

tatatattat atatataaat atatataaat atataacata tatattatat atataaatat    180

atattatata tttatatata taatatatat aaatatataa tatatattta tatatataat    240

atatataaat atataatata tatatttata tataatatat ataaatatat aatatataat    300

at                                                                   302
```

<210> SEQ ID NO 13
<211> LENGTH: 461
<212> TYPE: DNA
<213> ORGANISM: Homo sapiens
<220> FEATURE:
<221> NAME/KEY: misc_binding
<222> LOCATION: (1)..(461)
<223> OTHER INFORMATION: MAR of human chromosome 1, genomic contig; 6791827 to 6792287

<400> SEQUENCE: 13

```
tatataatat atattatata tacacatata taatatatat tatatataca catatataat     60

atatattata tatacacata tataatatat attatatata cacatatata atatatatta    120

tatatacaca tatataatat atattatata tacacatata taatatatat tatatataca    180

catatataat atatattata tatacacata tataatatat attatatata cacatatata    240

atatatatta tatatacaca tatgtaatat atattataca cacacatata atatatatta    300

tatacacata tataatatat attatatata catatataat atatattata tatacacata    360

tataatatat attatatata cacatatata atatatatta tatatacaca tataatatat    420

aatatataca catatataat atatatatta tatatgcaca t                        461
```

<210> SEQ ID NO 14
<211> LENGTH: 572
<212> TYPE: DNA
<213> ORGANISM: Homo sapiens
<220> FEATURE:
<221> NAME/KEY: misc_binding
<222> LOCATION: (1)..(572)
<223> OTHER INFORMATION: MAR of human chromosome 1, genomic contig; 163530 to 164101

<400> SEQUENCE: 14

```
atattataat tatatatatt atatataatt atataaaata tatattataa ttatatatat     60

tttatataat atatatatta taattaatat attatatata atatatatat tatatataat    120

atatatatta tatatattat atataatata tataatatat ataatatata atataatata    180

tatattatat ataatatata atatatataa tatattataa tataatatat ataatatata    240

atataatata tataatatat aatataatat ataatatata atatatataa tatataatat    300

aatatataat atatataata tataatataa tatataatat atataatata ttataatata    360

atatatataa tatataatat aatatatata atatataata taatatataa tatataatat    420

atatttaata tatttattaa ttatttgtta tatatttatt aatatataat atataatata    480

tttaatatat tataactata tattatatta taattatata tattatatat atacaattat    540

aattatatat tatatatact tataatatat at                                  572
```

<210> SEQ ID NO 15
<211> LENGTH: 357
<212> TYPE: DNA
<213> ORGANISM: Homo sapiens
<220> FEATURE:
<221> NAME/KEY: misc_binding
<222> LOCATION: (1)..(357)
<223> OTHER INFORMATION: MAR of human chromosome 1, genomic contig;
1842332 to 1842688

<400> SEQUENCE: 15
tatatctata tatatctata tatatataat atagataata tctatatata taatatagat 60
aatattatct atatataata tagataatat tatctatata taatatagat aatattatct 120
atatataaaa ttatattata tctatatata ttatatatat aaaattatat tatatctata 180
tataatatag ataatatcta tatataaata gataatatct atatatataa tatagatatt 240
atctatatta tagatataga taatattatc tatattatag atattatcta tatataatat 300
agataatatt atctatatta tatatataat atatctatat tatctataat attatct 357

<210> SEQ ID NO 16
<211> LENGTH: 399
<212> TYPE: DNA
<213> ORGANISM: Homo sapiens
<220> FEATURE:
<221> NAME/KEY: misc_binding
<222> LOCATION: (1)..(399)
<223> OTHER INFORMATION: MAR of human chromosome 1, genomic contig;
2309560 to 2309958

<400> SEQUENCE: 16
attatatata atatatatta tatattatat atatcaagca gcagatataa tatataatat 60
atataatata tataatatat attgtatatt atataatata taatatatat aatatatatt 120
gtatattata taatatataa tatatataat atatattgta tattatataa tatataatat 180
atataatata tattgtatat tatataatat ataatatatg taatatatta tgtaatatat 240
tatataatat atattatata ttatatataa tatatattat atataatata tattacataa 300
tatattacat atattacgta atatatgtta tatattacat ataatatata acatatatta 360
cgtaatatat gtaatatatt acatataata tatacatta 399

<210> SEQ ID NO 17
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of human chromosome 1, genomic contig;
2231759 to 2232152

<400> SEQUENCE: 17
atatatactt ataaattata tacttatata tacttataaa ttatatactt atatatactt 60
ataaattata tacttatata tacttataaa ttatatactt atatatactt ataaattata 120
tacttatata tacttataaa ttatatactt atatatactt ataaattata tacttatata 180
tacttataaa ttatatactt atatataatt ataaattata tacttatata taattataaa 240
ttatatactt atatataatt ataaattata tacttatata taattataaa ttatatactt 300
atatataatt ataaattata tacatatata taattataaa ttatatacat atataattat 360
aaattatata catatataat tataaattat atac 394

<210> SEQ ID NO 18
<211> LENGTH: 387
<212> TYPE: DNA
<213> ORGANISM: Homo sapiens
<220> FEATURE:
<221> NAME/KEY: misc_binding
<222> LOCATION: (1)..(387)

<223> OTHER INFORMATION: MAR of human chromosome 1, genomic contig;
7406524 to 7406910

<400> SEQUENCE: 18
tatattatat ataatatata ttatatataa tataaataat atatattata tataatatat 60
aaataatata taatatataa ataatatata atatataata tataaataat atataatata 120
taacatataa ataatatata taatatataa ataatatata taatatataa ataatatata 180
taatatataa aaatatataa tatataatac atatataaat aatatattat attatatatg 240
atacataata tattatatat aatatattat atgatacata atatattata tagaatatat 300
tatatgatac ataatatatt atatagaata tattatatga tacataatat attatatgat 360
acataatata ttatatataa tatatta 387

<210> SEQ ID NO 19
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of human chromosome 1, genomic contig;
9399572 to 9399941

<400> SEQUENCE: 19
catatataca tatatacaca tatatacaca tatatataca catacatatg tacacatata 60
tatacacata tgtatacaca tatatacaca tatatacaca catatataca catatataca 120
cacatatata cacatatata cacatatata cacatataca catatataca catatataca 180
tatatacaca tatatataat atacacacat atatatacac atatatacac acatatatac 240
acatatatac acatatatat acacatatat acacatatat acatatatac acatatatat 300
acatatatac acatatatac atatatacac atatatacat atatacacac atatatacac 360
atacatatac 370

<210> SEQ ID NO 20
<211> LENGTH: 377
<212> TYPE: DNA
<213> ORGANISM: Homo sapiens
<220> FEATURE:
<221> NAME/KEY: misc_binding
<222> LOCATION: (1)..(377)
<223> OTHER INFORMATION: MAR of human chromosome 1, genomic contig;
12417411 to 12417787

<400> SEQUENCE: 20
attatatata atacatataa ttatatattt atatataaat tataataaat acatataatt 60
atatatttat atataaatta tatataataa atacatataa ttacatatat ttataaatta 120
taataaatac atataattac atatatttat atatgaatta tatataataa atacatataa 180
ttatatatat ttatatgtag attatatata aatatatata atttatatat ataataatat 240
atataattta tatatataat tatatatata ataaatatat ataatttata tatataatta 300
tatatataat aaatatataa taatatatat aatttatata tataattata tatataataa 360
atatatataa tttatat 377

<210> SEQ ID NO 21
<211> LENGTH: 1524
<212> TYPE: DNA
<213> ORGANISM: Homo sapiens
<220> FEATURE:
<221> NAME/KEY: misc_binding
<222> LOCATION: (1)..(1524)
<223> OTHER INFORMATION: MAR of human chromosome 1, genomic contig;
1643307 to 1644830

<400> SEQUENCE: 21
tataaatata tataaatata taaatatata taaatatata aatatatata aatatatata 60
aatatataaa aatatataaa tatatataaa tatatataaa tatataaaaa cataaaaata 120
tatataaata tatataaata tataaaaata tataaatata taaatatata aaaatataca 180
aatatataaa tatatacata aatatatata aatatatata aatatataaa aatatatata 240
aatatataaa tatatataaa tatatataaa tatatataaa tatataaaaa tatatataaa 300
tatataaata tataaaaata tatataaata tataaatata taaatatata taaatatata 360
aatatataaa taaatataag tatttatgaa tatatatgaa tatataaata tataaaaaat 420
atatataaat atataaatat atataaatat ataaatatat acatatatac atatataaat 480
aaataaatat aagtatttat gaatatatat gaatatataa atatataaaa aatatatata 540
aatatataaa tatatataaa tataaatata taaaaatata taaaaatata tataaatata 600
taaatatata taaatatata aatatatata aatatatata aatatataaa tatatataaa 660
tatatataaa tatataaata tataaatata tataaatata tataaatata taaatatata 720
aatataaata tataaatata tataaatata tataaatata taaatatata taaatatata 780
taaatatata taaatatata taaatatata aatatatata aatatatata taaatatata 840
taaatatata aatatataaa tatataaaaa tatataacaa tatataaata tatataaaaa 900
tatataacaa tatataaata taaatatata taaaaatata taacaatata taaatataaa 960
tatatataaa tatataaata taaatataaa aaatatatat aaatatataa atatatataa 1020
atatataaat gtataaatat atataaaaat atataacaat atataaatat ataaatatat 1080
aacaatatat aaatatataa aaatatataa caatatataa atataaatat atataaaaat 1140
atataacaat atataaatat aaatatatat ataaatatat aaatataaat ataaaaaata 1200
tatataaata tataaatata tatataaata tatataaata tataaatgta taaatatata 1260
taaatatata aatatataaa aatatataaa tatatataaa tatatataaa tatataaata 1320
taaatatata aatatatata aatatataaa tataaatata taaacatata taaatatata 1380
taaataaaca tatataaaga tatataaaga tataaagata tataaatata taaatatata 1440
aagatatata aatatataaa gatatataaa tatataaaga tatataaata tataaagata 1500
tataaatata atatataaat atat 1524

<210> SEQ ID NO 22
<211> LENGTH: 664
<212> TYPE: DNA
<213> ORGANISM: Homo sapiens
<220> FEATURE:
<221> NAME/KEY: misc_binding
<222> LOCATION: (1)..(664)
<223> OTHER INFORMATION: MAR of human chromosome 1, genomic contig;
1398763 to 1399426

<400> SEQUENCE: 22
acacatatat atataaaata tatatatata cacacatata tataaaatat atatatatac 60
acacatatat ataaaatata tatatacaca catatatata aaatatatat atacacacat 120
atatataaaa tatatatata cacacatata tataaaatat atatatacac acatatatat 180
aaaatatata tatacacaca tatatataaa atatatatat acacacatat atataaaata 240
tatatataca cacatatata taaaatatat atatacacac atatatataa aatatatata 300

```
tacacacata tatataaaat atatatatac acacatatat aaaatatata tatacacaca    360

tatataaaat atatatatac acatatatat aaaatatata tatacacata tatataaaat    420

atatatacac acatatatat aaaatatata tatacacaca tatatataaa atatatatat    480

acacatatat ataaaatata tatatacaca tatatataaa atatatatat atacacatat    540

atataaaata tatatacaca catatatata aagtatatat atacacacat atatataaaa    600

tatatatata cacatatata taaaatatat atatacacat atatataaaa tatatatata    660

caca                                                                 664


<210> SEQ ID NO 23
<211> LENGTH: 1428
<212> TYPE: DNA
<213> ORGANISM: Homo sapiens
<220> FEATURE:
<221> NAME/KEY: misc_binding
<222> LOCATION: (1)..(1428)
<223> OTHER INFORMATION: MAR of human chromosome 2, genomic contig;
      17840365 to 17841792

<400> SEQUENCE: 23

aatttattat atattatata ttatatatat tatatatatt atatattata tatattatat     60

atattatata ttatatatat tatatattat atatttatat ataatatata tctaatatat    120

atattagata taatatatat ctaatatata tatattttat atatataata tatctctaat    180

atatatattt tatatgtata taatatatct ctaatatata tatattttat atgtatataa    240

tatatctcta atatatatat tttttatata taatatatct ctaatatata tattttatat    300

atataatata tatctaatat atataatata tatattagat atatataaaa tatatatgat    360

atatttatta tatatataat atataatata taatatatat attatattat atacatatat    420

attatataca atatatatta tatatatttt atatacatta tatattatat atattttata    480

tacaatatat attatatatt ttatatacaa tatatattat atatatttta tatttttata    540

tacaatatat attatatata ttttatatat aatatatatt atatatattt tatataatat    600

atattatata tattttatat ataatatata ttatataaat tatatataat atatattata    660

ataaattata atatttttta tatatataat atgtatttta tatataatat attataaatat    720

atattttata tataatatat tataatatat attttatata taatatatta taatatatat    780

tttatattat aatatattat aatatatatt ttatatataa tatattataa tatatatttt    840

atatataata tattataata tatattttat atataatata ttataaatata tatattataa    900

tatatatttt atatataata tattatcata tatatattaa atatatattt tatatataat    960

atattataat atatatatta taatatatat tttatatata atatattata atatatatat   1020

tataatatat attttatata taatatatta taatatatat tttatatata atatattata   1080

atatatattt tatatataat atattataat atatatttta tatataatat aatatatatt   1140

ttatatataa tatattataa tatatatttt atatataata tattataata tatattttat   1200

atataatata ttataatata tattttatat ataatatatt ataatatata ttttatatat   1260

aatatattat aatatatatt ttatatataa tatattataa tatatatttt atatataata   1320

tattataata tatattttat atataatata ttaattaaat ttattaattt attaattatt   1380

aatatttatt atattattaa ttaataatat ataaattatt aatatata                1428

<210> SEQ ID NO 24
<211> LENGTH: 4624
<212> TYPE: DNA
```

<213> ORGANISM: Homo sapiens
<220> FEATURE:
<221> NAME/KEY: misc_binding
<222> LOCATION: (1)..(4624)
<223> OTHER INFORMATION: MAR 1_6 of chromosome 1

<400> SEQUENCE: 24

```
ggatcttaaa tctattttat ttatttattt ttcatgtggc caataccctc cacccccttc     60
ttctgtctct ttcaacttat tgtggttacc ttgaggctac ctgagacagt aggcttgggt    120
ggggaagtat gcattctaag tgtaaagttt gatgagcttt gacaaatgtc aacccatgta    180
ccagaacatt ttcatcaccc ataaaatctc ccttgtgtca cttgccagtc agtgtctatt    240
ctagtatcca actcctggct ccaagaaacc attgaactgt tttctgtcac tataaattag    300
atttgtcttt tctagagttt catgtaaatg gaatcataca ctaagtactc tttgtgcctg    360
gcttctgctc agcataatgt ttttgagaat cattcatgct gctgcatgtt ttcagtagtt    420
catttttta aataggtgaa ttgtaactca ttctgtgaat ataccatatt ctgtcttcca     480
tttatctgtt agtggatctt taggtcgttt ctagttttgg gctattgcaa ataaagctgc    540
tgtaaatatt aatgcacaag ttttccatgt tcatatgttt catttcactt aggaaaatac    600
ctaagagagg aattgcacat attaaaaaaa ttttaaaaac tactaagctg ttctccaaaa    660
tggttgtaca atttttattc ccaagagcaa tatgagtgtt taattgctcc acattctcac    720
caacacttgg tgcttgttag ttttattttc attgttttca ttgttatgtc tgtgaggcag    780
cattgatgtg catgtctctg agtgtcatct tagcggtgat gctgagcatc agttcacgtc    840
cttataggcc gtttgtatat ctgctttgtg aaatgtctgt tcaaatcttt tgcctatttt    900
aaattgagtt gtgttcgtct tcttaggatt aagtaatgag ttaaaaatat ttctgataca    960
aatctttcat tatatatttc taatgctttc tcatctatag tttattttct catattcttt   1020
aactgtatct tttgaagagc aaattttact tttgattatg cccaatttat caagttttta   1080
tatggctctt ttgattatgc ccataatcac attagacttt gcctaaccca agtttgcaga   1140
gatttttctt tttatgcttt tatctagaaa ttttgtagtt ttaggtttta aaaaagttta   1200
atttatttat ttgagacagg gtattgctct ttacatatac tggagtgcag tgatgcaatc   1260
atggctcact gcagcctcaa cctcttgggc tcaagcggtt ctcccatctc agagtcctga   1320
gtagctggcc aggtgcatgc cagcttcaat gtgtttttca tttgcatttc cctgataatt   1380
attgacgttg agcatttttt tcatatatca gttagctatt tgtacgtctt cttttgagaa   1440
acatctattc gggtcttttg cccattttaa agtcagatgg tttgtttgtc agctattgag   1500
ttgtttgagt tccttgtata ttctggatat taccatcttg tcagatgcac agtttgcaaa   1560
ttttttttt ctattttgta ggttgtctct ttctctgttg tttcctccgg tatgcagaag     1620
ttttttagtg tgatgtaatt tcatttgtct gtttttgctt ttgttgcctg tactttctta   1680
ttcttatcca aaaaatcttt atctagatca atgtcacgaa gagtttctcc tctgttttct   1740
tcgagtagtt ttttataatt ttgggtatac atttaagtct ttaatctatt tggaattgat   1800
ttttgcatat ggtgagagat cagagtctaa tttcatactt ttggatgtgg aaagctagtt   1860
ttttcagcac catttattga agagactgtc tcttctccaa tgtgtgttct ttgtgccttc   1920
gtcaaaaatc agttggctgt gcgtggattt atttctgtgt tctctatttt gttccattgg   1980
tctagtttta gccttaaatt taggtctgca attttttttt ttttgtatat ggtgtgaagt   2040
aagagtcaaa gttcattatt tttcatatgg atatgtaatt actccagtac catcatttag   2100
tttgaatgga ctgtcctttc tccatggaat tacatgggca tcttttgtct gaaaccaatt   2160
```

-continued

```
atgtatgttt acgtatgtgt atgtttatgc atatgttata ggtttaatat atattaatat   2220
atataatata taatatataa atattaatat gtattatata atatatatta atatattata   2280
ttatattact atataaataa tattaatata ttatattaaa atattaataa atatatcata   2340
ttaaatatta tattaattaa atattaataa atatattata ttaatatatt tatatattaa   2400
acctataaca tatgcatata cttatttata tataacatgc atgtacttat ttatatatac   2460
aatatatatt tatatattat ataatatatt atatgtattt atatattata tatcatatat   2520
tatatgtatt tatatattat atatcatata atatatatat ttatattata tatattatat   2580
gatatataat attatataat gtattaatat atattaaacc tatatttata attctggact   2640
cactattttg tttcattggt gtctgtgtgt atctaaccct atgccaataa tgtactatct   2700
taattaccat agctttatag taagctttga aatcagatag tgtatttttt atcattgttt   2760
tttaaaataa tagtttatct ttttatttga atttgtaatc agctagtcag tttctgcaaa   2820
aagcttactg ggattttgct tggaattatg ttacatctgt agcatgtact atccaatatt   2880
ctagccttta tccacatgtg gctattaagg tttaaattaa ttaaattaaa atttaattaa   2940
ttaaaattaa aacttaataa ttggttcctc attcacacta ccatatgtca agtgttcaat   3000
agccacatat ggtcaatgtc ttggaaaagt caatacagta catttccatt attgcagtaa   3060
gttctgtcaa acagcactat cgtagaccga ttaggagaga actgacttaa cagtattgga   3120
tgctccagtc aatgaacatc tttttttttt tcatttattt cagtagtctc tgcagtatat   3180
tatagatttc agtttacata ttttgcatat attttattaa atgtataacg gtagaagtac   3240
tattattgga tgatgtgttc tatagatgta ttttaggtca agtttgttga tagtgttgtt   3300
taaatctcgt atacctcttg atttttttat ttacttgttc tttgaattac tgagacagga   3360
atgttatatc cttaactata tttgtgaatt tattcacttc ttccttcagt tctgttaact   3420
tttgcttagg tgctttttaa aaatgaaact ttcaatctct gccttttaat tgtagcattt   3480
agaccattta cattcaatgt aattatcaat atcagtttat ttaagtctga agttgtgcaa   3540
tttttcctct acctatatta taaatctttc tatatacaaa acacatgcta tgttttctgc   3600
atatgtttta aatgacaccc ggaaagcatt gacactattt ttgctttagg ttatctttca   3660
aagatgttaa aaatgagaaa gaaatattct gcatttatcc atacacttat tatttgcaaa   3720
ggttttttta aatacctttg tgtagatttc agttaccaac ttgtatttcc ttcagcttga   3780
agaacttaca atttcttgta ggacaggtct ctgacaacaa attatctcag cttttctttg   3840
tctaaaaaag ttattgcctt tatttttaaa atatattttc actggatatt gaattttagg   3900
tgataatctt tttttttttg ttagcacttt aaatatgtct tctaatgtcc tcttgctttc   3960
atagtttctg atgagaagtc tactgttatt agtatctctt tgtgtgtgtc tctctttttt   4020
ccctctctgc tattatggct attttttttt tttttttttt ttttggtcac tggtgtcagc   4080
aatttaatta tggtgtgcct tggtatgttt tgtgtgtgtg tgtgtgtgtg tgtgtgtgtg   4140
tgtgtgtgtg tagctgatgt tctttgagct ttagaatctg tgagtttgta gttttcatca   4200
attatttttt cttttcattc cttttattta ctcatgttcg tgttttattt tatattttta   4260
agaatttgt  gcgtatttgt aataactgtt taaatgtcat ttgtgaattc cattgcttct   4320
aggtaggatt ctattgacag atattttttc cctgacgaga ggtcatactt tccttattct   4380
tcatgtatct agtggttttt ggttgaatac tggatatttt gaattttatg ggagtgctga   4440
attctacaat attccttaaa aatgtgttgg attttgtttt agcagatagc tatcttactt   4500
gaagatcaat ttcatatttt ttgatgttca ttttttcatt tattaaagaa taggtccatg   4560
```

-continued gtagagttta ctgatatcaa cctttctggt gtctctaata aatgcaacat attcaataag 4620
atcc 4624

<210> SEQ ID NO 25
<211> LENGTH: 3616
<212> TYPE: DNA
<213> ORGANISM: Homo sapiens
<220> FEATURE:
<221> NAME/KEY: misc_binding
<222> LOCATION: (1)..(3616)
<223> OTHER INFORMATION: MAR 1_68 of chromosome 1

<400> SEQUENCE: 25
gactctagat tataccaacc tcataaaata agagcatata taaaagcaaa tgctcttatc 60
ttgcagatcc ctgaactgag gaggcaagat cagtttggca gttgaagcag ctggaatctg 120
caattcagag aatctaagaa aagacaaccc tgaagagaga gacccagaaa cctagcagga 180
gtttctccaa acattcaagg ctgagggata aatgttacat gcacagggtg agcctccaga 240
ggcttgtcca ttagcaactg ctacagtttc attatctcag ggatcacaga ttgtgctacc 300
tattgcctac catctgaaaa cagttgcttc ctatatttca tccagtttaa tatttattta 360
aaccaagaag gttaatctgg caccagctat tccgttgtga gtggatgtga aagtaccaat 420
tccattctgt tttactatta actatccttt gccttaatat gtatcagtag gtggcttgtt 480
gctaggaaat attaaatgaa tggcatgttt cataggttgt gtttaaagtt gttttttgag 540
ttaaatcttt ctttaataat actttctgat gtcaaaaaca cttagaagtc atggtgttga 600
acatctatat agggttggat ctaaaatagc ttcttaacct ttcctaacca ctgtttttgt 660
ttgtttgttt ttaactaagc atccagtttg ggaaattctg aattagggga atcataaaag 720
gtttcatttt agctgggcca cataaggaaa gtaagatatc aaattgtaaa aatcgttaag 780
aacttctatc ccatctgaag tgtgggttag gtgcctcttc tctgtgctcc cttaacatcc 840
tattttatct gtatatatat atattcttcc aaatatccat gcatgggaaa aaaaatctga 900
tcataaaaat attttaggct gggagtggtg gctcacgcct gtaatcccag cactttggga 960
ggctgaggtg ggcggatcat gaggtcaaga gatcgagacc atcctgacca atatggtgaa 1020
accccatctc tactaaagat acaaaactat tagctggacg tggtggcacg tgcctgtagt 1080
cccagctact cgggaggctg aggcaggaga acggcttgaa cccaggaggt ggaggttgca 1140
gtgagctgag atcgcgccac tgcactccag cctgggcgac agagcgagac tctgtctcaa 1200
aaaaaaaata tatatatata tatatataca catatatata taaaatatat atatatacac 1260
acatatatat ataaaatata tatatataca cacatatata taaaatatat atatatacac 1320
acatatatat aaaatatata tatacacaca tatatataaa atatatatat acacacatat 1380
atataaaata tatatataca cacatatata taaaatatat atatacacac atatatataa 1440
aatatatata tacacacata tatataaaat atatatatac acacatatat ataaaatata 1500
tatatacaca catatatata aaatatatat atacacacat atatataaaa tatatatata 1560
cacacatata tataaaatat atatatacac acatatataa aatatatata tacacacata 1620
tataaaatat atatatacac atatatataa aatatatata tacacatata tataaaatat 1680
atatacacac atatatataa aatatatata tacacacata tatataaaat atatatatac 1740
acatatatat aaaatatata tatacacata tatataaaat atatatatat acacatatat 1800
ataaaatata tatacacaca tatatataaa gtatatatat acacacatat atataaaata 1860
tatatataca catatatata aaatatatat atacacatat atataaaata tatatataca 1920

-continued

```
catatatata aaaatatata tatatatttt ttaaaatatt ccaattgtct cactttgtgg   1980

atgagaaaaa gaagtagtta gaggtcaagt aacttggcct acatcttttc tcaagattgt   2040

aaactcctag tgagcaataa ccacatcttc attttctttg tataaaacaa gaaagtttag   2100

catgaaaaag gtactcaatt acaaatgtgt tggattgaat tgaagaccct tggaagggga   2160

ttttgtacct gaggatctct ttcttttggc catattgttc aatggacaaa atttagcctt   2220

cgaaggcagg ccgatttgag gttaatacta cctttaccac ttgatagcta tgtgaccttg   2280

gccatgtggt ttcaacagtc tgaacctcat tttctctgtg tatgtgtggt cctccttaca   2340

agtttgtgaa aaatgtgaag tccttagcca tgatagccca atataacagg ctaaatgata   2400

ataggtttat gttcttttcc tttatattct cagataagca ctgtccaagt ttgaggtgtt   2460

ttgaggtctc gcctgatttg gattgtttga gtttatgcta ttctttgaat tctttgagct   2520

gttctgaagc agtgtatcat gaacaaaaac atccccagtt cagtccaaac ccctggttac   2580

atatcattct tatgccatgt tataaccagt ttgagagtgt tccctctgtt attgcattta   2640

agtttcagcc tcacacagaa attcagcagc caatttctaa gccctaagca taaaatctgg   2700

ggtggggggg ggggatggcc tgaagagcag cattatgaat agcaccatta taattaatga   2760

tctctcagga agatttacaa tcacaggtag cagataaaac aaatagtact gcttctgcac   2820

ttcccctcct tttattcgct atgaaatttt atgggaaatc agtccagtga aaaatgtaag   2880

ctcttaatct ttcccagaaa tcctacctca tttgatgaat actttgaggg aatgaattag   2940

agcatttttt tcttttatag tctacttcgc atttacgaag tgaggacggt agcttaggct   3000

gcctggccaa ctgatgagaa ggtcagaggc atttttagag acctctgttg tctttcattc   3060

atgttcattt tccacaaggc aagtaatttc caacaaatca gtgtcttcat tagtaataag   3120

attattaaca acaataatag tcatagtaac tattcagtga gagtccatta tatatcaggc   3180

attctacaag gtactttata tacatctgag taaacctcac acaattctac agggaggtat   3240

ttctatcccc atttaacaaa taaggaaacg aagtccaagt aaattaactt gcccaaggtc   3300

acacagatag tacctggcag aacaggaatt taaacctaaa tttgtccaac tccaaaagca   3360

gccttctatt tgttataaat gctgcctctc attatcacat attttattat taacaacaac   3420

aaacatacca attagcttaa gatacaatac aaccagataa tcatgatgac aacagtaatt   3480

gttatactat tataataaaa tagatgtttt gtatgttact ataatcttga atttgaatag   3540

aaatttgcat ttctgaaagc atgttcctgt catctaatat gattctgtat ctattaaaat   3600

agtactacat ctagag                                                   3616
```

<210> SEQ ID NO 26
<211> LENGTH: 4660
<212> TYPE: DNA
<213> ORGANISM: Homo sapiens
<220> FEATURE:
<221> NAME/KEY: misc_binding
<222> LOCATION: (1)..(4660)
<223> OTHER INFORMATION: MAR 1_42 of chromosome 1

<400> SEQUENCE: 26

```
gatcccttga ggtcagtagt ttaagaccag cctgaccaac atggtgaaac ccatctctac     60

taaaaataca aaaattagcc aggcgtggtg gcgggggcct gtaaccccag ctactcagga    120

ggctgaggca caagaatctc ttgaacccgg gaggcggagg ttgcagtgag ctgagattgt    180

gtcactgcac tccagcctgg gcaacagtgc cagactctgc cttaaaaaaa aaaaaaaaaa    240

aaaaaaggcc gggcgcggtg gctgacgcct gtaatcccag cactttggga ggccgaggcg    300
```

-continued

```
ggtggatcat gaggtcagga gatcgagacc acagtgaaac cccgtctcaa ctaaaaatac    360
aaaaaattag ccgggcgcgg tggtgggcgc ttgtagtccc agctactcag gaggctgagg    420
caggagaatg gcgtgaacct gggaggcgga gcttgcagtg agccgagatg gcaccactgc    480
actccagcct gggcgaaaga gtgagactcc gtctcaaaaa aaaaaaaaaa ttagctgggt    540
atggtggtgc gtgcctgtaa tcccagctac tcgggaggct gaggcaggag aatcccttga    600
acctgggagg cggaggttgc agtgatctgc catcctgtca ctgcatcact acactccagc    660
ctgggtgaca gagcgagact ctgtctcaaa aaaaaaaaaa aaaaaaaaag ctgggtgtgg    720
tggtatgcac cagctgtagt cccagctact tgggaggctg agttgggggg attgcctgag    780
ccagggaggt cgaggcttca gggagccatg attatgccac tgcactccag cctgggccac    840
agagtgaaac cttctgtcaa aaacaaaaaa acaaaaaaac acagtgtgtt agatcttgct    900
agacttggtg atataattaa gaggccatta tgggcagaac tgtgccccct tccaaaattc    960
atatataaat atatataaat atatataaat atataaatat atataaatat ataaatatat   1020
ataaatatat aaatatatat aaatatataa atatatataa atatatataa atatataaaa   1080
atatataaat atatataaat atatataaat atataaaaac ataaaaatat atataaatat   1140
atataaatat ataaaaatat ataaatatat aaatatataa aaatatacaa atatataaat   1200
atatacataa atatatataa atatatataa atatataaaa atatatataa atatataaat   1260
atatataaat atatataaat atatataaat atataaaaat atatataaat atataaatat   1320
ataaaaatat atataaatat ataaatatat aaatatatat aaatatataa atatataaat   1380
aaatataagt atttatgaat atatatgaat atataaatat ataaaaaata tatataaata   1440
tataaatata tataaatata taaatatata catatataca tatataaata aataaatata   1500
agtatttatg aatatatatg aatatataaa tatataaaaa atatatataa atatataaat   1560
atatataaat ataaatatat aaaaatatat aaaaatatat ataaatatat aaatatatat   1620
aaatatataa atatatataa atatatataa atatataaat atatataaat atatataaat   1680
atataaatat ataaatatat ataaatatat ataaatatat aaatatataa atataaatat   1740
ataaatatat ataaatatat ataaatatat aaatatatat aaatatatat aaatatatat   1800
aaatatatat aaatatataa atatatataa atatatatat aaatatatat aaatatataa   1860
atatataaat atataaaaat atataacaat atataaatat atataaaaat atataacaat   1920
atataaatat aaatatatat aaaaatatat aacaatatat aaatataaat atatataaat   1980
atataaatat aaatataaaa aatatatata aatatataaa tatatataaa tatataaatg   2040
tataaatata tataaaaata tataacaata tataaatata taaatatata acaatatata   2100
aatatataaa aatatataac aatatataaa tataaatata tataaaaata tataacaata   2160
tataaatata aatatatata taaatatata aatataaata taaaaaatat atataaatat   2220
ataaatatat atataaatat atataaatat ataaatgtat aaatatatat aaatatataa   2280
atatataaaa atatataaat atatataaat atatataaat atataaatat aaatatataa   2340
atatatataa atatataaat ataaatatat aaacatatat aaatatatat aaataaacat   2400
atataaagat atataaagat ataaagatat ataaatatat aaatatataa agatatataa   2460
atatataaag atatataaat atataaagat atataaatat ataaagatat ataaatataa   2520
tatataaata tataaagata tataaatata atataaaaat atataaatat atattaaaaa   2580
tatatacata taaatatatg tatatttttt tgagatgggg tctcgctcag ccacccacgc   2640
tggagtgcag tggcacgagc tcggctcact gcaaccactg tctctcgggt ccaagcaatt   2700
```

-continued ctgtctcagc ctcccaagta gctgggatta caggcacctg ccatcatgcc cggctaattt 2760
ttgtatttta gtagagatgg agtttcacca tgttggccag gttggtctcg aattcctgac 2820
ctcaggtgat ctgccggcct cggcctccca gtgctgggat tacaggcatg agtcaccacg 2880
cccggcccta tatatatttt tgagacaagc tctgtgtctc ccaggctgga gtgcagcagc 2940
atgatcatga ctcactgtag cctagacctc cagggctcaa gtgattctcc cacctcagcc 3000
tcccaagtag ctgggattac aggcatgcac caccacaccc agctaatttt tgttttgttt 3060
tgttttggag acagaatctc tctctgtcac ccaggctgga gtgcagtggt gtgatctcag 3120
ctcagtgcaa cctccacctc ctgggttcaa gtgattctca tgcctcagcc tcctgagtag 3180
ctgggactac aggcgtgagc caccacgccc tgataaattt tgtatttttt ttttcagatg 3240
gagtctcact ctgtcatact caggctggag tgcagtggcg tgattttggt ttattgcaac 3300
ctctgcttcc tgggttcaag cgattctcct gcctcagcct ccagagtagc tgggattaca 3360
ggcgcctgcc accatgccca cctagctaac tttttttttt ttttttttga gatagagtct 3420
cactctgtca cccaggctgg agtgcaatgg ggcgatattg gctcactaca acctccacct 3480
cccaggttca agcgattctc ctgcctcagc ctcctgagta gctgggatta caggtgggtg 3540
ccaccacgcc agactaatat ttgtattatt agtagagacg gggtttcacc acattggtca 3600
ggctggtttc gaactcctgg cctcaggtga tctgcctgcc tcggcctccc aaagtgctgg 3660
gattacaggc atgagccact gcggctggcc caatttttgc atttttttgg tagagacggg 3720
ggtttcacta tgcttcccag gctggtctca aactcctgga ctcaagcgat ctgcctgtct 3780
cagcctccca aagtgcaggg attacagtca tgagccacca ctgcacggcc ccaaaattta 3840
tttattttat tattattatt attttttaga tggagtctcc ttctgttgcc agattggaat 3900
gcagtgccac gatctcagct cactgcaacc tccccctcct gggatcaagt gattcttttt 3960
tttttaagac tctgtctcaa aaaaaaagaa aaaaaaaaaa aatatatata tatatatata 4020
tatacacgaa ttttgggcca ggcacagtgg cttatgcctg taatcccagc actttgggag 4080
ggccgaggtg ggtggatcac aaggtcagga gtttgagacc agcctggcca atatggtgaa 4140
accctgtctc tactaaaaaa tacaaaaatt agctgggcgt ggtggcacga gcctgtaatc 4200
ctggctactc tggaggctaa ggcaggagaa tcgcttgaac cggggaggca gaggttgcag 4260
tgagccagga tcgcatcact gcactccagc ctgggtaaca gagcaagact ctgtctcaaa 4320
aaacaaacaa aacaaaacaa aacaaaataa ataacggtgc aaaattgaat atgccttttt 4380
gactctctaa atgcctcaga tccatttacc ctggggattt gtcctttcta gccccaccac 4440
catctcccct ctggaagact gctgacctat aaggataaag accagactct tgagcaggca 4500
cttagggtct tcctgcccat ccctatcccc aactccccct cagtaatttt ggctactagt 4560
atttctccac atctgaggct atcgtgggtc tcccttcagt ggtcatgaag gacaaggttg 4620
gagaagtttg ccctcgtgag tctgatgagg gattgggtgg 4660

<210> SEQ ID NO 27
<211> LENGTH: 3354
<212> TYPE: DNA
<213> ORGANISM: Homo sapiens
<220> FEATURE:
<221> NAME/KEY: misc_binding
<222> LOCATION: (1)..(3354)
<223> OTHER INFORMATION: MAR X_S29 of chromosome X

<400> SEQUENCE: 27
gatcccttta taaaaccaca atataatgga gtgctataat ttcaaacagt gtttggtctg 60

-continued

```
ctggcagagt ggtcattcta acagcagtca cagtagagta gaaataagac tgcagtatat    120
ctaaggcaaa aagctgaggt ttcaggagct tgaaggtaaa gaggaagaaa gaaatgggaa    180
tgggaattgg aaagacaaat atcgttaaga gaaaattgct tttaggagag gggaaagaat    240
ctatgtgtac ttaagactat ggaatcaatc ccatttaagc tgggaaacta gtttcatata    300
taactaataa attttattta cagaatatct atttacctga tctaggcttc aagccaaagg    360
gactgtgtga aaaaccatca gttctgtcat attcctaaaa aaaaattaaa aagttaaaaa    420
taaataaata ataaaacttc ttttctttca aaataatcaa ggtgcttatt cacatccatt    480
ccaatttggg gaaatactta ttttcctatg attagcgaag agaaaagtaa cttgcatttc    540
aattcaagtt gatacatgtc acttttaaga ggtcaactaa tatttgctag ttgagctaac    600
catataggct ttaaatactt tcatagtaga aagaaaatga aaatcattag tgaactgtat    660
aaaatagatc atacttttttg aaagaatcag actgaagttt ccgaaaaaaa gaagtaagct    720
tcaatgaaaa ggtaagtgaa tttagcattt actcagcatc tactatggac ttaacaccta    780
acagtagata atctgaaggc aaacatattt gtatagggac tgcagaatga tagatgataa    840
atatcatctc ttctatttga atgaatattt tttcaaatct ttcacacaca gtggtttgct    900
atggaaagat ttgtagtaca ttaaacaaat ctgaagatgg agttagaaag cttaggctat    960
gttttgagca caacatataa tttctctgtg attgtttctt catctttcaa atgaggttac   1020
tgtgaagatt aaatgagata actaaatgat gataaaataa tgtaatctta gcagcacctt   1080
atttaatctg tgcaacaact ctgtgaagtg agtagggctc agcttcagtc acttctctgc   1140
catttattaa ctaagatagt ttggaaagtt acccatctct tcagctgtaa aatgatgagg   1200
atcataccta ttttatgggg ctgcttttag gtacaaatat acaggcaagc actttgttaa   1260
tactaaagca ttacaccaat tagttttact cttttccatt cacacatgaa attaatgtaa   1320
tcagaattct gtagattacc taaatcttct gttaacacgt gatatgcagt tcaggttaaa   1380
tgtcagttga gttaccaaag cacatacata ctcaccaccc tatccaaatc tacaagcctc   1440
ccagtttgtc ttcactattt tggttaaatt aatatgaatt cctagatgaa aatttcactg   1500
atccaaatga aataaaaaat atattacaaa actcacacct gtaatctcaa cattttggga   1560
ggccaaggca ggtagatcac ttgaggccag gagttcaaga ccagcctgat caacatggtg   1620
aaaccctgtc tctactaaaa atacaaaaat tagccaggtg tggtggcatg tgcctgtagt   1680
cctacctact cgggaggctg aggcacaaga atcgcttgaa tgtgggaggt ggaggttgca   1740
gtgacctgag atcgtgccac tgcactccag cctaggcaac agagtgagat catgtgtcat   1800
atatatatat atatatatat atatatatat atatatatac acacacacac acatatatat   1860
atacacatat atatacgtat atatatatat gtatatatat acatatatat acatatatat   1920
atatacgtat atatatacgt atatatatat caatgtaaat tatttgggaa atttggtatg   1980
aatagtcttc cctgtgaaca cagatcataa aatcatatat caagcagaca aataagtagt   2040
agtcacttat atgcttatac ttgtaactta aagtaaaaga attacaaaag catatgacaa   2100
agactaattt taagatatcc taatttaaat tgttttctaa aagtgtgtat accattttac   2160
ctatcatatg aataatttag aaacatgttt ataaaattaa tgtccaaatc cattcaaaag   2220
ttttgtaatg cagatcaccc acaacaacaa agaatcctag cctattaaaa aagcaacacc   2280
acctacatat aatgaaatat tagcagcatc tatgtaacca aagttacaca gtgaatttgg   2340
gccatccaac actttgagca aagtgttgaa ttcatcaaat gaatgtgtaa tcatttactt   2400
actaatgcca atacacttta aggtaatctt aagtagaaga gatagagttt agaattttt    2460
```

-continued aaatttatct cttgttgtaa agcaatagac ttgaataaat aaattagaag aatcagtcat 2520
tcaagccacc agagtatttg atcgagattt cacaaactct aactttctga tacccattct 2580
cccaaaaacg tgtaacctcc tgtcgatagg aacaacccac tgcagggatg tttctcgtgg 2640
aaaaaggaaa tttcttttgc attggtttca gacctaactg gttacaagaa aaaccaaagg 2700
ccattgcaca atgctgaagt acttttttca aatttaaaat ttgaaagttg ttcttaaaat 2760
ctatcattta ttttaaaata cggatgaatg agaaagcata gatttgataa agtgaattct 2820
tttctgcaat ctacagacac ttccaaaaat cactacagac actacagaca ctacagaaaa 2880
tcataaataa acaagtgcta gtatcaatat ttttaccaaa aaatggcatt cttagaattt 2940
tttataggct agaaggtttg tacaaactaa tctgccacgg attttaaaat atgagtgaat 3000
aaattatatt gcaaaaaaaa tcaggttaca gagaactggc aaggaagact cttatgtaaa 3060
acacagaaaa catacaaaac gtatttttaa gacaaataaa aacagaactt gtacctcaga 3120
tgatactgga gattgtgttg acatattagc attatcactg tcttgctaaa acataaaaat 3180
aaaaagatgg aagatgaaat tacaatacaa atgatgattt aaacatataa aaggaaaata 3240
aaaattgttc tgaccaacta ctaaaggaag acctactaaa gatatgccat ccagcacatt 3300
gccactctac atgtggtctg taaaccagca gcatagggat cctctagcta gagt 3354

<210> SEQ ID NO 28
<211> LENGTH: 677
<212> TYPE: DNA
<213> ORGANISM: Homo sapiens
<220> FEATURE:
<221> NAME/KEY: misc_binding
<222> LOCATION: (1)..(677)
<223> OTHER INFORMATION: MAR of chromosome 1 genomic contig;
      12803267..12803943

<400> SEQUENCE: 28
ttatatagta tatataatag tatatattat atagtataca taatagtata tattatatag 60
tatacataat agtatatatt ataatataca taattgtata tatcatatag tatacattat 120
agtatatatc atatagtata cattatagta tatatcatat agtatacatt atatagtata 180
tatcatatag tatacattat agtatatatc atatagtata cattatagta tatatcatat 240
agtatacgta atagtatata tcatatagta tacgtaatag tatatatcat atagtatacg 300
taatagtata tatcatatag tatacgtaat agtatatatc atatagtata cgtaatagta 360
tatatcatat agtatacgta atagtatata tcatatagta tacgtaatag tatatatcat 420
atagtatacg taatagtata tatcatatag tatacgtaat agtatatatc atatagtata 480
tattatatag tatatatcat atagtatata ttatatagta tatatcatat agtatatatt 540
atatagtata tatcatatag tatatattat atagtatata tcatatagta tatataatag 600
tatatatcat atagtatata taatagtata tatcatatag tatatatact atactatatt 660
atatatagta tacataa 677

<210> SEQ ID NO 29
<211> LENGTH: 332
<212> TYPE: DNA
<213> ORGANISM: Homo sapiens
<220> FEATURE:
<221> NAME/KEY: misc_binding
<222> LOCATION: (1)..(332)
<223> OTHER INFORMATION: MAR of chromosome 1 genomic contig;
      13079684..13080015

<400> SEQUENCE: 29

-continued

```
ttaattatat tatatatatt atataattat atattaatat atattaatta tattatatat     60

attatataat tatatattaa tatatattaa ttatattata tatattatat aattatatat    120

taatatatat taattatatt atatatatta tataattata tattaatata tattaattat    180

attatatata ttatatatta taattatata ttatataatt ataatatata tgttaatata    240

atatatataa ttaatatata attaaaacta tttaattata tgtatattat atataatatg    300

tattatttaa ataataaata tattatttat at                                  332
```

<210> SEQ ID NO 30
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAr of chromosome 1 genomic contig; 15682296..15682774

<400> SEQUENCE: 30

```
acaagtacat atatatatag tatatatata caagtacata tatatagtat atatatatat     60

acaagtacat atatatagta tatatatata tacaagtaca tatatatagt atatatatat    120

acaagtacat atatatagta tatatatata caagtacata tatatatagt atatatatat    180

acaagtacat atatatagta tatatatata caagtacata tatatatagt atatatatat    240

acaagtacat atatatagta tatatatata caagtacata tatatatagt atatatatat    300

acaagtacat atatatatag tatatatata tacaagtaca tatatatata gtatatatat    360

atacaagtac atatatatag tatatataca tatatacaag tacatatata tagtgtatat    420

atatatatac aagtacatat atatacttgt attagtatat atatatatat atacaagta     479
```

<210> SEQ ID NO 31
<211> LENGTH: 531
<212> TYPE: DNA
<213> ORGANISM: Homo sapiens
<220> FEATURE:
<221> NAME/KEY: misc_binding
<222> LOCATION: (1)..(531)
<223> OTHER INFORMATION: MAr of chromosome 1 genomic contig; 15694611..15695141

<400> SEQUENCE: 31

```
tataatatat ataatacata atagatatat tatattatat aatagatata taattataaa     60

cataataata tataatgaat ataatataaa ataaatataa taaaatatat aatatatcta    120

ttatgtatta tatattatat atgtttatat ataatataat tatatatgtt tatatataat    180

ataattatat atgtttatat ataatataat tatatattat atattataga tataatatat    240

aatatactat atattataga tataatatat aatatactat atattataga tataatatat    300

aatatactat atattataga tataatatat aatatactat atattataga tataatatat    360

aatatactat atattataga tataatatat aatatatatt atatattata gatataatat    420

ataatatatt atatattata tctatatata atatattgta tattatatat aatatattgt    480

atattatata taatatattg tatattatat ataatatatt gtatattata t             531
```

<210> SEQ ID NO 32
<211> LENGTH: 378
<212> TYPE: DNA
<213> ORGANISM: Homo sapiens
<220> FEATURE:
<221> NAME/KEY: misc_binding
<222> LOCATION: (1)..(378)

<223> OTHER INFORMATION: MAR of chromosome 1 genomic contig;
886276..886653

<400> SEQUENCE: 32
ttatattata tatcttacat aaattatata tatatattac ataaattata tacaatataa 60
attatataca atataattta tatataaaat ataaattata taaataattt atatataaaa 120
tataaattat ataaataatt tatatataaa atataaatta tgtataaaat ttatatataa 180
aatataaatt gtgtataaaa ttatatataa aatataaatt gtgtataaaa tttatatata 240
aaatataaat tatatataat ttatatatta taatataaat tatatataat atatatcata 300
aaatataaat tatatataat atatatcata agatataaat tatatataat atatatcata 360
agatataaaa tatataat 378

<210> SEQ ID NO 33
<211> LENGTH: 595
<212> TYPE: DNA
<213> ORGANISM: Homo sapiens
<220> FEATURE:
<221> NAME/KEY: misc_binding
<222> LOCATION: (1)..(595)
<223> OTHER INFORMATION: MAR of chromosome 1 genomic contig;
3326732..3327326

<400> SEQUENCE: 33
aaaatatata aatatatata aaaatatata aaaatatata aatatatata aaaatatata 60
aatatatata aatatatata aaaatatata aatatatata aatatatata aaatatataa 120
atatatataa aatatatata aatatatata aatatatata aaaatataaa tatatataaa 180
aatataaata tatataaata tatataaaaa tataaatata tataaatata tataaatata 240
taaatatata taaatatata taaatatata aatatatata aatatatata aatatatata 300
aatatataaa tatataaaaa tatatataaa tatataaata tatataaata tataaatata 360
taaaaatata tataaatata taaatatata taaatatata taaatatata tataaatata 420
tataaatata tatatatata aatatatata aatatatata taaatatata taaatatata 480
tatatatata taaatatata taaatatata taaatatata tataaatata tataaatata 540
tataaatata tatataaata tatataaata tatatataaa tatatataaa tatat 595

<210> SEQ ID NO 34
<211> LENGTH: 738
<212> TYPE: DNA
<213> ORGANISM: Homo sapiens
<220> FEATURE:
<221> NAME/KEY: misc_binding
<222> LOCATION: (1)..(738)
<223> OTHER INFORMATION: MAR of chromosome 1 genomic contig;
4485716..4486453

<400> SEQUENCE: 34
ataatagata atatatatta tatgatagat atataatata ttatataata tataatatat 60
tatatatcta tcatataata tatataatat ataatatatt atatatctat catataatat 120
aatatatata atatataata tatatcatat tatattgtat ataatatata tcatattata 180
ttgtatataa tatatatcat attatattgt atataatata tatcatatta tattgtatat 240
aatatatatc atattatatt gtatataata tatatcatat tatattgtat ataatatata 300
tcatattata ttgtatataa tatatatcat attatattgt atataatata tatcatatta 360
tattgtatat aatatatatc atattatatt gtatataata tatatcatat tatattgtat 420
ataatatata tcatattata ttgtatataa tatatatcat attatattgt atataatata 480

-continued tatcatatta tattgtatat aatatatatc atatattatc tattatattg tatataatat 540
atattatata ttatctatta tattgtatat aatatatatt atatattatc tattatattg 600
tatataatat atattatata ttatctatta tattgtatat aatatataat aaatatagta 660
tatataatag ataatatata gtatatatga tatattatat atactatata ttatatatca 720
tatatactat atactata 738

<210> SEQ ID NO 35
<211> LENGTH: 386
<212> TYPE: DNA
<213> ORGANISM: Homo sapiens
<220> FEATURE:
<221> NAME/KEY: misc_binding
<222> LOCATION: (1)..(386)
<223> OTHER INFORMATION: MAR of chromosome 1 genomic contig; 5423067..5423452

<400> SEQUENCE: 35
taaatatata aaaatatata taaaaatata aaaatattta tataaatata taaaaatatt 60
tatataaata tataaatata taaatatata tttatataaa tatataaata tataaatata 120
taaatatata tttatataaa tatataaata tatatttata taaatatata aatatatata 180
aaatatataa atatatattt atataaatat ataaatatat ataaaatata taaatatata 240
tattttatat aaatatataa atatatataa aatatataaa tatatatatt ttatataaat 300
atataaatat atataaaata tataaatata tatattttat atatttatat atataaatac 360
atatatttca tatatcacat atatga 386

<210> SEQ ID NO 36
<211> LENGTH: 584
<212> TYPE: DNA
<213> ORGANISM: Homo sapiens
<220> FEATURE:
<221> NAME/KEY: misc_binding
<222> LOCATION: (1)..(584)
<223> OTHER INFORMATION: MAR of chromosome 1 genomic contig; 5805559..5806142

<400> SEQUENCE: 36
taaatatttt taaaatatat atattttata atatataatt tatattataa tgtgtacata 60
atatatatta taatataata tatataatac tgtatattat attatatata ttataatata 120
tattattata tattatatta tatataatat aatatatatt ataatatatt atattataca 180
tattataatg tattataata tatattatat tatatattat aatatatatt atattatata 240
ttataatata tattatatta tatattataa tatatattat attatattat atatattata 300
atacatatta taatacatat tatataatat attataatat gtattataat acatattata 360
taatatatta taatatatta tatataataa tatattataa tacatattat atataatata 420
tattatgtat attatatata atatatatta caatgtatat tatgtatatt atatatatta 480
tatatcatat aatatatatt atatataata tgatatataa tatatattat ataatatatt 540
atatgatata tataatatgt attacatgta atatatatca taat 584

<210> SEQ ID NO 37
<211> LENGTH: 345
<212> TYPE: DNA
<213> ORGANISM: Homo sapiens
<220> FEATURE:
<221> NAME/KEY: misc_binding
<222> LOCATION: (1)..(345)
<223> OTHER INFORMATION: MAR of chromosome 1 genomic contig;

10802644..10802988

<400> SEQUENCE: 37
tgtatatata tactatatat atactatata tatagtgtat atatatacta tatatatact 60
atatatatag tgtatatata tactatatat atagtatata gtatatatag taatatatat 120
atatagtata tatatacact atatatagta tatatagtat atatatattg tgtatatagt 180
atatatatag tgtatatata gtatatatat attgtatata tagtatatat attgtgtata 240
tatagtatat atatagtata tatagtatat atagtatata tatagtatat atatactata 300
tatatagtat atatatattg tatatatata ctatatatat agtat 345

<210> SEQ ID NO 38
<211> LENGTH: 474
<212> TYPE: DNA
<213> ORGANISM: Homo sapiens
<220> FEATURE:
<221> NAME/KEY: misc_binding
<222> LOCATION: (1)..(474)
<223> OTHER INFORMATION: MAR of chromosome 1 genomic contig;
13496468..13496941

<400> SEQUENCE: 38
atattatata taatataatt atatctataa ttatatatta tatataatat aattatatat 60
ctataattat atattatata taatatatat tatatataat atataattat atataattta 120
tataatataa tatataatat ataattatat ataattatat aatataatat ataatatata 180
attatatata atttatataa tataatatat aatatataat tatatatatt tatataatat 240
aattatatat aatatataat tatatataat ttatataata taattatata taatatataa 300
ttatatataa tttatataat ataattatat ataattatat attatatata atttatataa 360
tataattata tataatatat aattatatat aatatataat tatatataat tatatataat 420
atataattat atataattta tataatataa ttatatatta tatatattat atat 474

<210> SEQ ID NO 39
<211> LENGTH: 483
<212> TYPE: DNA
<213> ORGANISM: Homo sapiens
<220> FEATURE:
<221> NAME/KEY: misc_binding
<222> LOCATION: (1)..(483)
<223> OTHER INFORMATION: MAR of chromosome 1 genomic contig;
2509163..2509645

<400> SEQUENCE: 39
caaaatacat aatatataat agtattatat aatagtatgt atagttataa tatatagtat 60
aattacaata tatgatatgg tttatatatt atatatagta taatataata taacataata 120
ctattataat atataaacta tataatatat actattataa tatatgaact attataatat 180
ataaactata tataatatat aatatgtact attataatat ataaactatt ataatataat 240
atataaacta ttataataca taaactatta taatatatat aatactatgt atacatatat 300
tacattatgt acatactaca ttatgtatta tgtatgtata tatacacaaa atacataata 360
tataatagta ttatataata gtatatatag ttataatata tagtataatt acaatatata 420
atatggttta tatattatat atagtataat acaatataac ataatactat tatatataaa 480
cta 483

<210> SEQ ID NO 40
<211> LENGTH: 641
<212> TYPE: DNA

-continued

<213> ORGANISM: Homo sapiens
<220> FEATURE:
<221> NAME/KEY: misc_binding
<222> LOCATION: (1)..(641)
<223> OTHER INFORMATION: MAR of chromosome 1 genomic contig;
2776349..2776989

<400> SEQUENCE: 40
tgttatatat atataacata gatattatat atacatgtta tatatataac atagatatta 60
tatatacatg ttatatatat aacatagata ttatatatat aacatagata ttatatatac 120
atgttatata taacatagat attatatata catgttatat ataacagata ttatatatac 180
atgttatata taacatagat attatatatg tatgttatat ataacataga tattatatat 240
gtttatataa tatataacat atgtttaaca tatataatat ataacatgtt tatataatat 300
ataacataat tatatgttat atatgatata aaacatatat attatatacg ttatatgtaa 360
tatataacat atattgtata cgttatatgt aatatataac atatattgta tacgttatat 420
gtaatatata acatatattg tatacgttat atgtaatata taacatatat tgcatacgtt 480
atatgtaata tataacatat attgtatacg ttatatgtaa tatgtaacat atattgtata 540
cgttatatgt aatatgtaat atataataca tataacatgt atatataaca tatatgtata 600
taacatatat ataacatata taacatatat gttatattat a 641

<210> SEQ ID NO 41
<211> LENGTH: 745
<212> TYPE: DNA
<213> ORGANISM: Homo sapiens
<220> FEATURE:
<221> NAME/KEY: misc_binding
<222> LOCATION: (1)..(745)
<223> OTHER INFORMATION: MAR of chromosome 1 genomic contig;
2858703..2859447

<400> SEQUENCE: 41
atatttatat atgtaataat atataatata tttatatgta tttgtatatg taataatata 60
tatataataa aatatgtaat aatatataat atatttatat ataaatatat tatattatat 120
atatattatt atatttataa tataatatat atttatatta tatattataa atatatatta 180
tataatatat attataaata tatattatat aatatatatt ataaatatat attatattat 240
atattataaa tatatattat ataatatata ttataaatat atattatata atatatatta 300
taaatatata ttatatttat aatatatatt tttgtatatt atatattata tattataaat 360
attattatat ttataatata ttatatattt tatatataat atatgatata tattataaat 420
atatcttata aatatatata tttatatata tatattataa atatataaat ataaatatat 480
aatataatat aatataatat aataaatata atatataata tatataatat ataataaata 540
taataaatat aaatatatca tataaatata aatataaata taaatatatc atataaatat 600
atatatttat atgatatatt atagtatata taaatatatt tatatattat aaaatattta 660
tataatatat aattataata tatttatata tataaattaa ctaatatata taaactaata 720
taatatataa tgtaataata tagta 745

<210> SEQ ID NO 42
<211> LENGTH: 307
<212> TYPE: DNA
<213> ORGANISM: Homo sapiens
<220> FEATURE:
<221> NAME/KEY: misc_binding
<222> LOCATION: (1)..(307)
<223> OTHER INFORMATION: MAR of chromosome 1 genomic contig;
945522..945828

<400> SEQUENCE: 42
catatataat atatattacc tatgttatat aggtcatata taacataaat atattacata 60
tatgtaatat atattaaata taaatatata acatatatgt gtaactatat atgtaaatat 120
gtacatatac atatatgtaa atatataata tatatttaca ttatattata taatatatat 180
ttacattata tatttatata tacattatat atatttacat tataaatatt tatataatat 240
atatttacat tatattacat tatataaaat acaatatatt acattataat acattataac 300
agataaa 307

<210> SEQ ID NO 43
<211> LENGTH: 357
<212> TYPE: DNA
<213> ORGANISM: Homo sapiens
<220> FEATURE:
<221> NAME/KEY: misc_binding
<222> LOCATION: (1)..(357)
<223> OTHER INFORMATION: MAR of chromosome 1 genomic contig;
3402743..3403099

<400> SEQUENCE: 43
aatattatat taaatataat atattaatat ttaatatatt taatataata ttaaataaat 60
atattataaa taaattataa tatataaata tatattatgt atttatgtat aatatataaa 120
aattatatat aatatatata tttttataaa tatataaata tataataaat aaatatatta 180
aataaataat aatatattaa atattaatat attaaatatt atatattaaa tataatatgt 240
aatatgaaat atattaaata ttatatatta aatataatat ataatgtgaa atatattaaa 300
tattatatat taaatataat atataatatg aaatatatta aatattatat attaaat 357

<210> SEQ ID NO 44
<211> LENGTH: 323
<212> TYPE: DNA
<213> ORGANISM: Homo sapiens
<220> FEATURE:
<221> NAME/KEY: misc_binding
<222> LOCATION: (1)..(323)
<223> OTHER INFORMATION: MAR of chromosome 1 genomic contig;
3485830..3486152

<400> SEQUENCE: 44
atatttatag actatatatt tatatattta gtgtatttgt atactatata tttatatagt 60
tagtatattt gtatactata tatttatata tttagtatat ttgtatacta tatatttata 120
tatttagaat atttgtatac tatatattta tatatttagt atatttgtat actatatatt 180
tagtatattt gtatactata tatttatata tttagtatat ttgtatacta tatatttata 240
tatttagtat atttatatac tatatactta tatatttagt atatttatat actatatact 300
tatatattta gtatatttat ata 323

<210> SEQ ID NO 45
<211> LENGTH: 498
<212> TYPE: DNA
<213> ORGANISM: Homo sapiens
<220> FEATURE:
<221> NAME/KEY: misc_binding
<222> LOCATION: (1)..(498)
<223> OTHER INFORMATION: MAR of chromosome 1 genomic contig;
3548336..3548833

<400> SEQUENCE: 45
aattattact atattgttaa tataattatt atataatata atataattat atcactatta 60

```
ttatattata gtattaatat aatagtgtat aacattaata taatatagta ttaatataat    120

agcgtataac attaatataa tatagtatta atataatagc gtataacatt aatataatat    180

agtattaata taatagtgta tattaatata atatagtatt aatatataat attaatataa    240

tatatcaata taatagtata taatataata taatatatca atataatagt atataatata    300

atataatata tcaatataat agtatataat ataatataat atatcaatat aatagtatat    360

aatattaata taatataata tcaatataat agtatataat attaatatat taatataata    420

gtatataata ttaatgtaat ataatattaa cataatgtat ataataatat aatagtatat    480

aatactaata taatataa                                                  498
```

<210> SEQ ID NO 46
<211> LENGTH: 400
<212> TYPE: DNA
<213> ORGANISM: Homo sapiens
<220> FEATURE:
<221> NAME/KEY: misc_binding
<222> LOCATION: (1)..(400)
<223> OTHER INFORMATION: MAr of chromosome 1 genomic contig;
4595109..4595508

<400> SEQUENCE: 46

```
aaatatatta tattatatat tatatattat tcaatatact ataatatata ttatatatgt     60

ttaatacaat atataatatt tacatatatt cccatttatt tatataacat atattatatg    120

atattatata ttactccata taatataata tattatacat aatatattac tcagtataat    180

acataatata tataatatat tactcggtat aatatataat attatatgtt atgcaatata    240

atatataata ttatatataa tacattattc aatataatat ataatattat atataataca    300

ttattcaata taatatataa tacactattc aatataatat acaatattat atataataca    360

ttattcaata taatatatat tatataatat atatatttat                          400
```

<210> SEQ ID NO 47
<211> LENGTH: 403
<212> TYPE: DNA
<213> ORGANISM: Homo sapiens
<220> FEATURE:
<221> NAME/KEY: misc_binding
<222> LOCATION: (1)..(403)
<223> OTHER INFORMATION: MAr of chromosome 1 genomic contig;
7205509..7205911

<400> SEQUENCE: 47

```
agtatatata tgtgtatata tatgagtata tatatgtgta tatatatgag tatatatatg     60

tgtatatata tgagtatata tatgtgtata tatatgagta tatatatgtg tatatatatg    120

agtatatata tgtgtatata tatgagtata tatatgtgta tatatatgag tatatatatg    180

tgtatatata tgagtatata tatgtgtata tatgagtata tatatgtgta tatatgagta    240

tatatatatg tgtatatatg tgagtatata tatgtgtata tatatgagta tatatgtgta    300

tatatatgag tatacatatg tgtatatata tgagcatata tgtgtatata tatgagtata    360

tatatgtgta tatatatgag tatatatgtg tatatatatg agt                      403
```

<210> SEQ ID NO 48
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig;
7507280..7507588

<400> SEQUENCE: 48
tataaaatat atattattta tatattatat ataaaatata tattatatta tatattatag 60
atataataaa taaataatat ataatatatt atataattat ttatacataa ttatatataa 120
ttatatgtaa ttgtacaatt atatataatt atatacaatt atacacataa ttatatacaa 180
ttatacaatt atatacataa ttatatatat aatatacata attatatatt aattatacaa 240
ttatatacat aattatatat aattatacaa ttatatacat aattattatg tatattatat 300
tatataata 309

<210> SEQ ID NO 49
<211> LENGTH: 516
<212> TYPE: DNA
<213> ORGANISM: Homo sapiens
<220> FEATURE:
<221> NAME/KEY: misc_binding
<222> LOCATION: (1)..(516)
<223> OTHER INFORMATION: MAR of chromosome 1 genomic contig;
3581085..3581600

<400> SEQUENCE: 49
atatatatat atatatatat atttatatat atatatatta atatatatta tatataaaaa 60
tatataaaat ttatatatat aatttatata tataaaaata tataaaattt atatatataa 120
tttatatata taaaaatata taaaatttat atatataatt tatatatata aaaatatata 180
aaatttatat atataattta tatatataaa aatatataaa atttatatat ataatttata 240
tatataaaaa tatataaaat ttatatatat aatttatata tataaaaata tataaaattt 300
atatatataa tttatatata taaaatatat aaattatata tataattata tatataatat 360
aaaattatat atataattat atatataata taaaattata tatataatta tatatataat 420
ataaaattat atatatattg tatatatata aaatatacaa aatttatata tataaaatat 480
aaaatataca taaaaataaa tatatataat ttatat 516

<210> SEQ ID NO 50
<211> LENGTH: 534
<212> TYPE: DNA
<213> ORGANISM: Homo sapiens
<220> FEATURE:
<221> NAME/KEY: misc_binding
<222> LOCATION: (1)..(534)
<223> OTHER INFORMATION: MAR of chromosome 1 genomic contig;
3084851..3085384

<400> SEQUENCE: 50
atataatata tatgactata tattttatat tatattctat ttcaataaaa tatttatatt 60
ttattatata ttataatata taattatata tgtaataata tataatatat aatatatatt 120
ttatattata ttttatattt atttttatat tttatattat atttattat atatattata 180 atatataatt atatatgcaa taatatatta tatattataa tatataatta tatatgcaat 240
aatatattat atattataat atataattat atatgcaata atatattata gattataata 300
tataattata tatgcaataa tatattatat attatatatt agataatata ttaatatata 360
ttataacata taatatataa catataatat ataatatatt atctaatata taatataaca 420
tataatatat aatatattat ataatatatt attacatata taatatattg taatatataa 480
tattacatat atcttcaaaa agagttatgt gtatataata catatatata ccat 534

<210> SEQ ID NO 51
<211> LENGTH: 583

<212> TYPE: DNA
<213> ORGANISM: Homo sapiens
<220> FEATURE:
<221> NAME/KEY: misc_binding
<222> LOCATION: (1)..(583)
<223> OTHER INFORMATION: MAR of chromosome 1 genomic contig;
160087..160669

<400> SEQUENCE: 51
tatttatata aaatatataa aatatattat atataaatat attatatata atatatttat 60
atattataca atatatttat atattatata taatatattt tatataatat acataatata 120
ttttatatat tatatataat atattttata tataatgtac aatatatttt atatattata 180
tataatatat tttatatata ctatacaata tattttatat attatatatt ttatatatat 240
ttttcatgta acatatatat tttatatata atatatatac catatataat atattttata 300
tataatatat ataccatata taatatattt tatatataat atgtatatca tatatagtat 360
attttatata taataggtat accatatata atatatttta tatataatag gtataacata 420
tataatatat tttatatata atatgtatac catatataat atattttata tattatagat 480
accatatgta atatacttta tatataatat agataccata tgtaatatac tttatatata 540
atatagatac catatgtaat atactttata tataatatag ata 583

<210> SEQ ID NO 52
<211> LENGTH: 314
<212> TYPE: DNA
<213> ORGANISM: Homo sapiens
<220> FEATURE:
<221> NAME/KEY: misc_binding
<222> LOCATION: (1)..(314)
<223> OTHER INFORMATION: MAR of chromosome 1 genomic contig;
4350424..4350737

<400> SEQUENCE: 52
tatgtgtata taaatatatg tatatatgtg tatataaata tatataaata tatgtatata 60
tgtatatata catatattta tatataaata tatgcatata tttatatata aaatatatgc 120
atatatgtat atatataaaa tatatacata tatgtatata tataaaatat atacatatat 180
gtatatatat aaaatatata catatatgta tatatataaa atatatacat atatgtatat 240
atataaaata tatacatata tgtatatata taaaatatat acatatattt atatatataa 300
aataccaagt ctta 314

<210> SEQ ID NO 53
<211> LENGTH: 828
<212> TYPE: DNA
<213> ORGANISM: Homo sapiens
<220> FEATURE:
<221> NAME/KEY: misc_binding
<222> LOCATION: (1)..(828)
<223> OTHER INFORMATION: MAR of chromosome 1 genomic contig;
8443267..8444094

<400> SEQUENCE: 53
tattatataa ttatatatac tatataatta tataatatat agttatatag tatatataat 60
atatataata tatactatag tatatataat atatataata tatactatag tatatataat 120
atataattat atataatata tataatatag tatatattat atatatatta tatatatata 180
atatatatat aatatatata atatagtata tataatatat aattatatat aatatataat 240
atagtatata taatatataa tatatatata attatatact ataatatata taatatataa 300
ttatatatta tatactatag tatatattat tatatataat agatataata tatataatta 360
ttatataata tagtatatat aatatataat tatatataat agatataata taatataatt 420
atatataata tagtatatat aatatataat tatattatat tatatataat atataattat 480
aatatataat tatattatat aatatatata atatataatt atattatata attatattat 540
ataatatata taatatataa ttatattata taatatatat aatatataat tatattatat 600
aatatatata atatataatt atattatata atatatataa tatataatta tattatataa 660
tatatataat atataattat atattatata taatatagta tatataatat gtaattatat 720
atcatataat atataacatt gtatataata tataattaca tattatataa tgtatataat 780
atataattat atacattata taatatagta tataattata tattatgt 828

<210> SEQ ID NO 54
<211> LENGTH: 573
<212> TYPE: DNA
<213> ORGANISM: Homo sapiens
<220> FEATURE:
<221> NAME/KEY: misc_binding
<222> LOCATION: (1)..(573)
<223> OTHER INFORMATION: MAR of chromosome 1 genomic contig;
8703190..8703762

<400> SEQUENCE: 54
tatattatat ataaaatata catataatat acctataata tacatataat atataatata 60
tattatgtac atataatata catataatat atataatata taatgtacat ataatataca 120
tataatatat gttatatatt atatataaaa tataggatat atataatata gaatatatat 180
actatattgt atatataaga tatataatat atagtatata tactatataa tatataatat 240
atagtatata taatatataa tatagaatat atatacaata tataatatag aatataggat 300
atatatagaa tatacatata taatatgtat atattatata ttatattata tattatataa 360
aaatatataa tatataatat aaaaatatat tatatattat ataatataaa atatattata 420
tattatatat tatataatat aaaatatatt atatattata tattatatat aaaatatatt 480
atatattata tattatatat aaaaatatat tatatattat atattatata taaaaatata 540
ttatatatta tatataaaaa tatatattat tac 573

<210> SEQ ID NO 55
<211> LENGTH: 597
<212> TYPE: DNA
<213> ORGANISM: Homo sapiens
<220> FEATURE:
<221> NAME/KEY: misc_binding
<222> LOCATION: (1)..(597)
<223> OTHER INFORMATION: MAR of chromosome 1 genomic contig;
8819076..8819672

<400> SEQUENCE: 55
acatatctta tatataaaat atataaatat acacatattt tatatataat atatattata 60
tatatgaaat atacacatat ttttatatat ataatatata tattatatat aatatatgca 120
tatattatat ataaaatata tatattatat ataaaatatg catatattat atataatata 180
tataatataa aatatataat atatattata tattatatat aatatatatt atatataata 240
catatatata atatataata tatataaaat ataatatata tattatataa tatatatata 300
aatatatata atatatatat aatatatata ttatatataa aatatatatt atatgtaaaa 360
tatataatat atataatata tatattatat gtaaaatata tattatatat aaaatatata 420
atatataaaa tatatattat atataaaata tataatatat aaaatatata atatatataa 480
aatatataat atatataaat atatattata tataaaatat ataatatata taaatatata 540

-continued ttatatataa aatatataat atatataaat atatattata tataaaatat atattat 597

<210> SEQ ID NO 56
<211> LENGTH: 646
<212> TYPE: DNA
<213> ORGANISM: Homo sapiens
<220> FEATURE:
<221> NAME/KEY: misc_binding
<222> LOCATION: (1)..(646)
<223> OTHER INFORMATION: MAr of chromosome 1 genomic contig;
759619..760264

<400> SEQUENCE: 56
taatatatat aatatatatt atataataat atataatata tattatatta taatatataa 60
tatattatat aataatatat attatataat atataataat atatataata catattattt 120
aataatatat aatatatatt atataataat atataatata tattatataa taatatacat 180
tatattatat aatatataat atatataata tatattatat aataatatat aatatatatt 240
atagaatgat atattagata ttatataatt atatatataa tattatatat tatataataa 300
tatataatat atattatata attatatata taatattata tattatataa ttatatataa 360
tatattatat aattatatat ataatattat atattatata attatatata atatatatta 420
tataattata tatataatac tatatattat ataattatat ataatactat atattatata 480
atttatataa ttatatatat tatatattat ataattatat atattatata ttatataata 540
acatatatat tatatattat ataataacat atatattata tattatataa tacatatata 600
ttatatatta tataatacat tattatataa tatataatat atatta 646

<210> SEQ ID NO 57
<211> LENGTH: 752
<212> TYPE: DNA
<213> ORGANISM: Homo sapiens
<220> FEATURE:
<221> NAME/KEY: misc_binding
<222> LOCATION: (1)..(752)
<223> OTHER INFORMATION: MAR of chromosome 1 genomic contig;
1226710..1227461

<400> SEQUENCE: 57
taaacatata tataaatata tataaatata tatataaata tatataaata tataaatata 60
taaatatata tgaatatata aatatatata aatatatatg aatatataaa tatatatata 120
aatatatata aatatatata taaatatata taaatatata taaatatata taaatatata 180
taaataaata tataaatata tataaatata taaatatata tataaatatg taaataaata 240
tatataaata tataaatata tataaatata tataaatata tatagaaata tatatagaaa 300
tatatataaa tatatataga aatatataga aatatatata gaaatatata taaatatata 360
taaatataga aatatatata aatatatata aatatatata gaaatatata atatatataa 420
atatatataa atatataaat atatatataa atatatatat aaatatatat aaatatatat 480
aaatatatat aaatatatat aaatatatat attaatatat aaatctatat taatatatat 540
taatatataa atctatatta atatatatta atatatatat taatatatat taatatataa 600
atatatatat taatatataa atatatataa atatatatgt aaatatatat ataaatatat 660
ataaatatat atataaatac atataaatat atatataaat atatataaat atatatataa 720
atatatataa atatatatat aaatatatat aa 752

<210> SEQ ID NO 58
<211> LENGTH: 300
<212> TYPE: DNA

<213> ORGANISM: Homo sapiens
<220> FEATURE:
<221> NAME/KEY: misc_binding
<222> LOCATION: (1)..(300)
<223> OTHER INFORMATION: MAR of chromosome 1 genomic contig;
1119049..1119348

<400> SEQUENCE: 58
taatatacat tttatataat atatgtaata tatattttat atatatgtaa tatatatttt 60
atataatata tgtaatatat attttatata tatgtaatat atattttata taatatatgt 120
aatatatatt ttatataata tatgtaatat atattttata taatatatgt aatatatatt 180
ttatataata tatgtaatat atattttata taatatatgt aatatatatt ttatataata 240
tatgtaatat atattttata taatatatgt aatatatatt ttatatatat gtaatacata 300

<210> SEQ ID NO 59
<211> LENGTH: 617
<212> TYPE: DNA
<213> ORGANISM: Homo sapiens
<220> FEATURE:
<221> NAME/KEY: misc_binding
<222> LOCATION: (1)..(617)
<223> OTHER INFORMATION: MAR of chromosome 1 genomic contig;
3603613..3604229

<400> SEQUENCE: 59
aaaatataat atatataata tataatatat ataatatatt atatataaaa tatataatat 60
ataatatata taataaaata tacataatat ataatgtata ataaaatata cataatatat 120
aatatataat aaatatataa tatataatat ataataaaat atataatata taatatataa 180
taaaatatat aatatattat atataataaa atatataata tattatatat aataaaatat 240
ataatatatt atatataata aaatatataa tatattatat ataataaaat atataatata 300
ttatatataa taaaatatat aatatattat atataataaa atatataata tataatatat 360
aataatatat ataatatata atatatataa taaaatatat ataatatata atatatataa 420
taaaatatat aatatataat atatataata aaatatatat gatatataat atatataata 480
aaatatatga tatataatat atataataaa atatataata tataatataa tatataatat 540
atatactaaa aaatatataa tatataataa aaaatatata atatataata tatataatat 600
ataataaaat atatata 617

<210> SEQ ID NO 60
<211> LENGTH: 674
<212> TYPE: DNA
<213> ORGANISM: Homo sapiens
<220> FEATURE:
<221> NAME/KEY: misc_binding
<222> LOCATION: (1)..(674)
<223> OTHER INFORMATION: MAR of chromosome 1 genomic contig;
2592460..2593133

<400> SEQUENCE: 60
taagcttata tatatatata agcttatata tatatatata agcttatata tatatagaaa 60
gcttatatat atatagaaag cttatatata taagaagctt atatataaaa gcttatgtat 120
aaatatatat aaatatattt atttatgctt atagatacat atataaatat atttatttat 180
atttatatat aaacatatat ttatatatat ttatataata tttatttatt atataaataa 240
atatataata aataataaat atatataata tatttattgt attatttata taaatttatt 300
aatataatat ataataaaat aataattata taaatatata aatatctata aatatatata 360
aatatatata atatctataa atatatataa atataaatat atataatatc tataaatata 420
gataaatata aatatatata atatctataa atatagataa atataaatat atataactat 480
atataaatat atataactat atataaatat atatataaat atatataact atatatataa 540
ctatatatat aaatatatat aactatatat ataaatatat atataaatat atataactat 600
atatataaat atatataact atatataaat atatatataa atatatataa ctatatatat 660
aaatatatat ataa 674

<210> SEQ ID NO 61
<211> LENGTH: 1694
<212> TYPE: DNA
<213> ORGANISM: Homo sapiens
<220> FEATURE:
<221> NAME/KEY: misc_binding
<222> LOCATION: (1)..(1694)
<223> OTHER INFORMATION: MAR of chromosome 1 genomic contig;
2891680..2893373

<400> SEQUENCE: 61
atatgtaata catatattat atatgcatat atacatgcat atgtatatac atatattata 60
tatgcatata tacatgcata tgtatataca tatataaagt atgattatat ataatatata 120
catgtatatg tatatacatg tatatattat attatatatt atttatacat attattatgt 180
ctatatataa tataatatat acatattaat aatataatac ataatataat ataatatatt 240
atataataca taatataata taatatatta tataatacat aatataatat aatatattat 300
atgatacata atataatata atatattata tgatacataa tataatataa tacatattaa 360
taatatatta ttattattaa tataatatat acatattaat atacatacat atatattata 420
ttatatataa tatacatata atataatatg taatattata tataatataa tacataatat 480
aatacatatt aataatatat tattaataag ataatatata tgtatctata atatatacat 540
atatgtatat gtatgtatat attatagata tacatgttta tacatgtata tattatagat 600
atatacatgt atatacatgt atatattata gatatataca tgtatatacg tatatattat 660
agatatacat gtatatatgt atatatatta tagatataat atatacaaga atataagaat 720
atatataata taatatataa tacacataat acgtatatat tatatataca tgtatattat 780
atatgtacat atatacatgt atattatata tacatgtata ttatatatac atgcatatta 840
tatatatttt tatatataat atccatgtat attatgtata tttgtgtata ttatatatac 900
atgtatatta tatatacatg catattatat atatttttat atataaatatc catatatatt 960 atgtatattt gtgtatatta tatatacaca tatattatat atacatggat attatatata 1020
cacatatatt atatatacat atatattata tatacacata tattatatat acatgtatat 1080
tatatataca cgtatattat atatacacac gtatattata tatacacgta tattatatat 1140
acacacgtat attatatata cacgtatatt atatatacac acgtatatta tatatacacg 1200
tatattatat atacacacgt atattatata tacacgtata ttatatatac acacgtatat 1260
tatatataca cgtatattat atatacacac gtatattata tatacacgta tattatatat 1320
acacacgtat attatatata cacgtatatt atatatacac acgtatatta tatatacatg 1380
tatattatat atacatgtat attatatata cacatgtata ttatatatac atgtatatta 1440
tatatacaca tgtatattat atatgcatgt atattatata tacacatgta tattatatat 1500
acacatgtat attatatata catatatatt atatatacat gtatattatg tatacatata 1560
tattatatat acatgtatat tatagataca tatatattaa atatacatgt atattatgta 1620
tacatatata ttaaatatac atgtatattg tatatacata tatattatat acatgtatat 1680
tacatgtata cata 1694

<210> SEQ ID NO 62
<211> LENGTH: 587
<212> TYPE: DNA
<213> ORGANISM: Homo sapiens
<220> FEATURE:
<221> NAME/KEY: misc_binding
<222> LOCATION: (1)..(587)
<223> OTHER INFORMATION: MAR of chromosome 1 genomic contig;
3432560..3433146

<400> SEQUENCE: 62
gaattatata tatatagctg aattatatac atatataata tatacaatat atattatata 60
tttatatatg atatatacaa tatatattac atattatata tacaatatat aatatataat 120
atataatatt atatattata tattgtatat aatatatatt atataacatt atataatata 180
taatattata tattatatat tgtatataat atatattata taacattata taatatatac 240
tattatatat tataatatat aatatataat aatatataat agtatatatt atatatattg 300
tatatattat atataaatat ataatatata atatatatta tataatatat attatataat 360
atatattatt atatattata tatttatata taatatatat tatatatatt atattttata 420
tataaatata taatatataa taatatataa tttaatatat ataatatata caatatataa 480
tatataatat attaatatat ataatatata caatatataa tatataatat ataatatata 540
atataaatta ttatatataa tatatattat atatagctga attatat 587

<210> SEQ ID NO 63
<211> LENGTH: 313
<212> TYPE: DNA
<213> ORGANISM: Homo sapiens
<220> FEATURE:
<221> NAME/KEY: misc_binding
<222> LOCATION: (1)..(313)
<223> OTHER INFORMATION: MAR of chromosome 1 genomic contig;
3805392..3805704

<400> SEQUENCE: 63
tatataatat gtatattatg taatatttta tatagcatat atgtatatta tatataatct 60
tttatatata gtatataata tgtatattat atattatata attatataat tatgtattat 120
ataaaatata ttatataata tataattata tattttttga aatatagatt atatataata 180
tatatggcag tgagctgaga tataatatat attatctata ctatataata tatattatat 240
atactctata ttatatatgt atatattata tataatatat acatatataa tgtgtatata 300
ttatatataa taa 313

<210> SEQ ID NO 64
<211> LENGTH: 349
<212> TYPE: DNA
<213> ORGANISM: Homo sapiens
<220> FEATURE:
<221> NAME/KEY: misc_binding
<222> LOCATION: (1)..(349)
<223> OTHER INFORMATION: MAR of chromosome 1 genomic contig;
4521378..4521726

<400> SEQUENCE: 64
ttatatacac tatataatat gtatttatat atacttatat acactatata tgtatttata 60
tataattata tacactatat aatatgtatt tatatataat tatatacact atataatatg 120
tatttatata taattatata cactatataa tatgtattta tatataattg tatacactat 180
ataatgtata tttatatata attgtataca ctatataatg tatatttatg tataattgta 240
tacactatat aatgtatatt tatgtataat tgtatacact atataatgta tatttatgta 300
taattgtata taccatataa tgtatattta tgtataattg tatatacca 349

<210> SEQ ID NO 65
<211> LENGTH: 500
<212> TYPE: DNA
<213> ORGANISM: Homo sapiens
<220> FEATURE:
<221> NAME/KEY: misc_binding
<222> LOCATION: (1)..(500)
<223> OTHER INFORMATION: MAR of chromosome 1 genomic contig;
3240166..3240665

<400> SEQUENCE: 65
ttaatatata atatatatta tatatttata tattaatata taatatatat ttatatataa 60
tatatattat atatttatat tacatatatt tatatgttaa tatatatttt atatatttat 120
atattttata tatttatata ttatatattt atatattata tttatatatt atatatttat 180
attatatatt tatatattat atttatatat tatatattta tattatatat ttatatattg 240
tatatttata ttatatattt atatattgta tttatatatt atatatttat atactatata 300
tatttatata tattatatat ttatatatta tatatattta tatatattat atatttatat 360
attatatata tttatatata ttatatattt atatattata tatatttata tatattatat 420
atatttatat atattatata tttatatata atatatatta tatattttat ctatatattt 480
atatattaat atatattata 500

<210> SEQ ID NO 66
<211> LENGTH: 866
<212> TYPE: DNA
<213> ORGANISM: Homo sapiens
<220> FEATURE:
<221> NAME/KEY: misc_binding
<222> LOCATION: (1)..(866)
<223> OTHER INFORMATION: MAR of chromosome 1 genomic contig;
409429..410294

<400> SEQUENCE: 66
atatatataa tatattatat atattatata ttatatatat aatacatata ttatatatat 60
aatatataat acatatatta tatatattat atattatata taatatataa tacatatatt 120
atatataata tataatatat aatatattat ataatataat tatataatta tataatataa 180
tataatatat aatattatat aattatataa tatatataat tatattatat attataaata 240
ttatataata tatatattac aaatatatat tatatatatt ataaatatta tataacatat 300
atattatata atatatataa tatataatat atataaaaat ataatatata agatatatat 360
aatatatgat atatatgata tataatatat gatatatatg atatatataa tatatgatat 420
atatgatata tatgatatat ataatatatg atatatatga tatatatgat atatgatata 480
tatgatatat gatatatatg atatatatga tatatgatat atatgatata tatgatatat 540
gatatatatg atatatatga tatatgatat gatatatata atatatgata tgatatatat 600
aatatatgat atatatgata tatgatatgt aatatatatg atatattata tataatatat 660
aatatataca taatatataa tatataatat ataatatata taatatgtga tatatataat 720
atatgatata tgatatatga tatatattat ataatatata taatatatat tatatataat 780
atatattata taatatatat aatatatatt atatataata tataagatat aagatataat 840
atatataata tataatatat ataata 866

<210> SEQ ID NO 67
<211> LENGTH: 335
<212> TYPE: DNA
<213> ORGANISM: Homo sapiens
<220> FEATURE:
<221> NAME/KEY: misc_binding
<222> LOCATION: (1)..(335)
<223> OTHER INFORMATION: MAR of chromosome 1 genomic contig; 614754..615088

<400> SEQUENCE: 67
acccaatata tgtgtatata tgtatgtata tatacatata catacataca tatatgtaca 60
tacatatata catacataca tatatatgta catacatata tacatacata catatataca 120
tataacatat atacacacat atatacagat atacatatat acatacatat atacatataa 180
catatataca tacatatata catataacac atacatacat acatatatac atacaacata 240
tatacataca tatatacata tgtatacata catatatgta tacatatatg tatacatata 300
tgtatacata tatgtatata tatattgtta tatat 335

<210> SEQ ID NO 68
<211> LENGTH: 455
<212> TYPE: DNA
<213> ORGANISM: Homo sapiens
<220> FEATURE:
<221> NAME/KEY: misc_binding
<222> LOCATION: (1)..(455)
<223> OTHER INFORMATION: MAR of chromosome 1 genomic contig; 1299520..1299974

<400> SEQUENCE: 68
ggatatatat attattagtt gttatattat tatatattat atatattatt atatataata 60
tattatatca tatatattat tatatataat atattatatc atatatatta ttatataata 120
tattatatca tatatattat tatatataat atatattata tatattatta tatataatat 180
atattatata tattattatg tataatatat atattatata ttatttatat atatataaat 240
tatataataa tatataatta attatacata tatacatata taagtataca tataatatat 300
ttatatagta tatataaata tatatacaat atatttatat attatatatt atatataaat 360
atatacaata tatttatatc atatatttta tatatgatac atataatata tattatatat 420
gatatataat atatatcata tatgatatat aacat 455

<210> SEQ ID NO 69
<211> LENGTH: 404
<212> TYPE: DNA
<213> ORGANISM: Homo sapiens
<220> FEATURE:
<221> NAME/KEY: misc_binding
<222> LOCATION: (1)..(404)
<223> OTHER INFORMATION: MAR of chromosome 1 genomic contig; 1970778..1971181

<400> SEQUENCE: 69
atatataata tgtataatat ataatatata tcatatattg ttctatgtat attacatata 60
atatgcatta tatattatat attgcatata atatgcatta tatattatat attgcatata 120
atatgcatta tatattatat attgcatata atatgcatta tatattatat attgcatata 180
atatgcatta tatattatat attgcatata atatgcatta tatattatat attgcatata 240
atatgcatta tatattatat aatatataca catataatat atataattta tatatattta 300
tatatattta catttattat atatttatta tatataaata tatttttata tattacttat 360
atattatata taatatatat aatatatata ttatatataa tata 404

<210> SEQ ID NO 70
<211> LENGTH: 605
<212> TYPE: DNA
<213> ORGANISM: Homo sapiens
<220> FEATURE:
<221> NAME/KEY: misc_binding
<222> LOCATION: (1)..(605)
<223> OTHER INFORMATION: MAR of chromosome 1 genomic contig; 3562918..3563522

<400> SEQUENCE: 70
tatatatata aaatacatat atattatata tattatatat aatacatata ttatatatta 60
tatataatac acgtatataa tatataatat ataatacata taatatatat gatatataat 120
acatataata tatatgatat ataatacata tataatatat atgatatata atacatatat 180
aatatatatt atatataata catatataat atatattata tataatacat atataatata 240
tattatatat aatacatata taatatatat tatatataat acatatataa tatatattat 300
ataatacata tataatatat attatataat acatgtatat aatatatatt atatataata 360
catatatatt atataataca tgtatataat atatattata tataatacat atatattata 420
tattatatat taatatattt atataatagt aatatataat attaatatat tatatatatt 480
aatattatat ataatacata tattatatat aatataaata tatataatac atatataata 540
cacatattat atataataca tatattatat ataatatata tattatatat aatatatatg 600
taata 605

<210> SEQ ID NO 71
<211> LENGTH: 317
<212> TYPE: DNA
<213> ORGANISM: Homo sapiens
<220> FEATURE:
<221> NAME/KEY: misc_binding
<222> LOCATION: (1)..(317)
<223> OTHER INFORMATION: MAR of chromosome 1 genomic contig; 189743..190059

<400> SEQUENCE: 71
tattttttat atttatatat tatatatatt tttatatgta atatattata tataaaatta 60
tataatttta ctacatataa tatataaaat tatataattt tactacatat aatatataaa 120
attatataat tttactatat ataatatata aaattatata attttatata taatatatat 180
tataatatat attatatgca atatatatta tatattatat tataatatat tgtatatttt 240
tgtatataaa atatataata tataatatat ttatagacaa taatatataa tataatatat 300
aaaattttat atataaa 317

<210> SEQ ID NO 72
<211> LENGTH: 522
<212> TYPE: DNA
<213> ORGANISM: Homo sapiens
<220> FEATURE:
<221> NAME/KEY: misc_binding
<222> LOCATION: (1)..(522)
<223> OTHER INFORMATION: MAR of chromosome 1 genomic contig; 229111..229632

<400> SEQUENCE: 72
gatatatata tttatatata taaaagatat atattattta tatataaaga tatatattta 60
tatatataaa agatatatat tatttatata tataaaagat atatatttat atatatgata 120
tatattattt atatatataa aagatatata tttatatata tgatatatat tatttatata 180
taaaagatat atataaaaga tatatattat ttatatatat aaaagatata tatataaaag 240

-continued

```
atatatatta tttatatata taaatgatat atattattta tatataaaag atatatatta    300

tttatatata aaagatatat attatttata tatataaaag atatacatat aaaagatata    360

tatttatata taaaagatat atatatttat atataaaaga tacatatatt tatatatata    420

aaagatatat atatttttat atataaaata tatattatat atataaaaga tatatataaa    480

tatatatatc ttttatatat aaaagatata tataaatata ta                       522


<210> SEQ ID NO 73
<211> LENGTH: 1110
<212> TYPE: DNA
<213> ORGANISM: Homo sapiens
<220> FEATURE:
<221> NAME/KEY: misc_binding
<222> LOCATION: (1)..(1110)
<223> OTHER INFORMATION: MAR of chromosome 1 genomic contig;
      1138030..1139139

<400> SEQUENCE: 73

tatgtatgta tacataatat attatatatg tatattatgt atacataata tattatatat     60

gtatattatg tatacataat atattatata tgtatattat gtatacataa tatattatat    120

attatatgta tattatgtat acataatata ttatatatta tatgtatatt atgtatacat    180

aatatattat atattatatg tatattatgt atacataata tattatatat tatatgtata    240

ttatgtatac ataatatatt atatattata tgtatattat gtatacataa tatattatat    300

attatatgta tattatgtat acataatata ttatatatta tatgtatatt atgtatacat    360

aatatattat atattatatg tatattatgt atacataata tattatatat tatatgtata    420

ttatgtatac ataatatatt atatattata tgtatattat gtatacataa tatattatat    480

attatatgta tattatgtat acataatatt tatatattat atgtatatta tgtatacata    540

atatattata tattatatgt atattatgta tacataatat gtacacataa tatttatata    600

ttatatgtat attatgtata cataatattt atatattata tgtatattat gtatacataa    660

tatttatata ttatatgtat attatgtata cataatattt atatattata tgtatattat    720

gtatacataa tatttatata ttatatgtat attatgtata cataatatat tatatattat    780

atgtatatta tgtatacata atatattata tattatatgt atattatgta tacataatat    840

attatatatt atatgtatat tatgtataca taatatttat atattatatg tatattatgt    900

atacataata tattatatat tatatgtata ttatgtatac ataatatatt atatattata    960

tgtatattat gtatacataa tatattatat attatatatg tatattatgt atacataata   1020

tattatatat tatatatgta tattatgtat tatattatat attatgtata ttatagatta   1080

tgtatgcata cataatatgt attgtatatt                                    1110


<210> SEQ ID NO 74
<211> LENGTH: 521
<212> TYPE: DNA
<213> ORGANISM: Homo sapiens
<220> FEATURE:
<221> NAME/KEY: misc_binding
<222> LOCATION: (1)..(521)
<223> OTHER INFORMATION: MAR of chromosome 1 genomic contig;
      2863407..2863927

<400> SEQUENCE: 74

aatatatata aatatataaa tatatataaa tatatataca tataaatata taaatatata     60

tatgtaaata tatgtaaata tatgtaaata tatgtatatg tatatatatg taaatgtatg    120

taaatatata taaatatatg taaatatata taaatatacg taaatatata aatatatata    180
```

actatatata aatatatata aatataaata tataaatata tataaatata tataaatata 240
taaataaata catataaata tataaataaa tacatataaa tatatataaa tatataaaaa 300
tatatataaa tatatatata aatatataaa catatataaa tatataaata tatataaata 360
tataaataca taaaatatat aaatatatat aaatatataa atatatataa atatagataa 420
atatagataa atatataaat atatataaat atataaatat agataaatat ataaatatat 480
aaatataaat atataaaaat atatataaat atataaaaat a 521

<210> SEQ ID NO 75
<211> LENGTH: 560
<212> TYPE: DNA
<213> ORGANISM: Homo sapiens
<220> FEATURE:
<221> NAME/KEY: misc_binding
<222> LOCATION: (1)..(560)
<223> OTHER INFORMATION: MAR of chromosome 1 genomic contig;
5712303..5712869

<400> SEQUENCE: 75
atataattat atatatatta tatattatat ataattatat attatatata atgtataatt 60
atatattata tataatatat ataaatatat atatttttta tataaatata ttatatattt 120
atatattata tataaattta tatatataaa tttttatata ttatatatat ttatatatta 180
tatattgtat atatttatat attacatatt gtatatattt atatattata tattatatat 240
ttatatatta tatattatat atttatatat tatatattat atatatttat atattatata 300
taaattattt atatataata tataaatata tattatataa tataaatttg tatatataat 360
atatatttat attatatata aaatatttat attatatata aaatataata taaatatata 420
catataatat atatattata tatttataat tatatattat atataataca tataatatat 480
aatatataat acatatatat catatatgaa atatatatca tatattatac atattatata 540
taacatatat attatatatc 560

<210> SEQ ID NO 76
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAR of chromosome 1 genomic contig;
8578812..8579290

<400> SEQUENCE: 76
tatggtatac atatagtata tatggggtac atatatggta tatatatggg ttatatatat 60
gatatatatt atatatgtat atggtatata tatggtatat atattataca tgcatatggt 120
atgtatatgg tatatatatg atatatacat atggtgtata tatatgttat atatgatata 180
tataaggtat atatatggta tatataaggt atatatagta tatatatggt atatataagg 240
tatatattgt atatatatgg tatatataag gtatatatat tgtatatatg gtatatatat 300
ggtttatata tatggtgtgt atatatggtg tttatataca cactttatat actatatatt 360
atatacacac tatatataat atatattata tatagttaaa tatatggtat atgcaattag 420
atatatggta tatgtaatta tatatatggt atatagatgg tgtatatatg gtatatata 479

<210> SEQ ID NO 77
<211> LENGTH: 477
<212> TYPE: DNA
<213> ORGANISM: Homo sapiens
<220> FEATURE:
<221> NAME/KEY: misc_binding
<222> LOCATION: (1)..(477)
<223> OTHER INFORMATION: MAR of chromosome 1 genomic contig;
      8579294..8579770

<400> SEQUENCE: 77
tatagtatat atacacacta taggtaatat actacatatt atatacacac tataaataaa     60
atatataata tataatattt tctatatagt atatattata tattgtatat actatatata    120
atatatacta tagacagtag atactttata tactatagac agtatatact atatactgta    180
tacactatag acagtatata ctatatactg tatacagtat atgtagtgta tatgtagtgt    240
atataatata tagtatatat tatctatact atatacagta tatatagtgt atacataata    300
tatattatat attatatata ctatatacag tatacatagt gtatatgtag tgtataaatat    360 atataatgtg tatataaaat atatatacta tatataatat atattatata taatatatac    420
actatatata ctatagatac actatatatt cactatatat actatatata ctatata      477

<210> SEQ ID NO 78
<211> LENGTH: 331
<212> TYPE: DNA
<213> ORGANISM: Homo sapiens
<220> FEATURE:
<221> NAME/KEY: misc_binding
<222> LOCATION: (1)..(331)
<223> OTHER INFORMATION: MAR of chromosome 1 genomic contig;
      8580024..8580354

<400> SEQUENCE: 78
actatatgtt atatacataa gatatagtat ataccatata ttatatacat tatatatagt     60
gtatactata tataatgtat ataatatata gtatatatac actatatata ctatgtatat    120
atacactata tatactatgt atatatacac tatatatact atgtatatat acactatata    180
tactatgtat atatacacta tatatactat gtatatatac actatatata ctatgtatat    240
atacactata tatactatgt atatatacac tatatatact atgtatatat agtgtatata    300
tactgtatat gttatagtgt atatatagta t                                   331

<210> SEQ ID NO 79
<211> LENGTH: 410
<212> TYPE: DNA
<213> ORGANISM: Homo sapiens
<220> FEATURE:
<221> NAME/KEY: misc_binding
<222> LOCATION: (1)..(410)
<223> OTHER INFORMATION: MAR of chromosome 1 genomic contig;
      8580705..8581114

<400> SEQUENCE: 79
tatagtctat attatataca gtctatataa tatatagtat atactatata tacttttcct     60
cattctgact atatactata tatatactat atatagtata tgtagtgtat atatacacca    120
tatatactat atatagtata cataccatat atagtatact atacatacca tatatagtat    180
acataccgta tatagtatac tatacttacc atatatagta tacatactat atataatata    240
tctggtgtat atatacacta tatatactat atatactata tatagtatat gtacactatt    300
tatagtattt atagtatata tactgtatat atagtatgta gtatatatac tatatattat    360
gtagactata tataatatag actatgtgta gagtatatat actatatata              410

<210> SEQ ID NO 80
<211> LENGTH: 433
<212> TYPE: DNA

<213> ORGANISM: Homo sapiens
<220> FEATURE:
<221> NAME/KEY: misc_binding
<222> LOCATION: (1)..(433)
<223> OTHER INFORMATION: MAR of chromosome 1 genomic contig;
      12979167..12979599

<400> SEQUENCE: 80
atatataata tatatatgtc ctatatataa aatatatcat atatataaat atatatgata 60
tattttatat attaaatata taattatata taaatatata tttatatata aatatattat 120
ttcaatatat ataaatatat ttaaatatat ttaaatagaa tattaaatat ataaatatat 180
aattatattt aatatataaa tatatattaa atatataatt atatttaata tatataaata 240
tatattaaat atataattat atatttatat atttattata tataaatata tatttgttct 300
aaataaatat atattctaaa tatataatat tttatattat ataatatata atataaaata 360
tataataaat atataatata taaataaata aatatttatt ataaaataca tataaatatt 420
aaatatatat taa 433

<210> SEQ ID NO 81
<211> LENGTH: 385
<212> TYPE: DNA
<213> ORGANISM: Homo sapiens
<220> FEATURE:
<221> NAME/KEY: misc_binding
<222> LOCATION: (1)..(385)
<223> OTHER INFORMATION: MAR of chromosome 1 genomic contig;
      16336644..16337028

<400> SEQUENCE: 81
tttatataaa tatctatata aataaatata taaatatata aatataaata tatataaata 60
tataaataaa tatataaata tatataaata taaatatata tataactatg aatttatatt 120
tatataaata tatatctata tgaatataaa tatatattta tataaatata aatatatata 180
taaatatata tatttatata gatataaata tatatataaa tatatatatt tatatagata 240
taaatatata tctatatatg aatatatatc tataggaata taaatatata tctatataaa 300
tataaatata tataagtata aatatatata aatatatatc tatataaata taaatatata 360
tataaatata aatatatata taaat 385

<210> SEQ ID NO 82
<211> LENGTH: 363
<212> TYPE: DNA
<213> ORGANISM: Homo sapiens
<220> FEATURE:
<221> NAME/KEY: misc_binding
<222> LOCATION: (1)..(363)
<223> OTHER INFORMATION: MAR of chromosome 1 genomic contig;
      20624448..20624810

<400> SEQUENCE: 82
tatatatata gttatatata tatttatata tatagttata tatatatttt tatatagtta 60
tatatatagt tatatatata gttatatata tatagttata tatatagtta tatatatagt 120
tatatatata tagttatata tatagttata tatatagtta tatatatagt tatatatata 180
tagttatata tatagttata tatatatagt tatatatata gttatatata tatagttata 240
tatatagtta tatatatagt tatatatata gttatatata tagttatata tatatagtta 300
tatatatata gttatatata tatagttata tatatagtta tatatatata gttatatata 360
tag 363

<210> SEQ ID NO 83
<211> LENGTH: 310
<212> TYPE: DNA
<213> ORGANISM: Homo sapiens
<220> FEATURE:
<221> NAME/KEY: misc_binding
<222> LOCATION: (1)..(310)
<223> OTHER INFORMATION: MAR of chromosome 1 genomic contig;
566025..566334

<400> SEQUENCE: 83
tatatataat atatattgta tatattatat attgtatata taatatatat tgtatatatt 60
atatattgta tatataatat atattgtata tattatatat tgtatatata atatatatat 120
tgtatatatt atatattgta tatataatat atatattgta tatattatat attgtatata 180
taatatatat attgtatata ttatatattg tatatataat atatatattg tatatattat 240
atattgtata tataatatat atattgtata tattatatat agtatatatt atatatagta 300
tatataatat 310

<210> SEQ ID NO 84
<211> LENGTH: 1236
<212> TYPE: DNA
<213> ORGANISM: Homo sapiens
<220> FEATURE:
<221> NAME/KEY: misc_binding
<222> LOCATION: (1)..(1236)
<223> OTHER INFORMATION: MAR of chromosome 1 genomic contig;
1171429..1172664

<400> SEQUENCE: 84
aaagtattat atgtattata tgtatatgta ttatatatta catatgtatt atatataata 60
tatattatat attattatat attatatatt atatattatt atttatataa tgtattatat 120
attatatagt atatatagta tatataatgt attatatatt atatagtata tatagtatat 180
ataatgtatt atatatagta tatataatgt attatatagt atatatacta tataatgtat 240
tacatattat gtatagtata tgtaatgtat tatatattat atagtatatg taatgtatta 300
tatgtattat atagtatata ttatatatga tgtattattt agtatatata atatatatga 360
tgtattatat aacatatata atatatatga tgtattatat agcatgtata gtatatatga 420
tgtattatat agcatgtata gtatatatga tgtattatat atagcatgta tagtatatat 480
gatgtattat atatagcatg tatagtatat atgatgtatt atatatagca tgtatagtat 540
atatgatgta ttatatatag catgtatagt atatatgatg tattatatat agcatgtata 600
gtatatatga tgtattatat atagcatgta tagtatatat gatgtattat atatagcatg 660
tatagtatat atgatgtatt atatatagca tgtatagtat atatgatgta ttatatatag 720
catgtatagt atatatgatg tattatatat agcatgtata gtatatatga tgtattatat 780
attatatatg gtatatatga tgtattatat attatatatg gtatatatga tgtattatat 840
attatatatg gtatatatga tgtattatat attatatata atatatatga tgtattatat 900
attatatata atatatatga tgtattatat atgatgtatt atatataata tatatgatgt 960
attatatata ttattatcta ttatatacga tgtattatat gcaagttatt atgtataata 1020
tataatgtat tatatattat ataatgtata atatataaat atataaatat ataattatgt 1080
ataaatatag aaatatatac attatacatt atatacatta taatgtataa tatataaata 1140
tattatatat aaatgtatac attatatata aatatattat atacattata tataaaatat 1200
gtatatagtt attatacctt atatatacta aacagt 1236

<210> SEQ ID NO 85
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig;
1925173..1925481

<400> SEQUENCE: 85
atatatttat ataaatatat tttatataaa tatatattat ataatattat aatatatgtt 60
atattatata tattttatac aatatataat atatattata tatattttat acaatatata 120
atatatatta tatatatttt atataatata taatatatat tatatatatt ttatacaata 180
tataatatat attatatatt atataatata tattatatat attttatata atatataata 240
tatattttat acaatatata atgtatatca ttatattata taatgtatat catattatat 300
aatgtatat 309

<210> SEQ ID NO 86
<211> LENGTH: 312
<212> TYPE: DNA
<213> ORGANISM: Homo sapiens
<220> FEATURE:
<221> NAME/KEY: misc_binding
<222> LOCATION: (1)..(312)
<223> OTHER INFORMATION: MAR of chromosome 1 genomic contig;
4396756..4397067

<400> SEQUENCE: 86
cacagtgtat atatagtata tatactgtat atatactgtg tatatacact gtatatacac 60
agtgtatata cagtatatat actatatata cactgtgtat atatagtata tataaattct 120
aggaatatat atactatata tatactatat atataaattc taggaatata tacacactat 180
atatacacta tatatacaca tatatacact atatatatta tacacatata ttatatatat 240
acactatata tacacgagat atataacata tacactatat actatacata acatatatac 300
tatatatact at 312

<210> SEQ ID NO 87
<211> LENGTH: 398
<212> TYPE: DNA
<213> ORGANISM: Homo sapiens
<220> FEATURE:
<221> NAME/KEY: misc_binding
<222> LOCATION: (1)..(398)
<223> OTHER INFORMATION: MAR of chromosome 1 genomic contig;
56057..56454

<400> SEQUENCE: 87
atatatatta catattatat atataatata tattatataa tatatattat attatataat 60
atataatata aatataatat aaattatatt atataatata taatataaat ataatataaa 120
ttatataaat ataatatata ttttattata taatataata tatattatat aaatataata 180
tataaattat ataatataat atatattata taatataata tattttatta tataaatata 240
tattatatta tataatatat attttattat ataatatata ttatatattt atagaatata 300
atatatattt tattatataa tatatattat ataatatata ttatatttat atataacata 360
tattattata taaaatatgt ataatatata ttatataa 398

<210> SEQ ID NO 88
<211> LENGTH: 391
<212> TYPE: DNA

<213> ORGANISM: Homo sapiens
<220> FEATURE:
<221> NAME/KEY: misc_binding
<222> LOCATION: (1)..(391)
<223> OTHER INFORMATION: MAR of chromosome 1 genomic contig;
56984..57374

<400> SEQUENCE: 88
tactataata catattatat ataatattat atactatata ttactatatt attatattat 60
atataattaa actatattat agtatataat atataatata tactatatgt aatattacta 120
tgatactgat attatattat atataattaa attatattat attaatatat aaattatata 180
taatacataa tatataaatt atattatatt atttatatat aatgtatgcc atataattta 240
tatataatgc attatatata atttatatat aatgcattaa atataaatta tatataatgc 300
attatatata attatatata atgcattata tataatttat atttaatata taaatttata 360
tttaatatat ttatatatta tatataataa a 391

<210> SEQ ID NO 89
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig;
469547..469855

<400> SEQUENCE: 89
atatatatgt aatatatatg ttatatatgt aatatatatg ttatgttata tatgttatat 60
atatgttata tataatatat atgttatata tacgttatat gttatatata tgttatatat 120
aatatatgtt atatatacgt tatatgttat atatgttata tataatatat gttatatata 180
atatatgtta tatatgttat atataatata tgttatatat attatatata atatatgtta 240
tatatattat atataatata taatatatgt gatatataat ataaaatata tgtgatatat 300
attatatat 309

<210> SEQ ID NO 90
<211> LENGTH: 441
<212> TYPE: DNA
<213> ORGANISM: Homo sapiens
<220> FEATURE:
<221> NAME/KEY: misc_binding
<222> LOCATION: (1)..(441)
<223> OTHER INFORMATION: MAR of chromosome 1 genomic contig;
546190..546630

<400> SEQUENCE: 90
atacacaaca tatgtgtata tatatagtat atatacacaa catatgtgta tatatatagt 60
atatatacac aatatatgtg tatatatata gtatatatac acaatatatg tgtatatata 120
gtataaatat atactatata tagtatatat agtataaata tatactatat atagtatata 180
catagtataa atatatacta tatatagtat atacatagta taaatatata ctatatatag 240
tatatacata gtataaatat atactatata tagtatatac atagtataaa tatatactat 300
atatagtata tacatagtat aaatatatac tatatatagt atatacatag tataaatata 360
tactatatat agtatataca tagtataaat atatactata tatagtatat acatagtata 420
aatatatact atatatagta t 441

<210> SEQ ID NO 91
<211> LENGTH: 1367

<212> TYPE: DNA
<213> ORGANISM: Homo sapiens
<220> FEATURE:
<221> NAME/KEY: misc_binding
<222> LOCATION: (1)..(1367)
<223> OTHER INFORMATION: MAR of chromosome 1 genomic contig;
124643..126009

<400> SEQUENCE: 91
atatttatat gatatataat atatataata ttatatataa tattatatat gatatataac 60
attatataat attatatatg atatatatta tatatattat atatgatata taatatatat 120
aatattatat atgatattat atatcatata taatatataa aatattatat atgatatata 180
atatatataa tattatatat attatatata ttatatatca tatataatat tctaaatata 240
taatattata tgatatataa gattatatac attatatata atatataata ttatatatga 300
tatataatat tatatacatt atatataata tataatgtat ataatattat atattatata 360
tttatattat atacaatgta tataatatta tatatcatat atatttatat tatatacaat 420
gtatataata ttatatatca tatataatat tatatacaat gtatataata tatattatat 480
atatttatat tatatacaat gtatataata tatattatat atatttatat tatatacaat 540
gtatataata tatattatat atatttatat tatatacaat gtatacaata ttatatatta 600
tatattatat atttatatta tatacaatgt atatattata tattatatat ttatattata 660
tacaatgtat atattatata ttatatattt atattatata caatgtatat attatatatt 720
atatatttat attatataca atgtatatat tatatattat atatttatat tatatacaat 780
gtatatatta tatattatat atttatatta tatataatgt atgtaatatt atatattata 840
tatttatatt atatataatg tatgtaatat tatatattat atatttatat tatatataat 900
gtatgtaata ttatatatta tatatttata ttatatataa tgtatgtaat attatatatt 960
atatatttat attatatata atgtatgtaa tattatatat tatatattta tattatatat 1020
aatgtatgta atattatata ttatatattt atattatata taatgtatgt aatattatat 1080
attatatatt tatattatat ataatgtatg taatattata tattatatat ttatattata 1140
tataatgtat gtaatattat atattatata tttatattat atataatgta tgtaatatta 1200
tatattatat atttatatta tatataatgt atataatatt atatattata tatttatatt 1260
gtatataata ttatatatta tatatttata ttgtatataa tatatattat atatttatat 1320
tgtatataat attatatatt atatatttat attatatata atgtata 1367

<210> SEQ ID NO 92
<211> LENGTH: 458
<212> TYPE: DNA
<213> ORGANISM: Homo sapiens
<220> FEATURE:
<221> NAME/KEY: misc_binding
<222> LOCATION: (1)..(458)
<223> OTHER INFORMATION: MAR of chromosome 1 genomic contig;
58908..59365

<400> SEQUENCE: 92
tatatgatat atatgatata tatgggatat atatgatata tatgatatat atggtatata 60
tatgatatat agtatatatg atatatatgg tatatatatg atatatagta tatatgatat 120
atatggtata tatgatatat agtatatatg atatatatgg tatatatggt atatatatga 180
tatatgatat atatgatata tatgatatat gatatatatg atatatatga tatatatggt 240
atatatgata tatatggtat atatggtata tatatgatat atatgatata tatggtatat 300
atatgatata tatgatatat atggtatata tatgatatat atgatatata tggtatatat 360
atgatatata tgatatatat ggtatatata tgatatatat gatatatatc atatatatgg 420
tatatatatg atatatatga tatatatcat atatatgg 458

<210> SEQ ID NO 93
<211> LENGTH: 330
<212> TYPE: DNA
<213> ORGANISM: Homo sapiens
<220> FEATURE:
<221> NAME/KEY: misc_binding
<222> LOCATION: (1)..(330)
<223> OTHER INFORMATION: MAR of chromosome 1 genomic contig;
306867..307196

<400> SEQUENCE: 93
ataatatata aatatatatg atatatatct atatatatca tatataaata tatatgatat 60
atatctatat atatcatata taaatatata tgatatataa atatatatga tatatatcta 120
tatatatcat atataaatat atatgatata taaatatata tgatatatat ctatatatat 180
catatataaa tatatatgat atatatctat atatcatata taaatatata tgatatatat 240
ctatatatat catatataaa tatatatgat atctatctat atatatcata tataaatata 300
tatgatatct atctatatat atcatatata 330

<210> SEQ ID NO 94
<211> LENGTH: 353
<212> TYPE: DNA
<213> ORGANISM: Homo sapiens
<220> FEATURE:
<221> NAME/KEY: misc_binding
<222> LOCATION: (1)..(353)
<223> OTHER INFORMATION: MAR of chromosome 1 genomic contig;
636899..637251

<400> SEQUENCE: 94
tatgtataca tatacacata tacgtatata tatacatata tacacatata cgtatatata 60
tacgtataca tacatatgta tatgtatacg tatacacaca tatgtatatg tatacgtata 120
cacacatata cgtatatatg tatacgtata cacacatata cgtatatgta tacatatata 180
tgtgtacata tacgtatata cgtatatgta tacatatata cgtttatgta tatatacgta 240
tatacgtata tatgtatatg tatacatata tacatatatg tgtatatacg tatatacgta 300
tatgtgtata tatacaatat acatacatgc acatatatgt gtatatgcac ata 353

<210> SEQ ID NO 95
<211> LENGTH: 345
<212> TYPE: DNA
<213> ORGANISM: Homo sapiens
<220> FEATURE:
<221> NAME/KEY: misc_binding
<222> LOCATION: (1)..(345)
<223> OTHER INFORMATION: MAR of chromosome 1 genomic contig;
1435510..1435854

<400> SEQUENCE: 95
atcatatata ttatatatca tatatatgat atataaaaat tatatatcat atatatgata 60
tataaaaatt atatatatca tatataatat atataatata ttatatatat aaattatata 120
taatatatat aaattatata tatcatatat atgatatata atttatatat catatatatg 180
atatatataa tatattattt atatataata tattatatat tatataatat gtaatatata 240
ttatatatta catattatat tatttataaa taatatttta taatatatat aatattatat 300
aatatagaat attatatatt atatattaca tattatataa tatat 345

<210> SEQ ID NO 96
<211> LENGTH: 521
<212> TYPE: DNA
<213> ORGANISM: Homo sapiens
<220> FEATURE:
<221> NAME/KEY: misc_binding
<222> LOCATION: (1)..(521)
<223> OTHER INFORMATION: MAR of chromosome 1 genomic contig; 39695..40215

<400> SEQUENCE: 96

```
tatatatata atagatatta tatatctatt atatatctat tatatatata atagatatta     60

tatatctatt atatatataa tagatattat atatctatta tatatataat agatattata    120

tatctattat atataatata tatctattat atattatata tctattatat ataatatata    180

tctattatat atattatata tctattatat atataataga tattatatat ctattatata    240

taatatatat ctattatata ttatatatct attatatata tgtatctatt atatatatta    300

tgtatctatt atatataata tatatctatt atatatatat tatatataat atatattata    360

tatattatat atctattata tataatatat atctattata tatattatat atctattata    420

tatattatat atctattata tataatatat atctattata tatattatat atctattata    480

tataatatat attatatata tattatatat tgtatatcta t                        521
```

<210> SEQ ID NO 97
<211> LENGTH: 484
<212> TYPE: DNA
<213> ORGANISM: Homo sapiens
<220> FEATURE:
<221> NAME/KEY: misc_binding
<222> LOCATION: (1)..(484)
<223> OTHER INFORMATION: MAR of chromosome 1 genomic contig; 1286007..1286490

<400> SEQUENCE: 97

```
atatcatata tattatatat catatatatg atatataaaa attatatatc atatatatga     60

tatatataaa ttatatatat catatataat atatataata tattatatat ataaattata    120

tataatatta tatataaatt atatatcaca tatatgacat ataaattata tatcacatat    180

atgatatata atttatatat cacatatatg atatataatt tatatatcat atatatgata    240

tataatttat atatcatata tatgatatat aatttatata tcatatatat gatatatata    300

atatattatt tatatataat atattatata ttatataata tgtaatatat attatatatt    360

atataatatg taatatatat tatatattac atattatatt atttataaat aatattttat    420

aatatatata atattatata atatagaata ttatatatta tatattacat attatataat    480

atat                                                                 484
```

<210> SEQ ID NO 98
<211> LENGTH: 244
<212> TYPE: DNA
<213> ORGANISM: Homo sapiens
<220> FEATURE:
<221> NAME/KEY: misc_binding
<222> LOCATION: (1)..(244)
<223> OTHER INFORMATION: MAR of chromosome 1 genomic contig; 73556..73879

<400> SEQUENCE: 98

```
attatatatt atattatata atatataata atattatata attatatatt acattatata     60

atatataata atattatata ataatatata attatataat atataataat attatataat    120

attatataat attatataat atataaatat ataataatat atattatatt atataatagt    180
```

atatattata ttatataata tatgttatta tattatataa tataaactat tatataatat 240
aata 244

<210> SEQ ID NO 99
<211> LENGTH: 463
<212> TYPE: DNA
<213> ORGANISM: Homo sapiens
<220> FEATURE:
<221> NAME/KEY: misc_binding
<222> LOCATION: (1)..(463)
<223> OTHER INFORMATION: MAR of chromosome 1 genomic contig;
179038..179500

<400> SEQUENCE: 99
tacaatatat tttctattat atatattttg tattatatat aatatacaat atattttcta 60
ttatatataa tatattttgt attatatata ttacaatata ttttgtatta tataatatat 120
aatacaatat aatatattgt attatataat atataatact atataatata ttgtattata 180
tattatatat aatactatat aatatatttt attatatatt atatataata ctatataata 240
tattttatta tatattatat ataatacaat atataatata ttgtattata atacaatgta 300
ttataatgta ttatatataa tatataatac aatatataat attatatata tttatatata 360
tatatatttt gtattatata ttttgtatta tatatatttt gtattatata tttatatttt 420
atattataat tatgttttgc attatatatt tcatattata tat 463

<210> SEQ ID NO 100
<211> LENGTH: 390
<212> TYPE: DNA
<213> ORGANISM: Homo sapiens
<220> FEATURE:
<221> NAME/KEY: misc_binding
<222> LOCATION: (1)..(390)
<223> OTHER INFORMATION: MAR of chromosome 1 genomic contig;
55617..56006

<400> SEQUENCE: 100
tgtataatat atatacttta tatataatat atatacttta tatatatact atatactaat 60
atatataata tatactatat ataatatata ctaatatata taatatatac actatatata 120
atatatacta atatatatta tatatacttt atataatata tactaatata tataatatat 180
atactttata tataatatat actaatatat ataatgtata tactttatat ataatatata 240
ctaatatata atatatatac tttatatata atatatacta atatatatta tatatacttt 300
atatatataa tatatactta tatattatat atgcttatat ataatatata cactaatata 360
taatatatat actttatata ttatatttta 390

<210> SEQ ID NO 101
<211> LENGTH: 582
<212> TYPE: DNA
<213> ORGANISM: Homo sapiens
<220> FEATURE:
<221> NAME/KEY: misc_binding
<222> LOCATION: (1)..(582)
<223> OTHER INFORMATION: MAR of chromosome 2 genomic contig;
1157405..1157986

<400> SEQUENCE: 101
tgtatatgta tatatacaca tacgcacata tatgtatatg tatatataca catacgcaca 60
tatatgtata tgtatatata cacatacgca catatatgta tatgtatatg tatatgtata 120
tatacacata tacacatata tgtatatgta tatatacaca tatacacata tatgtatatg 180

-continued

```
tatatataca catatacaca tatatgtata tgtatatata cacatacaca tatatgtata    240

tgtatatgta tatatacaca tacacatata tgtatatgta tatgtatata tacacatata    300

cacatatata catatatgta tacatatatg tgtatatata tacacatata tatacatata    360

tgtatacata tatgtgtata tatacacata tatatacata tatacatata catatatatg    420

tgtatgtata tatacacata tacatatata tgtatatgtg tatatatatt agacagatat    480

atatgtacat atacatatat atgtatatgt atatgtatat gtatatgtat atgtatatgt    540

atatgcatat ataatataca tatacatata tgtatatgta ta                       582
```

<210> SEQ ID NO 102
<211> LENGTH: 322
<212> TYPE: DNA
<213> ORGANISM: Homo sapiens
<220> FEATURE:
<221> NAME/KEY: misc_binding
<222> LOCATION: (1)..(322)
<223> OTHER INFORMATION: MAR of chromosome 2 genomic contig; 1858638..1858959

<400> SEQUENCE: 102

```
acaccatata tacaccatat atatacatac catatatata ccatatatat acataccata     60

tatataccat atatatacat accatatata caccatatat atacatacca tatatataca    120

ccatatatat acataccata tatataccat atatatacat accatatata taccatatat    180

atacatacca tatatataca ccatatatat acataccata tatatacacc atatatatac    240

ataccatata tataccatat atacaccata tatatacacc atatatacac accatatata    300

ccatatatat acaccatata ta                                             322
```

<210> SEQ ID NO 103
<211> LENGTH: 914
<212> TYPE: DNA
<213> ORGANISM: Homo sapiens
<220> FEATURE:
<221> NAME/KEY: misc_binding
<222> LOCATION: (1)..(914)
<223> OTHER INFORMATION: MAR of chromosome 2 genomic contig; 5712196..5713109

<400> SEQUENCE: 103

```
aaatatatat tctatatata gaaaatatat attctatata tatagaatat atatagaata     60

tatattctat atatattcta tatatataga atatatatat aaaacatata ttctatatat    120

aaaatatata ttctatatat ataaaatata tattctatat atatagaatg tatataaaat    180

atatattcta tatatataga atgtatataa aatatatatt ctatatatat agaatgtata    240

taaaatatat attctatata tatagaatgt atataaaata tatattctat atatatagaa    300

tatatataac atatatatga aatatatata aaatatatat aaatacatat ttctatatat    360

aaatatatat aaatacatat ttctatatat aaatatatat caatacatat ttctatatat    420

aaatatatat aaatatatat tcatatatat aaaaatatat aaatatatat tcatatatat    480

aaaatatata tgaatatata ttctctatat ataaaatata tataatatat attatatata    540

taaaatatat ataatatata ttatatatat aaaatatata taatatatat tcatatatat    600

aaattatata taaatatata ttcatatata taatatatat aaatatttat ttcatatata    660

aaatatattt aaatatatat ttctatatag aatatatatt ctatatataa aatatatata    720

taaatatatt ttctatatag aaatatatat gaaatatata gaatatatat aaatatatat    780

tatatatact atatatacaa tatatattat atataaaata tatatacaat atatattcta    840
```

```
tatattaata tatagaatat atattaacat atatttcaat atattaatat atgaaatata    900

tataaatatt tcat                                                      914


<210> SEQ ID NO 104
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of chromosome 2 genomic contig;
      5713613..5713982

<400> SEQUENCE: 104

tatttcatat ataatatata tataaaatat atatttcata tacataatat atataatata     60

aataaaatat atatttcata tatataatat atataatata tataaaacat atatttcata    120

tataatatat ataaactata tatttcatat ataatatata taaactatat atttcatata    180

cataatatat ataatatata tttcatttat attatatata taatatatat ttcatatata    240

taatatataa aatagatata aatatatata aatatatatt tcatatataa tatatataaa    300

atatatatta atatatattt tatatataat atatatattt catatataaa tataaaaaaa    360

tatatatttc                                                           370


<210> SEQ ID NO 105
<211> LENGTH: 442
<212> TYPE: DNA
<213> ORGANISM: Homo sapiens
<220> FEATURE:
<221> NAME/KEY: misc_binding
<222> LOCATION: (1)..(442)
<223> OTHER INFORMATION: MAR of chromosome 2 genomic contig;
      7481647..7482088

<400> SEQUENCE: 105

atataaatta tataatatgt tatataatat ataaatatat tatataacat gttatataat     60

atataacatg ttatataata tataacatgt tatataatat ataacatgtt atataatata    120

taacatgtta tataatatat tatgtaatat gttatataat atataatata ttatataaca    180

tgttatataa tatataacat gttatataat atgttatata atatataaat atattatatt    240

atatgttata taatatataa atatattata ttatatgtta tataatatat aaatatatta    300

tattatatgt tatataatat ataaatatat tatattgtat gttatataat atataaatat    360

attatattgt atgttatata atatataaat atattatatt gtatgttata taatatataa    420

atatattata ttatatatgt ta                                             442


<210> SEQ ID NO 106
<211> LENGTH: 338
<212> TYPE: DNA
<213> ORGANISM: Homo sapiens
<220> FEATURE:
<221> NAME/KEY: misc_binding
<222> LOCATION: (1)..(338)
<223> OTHER INFORMATION: MAR of chromosome 2 genomic contig;
      9594557..9594894

<400> SEQUENCE: 106

tatataaata tataccatat atataaatat atatattcca tatataaata tatatattcc     60

atatatataa atatatatat tccatatata aatatatata ttccatatat ataaatatat    120

atataaatat atatattcca tatatataaa tatatatata aatatatata ttcatatata    180

aatatatata tattccatat ataaaaatat atatatattc catatataaa aatatatata    240
```

tattccatat atataaatat atatatattc catatatata aatatatata tattccatat 300
atataaatat atatatattc catatatata aatatata 338

<210> SEQ ID NO 107
<211> LENGTH: 364
<212> TYPE: DNA
<213> ORGANISM: Homo sapiens
<220> FEATURE:
<221> NAME/KEY: misc_binding
<222> LOCATION: (1)..(364)
<223> OTHER INFORMATION: MAR of chromosome 2 genomic contig;
10519720..10520083

<400> SEQUENCE: 107
ttatatatat ttataataat atatataagc tatatatatt tatatataat atattatata 60
tattagctat atatatttat ataataatat attatatatt agctatatat atttatatat 120
aataatatat ataagctata tatttatata tattatatat tagctatata tatttatata 180
taatatatta tatattagct atatatttat atataataaa taatatatat attagctata 240
tatatttata tataataata tatataagct atatatttat atataatata ttatatatta 300
gctatatata tttatatata ataatatatt atatattagc tatatatatt tatatataat 360
atat 364

<210> SEQ ID NO 108
<211> LENGTH: 342
<212> TYPE: DNA
<213> ORGANISM: Homo sapiens
<220> FEATURE:
<221> NAME/KEY: misc_binding
<222> LOCATION: (1)..(342)
<223> OTHER INFORMATION: MAR of chromosome 2 genomic contig;
11481943..11482284

<400> SEQUENCE: 108
tacatataat atataattat atataatata tattatatat tacatatata atatatatat 60
tacatatgta atatatatat tatatatgta atatatatta tatatgtaat atatatatta 120
tatatgtaat atatattata tatatgtaat atatatatta tatatgtaat atatatatta 180
tatgtaatat atatatgtaa tatatatata atatatatgt aatatatata taatatatat 240
gtaatatata tataatatat atgtaatata tatattatat atatgtaata tatatcatat 300
atatgtaata tatatcatat atatgtaata tatatcatat at 342

<210> SEQ ID NO 109
<211> LENGTH: 415
<212> TYPE: DNA
<213> ORGANISM: Homo sapiens
<220> FEATURE:
<221> NAME/KEY: misc_binding
<222> LOCATION: (1)..(415)
<223> OTHER INFORMATION: MAR of chromosome 2 genomic contig;
13499598..13500012

<400> SEQUENCE: 109
tatatatata tatatatata atataatata atatatatat aaatatatat aatataaatt 60
tatatatata tatttatata tacatatata aatatatatt tatatttata tataaatata 120
tataaatata tataaatata tatttatata tacatatata aatatatatg ttcatataaa 180
tatatatgta tatatacata tataaatata tattatatat gtatatatat aatataatat 240
ataataataa tataatatat attatataaa tataatatat tatatataat atatataata 300

-continued tataatatat aatatataat atataatata tattatatat tatataatat ataaaatata 360
tattatataa tatatataca taatatatat aaataaatat atataaagat ataaa 415

<210> SEQ ID NO 110
<211> LENGTH: 330
<212> TYPE: DNA
<213> ORGANISM: Homo sapiens
<220> FEATURE:
<221> NAME/KEY: misc_binding
<222> LOCATION: (1)..(330)
<223> OTHER INFORMATION: MAR of chromosome 2 genomic contig;
16370976..16371305

<400> SEQUENCE: 110
catttacata tgtatgtata agtatgtata ttacatactt atacatacat acttataaat 60
atataagtat aatacataca tacttataaa tatataagta taatacatac atacttatac 120
atatataagt ataatacata catacttata catatataag tataatacat acatacttat 180
acatatataa gtataataca tacatactta tacatataag tataatacat acatacttat 240
acatatataa gtataataca tacatactta tacatatata agtataatac atacttatta 300
catatgtata taagtatatt acatacttat 330

<210> SEQ ID NO 111
<211> LENGTH: 702
<212> TYPE: DNA
<213> ORGANISM: Homo sapiens
<220> FEATURE:
<221> NAME/KEY: misc_binding
<222> LOCATION: (1)..(702)
<223> OTHER INFORMATION: MAR of chromosome 2 genomic contig;
626641..627342

<400> SEQUENCE: 111
tatatataca catatacata tataatatat atacatatac atatatatta tatatacata 60
tatattacat atatcatata tacatatata ttatatatac atatatatta tatatatcat 120
atatacatat atatattata tattatatat atcatatata catatatatt atatatatta 180
tatatatcat atatacatat atattatata tattatatat acatatatat tatatatatc 240
atataaacat atatattata tatatcatat atacatatat attatatata ttatatatat 300
catatataca tatatattat atatatcata tataatatat attatatata ttatatataa 360
tatatattat atatacatat atattatata tacatatata ttatatatac atatatatta 420
tatatacata tatattatat atacatatat attatatata tacatatata ttatatatac 480
atatatatta tatatacata tattatatat acatatatat tatatataca tatattatat 540
atatacatat atattatata tacatatatt atatatatac atatatatta tatatacata 600
tattatatat atacatatat attatatata catatattat atatacatat atattatata 660
tacatatata ttttatatat atataatata tattttatat at 702

<210> SEQ ID NO 112
<211> LENGTH: 679
<212> TYPE: DNA
<213> ORGANISM: Homo sapiens
<220> FEATURE:
<221> NAME/KEY: misc_binding
<222> LOCATION: (1)..(679)
<223> OTHER INFORMATION: MAR of chromosome 2 genomic contig;
3196047..3196725

<400> SEQUENCE: 112
atatattata tattcatata tcataaatat atatattata tattcatata ttatatatct 60
atatatttat atattcatat attatatatc tatatattta tatattcata tattatatat 120
ctatttatat attcatatat tatatatcta tatattttat atattcgtat attatatatc 180
tatatattat atattcgtat attatatatc tatatattat gtattcatat atatctatat 240
attatatata ttcatatata ttataaatta tattcatata gtatatatct attataaatg 300
tatattcata tagtatatat ctatatatta taaatataca tatattatat atttatatat 360
tatatattca tatagatcta tatattatat atattcatat atgaatatat atattatatg 420
tatatatatt ataaatatat ttatatagta tagatattat atagtatatg catatttata 480
ttataaataa tttacatagt atatgtatat ttataaatta tatatattta catattacat 540
gtatatttat atattataaa tacatattta catattataa atatatttat atattatgaa 600
tataatttat atattattac atatttacat atatgcatag ttatatatta taaatatgca 660
tttatgtaaa tatatattt 679

<210> SEQ ID NO 113
<211> LENGTH: 728
<212> TYPE: DNA
<213> ORGANISM: Homo sapiens
<220> FEATURE:
<221> NAME/KEY: misc_binding
<222> LOCATION: (1)..(728)
<223> OTHER INFORMATION: MAR of chromosome 2 genomic contig;
3196778..3197505

<400> SEQUENCE: 113
tacataaata tatatttaca atatgtaaat atctgatatg taaatatgta tttataatat 60
ataaatatac atataatatg taaatatata aatatacata tactatgtaa atatatgtta 120
tatatacata tactatataa atatagaata tataaatata catatactat ataaatatgt 180
aatatataaa tatatactat ataaatatac atatactata taaatgtatt tataatatat 240
aaatatacat atactatata aattcatata tgaatatata atatataaat atatataata 300
tatgaatata tactcatata taaatatata tgaatatata tttataatat atagatataa 360
tatgaatata tatttataat atatagatat atattatatg aatatatatt tataatatat 420
agatatatac catatgaata tatattatac actatatgaa tatatattta taatatataa 480
atagatatat actatatgaa tatataatat atatactcta tgaatatata atatatatac 540
tatatgaata tattatatac tgtatgaata tataatatat agatgtatac tatatgaata 600
tataatatat agatatatat actatatgaa tatatataat atatagatat atactatatg 660
aatatatatg atatatagat atatactata tgaatatata atatatagat atatatttat 720
gatatatg 728

<210> SEQ ID NO 114
<211> LENGTH: 413
<212> TYPE: DNA
<213> ORGANISM: Homo sapiens
<220> FEATURE:
<221> NAME/KEY: misc_binding
<222> LOCATION: (1)..(413)
<223> OTHER INFORMATION: MAR of chromosome 2 genomic contig;
2560638..2561050

<400> SEQUENCE: 114
atataaatat atatttatat attttatata aatatatata tttatatatt tttatataaa 60
tatatatatt tatatatatt tatataaata tatatattta tatatattta tataaatata 120
taaatatata tatttatata aatatataaa atatataaat atatttatat aaatatataa 180
aatatataaa tatatttata taaatatata aaatatataa atatatttat atataaatat 240
ataaaatata taaatatctt tatatataaa tatataaaat atataaatat ctttatatat 300
aaatatataa aatatataaa tatatttata tataaatata taaaatatat aaatatattt 360
atatacaaat atataaaata tataaatata tttatatata aatatataaa ata 413

<210> SEQ ID NO 115
<211> LENGTH: 361
<212> TYPE: DNA
<213> ORGANISM: Homo sapiens
<220> FEATURE:
<221> NAME/KEY: misc_binding
<222> LOCATION: (1)..(361)
<223> OTHER INFORMATION: MAR of chromosome 2 genomic contig; 4965309..4965669

<400> SEQUENCE: 115
tatacgtata tatacatata tatacgtata tatatacata tatatacgta tatatacata 60
tgtatatatg tgtgtacatg tatatatata catatgtaca tatatatgta cacatatata 120
tatacatata tatgtacaca tatacatata tatgtacaca tatacatata catatatatg 180
tacacatata tatacatata tatgtacaca catatatata catatatatg tacacacata 240
tatacgtata tatgtacaca catatatacg tatatatatg tacacacata tatacgtata 300
tatatgtaca cacatatata tacgtatata tatgtacaca tatatatata cgtatatata 360
t 361

<210> SEQ ID NO 116
<211> LENGTH: 325
<212> TYPE: DNA
<213> ORGANISM: Homo sapiens
<220> FEATURE:
<221> NAME/KEY: misc_binding
<222> LOCATION: (1)..(325)
<223> OTHER INFORMATION: MAR of chromosome 2 genomic contig; 5258150..5258474

<400> SEQUENCE: 116
tacacacaca tatacatata tacatatata cgtgtatacg tatacgtata tacgtatata 60
tacatatatg tatacgtata cgtatatacg tatatataca tatatgtata cgtatacgta 120
tatacgtata tatacatata tgtatacgta tacgtatata cgtatatata catatatgta 180
tacgtatacg tatatacgta tatatacata catatgtata cgtatacgta tatatgtata 240
tatacgtata tgtatacgta tacatatata cgtatatata cgtatatgta tatgtatata 300
cgtatatgta tatatgtaca tatac 325

<210> SEQ ID NO 117
<211> LENGTH: 1508
<212> TYPE: DNA
<213> ORGANISM: Homo sapiens
<220> FEATURE:
<221> NAME/KEY: misc_binding
<222> LOCATION: (1)..(1508)
<223> OTHER INFORMATION: MAR of chromosome 2 genomic contig; 6057499..6059006

<400> SEQUENCE: 117
atataatata tataaattat ataatatata aaaattaata tataatatat ataaattata 60
taatatataa attaattata taatatatat aaattatata atatataaat taattatata 120
atatatataa attatataat acatataaat taattatata atatataaat tatataatat 180

-continued atacaaatta tatactatat taattatata ttatataatt aattatataa tatatataaa 240
ttatatatta ttaaattaat tatataatat ataaattata taatatataa attaattata 300
taatatataa attatataat atataaatta attatataat atataaatta tataatatat 360
aaattaattg tataatatat aaattaatta tataatatat aatatataat taataaataa 420
ttatatatta attatataat taataaataa ataataaata tatataatta atatataata 480
tacatcatat atatcacata tagattatat aatagttata tattatataa taaattatat 540
ataatatata ataaacatat ataacatatg ttatatatta cataatatag tataatatat 600
aacatatgtt atatattaca taatatagta taatatataa catgttatat attacataat 660
atagtataat atataacata tgttatatat tacataatat agtataatat ataacatatg 720
ttatatatta cataatatag tataatatat aacatatgtt atatattaca taatatagta 780
taatatataa catatgttat atattacata atatagtata atatataaca tatgttatat 840
attacataat atagtataat atataacata tgttatatat tacataatat agtataatat 900
ataacatatg ttatatatta cataatatag tataatatat aacatatgtt atatattaca 960
taatatagta taatatataa catatgttat atattacata atatagtata atatataaca 1020
tatgttatat attacataat atagtataat atataacata tgttatatat tacataatat 1080
agtataatat ataacatatg ttatatatta cataatatag tataatatat aacatatgtt 1140
atatattaca taatatagta taatatataa catgttatat attacataat atagtataat 1200
atataacata tgctatatat tacataatat agtataatat atatgttata tattacataa 1260
tatagtataa tatataacat atgttatata ttacatatta tagtataata tatatgttat 1320
atattatata atatagtata atatataatg tatgttatat attatataat atagtataat 1380
atataacatg ttatatatta tataatatag tataatatat atgttatata ttatataata 1440
tagtataata tataatatat gttatatatt atataatata gtataatata tatgttatat 1500
attatata 1508

<210> SEQ ID NO 118
<211> LENGTH: 415
<212> TYPE: DNA
<213> ORGANISM: Homo sapiens
<220> FEATURE:
<221> NAME/KEY: misc_binding
<222> LOCATION: (1)..(415)
<223> OTHER INFORMATION: MAR of chromosome 2 genomic contig;
7996866..7997280

<400> SEQUENCE: 118
caattatata atatacatat tatataattg tataaattat acaatcatat aattatatta 60
tatataatat acatataata taattatata taattatata attttataat ataattatat 120
ataattatat aattatatat aatatatatt ataattatat atataatata tatattatat 180
atattatata taatatataa ataatatata taatatatat ataattatat ataataaatat 240 atgtaatata tataatatat atataatata ttatttataa ttatatatta tatatatatt 300
ataatatata taattataaa taatatatat tataatatat ataataatat atatataatt 360
atatataata atatatatta taattatata taataatata tataatttat ataat 415

<210> SEQ ID NO 119
<211> LENGTH: 526
<212> TYPE: DNA
<213> ORGANISM: Homo sapiens
<220> FEATURE:
<221> NAME/KEY: misc_binding
<222> LOCATION: (1)..(526)
<223> OTHER INFORMATION: MAR of chromosome 2 genomic contig;
8300930..8301455

<400> SEQUENCE: 119
tatatcatat gatatattat acaatatatc atataatatg atatattata tgatatattg 60
tacaatatat catatgatat atgatatatt atacaatata tcatataagg tatatattat 120
atcatatata atatataata taatatatga tataatatat gatatatgat atataatata 180
tgatatatga tatatgatat ataatatatg atatatgata tatgatatat aatatatgat 240
atatgatata tgatatataa tatatgatat atgatatatg atatgatata tgatatatga 300
tataatatat gatataatat atgatatata ttatatgata tataatatat gatataattt 360
atatgatata taatatatga tatataatat ataatatatg atatgatata tattatatca 420
tatataatat ataatataat atatgatata tattatatat ttttatacat tatatatata 480
aactatataa caatataaca tattatgtgt ataatatata ttacat 526

<210> SEQ ID NO 120
<211> LENGTH: 402
<212> TYPE: DNA
<213> ORGANISM: Homo sapiens
<220> FEATURE:
<221> NAME/KEY: misc_binding
<222> LOCATION: (1)..(402)
<223> OTHER INFORMATION: MAR of chromosome 2 genomic contig;
8576553..8576954

<400> SEQUENCE: 120
atgtatatta tatacaatat agtatatcat atatagtata tattatatag taatgtatta 60
tatataatgt ataatgtata aatatataat atatactaca tactatacta ttatatatac 120
tatatattat atatgataca tatactatat aatatgctat atattatact atataatatg 180
ctatatatta tactatataa tatgctatat attatactat ataatatgct atatattata 240
ctatataata tgctatatat tatactatat aatatactat ataatatgct atatattata 300
ctatataata tactatatat tatactatat aatatactat ataacatact atatattata 360
tatgatacat atactatatt acatatataa tatatatata ta 402

<210> SEQ ID NO 121
<211> LENGTH: 477
<212> TYPE: DNA
<213> ORGANISM: Homo sapiens
<220> FEATURE:
<221> NAME/KEY: misc_binding
<222> LOCATION: (1)..(477)
<223> OTHER INFORMATION: MAR of chromosome 2 genomic contig;
8785649..8786125

<400> SEQUENCE: 121
tatttatata tatatttata tatatattta tatatattta tatatatatt tatatatata 60
tttatatata tatttatata tttatatata tatattttta tatatttata tatatattta 120
tatatttata tatatttata tttatatata tatttatata tatttatata tatttatata 180
tatatattta tatatattta tatatatata tttatatata tttatatata tttatatata 240
tatttatata tatatttata tatatattca tatatattta tatatatatt catatatatt 300
tatatatata ttcatatata tttatatata tatttatata tatatttata tatatttata 360
tatatttata tatatattta tatatatatt tatatatata tatttatata tatatttata 420
tatatatatt tatatatata tttatatata tatatttata tatatattta tatatat 477

<210> SEQ ID NO 122
<211> LENGTH: 773
<212> TYPE: DNA
<213> ORGANISM: Homo sapiens
<220> FEATURE:
<221> NAME/KEY: misc_binding
<222> LOCATION: (1)..(773)
<223> OTHER INFORMATION: MAR of chromosome 2 genomic contig;
10064737..10065509

<400> SEQUENCE: 122
atattatata tattacatat atattatatt gtatataata tatatattat attgtatata 60
atatatatat tatattgtat ataatatata tattatattg tatataatat atatattata 120
ttgtatataa tatattatat tgtatatatt atattgtata tattatattg tatacaatat 180
atattatatt gtatacaata tatattatat tgtatataat atattatatt gtatataata 240
tattatattg tatatattat attgtatata atatattata ttgtatataa tatattatat 300
tgtatatatt atattgtata taatatatta tatgtatata atatagtgta tactatatta 360
tataatatat attatataca atatataata tattgtatat catatatgat atattgtata 420
taatatataa tatatgatat attgtatata atatattata tatgatatat tgtatattat 480
atattatata tgatatattg tatattatat attatatatt gtatattgta tattatatat 540
tatatattgt atataatatg ttatatattg tatataatat gttatatatt atatattgta 600
tatatgttat atattatgta ttgtatataa tatgttatat attatatatt gtatataatg 660
tattatatat tatatatatt atatattgta tataatgtat tatatattgt atattatata 720
ttatatattg tatataatat attatataca ttatattata tattatatat tgt 773

<210> SEQ ID NO 123
<211> LENGTH: 1554
<212> TYPE: DNA
<213> ORGANISM: Homo sapiens
<220> FEATURE:
<221> NAME/KEY: misc_binding
<222> LOCATION: (1)..(1554)
<223> OTHER INFORMATION: MAR of chromosome 2 genomic contig;
1039775..1041328

<400> SEQUENCE: 123
ataatatatt aaatgtatat ataatatatt aaatataaat atatttataa tatataaata 60
tttatataaa tataaaatat atattaaata taaatatata taaaatatat attaaatata 120
taaaatataa atatatatta aatatatatt aaatatataa aatataaata tatattaaat 180
atattttaaa tatataaaat ataaatatat attaaatata ttttaaatat attaaatata 240
aatatatatt aaatatattt taaatatatt aaatataaat acatatatta aatatatatt 300
atatatataa aatatataaa atataaatat atattaaata tatataaaat atatatgtta 360
aatatataaa agatatataa aatataaata tatattaaat atatataaaa tatatatata 420
ttaaatatat atattaaata taaatatata taaaatataa atatatgtat taaatatata 480
tattaaatat aaatatatgt attaaatata tattaaatat gaatatatgt attaaatata 540
tattaaatat aaatatatgt attatatata tagaatataa atatatgtat taaatatagt 600
atattaaata taaatatata taaaatatat attaaatatg aatatatata aaatatatat 660
attaaaaata tatataatat aaatatatat aaaatatata tattaaaaat atatataata 720
taaatatata taaaatatat atattaaaaa tatatataaa atatatatat taaaaatata 780
tataaaatat atatattaaa aatatatata aaatatatat attaaaaata tatattaaat 840

-continued

```
ataaatatat atattaaaaa tatatattaa atataactat atattaaata tatattaaat    900

ataactatat attaaatata tattaaatat aactatatat taaatatata ttaaatataa    960

ctatatatta aatatatatt aaatataact atatattaaa tatatattaa atataactat   1020

atattaaata tatattaaat ataactatat attaaatata tattaaatat aactatatat   1080

taaatatata tgaaatataa ctatatatta aatatatatt aaatataact atatgtatta   1140

aatataaata tatgtcttaa atatatatta aatataaata tatgtattaa atatatatta   1200

aatataaata tgtgtattaa atatatatta aatataaata tgtgtattaa atatatatta   1260

aatataaata tgtgtattaa atatatatta aatataaata tgtgtattaa atatctatat   1320

taaatataaa tatatgtatt aaatatatat taaatataaa tatatattaa atatatatat   1380

taaatataaa tatatattaa atataaatat atatattaaa tatatatatt aaatataaat   1440

atatataaaa tatatatatt aaatataaat ataaatataa aatatatatt aaatataaat   1500

acatatatta aatatatgta ttaaatatat atataaaata tatgtattaa atat         1554
```

<210> SEQ ID NO 124
<211> LENGTH: 650
<212> TYPE: DNA
<213> ORGANISM: Homo sapiens
<220> FEATURE:
<221> NAME/KEY: misc_binding
<222> LOCATION: (1)..(650)
<223> OTHER INFORMATION: MAR of chromosome 2 genomic contig;
      3944813..3945462

<400> SEQUENCE: 124

```
catgatatat tatgtataat atatattata gattacatat aaattatata tataatatat     60

aattatataa tatataatat tatataatat attatatata ttatacaatt atataatata    120

tataatatac aattatataa tatataatat acaattatat aatatataat acaatataat    180

atatatttaa tatattatat aatacatatt taatatatta tatattatat gttatatact    240

aaatatataa tatgtattta atatatacta ttatatatgt aatatattat ataatttatg    300

taacatatta tatattatat atgcaatata ttacatgtta catatatatt acatataata    360

tatgtaatat ataatataca ctatattatt atagtatata atatactata ttatgtaatt    420

atataatata gtatattata cactatatta tattatcata taattatata ttatatacta    480

tattacatat atattatgta atataatatg caatatgtta catatataat atatatgtat    540

tatatagtat atatactata gtatatataa aatatatgct ataatatata ttttatatat    600

tatataatac atataatgta tcatatatta tatataatat attttataat              650
```

<210> SEQ ID NO 125
<211> LENGTH: 441
<212> TYPE: DNA
<213> ORGANISM: Homo sapiens
<220> FEATURE:
<221> NAME/KEY: misc_binding
<222> LOCATION: (1)..(441)
<223> OTHER INFORMATION: MAR of chromosome 2 genomic contig;
      5314265..5314705

<400> SEQUENCE: 125

```
tataaatata tatgaaatat atataaatta tatataattt atatatacat atataaatta     60

tatataaatt atatataaat tatatataca tatataaatt atatattata tataaaattg    120

tatatattta tatataaatt gtatatataa tttatatata aattgtatat ataatttata    180

tatacaatgt atatattaat ttatatatac attgtatata taatttatat atacattgta    240
```

-continued

```
tatacaattt atatatacat tgtatataca atttatatat acattgtata tacaatttat    300

atataaatta tattatttat atatagtata tataaatata tatactatat ataaattata    360

tatttattta tatattatat tatttatata taaattatat attatttata tatacattat    420

atataaatta tatattattt a                                              441
```

<210> SEQ ID NO 126
<211> LENGTH: 1169
<212> TYPE: DNA
<213> ORGANISM: Homo sapiens
<220> FEATURE:
<221> NAME/KEY: misc_binding
<222> LOCATION: (1)..(1169)
<223> OTHER INFORMATION: MAR of chromosome 2 genomic contig; 5953971..5955139

<400> SEQUENCE: 126

```
atgtattcat attatatatt tatatataaa taatatacat tcatattata tatttatata     60

taaataatat atattcatat tatatattta tatataaata tataatatat ttatgtataa    120

ataatatata tattcatatt atatatttct atataaataa tatatatatt catattatat    180

atttatatat aaatatataa tatatttata tataaatata taatatattt atatataata    240

tatatattca tattatatat ttatatataa atatataata tatttatata taaataatat    300

atatattcat attatatatt tatatataaa taatatatat tcatattata tatttatata    360

taaataatat atattcatat tatatactta tatataaata atatatattc atattatata    420

cttatatata aataatatat attcatatta tatatttata taaaaataat atatattcat    480

attatatatt tatatataat atatatattc atattatata tttatatatt ctatatattc    540

atattatata tttatatata aataatgtat attcatatta tatatttata tataaataat    600

gtatattcat attatatatt tatatataaa tatatattca tattatatat ttatatataa    660

atatatattc atattatata tttatatata aatatatatt catattatat atttatataa    720

aatatatata ttcatattat atttatatat aaatatatat attcatatat atatttatat    780

ataatatata tattcatatt atatatttat atataaatata tatattcata ttatatattt    840

atatataaat aatatatata ttcatattat atatttatat ataaataatg tatattcata    900

ttatatattt atatataaat aatgtatatt catattatat atttatatat aaatatatat    960

attcatatta tatatttgta tataaatata tattcatatt atatatttgt atatatattc   1020

atatatattt atatataaat atataatatt catattatat ataaatatat atattcatat   1080

tatatattta tatatataaa taatatatat tcatattatt tatatatata aataatatat   1140

attcatatta tttatatata taaataata                                     1169
```

<210> SEQ ID NO 127
<211> LENGTH: 653
<212> TYPE: DNA
<213> ORGANISM: Homo sapiens
<220> FEATURE:
<221> NAME/KEY: misc_binding
<222> LOCATION: (1)..(653)
<223> OTHER INFORMATION: MAR of chromosome 2 genomic contig; 6427669..6428321

<400> SEQUENCE: 127

```
tatatatgta tacatatatg tatatatgtg tatatatgta tacatatatg tatatatgtg     60

tatatatgta tacatatatg tatatatgtg tatatatgta tacatatatg tatatatgtg    120

tatatatgta tacatatatg tatatatgtg tatatatgta tacatatatg tatatatgtg    180
```

-continued

```
tatatatgta tacatatatg tatatatgtg tatatatgta tacatatatg tatacatgtg    240

tacatgtgta tacatatatg tatacatgtg tacatgtgta tacatatatg tatacatgtg    300

tacatgtgta tacatatatg tatatatgtg tatacatata tgtatatatg tgtatatatg    360

tatacatata tgtatataag tgtatatatg tgtatatgta tataagtgta tatatgtgta    420

tatgtatata agtgtatata tgtgtatatg tatataagtg tatatatgtg tatatatgta    480

tacatatatg tatatatgtg tatatatgtg tatatgtata taagtgtata tatgtgtata    540

tatgtataca tatatatgtg tatatatgta tacatatatg tatatatgtg tatatatgta    600

tacatatatg taaatatgtg tatatatgtg tatatgtata taagtgtata tat           653
```

<210> SEQ ID NO 128
<211> LENGTH: 414
<212> TYPE: DNA
<213> ORGANISM: Homo sapiens
<220> FEATURE:
<221> NAME/KEY: misc_binding
<222> LOCATION: (1)..(414)
<223> OTHER INFORMATION: MAR of chromosome 2 genomic contig; 10890453..10890866

<400> SEQUENCE: 128

```
tatattttgt aaatatatat atagtaaata tatgtaaata tatatatttt gtaaatatat     60

atatattttg taaatatatg taaatatata tattttgtaa atatatgtaa atatatatat    120

tttgtaaata tatgtaaata tatatatttt gtaaatatat gtaaatatat atattttgta    180

aatatatgta aatatatata ttttgtaaat ttatgtaaat atatatattt tgtaaatata    240

tgtaaatata tatatatttt gtaaatatat atacatatat attttgtaaa tatataaaca    300

tatatatttt ataaatatat ttataaatat atatattgta aatatattta taaatatatt    360

tataatatat atattgtaaa tatgtttata aatatatata ttgtatatat aaat          414
```

<210> SEQ ID NO 129
<211> LENGTH: 496
<212> TYPE: DNA
<213> ORGANISM: Homo sapiens
<220> FEATURE:
<221> NAME/KEY: misc_binding
<222> LOCATION: (1)..(496)
<223> OTHER INFORMATION: MAR of chromosome 2 genomic contig; 13952568..13953063

<400> SEQUENCE: 129

```
taatatacat attatatatt atatattgta tatataatat acatattata tattatatat     60

tgtatatata atatacatat tatatattat atattgtata tataatatac atattatata    120

ttatatattg tatatataat atacatatta tatattatat attgtatata taatatacat    180

attatatatt atatattgta tatataatat acatattata tattatatat tgtatatata    240

atatacatat tatatattat atattgtata tataatatac atattatata ttatatattg    300

tatatataat atacatatta tatattatat attgtatata taatatacat attatatatt    360

atatattgta tatataatat acatattata tattatatat tgtatatata atatacatat    420

tatatattat atattgtata tataatatac atattatata ttatatattg tatatataat    480

atacatatta tatatt                                                    496
```

<210> SEQ ID NO 130
<211> LENGTH: 317
<212> TYPE: DNA
<213> ORGANISM: Homo sapiens
<220> FEATURE:

<221> NAME/KEY: misc_binding
<222> LOCATION: (1)..(317)
<223> OTHER INFORMATION: MAR of chromosome 2 genomic contig; 16942865..16943181

<400> SEQUENCE: 130

```
tctcctagta gttatatata tatatatgtg tatatatata tatcctagta gatatatata     60

tatatatatc ctagtagata tatatatata tatatcctag tagatatata tatatatata    120

tcctagtagt tatatatata tatatatcct aacagttata tatatatata tcctagtagt    180

tatatatata tatatcctag tagttatata tatatatata tcctagtagt tatatatata    240

tatatcctag tagttatata tatatatatc ctagtagtta tatatatata ttatatatta    300

tataatatat atataat                                                   317
```

<210> SEQ ID NO 131
<211> LENGTH: 464
<212> TYPE: DNA
<213> ORGANISM: Homo sapiens
<220> FEATURE:
<221> NAME/KEY: misc_binding
<222> LOCATION: (1)..(464)
<223> OTHER INFORMATION: MAR of chromosome 2 genomic contig; 17217049..17217512

<400> SEQUENCE: 131

```
acatactata tatatacaca tactatatat actatataca gtatatagta tacatatact     60

atacatatac atatactata catatacata tacatatact aagtatacgt atatacagta    120

catagtatat gtatactata tagtatgtat atatagcata tagtatgcgt atactctata    180

tagcatatag tatgcatata cgctatatag catatagtat gcatatacta tatatagtat    240

agagtatgcg tatactatat atatagtata gagtatgcgt atactatata tatagtatag    300

agtatgcgta tactatatat atagtataga gtatgcgtat actatatata tagtatagag    360

tatgcgtata ctatatatat agtatagagt atgcgtatac tatatatata gtatagagta    420

tgcgtatact atatatatag tatagagtat gtatatatat agta                     464
```

<210> SEQ ID NO 132
<211> LENGTH: 430
<212> TYPE: DNA
<213> ORGANISM: Homo sapiens
<220> FEATURE:
<221> NAME/KEY: misc_binding
<222> LOCATION: (1)..(430)
<223> OTHER INFORMATION: MAR of chromosome 2 genomic contig; 19647266..19647695

<400> SEQUENCE: 132

```
tgtaaatata tgtaaatata tatttatatt atatattata taaaaatata atatataata     60

tataatatat aaactatata ttaatataat atatataaac tattatataa atacatatta    120

aatatattat atttttaata tttatatatt aaatataata tatatttaat atttatatat    180

taaatatata atatatttaa tatttatata atatatagca tattttatat ttatattata    240

tataacattt tatatttata tttatattta tatatattta atttatattt atattatatt    300

tatatttata ttatatataa cataattata tatattttca tattgtatat aataaagaaa    360

tgtatatttg ttatatataa tatatattat ataatttatt atatattata taatatatat    420

tatataatat                                                           430
```

<210> SEQ ID NO 133
<211> LENGTH: 2131

<212> TYPE: DNA
<213> ORGANISM: Homo sapiens
<220> FEATURE:
<221> NAME/KEY: misc_binding
<222> LOCATION: (1)..(2131)
<223> OTHER INFORMATION: MAR of chromosome 2 genomic contig;
20481223..20483353

<400> SEQUENCE: 133

```
tatatataaa tatatttata tttaatatat atttatataa atatattttt atataaatat     60

atatttaata taaatatctt tatatttaat atatatttaa tataaatatc tttatattta    120

atatatattt atatataaat atatatttat atttaatata tattaatatt taatatacgt    180

ttatatttaa tatatatttc tatataaata tatttatatt aacatatatt tatatataaa    240

tatatttata tttaatatat ttacatataa atatatttat atgtaatata tttacatata    300

aatatattta tatttaatat atatgcatat gtaaatatat ttatatttaa taatatttat    360

atataaatat atttatattt aataatattt atatataaat atatttatat ttaatatata    420

ttaaatatat atttatattt aatatatatt aatatttaat atatatttat atttaatata    480

tattatatat aaacatatat ttatatttaa tatatattat atataaacat atatttatat    540

ttaatatata ttatatataa acatatattt atatttaata tatatttata tttaatatat    600

tatatataaa catatattta tatttaatat atatttatat taaatatata ttatatataa    660

acatatattt atatttaata tatatttata ttaaatatat atttatattt aatatatata    720

tattaaatat atatttatat ttaatatata tttatattaa atatatattt atattaaata    780

tatttatatt taatatatat ttatattaaa tatatattaa atatttaata tatatttata    840

tttaatatat acatatatat ttatatttaa tatatacata tatatttata tttaatatat    900

acatatatat ttatatttaa tatatacata tatatttata tttaatatat aaatttatat    960

tttatatata taaaaatata tatttatatt taatatatat aaatatatat ttatatttaa   1020

tatatatatt tatattgaat atatacataa atatatattt atatttaata tataaacata   1080

tatttatatt tatatattaa atatatattt atatttaata tataaatata tatttatatt   1140

taatatattt atatatacta atatatttat atttaatata tttatatata gatatattta   1200

tatttaatat atttatgtgt attaatatat ttatatttaa tatatttata tattaatata   1260

tttatatttt atatttatat attaatatat ttatatttta tatttatatt ttatatattt   1320

atatattaat atatttatat ttatatatat ttttatatat taataaattt atattttata   1380

tatttatata ttaataaatt tatattttat acagttatat aaatatattt atattttata   1440

cagttatata aatatattta tattttatag ttatataaat atatttatat tttatacagt   1500

tatataaata tatttatatt ttatacagtt atataaatat atttatattt tatacagtta   1560

tataaatata tttatatttt atacagttat ataaatatat ttatatttta tacagttata   1620

taaatatatt tatattttat acagttatat aaatatattt atattttata cagttatata   1680

aatatattta tattttatac agttatataa atatatttat attttataca gttatataaa   1740

tatatttatg ttttatacat ttatataaat atatttatat tttatacatt tgtatttaat   1800

atatatttat atataaatat attttatatt taatatattt atatataaat atatattgat   1860

atttaatata tatttatata taaatatata ttgatattta atatgtttat atataaatat   1920

atatttatat ttaatatata tgtttatata tcaatatata tttatattta atatatattt   1980

acatataaat atatatttat atttgatata tatttatatt tgatatatat tttatatata   2040

ttaatatatt tacatttgat atatatttta tatatattaa tatatttaca tttgatatat   2100
```

attttatata tattaatata tttacatttg a 2131

<210> SEQ ID NO 134
<211> LENGTH: 842
<212> TYPE: DNA
<213> ORGANISM: Homo sapiens
<220> FEATURE:
<221> NAME/KEY: misc_binding
<222> LOCATION: (1)..(842)
<223> OTHER INFORMATION: MAR of chromosome 2 genomic contig;
20483478..20484319

<400> SEQUENCE: 134
tatatattta tgtttaatat atatttatag ataaatatat atttacgttt aatatatatt 60
tatagataaa tatatattta cgtttaatat atatttatct ataaatatat ttacgtttaa 120
tatatattta tatattaata tatttatgtt taatatatat ttatatatat taatatattt 180
atgtttaata tatatttata tattaatata tttatgttta atatatttat atatattaat 240
atatttatgt ttaatatata tttatatgtt aatatattta ggtatatata tatttatatg 300
ttaatatata tttatattaa tatattatat ttatatataa aagtatatat aatatataaa 360
tattatataa attattatat agtatttta tatatattta tatataaatt ttatatattt 420
tatatatata aatatatatt tatatataca ttttatatat aaatatatat ttatatatac 480
attatatata taaatatata tatttatatt ttatatataa atatatatat ttatatatac 540
attttatata ttttatatat gtaaatatat atataaattt tatatattgt atatatattt 600
ataaatttta tatatatatt tatatatata atatatataa tatatataaa ttttatatat 660
attatatata tttatatttt atatattata tatttattta tatatattta tatgttatat 720
atatttatat ttatatttat tttttattta tatattttat atatatattt atatatgtat 780
attatatata ttatatatta tataatatat tatatatatt atattatata tttatattat 840
at 842

<210> SEQ ID NO 135
<211> LENGTH: 645
<212> TYPE: DNA
<213> ORGANISM: Homo sapiens
<220> FEATURE:
<221> NAME/KEY: misc_binding
<222> LOCATION: (1)..(645)
<223> OTHER INFORMATION: MAR of chromosome 2 genomic contig;
20897566..20898210

<400> SEQUENCE: 135
gtatatttat attatatatt atataatata tattatatat taataaatta tatataatat 60
aatatatatg tatatttata tttatgttat aatatacata taattatata tgtatgtata 120
catgtataca tatacgtata tgtgtatatg tatacatata ggtatatgtg tacatgtata 180
catataggta tatgtatatg tatacatgta tacatataat ataattacat atgtatgtat 240
acatacatat gtaattatat tatatatgta tatgtatatt tatataatat ataatatgta 300
ttatatatta tacatgcata tttatatgta tattatatat acacatataa tataattata 360
tatgtatgta tatatacaca tatatattta tattatatat gtatattata tacatatatt 420
tatattatat atgtatatat atttatcata tttatatgta atatgcatgt gtaataaata 480
atatacacat ttatatatgt atattatata catatattta tattgtatat gtatatatat 540
ttatatatat ttgtatatca tatatttata tattgtatat ttatgtatat tatatattta 600
tatattatat atgtattata taatatatat gtaaatatat attat 645

<210> SEQ ID NO 136
<211> LENGTH: 722
<212> TYPE: DNA
<213> ORGANISM: Homo sapiens
<220> FEATURE:
<221> NAME/KEY: misc_binding
<222> LOCATION: (1)..(722)
<223> OTHER INFORMATION: MAR of chromosome 2 genomic contig;
21664541..21665262

<400> SEQUENCE: 136
tataatatat attatattct atataatatg taaaatatat attatattct atataatgta 60
ttatatatag aatataatat attctatgta ttctataatc tatataatac atattatata 120
ttatatagaa tattataaat aatatattct atattatata tagaatatat tctatatgtt 180
tatattctat atattatata tgaaatagta tataaaatat atataatata tataaaatat 240
gatatataat atatataaaa taatatataa tgtataatat ataaaataat atataatgta 300
taatatataa aataatatat aatgtataat atataaaata atatataatg tatattatat 360
aaaataatat ataatgtata ttatatataa aataatatat aatgtatatt atatataaaa 420
taatatataa tgtatataaa ataatatata atatattata tataaaataa tatataatat 480
attatatata aaataatata tattatatat aaaataatat ataatatatt atatataaaa 540
taatatatat tatatataaa ataatatata atatattata tataaaataa tatatattat 600
atataaaata atatatatta tatataaaat aatataatat atattatata taaaataata 660
tataatatat tatataaaaa tataaatata ttatataaaa atataaaata taaaatatta 720
ca 722

<210> SEQ ID NO 137
<211> LENGTH: 305
<212> TYPE: DNA
<213> ORGANISM: Homo sapiens
<220> FEATURE:
<221> NAME/KEY: misc_binding
<222> LOCATION: (1)..(305)
<223> OTHER INFORMATION: MAR of chromosome 2 genomic contig;
22834991..22835295

<400> SEQUENCE: 137
aatataaaat atatgatata taatacgtat tatatatgta taatacgtat tatatattaa 60
tatataatat ataatacata ttatatatgt atataatata tactaatata tataatgtat 120
acattatata tttacataat atataataca taatatagaa ttataattat atataataca 180
taatatataa ttatatatat tattatatat gtatttatat tatatataat atattatata 240
taatatatat tatataatta tataagtata taattatgtt atatacataa taatatataa 300
tatat 305

<210> SEQ ID NO 138
<211> LENGTH: 352
<212> TYPE: DNA
<213> ORGANISM: Homo sapiens
<220> FEATURE:
<221> NAME/KEY: misc_binding
<222> LOCATION: (1)..(352)
<223> OTHER INFORMATION: MAR of chromosome 2 genomic contig;
25277762..25278113

<400> SEQUENCE: 138
taatatatat aatatattat atattatata taatatattt tataatatat aaaatatatt 60
atatataata tataatatat tttataatat atataatata ttatatataa tatataatat 120
attttataat atatataata tattatatat attatatatt tatatttatt tatatattca 180
taaatatata tttatatata atatatttta taatatatta tatataatat ataatatatt 240
ttataatata ttataatata taatatataa tatattttat aatatatata atatataata 300
tattatatat ttatatttat ttatatattc ataaatatat atatttatat ta 352

<210> SEQ ID NO 139
<211> LENGTH: 342
<212> TYPE: DNA
<213> ORGANISM: Homo sapiens
<220> FEATURE:
<221> NAME/KEY: misc_binding
<222> LOCATION: (1)..(342)
<223> OTHER INFORMATION: MAR of chromosome 2 genomic contig;
25378452..25378793

<400> SEQUENCE: 139
tatgtacata tatattttat atattatata taatatatat tatatgatat atataatata 60
ttatataata taatatataa aatatatata atatatatta tattatataa attatattat 120
atatatcata taatatattt tatatattat ataatatata ttatattata tatattttat 180
atattatatt atatattata tatatcatat aatatatatt atattatata ttttatatat 240
tatataatat atattatata tttttatata ttatataata tatattatat attttatata 300
ttatataata catatattat atataatata atatatatta ta 342

<210> SEQ ID NO 140
<211> LENGTH: 663
<212> TYPE: DNA
<213> ORGANISM: Homo sapiens
<220> FEATURE:
<221> NAME/KEY: misc_binding
<222> LOCATION: (1)..(663)
<223> OTHER INFORMATION: MAR of chromosome 2 genomic contig;
30209437..30210099

<400> SEQUENCE: 140
aatatatatt acatattgta tatatagtat atgtaatgta tataatatag tatattctat 60
attgtataat agtaatatat agtatatgat atactatata ttacttatca tatatacaat 120
atatattata tcgtatattg tatattatat attgtatata tgtaatatat gatatgtaca 180
tatgttatat atgtatataa tatactatat tatatattgt atattatata catatataac 240
actattatac aatatataat atagcatatt atatacaata tagcatatac aatatataat 300
atagcatatt atatataata tagtatatta tatacaatat ataatatagc atattatata 360
taatataata tagtatatta tatacaatat ataatatagc atatacaata tagtatacaa 420
tatataatat agcatataca atatagtata ttatatataa tatataatat agcatgtaca 480
atatagtatg ttatatacaa tatataatat agcatataca atatagtata ttatatacaa 540
tatataatat agcatataca atatattata ttatatacaa tatataatat agcatataca 600
atatagtata ttatatacaa tatataatac agcatataca atatagtata ttacatacag 660
tat 663

<210> SEQ ID NO 141
<211> LENGTH: 1200
<212> TYPE: DNA
<213> ORGANISM: Homo sapiens
<220> FEATURE:
<221> NAME/KEY: misc_binding
<222> LOCATION: (1)..(1200)
<223> OTHER INFORMATION: MAR of chromosome 2 genomic contig;

31725089..31726288

<400> SEQUENCE: 141

```
tgtacttata tattataatg tatatataaa gtatatactt tatatatact tatatattat     60
aatgtatatt attgtatata agtatatatc ataatatata cttacatatg ctcacatata    120
ttataatgta tattgtatat attatataca tattatatat gtataatgta tatatacatt    180
atatatgtat aatgtatata tacattatat atgtataatg tatatataca ttatatatgt    240
ataatgtata taatatatac aatatatgta taatatataa tatatacaat atatgtataa    300
tatacaatat atgtataata tacaatatat gtatagtata taatatatat tatatatgta    360
tagtatatta tatattatat atgtatagta tataatatgt ataatgtata tattataata    420
tattatatat aatatctata acaatataat atattgtata tattatatat aatatatatt    480
tatataatat atattatata taatatatta tgtatttatt tatattatat ataatataaa    540
tatatataat ataaataata tttattatat attaatataa atatttatat taatatatat    600
ttattatata taaataatat ctatgatata aataatatat aatatacatg tatatgttat    660
aatatataca tataatatac atgtgtatat atactataca tgtatatata acatgtatat    720
atatacatgt atatatatta tgtatacatg tatagtatat atacatgtat atatatacat    780
atatactata catgtatata tacatgtata tatatacata tatactatac atgtatatat    840
acatgtatat atacacatat atactataca tgtatatata catgtatata tatacatgta    900
tgttatatac attattataa tatacatata tagtatacat tatatacatt atataatatg    960
cattattata atataatata cattattata atatacatta ttataatata atatacatta   1020
ttataatata cattattata atatacatta taataatata cattattata atatacatta   1080
taatattgaa gtatatatac tataatatat gtatatatta taatgtatat aatatacatt   1140
attatatata agtatgtatt atatataagt atatattata atatatgtat atacatatat   1200
```

<210> SEQ ID NO 142
<211> LENGTH: 325
<212> TYPE: DNA
<213> ORGANISM: Homo sapiens
<220> FEATURE:
<221> NAME/KEY: misc_binding
<222> LOCATION: (1)..(325)
<223> OTHER INFORMATION: MAR of chromosome 2 genomic contig;
      32147252..32147576

<400> SEQUENCE: 142

```
aaatacaaat atttatttat atataatata taatataata tatttattta tatataatat     60
ataatttata attatataaa tatataatat atttatatat aatatataat tttattatat    120
attaattata tatataataa atatatataa tatataattt tattatatat taattatata    180
tataataaat atatataata tataataata ttatatacat tatatataaa tataaatatt    240
tatataatat ataatataat atatttattt atatataaat atataatata taattatata    300
aatatataat atatttatat ataac                                          325
```

<210> SEQ ID NO 143
<211> LENGTH: 507
<212> TYPE: DNA
<213> ORGANISM: Homo sapiens
<220> FEATURE:
<221> NAME/KEY: misc_binding
<222> LOCATION: (1)..(507)
<223> OTHER INFORMATION: MAR of chromosome 2 genomic contig;
      32312662..32313168

<400> SEQUENCE: 143
attatttata taaatattat atttatatta tttatataaa tattatattt atattattta 60
tataaatatt atatttatat tatttatata aatattatat ttatattatt tatataaata 120
ttatatttat attatttata taaatattat atttatatta tttatataaa tattatattt 180
atattattta tataaatatt atatttatat tatttatata aatattatat ttatattatt 240
tatataaata ttatatttat attatttata taaatattta tttatattat ttatataaat 300
attatattta tattatttat ataaatattt atttatatta tttatataaa tatttattta 360
tatttatata aataatatat aaataaatat tttatatgta tataaatatt atttatatta 420
tttatttaaa taaataatat aaattaatat aaatattaat attatttatt ttattataaa 480
taatataaat attatattta tatttat 507

<210> SEQ ID NO 144
<211> LENGTH: 339
<212> TYPE: DNA
<213> ORGANISM: Homo sapiens
<220> FEATURE:
<221> NAME/KEY: misc_binding
<222> LOCATION: (1)..(339)
<223> OTHER INFORMATION: MAR of chromosome 2 genomic contig;
33651118..33651456

<400> SEQUENCE: 144
aaatataata tattatttat atataatata aatgatatat tatgtatata taaaatataa 60
ataatatatt atgtatatat aaaatataaa tattatttat atataaaata taaataatat 120
ttatatataa aatataaata ttatattatt tatatataaa atataaataa tatattattt 180
atatataaaa tataaataat atattattta tatataaata atatataaaa tataaatata 240
tattatatat aaataaaata tatatattat atatataaat ttatatataa tatataaaat 300
ataatatata tatttaatat ttattatata atatataat 339

<210> SEQ ID NO 145
<211> LENGTH: 461
<212> TYPE: DNA
<213> ORGANISM: Homo sapiens
<220> FEATURE:
<221> NAME/KEY: misc_binding
<222> LOCATION: (1)..(461)
<223> OTHER INFORMATION: MAR of chromosome 2 genomic contig;
45073053..45073513

<400> SEQUENCE: 145
tgtgtataca tatatacgtg tacatataca tatatacatg tgtatatata tacgtgtaca 60
tatacatata tacatgtgta tatatatgta catatacata tatacatgtg tatacataca 120
tatatacatg tacatataca tatatacatg tgtatacata catatataca tgtacatata 180
catatataca tgtgtatact tacatatata catgtacata tacatatata catgtgtata 240
tatacatata tacacgtaca tatacatata tacatgtaca tatatacatg tatacatata 300
tacatgtaca tatgtacata tatacatgta tacatatata catgtacata tgtacatata 360
tacatgtata catatataca tgtacatatg tacatatata catgtataca tatatacata 420
tgtacatacg cacagataga catatataca tatgtacata c 461

<210> SEQ ID NO 146
<211> LENGTH: 1162
<212> TYPE: DNA
<213> ORGANISM: Homo sapiens
<220> FEATURE:

<221> NAME/KEY: misc_binding
<222> LOCATION: (1)..(1162)
<223> OTHER INFORMATION: MAR of chromosome 2 genomic contig; 45487691..45488852

<400> SEQUENCE: 146
attatattat ctatataaat ctattatatc tattatatta tctatataat atctattata 60
tatattatat tatctatata aatctattat atatattata ttatctatat aaatctatta 120
tatatattat attatctata tatctattat atattatatt atattatatt atatataata 180
tctattatat atattatatt atattatatt atatataata tctattatat atattatatt 240
atctatataa tatctattat atattatata ttatattata tataatatct attatatata 300
ttatattata ttatatataa tatctattat atctattata tatattatat atatctatta 360
tatctattat atatattata tataatatct attatatcta ttatatatat tatatataat 420
atctattata tctattatat tatattatat ataatatcta ttatatctat tatatatatt 480
atatatatct attatatcta ttatatatat tatatataat atctattata tctattatat 540
atattatata taatatctat tatatctatt atatattata tatataatat ctattatatc 600
tattatatat tatatatata atatctatta tatctattat atctattata tatatatcta 660
ttatatctat tatatatatt atatacataa tatctattat atctattata tatattatat 720
atataatatc tattatatct attatatata tactatctat tatatctatt atatatatta 780
tatatgtact atctattata tctattatat ctattatata tatactatct attatatcta 840
ttatatatat tatatatata ctatctatta tatctattat atatattata tatatactat 900
ctattatata tctattatat atattatttt atattatata tagtatctat tacatatatt 960
atattatatt atatataata tctattatat atattatatt atattataaa taatatatat 1020
aatatctgtt atatataata gatattatat ataatatata atatatataa tagatattat 1080
atatattata ttatataata tataatatat aatataatta atataaaata tatataatat 1140
ataattaata taatatgtaa ta 1162

<210> SEQ ID NO 147
<211> LENGTH: 562
<212> TYPE: DNA
<213> ORGANISM: Homo sapiens
<220> FEATURE:
<221> NAME/KEY: misc_binding
<222> LOCATION: (1)..(562)
<223> OTHER INFORMATION: MAR of chromosome 2 genomic contig; 45516233..45516794

<400> SEQUENCE: 147
acatattata tatattatat ataatatata ttatatatac atattatata tattatatat 60
aatatatatt atatatacat attatatata ttatatatac atatatatat tgtatataat 120
atatacatat tatatatatt atatatacat attatatatt atatataata tatacatatt 180
atatattata tataaatatt atatattata tataaatatt atatatataa atattatata 240
ttatatataa atattatata tcttatatat aaatataata tataatatat ataatattta 300
tatattatat ataaatatta tatatattat ataatattat atataatata taaatatata 360
tattatataa atattgtata tattatataa atattatata tattatatat aaatattata 420
tatattatat aaatatatat aaatatataa aatatataaa tatgtaaaat ttatatttat 480
aaatatataa tataaatata taaatataaa tataaattat atataatata taatatatta 540
tacataatat atactatata ta 562

-continued

<210> SEQ ID NO 148
<211> LENGTH: 801
<212> TYPE: DNA
<213> ORGANISM: Homo sapiens
<220> FEATURE:
<221> NAME/KEY: misc_binding
<222> LOCATION: (1)..(801)
<223> OTHER INFORMATION: MAR of chromosome 2 genomic contig;
45727251..45728051

<400> SEQUENCE: 148
atatatatat ataatatata catatataga atatatatat tattatattc tatatataga 60
atatatatat agaatatata tatatagaat atatatatag aatatatata tagaatatat 120
atatagaata tatatataga atatatatat atagaatata tatatagaat atatatatat 180
agaatatata tatatagaat atatatatat agaatatata tatatagaat atatatatag 240
aatatatata tagaatatat atatatagaa tatatatata gaatatatat atatagaata 300
tatatataga atatatatat atagaatata tatatagaat atatatatat agaatatata 360
tatagaatat atatatatag aatatatata tagaatatat atatatagaa tatatatata 420
gaatatatat atatagaata tatatataga atatatatat atagaatata tatatagaat 480
atatatatat agaatatata tatagaatat atatatatag aatatatata tagaatatat 540
atatatagaa tatatatata gaatatatat atatagaata tatatataga atatatatat 600
atagaatata tatatagaat atatatatat agtatatata gaatatatat atatagtata 660
tatagaatat atatatatag aatatatata tagaatatat atatatagaa tatatatata 720
gaatatatat atatagaata tatatataga atatatatat atatagaata tatatataga 780
atatatatat atatatagaa t 801

<210> SEQ ID NO 149
<211> LENGTH: 346
<212> TYPE: DNA
<213> ORGANISM: Homo sapiens
<220> FEATURE:
<221> NAME/KEY: misc_binding
<222> LOCATION: (1)..(346)
<223> OTHER INFORMATION: MAR of chromosome 2 genomic contig;
50937238..50937583

<400> SEQUENCE: 149
taaaattata tatattatat ataatatata atatattata tataatatat attataatat 60
atataatata tattatataa aatatattct atagaatata tattctatta tataatatat 120
attctattat aatatatatt atatataata tatattctat tataatatat attatatata 180
atatattcta ttatgatata tattatatat aataacatat attatatata atatatattc 240
tattatataa aatatatatt atataaaata tatattctat tatataaaat atatattata 300
taaaatatat attatattat ataaaatata tattatacta tatata 346

<210> SEQ ID NO 150
<211> LENGTH: 462
<212> TYPE: DNA
<213> ORGANISM: Homo sapiens
<220> FEATURE:
<221> NAME/KEY: misc_binding
<222> LOCATION: (1)..(462)
<223> OTHER INFORMATION: MAR of chromosome 2 genomic contig;
55672627..55673088

<400> SEQUENCE: 150
taaatatata ttatatatta tattatatat aatatattta tatttatata tactataatt 60
tatatataat atatattata tatataatat atttataata tatatcatat aaataatata 120
tatttataat atatatcata taaataatat atatttataa tagatatcat ataaataata 180
tatatttata atagatatca tataaataat atatatttat aatagatatc atataaataa 240
tatatattta taatagatat catataaata atatatattt ataatatata tcatataaat 300
aatatatatt tataatatat atcatataaa taatatatat ttataatata tatcatataa 360
ataatatata tttataatag atatcatata aataatatat atttataata gatatcatat 420
aaataatata tatttataat agatatcata taaataatat at 462

<210> SEQ ID NO 151
<211> LENGTH: 401
<212> TYPE: DNA
<213> ORGANISM: Homo sapiens
<220> FEATURE:
<221> NAME/KEY: misc_binding
<222> LOCATION: (1)..(401)
<223> OTHER INFORMATION: MAR of chromosome 2 genomic contig;
56081352..56081752

<400> SEQUENCE: 151
tatacatgta tgtattcgta tatgtatgtt atatatgtat atgtgttata tacatataca 60
tatatacatg tatatgtgtt atatacatat acatatatac atgtatatgt gttatataca 120
tatacatata tacatgtata tgtgttatat acatatacat atatacatgt atatgtgtta 180
tatacatgtg tatgtgtata tgtatatata catatatgtg tatgtgcatg tgtatatata 240
catatatgta tatgtgtata tgtatatata catatatgta tatgtgtatg tgtatacgta 300
tatatacata tatgtgtatg tgtatgtgta tacgtatata tatacatata tgtgtatgtg 360
tatacgtaca tatacatata tgtgtatgtg tatacgtaca t 401

<210> SEQ ID NO 152
<211> LENGTH: 765
<212> TYPE: DNA
<213> ORGANISM: Homo sapiens
<220> FEATURE:
<221> NAME/KEY: misc_binding
<222> LOCATION: (1)..(765)
<223> OTHER INFORMATION: MAR of chromosome 2 genomic contig;
56404208..56404972

<400> SEQUENCE: 152
tatattatat aaagaatata tattatataa tatgtaaaga atatatatta tataatatgt 60
aaagaatata tattatatat tatgtaaaga atatatatta tatataatat ataaagaata 120
tatattatat aatatataaa gaatatatat tatatattat ataaagaata tatattatat 180
ataatatata aagaatatat aatatataat atataaagaa tatatattat atataatata 240
taaagaatat atattatata taatatataa agaatatata ttatatatta tataaagaat 300
acatatatat aatatataaa gaatatatat tatatataat atataaagaa tatatattat 360
atataatata taaagaatat atattatata taatatataa agaatatata ttatatataa 420
tatataaaga atatatatta tatataatat ataaagaata tatattatat atattatata 480
aagaatatta tatattatat aaagaatata tattatatat aatatataaa gaataaacat 540
atatactata tataaagaat atacattata tatactatat ataaagaata tacattatat 600
atactatata taaagaatat atataatata taaagaatat acattatata taatatataa 660
agaatatatt atatattata taaagaatac attataatat aaagaataca ttatatataa 720
tataaagaat acattataat atataaagaa tatatataat atata 765

<210> SEQ ID NO 153
<211> LENGTH: 443
<212> TYPE: DNA
<213> ORGANISM: Homo sapiens
<220> FEATURE:
<221> NAME/KEY: misc_binding
<222> LOCATION: (1)..(443)
<223> OTHER INFORMATION: MAR of chromosome 2 genomic contig;
61953416..61953858

<400> SEQUENCE: 153
tttatatatt atagataaaa ttatattata ttacatgtaa tatataatat gtaaaatata 60
ttatattaca tatataatat ataatatgta aaatatatta tattacatat ataatatata 120
atatgtaaaa tatattatat tacatatata atataaaata ttacatataa tatattttac 180
ataaatatat attatctatt acatatttat tatatgtaat aatatgtaca tatgtataaa 240
tatgtatata tttatacata tgtatatatt atatatacat atatatgtat atattatata 300
tacatatata tgtatatatt atattatata tacatatata tgtatatatt atattatata 360
tacatatata tgtatatatt atattatata tacatatata tgtatatata ttataaatat 420
gtataataaa gatttatatg taa 443

<210> SEQ ID NO 154
<211> LENGTH: 372
<212> TYPE: DNA
<213> ORGANISM: Homo sapiens
<220> FEATURE:
<221> NAME/KEY: misc_binding
<222> LOCATION: (1)..(372)
<223> OTHER INFORMATION: MAR of chromosome 2 genomic contig;
62076211..62076582

<400> SEQUENCE: 154
tatatataat tatatatgta attatatatc agtatatata attatatata attatcaata 60
tatataatta tatataatta tcaatatata taattatcaa tagatatata taattatata 120
tataattata tataattata tatcagtata tatacttata taattatata tatgtatata 180
taattatatg tataaattat ctataagtat atataactat aatatatatc aattatatat 240
acttatgtat aattatatat actgatatat aattatacat aattatatat atcaattata 300
tataattatg tataattata tatacatata tataattata tatataaatt atatgtaatt 360
atataattac ac 372

<210> SEQ ID NO 155
<211> LENGTH: 484
<212> TYPE: DNA
<213> ORGANISM: Homo sapiens
<220> FEATURE:
<221> NAME/KEY: misc_binding
<222> LOCATION: (1)..(484)
<223> OTHER INFORMATION: MAR of chromosome 2 genomic contig;
62158581..62159064

<400> SEQUENCE: 155
attatatata atataaaaat tatacatatt attttattat atattatata cataatatat 60
atatttcata tataatatat attatatata atataaaata tatattatgt ataattatat 120
ataaaatata ttatataatt atatataaca taaaatatat ataatatata attatatata 180
atataaaata tatatataat ataaaatata tattatatgt aattatatat aatataaaat 240
atatatataa tataaaatat atattatata taattataat ataaaatata tattatatag 300

```
tatatattat ataaaatata tattatatat aattatatat tatataaaat atatattata    360

tataattata taatataaaa tatatattgt atataattat atataatata aaatatatat    420

aatatatgaa ataagatata tactatatat aatatatata atttacatat aagatatata    480

tcat                                                                 484


<210> SEQ ID NO 156
<211> LENGTH: 644
<212> TYPE: DNA
<213> ORGANISM: Homo sapiens
<220> FEATURE:
<221> NAME/KEY: misc_binding
<222> LOCATION: (1)..(644)
<223> OTHER INFORMATION: MAR of chromosome 2 genomic contig;
      68145036..68145679

<400> SEQUENCE: 156

tatatatatg ctaatatatg taatatatat tatatatatg ctaatatata tatgctaata     60

tataatatat attatatata aatatataat atatatttat ataaatatat aatatattat    120

atataaatat ataatataaa tatatataat atatactata ttatatatta tgtataacat    180

ataatacata tttgttatat ataatatata tattatatgt tatatattat atattatata    240

taatataaca atatatttta tatattatat gttatatatt atatattata tataatataa    300

cataatatat aatatatatt atattatata ttacatatat tagcaatatt atatataaaa    360

tatatataat atatataaaa tatatataaa aatataaaat atatatcaaa atataaacta    420

tataatatat aaaaatatat tatatataat atataaaaat ataaactata taatatataa    480

aaatatatta tatataatat ataaaaatat attatatatt atatataaaa atatattata    540

tataatatat aaaaatatat ataaaatata aaaaatatat ataaaatata aaaaatatat    600

aaaataatat aaaatatata atatataata atataatata taat                     644


<210> SEQ ID NO 157
<211> LENGTH: 530
<212> TYPE: DNA
<213> ORGANISM: Homo sapiens
<220> FEATURE:
<221> NAME/KEY: misc_binding
<222> LOCATION: (1)..(530)
<223> OTHER INFORMATION: MAR of chromosome 2 genomic contig;
      71257289..71257818

<400> SEQUENCE: 157

atatctatta tatttatata ctttatataa attatatcta ttatatttat atactttata     60

taaattatat ctattatatt tatatacttt atataaatta tatctattat atttatatac    120

tttatataaa ttatatctat tatatttata tactttatat aaattatatc tattatattt    180

atatacttta tataaatata taattatatt tatatacttt atataaatat aattataaat    240

atatttatat actttatata aatataatta taaatatatt tatatacttt atataaatat    300

aattataaat atatttatat actttatata aatataatta taaatatatt tatatacttt    360

ataattatat gttatattta taattatatt tatataattc ataattatat acattatgtt    420

tatagttata taatttataa ttatatacat tatatttata tttatataat ttataattat    480

ataaattata taaattatat aaattatctt taatttatat tatataatct               530


<210> SEQ ID NO 158
<211> LENGTH: 337
<212> TYPE: DNA
<213> ORGANISM: Homo sapiens
<220> FEATURE:
```

<221> NAME/KEY: misc_binding
<222> LOCATION: (1)..(337)
<223> OTHER INFORMATION: MAR of chromosome 2 genomic contig;
73413615..73413951

<400> SEQUENCE: 158

```
acttatatta tatataacta tattattgta tattaatata aattaatgat atataatata     60

ttaattatat attattatat gtgatataaa atacttatat ttatactgta tatatgtata    120

tacacacata tatgtatata tgtatatata cacatatgta tatatgtata tgtatatatg    180

tatactgtat atatgtatat acacacatat atgtatatat gtatatgtat atatgtatac    240

tgtatatatg tatatacata tatacatata tgatatatat cacatatatg tgatatataa    300

atatatttat ataaatataa tattaatatt tatatta                             337
```

<210> SEQ ID NO 159
<211> LENGTH: 1340
<212> TYPE: DNA
<213> ORGANISM: Homo sapiens
<220> FEATURE:
<221> NAME/KEY: misc_binding
<222> LOCATION: (1)..(1340)
<223> OTHER INFORMATION: MAR of chromosome 2 genomic contig;
77011049..77012388

<400> SEQUENCE: 159

```
atgtatttta tatagtatat attatgtatt atattgatat aattatataa caattattta     60

tatataaaat aacaaataaa tatataaaat aataaatata tatttattat taaataataa    120

atatatattt attattaaat aataaatata taaagtaata aatatatatt tatatattaa    180

ataattcata tatatttata tattaaataa ttcatatata tttaaataat taatacatat    240

ttaaataatt aatatatatt tatataatat atatttatat attaaataat taatatatat    300

ttatagatta aattaatata tatttatata ttaaattaaa tttaatatat tatatattta    360

tataatttaa atttaataat ttatataatt taatttaatt taatataatt aaaatatatt    420

aaacattata taatatataa tatatttaat atataatata tatttaatat ataatatatt    480

taatatataa tatatttaat atataatata tatttaatat ataatatatt taatatataa    540

tatatttaat atataatata tatttaatat ataatatatt taatatataa tatatattta    600

atatataata tatttaatat ataatatata tttaatatat aatatattta atatataata    660

tatatttaat gtataatata tttaatatat aatatatatt taatgtataa tatatttaat    720

atataatata tatttgatgt ataatatatt taatatatat ttgatgtata atatatttaa    780

tatataatat atatttgatg tataatatat ttaatatata atatatattt gatgtataat    840

atatttaata tataatatat atttgatgta taatatattt aatatataat atatatttga    900

tgtataatat atttaatata taatatatat ttgatgtata atatatttaa tatataatat    960

atatttgatg tataatatat ttaatatata atatatattt gatgtataat atatttaata   1020

tataatatat atttgatata taatatattt aatatataat atatatttga tatatattta   1080

atatataata tatatttgat atataatata tttaatatat aatatatatt tgatatataa   1140

tatatttaat atataatata tatttgatat ataatatatt taatatataa tatatatttg   1200

atatataata tatttaatat ataatatata tttgatatat aatatattta atatataata   1260

tatatttgat atataatata ttttcttatt aattatttat atataatata taaatatata   1320

ttaattaatt atatattaaa                                                1340
```

<210> SEQ ID NO 160

<211> LENGTH: 937
<212> TYPE: DNA
<213> ORGANISM: Homo sapiens
<220> FEATURE:
<221> NAME/KEY: misc_binding
<222> LOCATION: (1)..(937)
<223> OTHER INFORMATION: MAR of chromosome 2 genomic contig;
78226855..78227791

<400> SEQUENCE: 160
tgtgtatata tacatatatg tgtatctatg tgtatatata catatgtgta tatatacata 60
tatgtgtata tatacatatg tgtatatatg tgtatatatg tgtatatata catatatgtg 120
tatatatgtg tatatatgtg tatatataca tatatgtgta tatatgtgta tatatacata 180
tgtgtatata tgtgtatata tacatatatg tgtatatatg tgtatatata catatatgtg 240
tatatatgtg tatatataca tatatgtgta tatatgtgta tatatgtgta tatatacata 300
tatgtgtata tatgtgtata tatacatata tgtgtatata tgtgtatata tacatatatg 360
tgtatatatg tgtatatgtg tgtatatata catatatgtg tatatacaca catatatgtg 420
tatatatgtg tatatataca tatatgtata tatacatata tgtgtatata tgtgtatata 480
tacatatatg tgtatatatg tgtatatata catatatgtg tatacataca tatatgtgta 540
tatatgtgta tatatacata tatgtgtata catacatata tgtgtatata tgtgtataca 600
tacatatatg tgtatacata catatatgtg tgtatatgtg tatacataca tatatgtgtg 660
tatatatgtg tatacatatg tgtgtatatg tgtatatata catatatgtg tgtatatatg 720
tgtatatata catatatgtg tgtatatatg tgtatatata catatatgtg tgtatatatg 780
tgtatatata catatatgtg tgtatatatg tgtatatata catatatgtg tgtatatatg 840
tgtatatata catatatgtg tgtatatatg tgtatatata catatatgtg tgtatatatg 900
tgtatatata catatatgtg tgtatatatg tgtatat 937

<210> SEQ ID NO 161
<211> LENGTH: 1350
<212> TYPE: DNA
<213> ORGANISM: Homo sapiens
<220> FEATURE:
<221> NAME/KEY: misc_binding
<222> LOCATION: (1)..(1350)
<223> OTHER INFORMATION: MAR of chromosome 2 genomic contig;
79287748..79289097

<400> SEQUENCE: 161
tatatatatt atatatatag taactgttct attatatata tattatatat atttctgttc 60
tattatatat tatatatatt atattatata ttatatgtaa tatattatat atattataag 120
taatatatta tatatattat atgtaatata ttatatatat tatatgtaat atattatata 180
tattatatgc aatatgttat atatattata tgcaatatgt tatatatatt atatgcaata 240
tattatatat attatatgca atatattata tataatatat gtaatatatt atattatata 300
ttatatgtaa tatcttatat attatatgta atatattata tatattatat gtaatatctt 360
atatatatta tatgtaatat attatatatt atatgtaata tattatctta tatatattat 420
atgtaatata ttatattata tattatatgt aatatatatt atatgtaata tattacatat 480
tatatgtaat atatattata tgtaatatat tacatattat atgtaatata tattatatgt 540
aatatattac atattatatg taatatatta catattatat gtaatatatt atatgtatta 600
tatgtaatat attatatgta ttatatgtaa tatattatat gtattatatg tattatatgt 660
aatatattat atgtattata tgtaatatat tatatattat atgtaattat attatatgta 720
atatattata ttatatatta tatatattat atgtaatata ttatattata tattatatat 780
attatatgta atatattata ttatatatta tatatattat atgtaatata ttatattata 840
tattatatat attatatgta atatattata ttatatatta tatatattat atgtaatata 900
ttatattata tattatatat attatatgta atatattata ttatatatta tatatattat 960
atgtaatata ttatattata tattatatat attatatgta atatattata ttatatatta 1020
tatatattat atgtaatata ttatattata tattatatat attatatgta atatattata 1080
ttatatatta tatatattat atgtaatata ttatattata tattatatat attatatgta 1140
atatattata ttatatatta tatatattat atgtaatata ttttatatta tatatattat 1200
attatatatt atatgtaata tattatatta tttattatat attatatatt atatgtaata 1260
tattatatta tttattatat atattatatt atttattata tataatatat tatattatat 1320
atattatatt atatatattt ctgttctaat 1350

<210> SEQ ID NO 162
<211> LENGTH: 332
<212> TYPE: DNA
<213> ORGANISM: Homo sapiens
<220> FEATURE:
<221> NAME/KEY: misc_difference
<222> LOCATION: (1)..(332)
<223> OTHER INFORMATION: MAR of chromosome 2 genomic contig;
81142998..81143329

<400> SEQUENCE: 162
ctatgtatat aactatatat aactattata taacttaata agatatataa ctattatata 60
acttaataag ttatatataa ctattatata taacttaata agttatatat aactattata 120
taacttaata agttatatat aactattata taacttatta agttatatat aactatatat 180
aacttaataa gttatatata actattatat aacttaataa gttatatata actattatat 240
aacttaataa gttatatata actattatat aacttaataa gttatatata actatatata 300
acttatatac aacttattaa gctatatata ta 332

<210> SEQ ID NO 163
<211> LENGTH: 327
<212> TYPE: DNA
<213> ORGANISM: Homo sapiens
<220> FEATURE:
<221> NAME/KEY: misc_binding
<222> LOCATION: (1)..(327)
<223> OTHER INFORMATION: MAR of chromosome 2 genomic contig;
84019536..84019862

<400> SEQUENCE: 163
actgacagta tacatactgt atatatatac agtatgtata catatacagt atgtatacta 60
tatacagtat gtatactgta tatatatata cagtatgtat actgtatata tatacagtat 120
gtatacgtat gtatactgta tatatgtatt atagtgtata tatgtattat agtgtatata 180
tgtattatat atattatagt gtatgtatta tatgtgtata tacatataat atattataca 240
tatacatatg cacaatatgt atatgtatta tatgtattca tatacatata tgtatatgta 300
taatatatgt atacatataa tacacat 327

<210> SEQ ID NO 164
<211> LENGTH: 407
<212> TYPE: DNA
<213> ORGANISM: Homo sapiens
<220> FEATURE:
<221> NAME/KEY: misc_binding
<222> LOCATION: (1)..(407)

<223> OTHER INFORMATION: MAR of chromosome 2 genomic contig;
1448030..1448436

<400> SEQUENCE: 164
tatataatat atattacata tatattatat ctatattatt tatattacat atgtaatata 60
tattatattt atattattta tataatatat tatatatatt atattattta tatgtaatat 120
atttatattg tttatatata ttatatttat attatttata tataatacat attatattta 180
tattatttat atataatata tataataaat atataatata tataaaaata tatatattta 240
atatatctat aatatatatt atatatatta tatataatat atataattgt acatatattt 300
attatatata ttatatatat aatatatatt ataaatataa tatataaata tatttataaa 360
tatatataaa tattatattt atacattata tttatataca tattata 407

<210> SEQ ID NO 165
<211> LENGTH: 1959
<212> TYPE: DNA
<213> ORGANISM: Homo sapiens
<220> FEATURE:
<221> NAME/KEY: misc_binding
<222> LOCATION: (1)..(1959)
<223> OTHER INFORMATION: MAR of chromosome 2 genomic contig;
2117630..2119588

<400> SEQUENCE: 165
tatacatgtt atagtgtata tagtatacta atatataatg tatgtatgtg tatacatata 60
cacatataat atacacatat ataatatata tagtatataa taatgtataa tatataatat 120
ataatataaa atgtatagta tactacatat ttatatatag tatatagtat gcatagtaca 180
tatatactat atatgtagta tactatagtg tatatatagt acaccatata tagtataaat 240
atactatata gtatatgtac tatatatata ctatatagta tatacagtat acatatatag 300
tatacctata ctatatagta tatatagtgt gcgtatacta tatagtatat atagtgtgcg 360
tatactatat agtatatata gtgtgcgtat actatatagt atatatagtg tgcgtatact 420
atatagtata tatagtgtgc gtatactata tagtatatat agtatacata tatagtgtgc 480
gtatactata tagtatatat agtatacata tatagtatgc gtatactata tatagtatac 540
atatatagta tatctagagt atatgtagta tgtatagtat atatagtcta catactgtat 600
atacagtata tatatactct atagtatact atacagtata gtatactata tagtatacaa 660
tatatgtata ctatagaaac acactatata tagtatacta tatatactat atactatata 720
ctatatatag tatactatat atactacata ctatatatag tgtatgtata gtatatataa 780
actatatata gtgtatatag tatatatatt atatataata tatattatat tatattatac 840
tatatattat atgtatatta tagtatatta tactattata tattatatat tatattatat 900
attatataat ataatataat tatatattat aaaatatata tttttatatt atatattttt 960
aaatatttta taatatatat tttataatat atatattata attattttat atataatata 1020
aaatataata aatattttat aatatatatt tttaaaatat aatatttata tattataaaa 1080
atataaatat ataatatatt atatattata tatagtataa tatataatat gttatatagt 1140
atcttatact attatactat atatattata tagtgtatat atagtatact atatatagtg 1200
tatatagtgt atactatagt gtatatagtg tatactatag tgtatatagt gtatactata 1260
tacactgtat atagtagtgt atactatata cactgtatat agtagtgtat actatataca 1320
ctgtatatag tagtgtatac tatatacact gtatatagta gtgtatacta tatacactgt 1380
atatagtagt gtatactata tacactgtat atagtagtgt atactatata cactgtatat 1440
agtagtgtat actatataca ctgtatatag tagtgtatac tatatacact gtatatagta 1500
gtgtatacta tatacactgt atatatagta tattatatat actatatatg tatatatagt 1560
atacatatat attatatata cagtatatat agtatatata ctatgtagta tatatagtat 1620
atatactata tagtatgtat agtatactat atagtatata tagtatatta tatagtatat 1680
atactatata gtatatatag tatattgtat atatagtata tatactatat agtatatata 1740
gtatattgta tatatagtat attgtatata tagtatacat agtatgtata tatagtatat 1800
atagtataca tatatagtat gtacacagta tatatagtct atatgtatac tacatatagt 1860
atacatgtat actatactac atatagtata catgtatact atactacata tagtatacat 1920
gtatagtata ctacatatac tatacatgta tagaatact 1959

<210> SEQ ID NO 166
<211> LENGTH: 520
<212> TYPE: DNA
<213> ORGANISM: Homo sapiens
<220> FEATURE:
<221> NAME/KEY: misc_binding
<222> LOCATION: (1)..(520)
<223> OTHER INFORMATION: MAR of chromosome 2 genomic contig;
2119984..2120503

<400> SEQUENCE: 166
tatgtatgca tcgtatacat atatagtata tatatgtatg catcgtatac atatatacag 60
tatatatagt atgcatcgta tacatacagt atactatata tacagtatat acagtatact 120
atatatacag tatatacagt atactatata tacagtatat acagtatact gtatatacag 180
tatatacagt atatatagta tactatatat acagtatata tactatgtat tctatatata 240
gtatagtgta catagtatac atatagtata cactatacta tatatagtat actatatata 300
ctctatatag tatatatagt atactatata tagtatatat gtatactata tatagtgtat 360
atatatacta tatatagtgt atatatatac tatatatagt atatatatac actatatatt 420
gtatagtata gtgtatatat agtatagtat atgtatatat acacatgtat acatgtatat 480
atgtatacta atatatacta atatatgtat aaatatatat 520

<210> SEQ ID NO 167
<211> LENGTH: 954
<212> TYPE: DNA
<213> ORGANISM: Homo sapiens
<220> FEATURE:
<221> NAME/KEY: misc_binding
<222> LOCATION: (1)..(954)
<223> OTHER INFORMATION: MAR of chromosome 2 genomic contig;
2578285..2579238

<400> SEQUENCE: 167
tattatatat aactttataa tatataatat atattatata taactttata atatataata 60
tatattatat ataactttat aatatataat atatattata tataacttta taatatataa 120
tatatattat atataacttt ataatatata atatatatta tatataactt tataatatat 180
aatatatatt atatataact ttataatata taatatatat tatatataac tttataatat 240
ataatatata ttatatataa ctttataata tataatatat attatatata actttataat 300
atataatata tattatatat aactttataa tatataatat atattatata taactttata 360
atatataata tatattatat actatatata atatataact ttataatata taatatatat 420
tatatactat atataacttt ataatatata atatatatta tatattatat ataactttat 480
aatatataat atatattata tataacttta taatatataa tgtatattat atattatata 540
ttatatatta tatataactt tataatatat aatgtatatt atatattata tataacttta 600
taatatataa tatataatat aatatataac tttataatat atatatcata tattatatat 660
aactttataa tatatatcat atattatata taactataat atatatatca tatattatat 720
ataactataa tatatatatc atatattata tataacttta taatatatat atcatatatt 780
atatataact ttataatata tatcatatat tatatataac tttataatat atatcatata 840
ttatatataa ctttataata tatattatat ataactttat aatatatatc atatattata 900
tataacttta taatatatat catatattat atataacttt ataatatata tcat 954

<210> SEQ ID NO 168
<211> LENGTH: 452
<212> TYPE: DNA
<213> ORGANISM: Homo sapiens
<220> FEATURE:
<221> NAME/KEY: misc_binding
<222> LOCATION: (1)..(452)
<223> OTHER INFORMATION: MAR of chromosome 2 genomic contig;
3836217..3836668

<400> SEQUENCE: 168
tttatatata aatatatatc ttatatatat ttatatataa tacatatata tcttatatat 60
ataaaatata tatacatatt tatatataaa atacatatgt attatataca tttatatata 120
atacatatgt attatataca attatataat acatatgtat tatatacaat tatataatac 180
atatttataa atatatatat ttatatttat atatatttat atataaataa atatatattt 240
atagatttat ttatataaat atatatttat ataaatatat atttatatat atttatataa 300
atatatattt atatatattt ctatatatat atataaatat atgtataaat atatatattt 360
atacatatat tcatataaat atatatattt atacatgtat ttatatgaat atatatttat 420
acatgtaatt atatgaatat atatttatac at 452

<210> SEQ ID NO 169
<211> LENGTH: 417
<212> TYPE: DNA
<213> ORGANISM: Homo sapiens
<220> FEATURE:
<221> NAME/KEY: misc_binding
<222> LOCATION: (1)..(417)
<223> OTHER INFORMATION: MAR of chromosome 2 genomic contig;
3837666..3838082

<400> SEQUENCE: 169
gatatatata tttatataaa tatatatata aagagatata tttatatatt tatttatata 60
aatatatttc tttatataaa gatatatgta aatatattta tttatataaa tatatttata 120
tatgtaaata tatatttata tatttatata tttatatatt tatttatata aatatatata 180
tttatatatt tatttatata tataaaaata tataaatata aatatatata aatatatata 240
attataaata tagaaataaa tataaatata aatatataaa tatatataaa tataaatata 300
tataaatata aatatatata aatataaata tataaatgta taaatatata aatataaata 360
tatataaata tgtataaata tataaatata taaatatata aaaatatata taaatac 417

<210> SEQ ID NO 170
<211> LENGTH: 1197
<212> TYPE: DNA
<213> ORGANISM: Homo sapiens
<220> FEATURE:
<221> NAME/KEY: misc_binding
<222> LOCATION: (1)..(1197)
<223> OTHER INFORMATION: MAR of chromosome 2 genomic contig;
6294846..6296042

<400> SEQUENCE: 170
tatatactaa tatgtatata taaatatata aatatatata cacgtgtata tataaatata 60
tatgtatata taaatatata tacatatatg tatataaaaa tatatacgta tatacgtata 120
tacgtatata tagatatata cgtatatacg tatatacgta tatatagata tatacgtata 180
tacgtatata tagatatata cgtatatacg tatatacgta tacatgtgta tatacgtata 240
tacacatata cgtatacatg tgtatatacg tatatgtata cattatatat acgtatatat 300
acatatatgt atacatgtat atataaatat atacatatat gtatatatta tacatatatg 360
tatatataat atatatatta tatataatat atatattata tataatatat atattatata 420
taatatatat attatatata atatattata tattatatat aatatataca tatataatat 480
attatatatg tacatatgta cataatgtat atatgtatat atataatata tatgcacatg 540
tatatataat atatgtatat tatatataca tatgtatata tgtacatatt atatatgtat 600
atatgtacct attatatata catatgtata tatgtaccta ttatatatac atatgtatat 660
atgtacatat tatatataca tatgtatata tgtacatatt atatatacat atgtatatat 720
gtgcatgcat atataatata taatatatta tagattataa tattatatac atatcatata 780
ttatatactt atatatacat gtatatatta tatacatatt atatattata tacatataat 840
atatgtatat aatatataca tatattatat attatatata atacattatg ttatatatta 900
tgttatataa tatatattat ataatataca tatattatat ataatatata catatataat 960
aaataatata taattatata tataatatat gcatataaat atgtaatata ttttatatta 1020
tatatgatca tatataatat gacatattat atatgattat atatatgata tattatatat 1080
gattatatat attatatata aatatatgat tatatataat catatatata aatatatgat 1140
tatatgatta tatataaata tatatatatg attatatgat tatatataat tgattat 1197

<210> SEQ ID NO 171
<211> LENGTH: 362
<212> TYPE: DNA
<213> ORGANISM: Homo sapiens
<220> FEATURE:
<221> NAME/KEY: misc_binding
<222> LOCATION: (1)..(362)
<223> OTHER INFORMATION: MAR of chromosome 2 genomic contig; 6506971..6507332

<400> SEQUENCE: 171
tatatatagt gtatactata tatacgctat atgcacacat aaactatata tacagtatat 60
aatatgcgta tactatatac acagtatata ctacatgtat actatatata gtatataaga 120
tatatactat gtatataata tatatactag gtatatatat ccatatatat actatatact 180
atagtatata catatatatg tacgtatata tgtatatgta catatatatg tagtatgtat 240
atatatacat atatacacac tatagtatat acatatatat actatatata ccctatatag 300
agtatattat atacagtata ctatatatac tatatatacc ctatatagag catgtctatg 360
ct 362

<210> SEQ ID NO 172
<211> LENGTH: 2578
<212> TYPE: DNA
<213> ORGANISM: Homo sapiens
<220> FEATURE:
<221> NAME/KEY: misc_binding
<222> LOCATION: (1)..(2578)
<223> OTHER INFORMATION: MAR of chromosome 2 genomic contig; 6507395..6509972

<400> SEQUENCE: 172
ggtatactat atatactata gagtatactt tatagtatat atacctatat tatatatata 60
tacatacact gtatagtata tatggtatat atactatata tggcatatat agtttatata 120
tatactatat atggtatata tagtttatat atatactata tatggtatat atagtttata 180
tataccatat atggtatata tagtttatat agtacatata gtatatatac acactgtata 240
gtatatatta tgtagtatat atactatata tactgtatat atagtataaa tactatatat 300
agtatacact atatactata cactatatat actatatact atatactata tatagtatac 360
tatatagtat atagtatact ctatatgtac tatagagtat actatatata ctatacataa 420
aatattttta tatatagtac agcgtatact atatactata tatagtatac tctatatgta 480
ctatagagtg tagtatatac tatacagtat actctatata tactatacag tacactatat 540
atactatata tagtatattt tatatatagt acagtatata cagtatatat attatactat 600
atgtagtaca tatatagttt agtatatata gtatatatac tatactatat gtactacata 660
tataatagta tatatagtat atatactata ctatatgtag tacatatata gtttagtata 720
tatactagta tatagatata tagttatata gatatataat agtatatata gtatatatag 780
catatatagt atatatgcta tatatactat atagcatata ctatatacta tatatacagt 840
atatatagca tatatagcat atataatata tatacttttg atatacatac tatatacagt 900
atatatagta tatatactgt ataaatatac tatatatacc gtatatgcac actatatgct 960
atatatacta tatacactat atacagtata tatagtacac tatactatat aaagtatata 1020
tagtatacag tacactatac tatatacatt atatatagta tatattatac atagtatata 1080
gtatataaat agtatatata gtatatacag tatatatata gcatacttta tatagtatac 1140
acagtatata gatactatat atgctatata tagtatctat atactgtata ttatatatac 1200
taatatagta tatatgtata tatatactgt atatataata tatacatata tagtatatat 1260
actatacata cacactatac atatgtatat atactataca tactatatac tatatatcct 1320
atatatacta tatagtatat tatatatcct atatatacta tatagtatat tatatatcct 1380
atatatacta tatagtatat tatatatact atataccata tatactatat atactgtata 1440
gtatactata tatactatat agtatactgt atatactata tagtatactg tatatactat 1500
atagtatact gtatatacta tatagtatac tgtatatact atatagtata ctgtatatac 1560
tatatagtat actgtatata ctatatatac tatatagtat actgtatata ctatatagta 1620
tactatatat actatatacc atatatacta tgtatatact atatatagta tatactatgt 1680
atatgctata tatagtatat atagtatata tgctatatat agtatatata gtatatatgc 1740
tatatataca gtctatatat agtatatata ctatatagac tatatatata gcatatatac 1800
tatatatact atatataata tatatggtat atacatagta tctatatgta gtatctatat 1860
atagtaccta tatatactat atataggtac tatatatagt atatatactt tatatagata 1920
ctatatatag tatatatact ttatatagta tatatagtat atgtagcata tatagtatat 1980
atagtatata tagtatatag tatgtatagt atatatagat tatattgtat atacagtata 2040
tatactgtat atactatata aatagtacat acagtatata cagtatatat gtactatata 2100
tagtatatac agtatataca gtatatatgt accatatata gtatatacag tatatacagt 2160
atatatgcac tatatgttat atacagtata tacagtatat atgtactata taaatagaat 2220
atactctata tacagtatat atgtactata taaatatata cactatgtac agtatatatg 2280
tactatataa atagtatata cactatatac agtatatatg tactatatag tgtatacagt 2340
atatacagta tataggtact atatatggta tatacagtat atatgcacta tatggtatat 2400
acagtatata tgcactatat atggtatata cagtatatat gtactatata tggtatatac 2460
agtatatatg tactatatat ggtatataca gtatatatgt actatatatg gtatatacag 2520
tttatacagt atatatgcac tatatatggt atatacagta tacatgtact atatatgg 2578

<210> SEQ ID NO 173
<211> LENGTH: 598
<212> TYPE: DNA
<213> ORGANISM: Homo sapiens
<220> FEATURE:
<221> NAME/KEY: misc_binding
<222> LOCATION: (1)..(598)
<223> OTHER INFORMATION: MAR of chromosome 2 genomic contig;
7770400..7770997

<400> SEQUENCE: 173
gtgtattgta tatacatata cgtatctacg tatatacata tatgtattgt atatacatat 60
atgtattgta tatacatata tgtatatacg tatatacata tatgtattgt atatacatat 120
atgtatatac gtatatacat atatgtatat acgtatatag atatacatat atatgtattg 180
tatatacata tatgtatata catatataca tatatattga tatacatata tatgtattgt 240
atatacatat acaatatatg tatatataca tatacatata caatatatgt atatacatat 300
atatgtattg tatatacata tatatgtatt gtatatacat atattgatat acatatatgt 360
atatatacat atatgcatat atgtatatat acatatatgc atatatgtat atatacatat 420
atacatatgt acatatatac atatatacat atatgtatat atacatatat acatatgtac 480
atatatacat atatacatat gtacatatat acatatatac atatgtacat atatacatat 540
atagatatat atacacatat atagatatac ttatatgtat atatacatac atacatat 598

<210> SEQ ID NO 174
<211> LENGTH: 1048
<212> TYPE: DNA
<213> ORGANISM: Homo sapiens
<220> FEATURE:
<221> NAME/KEY: misc_binding
<222> LOCATION: (1)..(1048)
<223> OTHER INFORMATION: MAR of chromosome 2 genomic contig;
8332422..8333469

<400> SEQUENCE: 174
cattatatat aatatataat atattattat atataatata tataacatta tatatagtat 60
atatgacata tataacatat attatatata acatatataa aatataacat attatatata 120
acatatataa aatataacat atattatata taacatatat aaaatataac atatattata 180
tataacatgt ataaaatata acatatatta tatataacat gtataaaata taacatatat 240
tatataacat gtataaacta taacatatat tatatataaa atatattata tgttatatat 300
tataaataaa atatattata tgttatatat tataacatat tatataaata atatataata 360
tataacatat attatataaa taatatataa catatattat ataaataata tataacataa 420
catatattat ataacatata acatataaca tatattatat ataacatata acatataaca 480
tatattatat ataacatata acatataaca tatattatat ataacatata acatatatta 540
tattatatat aacatataac atatattata ttatatataa catataacat atattatatt 600
atatataaca tataacatat attatattat atataacata taacatatat tatattatat 660
ataatatata acatatatat tatatataat atataacata taacatatat tatatataat 720
ataatatata acatatatta tatataatat aatatataac atatattata tataatataa 780
tatataacat atattatata taatataata tataacatat attatatata atataatata 840
taacatatat tatatataat ataatatata acatatatta tatataatat aatatataac 900
atatattata tataatataa tatataacat atataatata taacatatag catatataat 960
atataacata taacatatat tatatataac atataacata tattatatat aacatataac 1020
atatataata tgtaacatta tatataac 1048

<210> SEQ ID NO 175
<211> LENGTH: 375
<212> TYPE: DNA
<213> ORGANISM: Homo sapiens
<220> FEATURE:
<221> NAME/KEY: misc_binding
<222> LOCATION: (1)..(375)
<223> OTHER INFORMATION: MAR of chromosome 2 genomic contig;
8909678..8910052

<400> SEQUENCE: 175
tatatacaca tatatacgta tgaatatata tacacatata cgtatgaata tatataccca 60
tatacgtatg aatatacaca tatatatacg tacgtatata tatacacata tatacgtacg 120
tatatatata cacatatata cgtacgtata tatatacaca tatatacgta cgaatatata 180
tacacatata tacgtacgaa tatatataca catatatacg tacgaatata tatacacata 240
tatacgtacg aatatatata cacatatata cgtacgaata tatatacaca tatatacgta 300
cgaatatata tacacatata tacgtacgaa tatatataca catatatacg tacgaatata 360
tatacacata tatac 375

<210> SEQ ID NO 176
<211> LENGTH: 563
<212> TYPE: DNA
<213> ORGANISM: Homo sapiens
<220> FEATURE:
<221> NAME/KEY: misc_binding
<222> LOCATION: (1)..(563)
<223> OTHER INFORMATION: MAR of chromosome 2 genomic contig;
10572503..10573065

<400> SEQUENCE: 176
atttataata tatatgtata aatatatgta tatatttata tttaaatata tgtatatata 60
tttatattta aatatacgta tatatattta tatttaaata tacgtgtata tatttatatt 120
taaatatacg tgtatatatt tatatttaaa tatacgtgta tatatttata tttaaatata 180
cgtgtatata tttatattta aatatacgtg tatatattta tatttaaata tacgtgtata 240
tatttatatt taaatatacg tgtatatatt tatatttaaa tatacgtgta tatttatatt 300
taaatatacg tgtatattta tatttaaata tatgtatgta tttataaata tatatttaaa 360
gtatatattt ataaatgtat acatgtatat ataaatatat atattttaaa tatatattta 420
tatatatatt tatatattta tataagtata tatatattta aatatatgta tatatttata 480
tatttatata agtatatata tttaaatata tgtatatatt tataatatat attttaaata 540
tatatttata tatttattat ata 563

<210> SEQ ID NO 177
<211> LENGTH: 595
<212> TYPE: DNA
<213> ORGANISM: Homo sapiens
<220> FEATURE:
<221> NAME/KEY: misc_binding
<222> LOCATION: (1)..(595)
<223> OTHER INFORMATION: MAR of chromosome 2 genomic contig;

11609694..11610288

<400> SEQUENCE: 177
tataaatact atatatagta tatataatat tatatatact atatataaat atatgtagta 60
taaataatat ataatataga tatataatat aatataatat gttataaata taaatatatt 120
tatataattt aatttataat atataatata taatatataa tttaatttta taatatataa 180
tatataattt aattttataa tatataatat ataatatgta aattatatat aatttaatat 240
atctaaatta tataatttaa atataaatat aatataaata tatctaacat aatatacata 300
acataaatat atatagtata tatagtacat ataaatatat atagtacata tagtatatat 360
aaatatatag tatatataaa tatagtatat ataaatatat agtatatata tagtatatat 420
aaatatatag tatatataaa tatatatagt atatataaat aatatatagt atataaataa 480
tatatattat taaatataat aataatttat tatatatact atatattatt atgtattata 540
ttatatatat tattttatat ttaatatata ttattttata tattatattt aatat 595

<210> SEQ ID NO 178
<211> LENGTH: 662
<212> TYPE: DNA
<213> ORGANISM: Homo sapiens
<220> FEATURE:
<221> NAME/KEY: misc_binding
<222> LOCATION: (1)..(662)
<223> OTHER INFORMATION: MAR of chromosome 2 genomic contig;
12699804..12700465

<400> SEQUENCE: 178
gtatatatat atatatatat atggtgtata tatatatata tatatatggt gtatatatat 60
atatatatat atggtgtata tatatatata tggtgtatat atatatatgc tgtatatata 120
tatggtatat atatatggta tatatatatt tgctatatat atagcagatc tgctatatat 180
atatatttgc tatatatata gcagatctgc tatatatatt tgctatatat atgctatata 240
tatgctacat atatgctata tatatgctat atatatgcta tatatatgct atatatatgc 300
tatatatatg ctacatatat gctatatata tgctacatat atgctatata tatgctatat 360
atatatgcta tatatatgct atatatatat gctatatata tgctatatat atatgctata 420
tatatgctat atatatatgc tatatatatg ctatatatat gctatatata tagcatatat 480
atatagctat atatatgcta tatatatagc ttatatatat gctatatatg ctatatatat 540
gctatatata tagctatata tatgctatat atagctatat atatgctaca tatatgctat 600
atatatgcca tatgtatgct atatatatgc tatatatata tgctatatat atgctatata 660
ta 662

<210> SEQ ID NO 179
<211> LENGTH: 649
<212> TYPE: DNA
<213> ORGANISM: Homo sapiens
<220> FEATURE:
<221> NAME/KEY: misc_binding
<222> LOCATION: (1)..(649)
<223> OTHER INFORMATION: MAR of chromosome 2 genomic contig;
12821904..12822552

<400> SEQUENCE: 179
tatgtaatat tatatatata aattatatat tatacatatg taatattata tatatataaa 60
ttatatatta tacatatgta atattatata tatataaatt atatattata catatgtaat 120
attatatata tataaattat atattataca tatgtaatat tatatatata taaattatat 180
attatacata tgtattatat atataaatta tatattatac atatataata tatatataaa 240
ttatatatta tacatgtata atatatataa attatatatt atacatatat aatatatata 300
aattatatat tatacatata taatatatat aaattatata ttatacatat ataatatata 360
taaattatat attatacata tataatatat ataaattata tattatacat atataatata 420
tataaattat atattataca tatataatat atataaatta tatattatac atatataata 480
tatataaatt atatattata catatataat atatataaat tatatattat acatatataa 540
tatatataaa ttatatatta tacatatata atatatataa attatatatt atacatatat 600
aatatatata aattatatat tatacatata taatatatat aaattatat 649

<210> SEQ ID NO 180
<211> LENGTH: 3191
<212> TYPE: DNA
<213> ORGANISM: Homo sapiens
<220> FEATURE:
<221> NAME/KEY: misc_binding
<222> LOCATION: (1)..(3191)
<223> OTHER INFORMATION: MAR of chromosome 2 genomic contig;
15356889..15360079

<400> SEQUENCE: 180
tacaattata tataactata aatataatat aatatatatt atctatatta catattaata 60
tataatatat attacctatt aatatataat ataatatata taatatatat tacctattaa 120
tatataatat aatatatata atatatatta cctattaata tataataaaa tatatataat 180
atatattaca tattattata taatatatat tatataacat atataacata tactatatat 240
tatataacat atataattgt atatgtatta tatatattat atatacttat acataatata 300
taaataatta aatatatgtt ataaatataa caaatatata acatatataa catatataac 360
atatatataa ttacataaaa tatataatac ataatatata ttatgcaaca tattatataa 420
tatataacat ataatgtata ttatattata tcatatataa tacataatat ataatatatg 480
atataatata atatattata tatgatataa tataatatat tatatatgtt ataatataat 540
atatattata tataggatat attataacat attacatatg atataataaa ttttatctta 600
tatataggat atattataat atatcacata tagcatatat taaaatatat tacatatagt 660
atattatata tactatatgt atatatacat atagtatatt atagtatatt atacagtata 720
tattatatat actatatata gtagtataca gtatatatta tatatactat atatagtagt 780
atacagtata tattatacag tatatattat atacactata ttatatatta tgtataaatat 840 atactatata tagtatatta tgtagtatat attaaacata atagatatat agtatatact 900
atagataata gatattatat agtatatagt atatattata tataatatat ataatatata 960
ttatatacat atatgatata tgatatatta tatataatat atataatata taatatatgt 1020
aatataatac atattatata taatatatgt aatataatat aatatataat atatgtaata 1080
taataatata tattatataa tataacatat ataaatataa taatatatat tatatgatat 1140
aacatacata aatataataa catatataat atatattata tattatattg tatatatgat 1200
atactatata ttacacatta tacattattt ataatatata attaatatat aacatatatt 1260
agataacata taattatatc tgtaacatat ataagatata attacatata taacatatat 1320
aattatatat atatttatct aattatatat gaaattatat atgacatata aaattatata 1380
ttatatatgt tatatgtatt atatattata tatgttatat atgttatata taacatatat 1440
aacatatata acacacacat ataacatata taacatatat tacatatata acatatataa 1500
cacatatata attatctaac atagataata tatataatat ataatataac atatatatta 1560
tatattatac actctattat attatatata ttatacataa tatataatat atatgatata 1620
atataataca ttgtatatac gatataatat atattgtaca tagtataata tacatatata 1680
gtatattatg tataacataa tatatagtat attatgtata acataatata tagtatatta 1740
tgtataacat aatatatagt atattatgta taacataata tatagtatat tatgtataac 1800
ataatatata gtatattatg tataacataa tatatagtat attatgtata acataatata 1860
tagtatatta tgtataacat aatatatagt atattatgta taacataata tatagtatat 1920
tatgtataac ataatatata gtatattatg tataacataa tatatagtat attatgtata 1980
tataatatac atattatata gtatattatg tatatataat atacatatta tatagtatat 2040
tatgtatata taatatacat attatatagt atattatgta tatataatat acatattata 2100
tagtatatta tgtatatata atatacatat tatatagtat attatgtata tataatatac 2160
atattatata gtatattatg tatatataat atacatatta tatagtatat tatgtatata 2220
taatatacat attatatagt atattatgta tatataatat acatattata tagtatatta 2280
tgtatatata atatacatat tatatagtat attatgtata tataatatac atattatata 2340
gtatattatg tatatataat atacatgtta tgtagtatat tatgtatata taatatacat 2400
gttatgtagt atattatgta tatataatat acatgttatg tagtatatta tgtatatata 2460
atatatataa ggtgtatata tattatgtat atataatata taaggtatat atattatgta 2520
tatataatat atataaggtg tttatataat gtatatataa tatataaggt atgtatatta 2580
tgtatatata atatgtatat tatatataat atatattatt tatatacatt atgtatctat 2640
ataatatata ttatgtatat attaggtatc tatataatat atattatgta tatatattat 2700
gtatctatat aatatatata ttatgtatat atattatgta tctatataat atatatatta 2760
tatgtatatt atgtatctat ataatatata taatgtatat agatatatta tatattatgt 2820
atatatatta tgtatctatt ttatatataa tgtatataga tatacaatat atattatgta 2880
tatattatgt atctatataa tatatattat ttatatagat atatatatta tgtatatata 2940
cataatatat tacatattat gtatatatac ataatatata atatattatg tatatataca 3000
taatatataa tatattatat attacatata ttatatataa tatattatat tatgtatata 3060
tattatgtat atataatgta tatataatat ataaagtgta tatatattgt gtatatataa 3120
tgtatatata ttacatatat tatgtgtata tatattatac ataatatata tactacatta 3180
tacataatat g 3191

<210> SEQ ID NO 181
<211> LENGTH: 314
<212> TYPE: DNA
<213> ORGANISM: Homo sapiens
<220> FEATURE:
<221> NAME/KEY: misc_binding
<222> LOCATION: (1)..(314)
<223> OTHER INFORMATION: MAR of chromosome 2 genomic contig;
728676..728989

<400> SEQUENCE: 181
tgtgtatata tgtatatata atatatatta tataatatgc atatgtataa aatatgtata 60
ttatatatgt atattttata tatatgtata tattatatgt atattttata tatgtatatt 120
ttatatatat gtatatatta tatatgtata ttttatatat atgtatatat tatatgtata 180
ttttatatat atgtatatat tatatatgta tattttatat atatgtatat attatatatg 240
tatattttat atatatgtat attttatata tatgtatatc atatatatgt atatattata 300
tatatgtata tctt 314

<210> SEQ ID NO 182
<211> LENGTH: 423
<212> TYPE: DNA
<213> ORGANISM: Homo sapiens
<220> FEATURE:
<221> NAME/KEY: misc_binding
<222> LOCATION: (1)..(423)
<223> OTHER INFORMATION: MAR of chromosome 2 genomic contig; 737493..737915

<400> SEQUENCE: 182
ataatatata gtgtctttta tattatctaa tatgtaatat aatgtatttt atattatgta 60
ttttatatta tataatatat aatataatgt attttatatt atatgttata taatatatag 120
tgcattatat attatgttat attatatata ttttatttat ataaattata tattatatgt 180
tattttatat atattatata acatataata taacaatgca ttatatatta taaaatatat 240
aatacattac atatattata taatatataa tacattacat atattatata atatataata 300
cattatcata tattacaaat attacattag tataatagta attataatat aatatattat 360
atattacata tattatatta atgtaatagt aattataata taatatatat tatattttat 420
att 423

<210> SEQ ID NO 183
<211> LENGTH: 724
<212> TYPE: DNA
<213> ORGANISM: Homo sapiens
<220> FEATURE:
<221> NAME/KEY: misc_binding
<222> LOCATION: (1)..(724)
<223> OTHER INFORMATION: MAR of chromosome 2 genomic contig; 1069556..1070279

<400> SEQUENCE: 183
tattataata tattatatac attatattgt atatatacta tatatggtat atatagtata 60
cataatataa aatgtatatt gtaatataca ttatatatat acatagtgta cattatataa 120
tataatataa tgtatattat aatatacatt ataatataat agtgtactat gtatatagta 180
tatataatgt atattataat gtattatata gtataatata atataatata cattatatag 240
tattgcatta tatatgctat ataatatata atatattatg tatatataca ttatatatac 300
tatattatat agtacatata atgtatatta tatagtatat ataatataat acattataca 360
tacaatatat aatgtatatt atatagtatg tataatgtaa tacattatac atagtacata 420
aagtatatta taatatatta taatatataa tatacattat atattataat gtatataata 480
tattgtatat atactatata taatgtatat acaattatat ataattgtat atatacatgt 540
atatgtatat gtatatatac atgtatatgt atgtgtatat atacatatat gtatatgtat 600
gtgtatatat gtatatgtat atatgtatat gtatacgtat atatgtatat acaatgtata 660
tataatgtat ataaaaatat ataatatata caatatgtat ataatgtata taattatata 720
atat 724

<210> SEQ ID NO 184
<211> LENGTH: 383
<212> TYPE: DNA
<213> ORGANISM: Homo sapiens
<220> FEATURE:
<221> NAME/KEY: misc_binding
<222> LOCATION: (1)..(383)
<223> OTHER INFORMATION: MAR of chromosome 2 genomic contig; 2719918..2720300

<400> SEQUENCE: 184
atatttatat tttatatatt atttatatat aaatatatat ttatatttta tatattattt 60
atatataaat atatatttat attttatata ttatttatat ataaatatat atttatattt 120
tatatattat ttatatataa atatatattt atattttata tattatttat atataaatat 180
atatttatat tttatatatt atttatatat aaatatatat ttatatttta tatattattt 240
atatataaat atatatttat attttatata ttatatattt atatattata tatatttata 300
ttaatttgtg tataatatat attattaaat ataataaata tatttatttt tatatattat 360
ataaaaatat ataatatata aaa 383

<210> SEQ ID NO 185
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 2 genomic contig;
4994249..4994557

<400> SEQUENCE: 185
tataatatat aattgttata acattataac aattatatat tatatataat acaattatat 60
aatatatatt atataattgt aatatataat ataattatat aatatatatt atataatata 120
atatataata tatcatatat gttatatatt ttattatata atatatatta tatataatat 180
tatatataat atatattata tataatatta tatataatat atattatata taatatattt 240
atatatatta tatataatat atattatata ttaaatatta tatatataat atatataaca 300
ttattgtta 309

<210> SEQ ID NO 186
<211> LENGTH: 740
<212> TYPE: DNA
<213> ORGANISM: Homo sapiens
<220> FEATURE:
<221> NAME/KEY: misc_binding
<222> LOCATION: (1)..(740)
<223> OTHER INFORMATION: MAR of chromosome 2 genomic contig;
5034916..5035655

<400> SEQUENCE: 186
tttatatata aaatattata tataatatta tatataatat tttctatata aaatgtgtat 60
ataattatat ataattatat aaaatataat atagaatatc taataatgta taatatataa 120
catataaaaa taatattatt taatatataa tattttatat ataatatttt tatatataat 180
ataatatata ttttatatat aattattaat tatataatta atatataata tatattttat 240
acataattat taattatata taattaatat ataatatatc ttatacataa ttatcaatta 300
tatataatta atatataata tatattttat acataattat taattatata taattaatat 360
ataatatatc ttatacataa tatatataaa tatattatat ataatatata ttatatataa 420
tattatatat aatatatatt atatatataa aatttatata taatattata tataatatta 480
tatattttat atacaatatg atatataata taatttatat attatatata tttatatata 540
attattatat aaattatata aatataaatt atatatttat atataattat tatataaatc 600
attatataat tattataatt ataatatata atataatata atattatata taatatatag 660
tattctatat aaataatata acatatattt tatatagaat attatatata atataatata 720
tattttatat agaatattat 740

<210> SEQ ID NO 187
<211> LENGTH: 847
<212> TYPE: DNA
<213> ORGANISM: Homo sapiens
<220> FEATURE:
<221> NAME/KEY: misc_binding
<222> LOCATION: (1)..(847)
<223> OTHER INFORMATION: MAR of chromosome 2 genomic contig;
6074678..6075524

<400> SEQUENCE: 187
aatatagaca taaatatata tgcataaata tatatatgca taaatatata taaaaatata 60
tataaatata tacataaata tatataaata tatacaaaaa tatatataaa tatataaaaa 120
aatatataaa tatatataca catatataaa tatatataca tacatatata aacatatata 180
cataaatata tatgtataaa tatatataca cataaatata tgtatgaata tatatacata 240
aatatatatg tataaatata tatacataaa tatataaaga tatatacata aatatatata 300
aatatatata cataaatata tataaatata tataaataga tatataaata tatatataaa 360
tatataaata tatatataaa tatataaata tataaaaata gatatataaa tatatatata 420
aatatataaa tatatatata aatatatata aatatataaa tatatatata aatatatata 480
aatatataaa tatatataaa tatataaata tatatataaa tatatataaa tatataaata 540
tatataaata tatataaata tataaatata tatataaata tatataaata tataaatata 600
tatataaata tataaatata taaatatata tataaatata taaatatata taaatatata 660
taaatatata aatatatata aatatatata aatatataaa tatatataaa tatatataaa 720
tatatataaa tatataaata tatataaata tatataaata tatataaata tatataaata 780
tataaatata tatataaata taaatatata taaatatata aatatatata taaatatata 840
taaatat 847

<210> SEQ ID NO 188
<211> LENGTH: 784
<212> TYPE: DNA
<213> ORGANISM: Homo sapiens
<220> FEATURE:
<221> NAME/KEY: misc_binding
<222> LOCATION: (1)..(784)
<223> OTHER INFORMATION: MAR of chromosome 2 genomic contig;
6108986..6109769

<400> SEQUENCE: 188
atttatttat atatttaata tataaaatat atatttaata tataaaatgt atatatatac 60
atatattata tataatacaa tatatattat atataatata tattatatat aatattatat 120
attatattat aatataatat atattatata taatataata tatattatat attattatat 180
ataatataat atatattata tattattata tataatataa tatatattat atattattat 240
atataatata atatatatta tatattatta tatataatat aatatatatt atatatatat 300
tttatatata taatatataa tatatatatt atatatatat tttatatata taatatataa 360
tatatatatt atatatatat tttatatata taatatataa tatatatatt atatatatat 420
tttatatgta taatatataa tatatatatt atatatatat tatatatata taatatgtaa 480
tatatatatt atatatatat tatatatata atatatatta tacataaaat atatattata 540
tataatatat ataatatata ttatatataa aatatatttt atgtataata tatattatat 600
ataatatata atgtatattt atatataaaa tatatattta tatacaatgt atatttatat 660
ataaaatata tatttatata caatgtatat ttatataaat atgtgtttaa tatatgaaat 720
atatatttat atataatata tatttaatct ataaaatata tattaaatat atatttatat 780
ttaa 784

<210> SEQ ID NO 189
<211> LENGTH: 381
<212> TYPE: DNA
<213> ORGANISM: Homo sapiens
<220> FEATURE:
<221> NAME/KEY: misc_binding
<222> LOCATION: (1)..(381)
<223> OTHER INFORMATION: MAR of chromosome 2 genomic contig;
10389032..10389412

<400> SEQUENCE: 189
tatacacata tagagtatat agagtatata tagagtatat ctatagagta tatatgtata 60
tagagtatat aatacagcct accatatata tagtatacat atatatatac tctatatact 120
atatatatag tgtgtatata tatagtatag accctaccat atatatatat aggagtatat 180
atatatacac actcctacta tatatagtat gtatatagag agtatataga gtatatatac 240
agtatatata cacagtatat atatgccata tatagtatct atatacttat atatagtatg 300
tatctatata cttatatata gtatgtatct atatactata tatagtatgt atctatatac 360
tatatagagt atatatgtat a 381

<210> SEQ ID NO 190
<211> LENGTH: 507
<212> TYPE: DNA
<213> ORGANISM: Homo sapiens
<220> FEATURE:
<221> NAME/KEY: misc_difference
<222> LOCATION: (1)..(507)
<223> OTHER INFORMATION: MAR of chromosome 2 genomic contig;
11097807..11098313

<400> SEQUENCE: 190
aattatatat aatttattat atataatttt atatttataa tatttttata tacatatttt 60
atatatcttt ataattatat attacatata taatattata taatatatat aatatatata 120
atatatatta tatattatat aatatatatt atatatatta tatataatat atataatata 180
tataatatat ataatatata taatatataa tatatattat ataatatata ttatatataa 240
tatatattat atataatata tattatatat aatatataat atatataata tatataacat 300
ataataatat attatacata atttatatat aatttttata taattatata tatttatata 360
tttttatata attatatata tttatatatt tttatataat tatatatatt tatatatttt 420
tatataatta tatatataat ttttatataa atatatataa ttttatataa ttttatataa 480
ttataaaata tataattata tataatt 507

<210> SEQ ID NO 191
<211> LENGTH: 329
<212> TYPE: DNA
<213> ORGANISM: Homo sapiens
<220> FEATURE:
<221> NAME/KEY: misc_binding
<222> LOCATION: (1)..(329)
<223> OTHER INFORMATION: MAR of chromosome 2 genomic contig;
11234628..11234956

<400> SEQUENCE: 191
ttatagttaa atatataaat ataaaatata cagttttata cagtatatat aaaatataca 60
atatataata cataatacat tagttatata tactatatat actatatata ctacacgtat 120
agtatatata tgaaactata tatatactat acgtgtagta tatatatgaa actatatata 180
tactatacgt gtagtatata tatgaaacta tatactatac gtatagtata tatatgaaac 240
tatatatact atatatactt aactataatt gtatatagtt aaaaatataa atataaaata 300
tacagttaaa tatattaata tataatagt 329

<210> SEQ ID NO 192
<211> LENGTH: 584
<212> TYPE: DNA
<213> ORGANISM: Homo sapiens
<220> FEATURE:
<221> NAME/KEY: misc_binding
<222> LOCATION: (1)..(584)
<223> OTHER INFORMATION: MAR of chromosome 2 genomic contig;
797844..798427

<400> SEQUENCE: 192
tattatttta tgttataaat agataaaaat atatactaat atatatgtac ttatatatac 60
atcaatatat aatgttatat tttatactaa cgtatattat atatactagt atataatcta 120
tattatttta tatgttataa atatataata aaatatataa atattttatg catatattaa 180
tatataatat atactaacat gctaatttat atatacttat atataattta tatagtatat 240
aatatataaa tgtatataat acataattta tatatttata tattaatagt ttatatatta 300
gtatatatac taattttata tactaataaa taaattatat aatatataaa ttatatatta 360
tagtacataa tatatattat atagttaaat aactatgtaa ctataatata taactatata 420
tgatatacag ttatatataa tataaatttt acatacagta tataaattat atactataca 480
tttatataca tatggtatat aaattatata ctatacattt atatacatat ggtatataaa 540
ttgtatacta tataatgtgt attagtatat atactaatat atac 584

<210> SEQ ID NO 193
<211> LENGTH: 363
<212> TYPE: DNA
<213> ORGANISM: Homo sapiens
<220> FEATURE:
<221> NAME/KEY: misc_binding
<222> LOCATION: (1)..(363)
<223> OTHER INFORMATION: MAR of chromosome 2 genomic contig;
1093824..1094186

<400> SEQUENCE: 193
tatacacaca catatatata cacatatata tacacatata tatatacaca tatatataca 60
catatatata cacgtatata tgtatacaca tatatatgta tatatataca catatataca 120
cacatatata cgtgtatata cgtatatacg tacatatata cgtgtatata cgtatatgcg 180
tacatatata cgtgtatata cgtatatgcg tacatatata cgtgtatata cgtatatgcg 240
tacatatata cgtgtatata cgtatatgcg tacatatata cgtgtatata cgtatatgcg 300
tacatatata cgtgtatata cgtatatgcg tacatatata cgtgtatata cgtatatgcg 360
tac 363

<210> SEQ ID NO 194
<211> LENGTH: 545
<212> TYPE: DNA
<213> ORGANISM: Homo sapiens
<220> FEATURE:
<221> NAME/KEY: misc_binding
<222> LOCATION: (1)..(545)
<223> OTHER INFORMATION: MAR of chromosome 2 genomic contig;
3456187..3456731

<400> SEQUENCE: 194

```
tattataata tatatttata tattataata tatattatat tatatattta tatattataa     60

tatatattat attatatatt tatatattat aatatatatt atattataat atatatttat    120

attataatat attatattat aatatatatt atattattat atattataat ataatatata    180

ttataatata tattatatta taatttatat attatatata ttataatata tattatatta    240

tatatatatt tatattataa tatatattat tatatattat atattataat ttatattata    300

ttacaatata tattataaat atatatatta tattataaat atatattttt atattacaat    360

atatattata aatatatatt ttatattaca atatatatta taaatatata tattatatta    420

caatatatat tataaatata tattatatta caatatatat tatattataa tatatattta    480

tatatgatat attatattta atatattata taacataata tataatatat aatatattaa    540

tataa                                                                545
```

<210> SEQ ID NO 195
<211> LENGTH: 356
<212> TYPE: DNA
<213> ORGANISM: Homo sapiens
<220> FEATURE:
<221> NAME/KEY: misc_binding
<222> LOCATION: (1)..(356)
<223> OTHER INFORMATION: MAR of chromosome 2 genomic contig;
5001567..5001922

<400> SEQUENCE: 195

```
tataaaatat atgttatata tataatatat attatataat atataatata tataatatat     60

aaaatatata aaatatataa tatataatat aatatataat atatataata tataaaatat    120

atataatata aaatatatat aatatataat atatataata tataatacat ataatatata    180

atatataata tataatatat ataatatata atatataata tataatatat ataatatata    240

atatataata tatataatat ataatatata atatataata tataaatata taaatatata    300

tacacacata cacacacata tatgcatata tatacatata catgtgtaca tagata        356
```

<210> SEQ ID NO 196
<211> LENGTH: 321
<212> TYPE: DNA
<213> ORGANISM: Homo sapiens
<220> FEATURE:
<221> NAME/KEY: misc_binding
<222> LOCATION: (1)..(321)
<223> OTHER INFORMATION: MAR of chromosome 2 genomic contig;
5457330..5457650

<400> SEQUENCE: 196

```
tatacaatat attataaatt atatataatt tatatataat atatattata tataaattat     60

atataattta tataatatat aaattatata taatataaat tatatataat ttatataata    120

tataaattat atattatata aattaaatat aatttatatt atatataaat tatatttaat    180

ttatataata tataaattat atttaattta tatataatat aaattatatt tttatatatt    240

atgtataatt tatatattta tacatatata cattataata tattgtatag tatatataat    300

atatagtata tataaagcat a                                              321
```

<210> SEQ ID NO 197
<211> LENGTH: 361
<212> TYPE: DNA
<213> ORGANISM: Homo sapiens
<220> FEATURE:
<221> NAME/KEY: misc_binding
<222> LOCATION: (1)..(361)
<223> OTHER INFORMATION: MAR of chromosome 2 genomic contig;

8124469..8124829

<400> SEQUENCE: 197
tatatataat atatattata tatattatat aaattatata taatatgtaa tataaatttt 60
gtaatataaa ttatatatat aaattatata taatatatat taatatatat aatataaatt 120
aatatatata atatataatt atatataatt tatatgatat atataaatat atattatata 180
taaattatat atatcataaa ttatatatca tataaattat atataatata cattatgtac 240
ataatatatg atatataata tataatatat attatatata attatatata tataattata 300
taatatatat aaattataat atataatata tataaattat aatatataat atatataaat 360
t 361

<210> SEQ ID NO 198
<211> LENGTH: 418
<212> TYPE: DNA
<213> ORGANISM: Homo sapiens
<220> FEATURE:
<221> NAME/KEY: misc_binding
<222> LOCATION: (1)..(418)
<223> OTHER INFORMATION: MAR of chromosome 2 genomic contig;
11151485..11151902

<400> SEQUENCE: 198
atgtaactat atatatagta tatatagtat atatatacta tatagtgtgt atatatagta 60
tatatatact atatagtgtg tatatatagt atatatatag tgtatatatc gtatatacac 120
tatatactat atagtgtata tatagtatat gtagtatata tagtatatat agtatagtat 180
atatagtata tatagtgtat atatactgta tatatagtgt acatagtata ctatatagta 240
tacatatagt acactgtata gtatatatag tatagtatat atagtataca tagtatacta 300
tatatagtat agtatacata gtatactata tagtatatag agtatatata cagtatacta 360
tatagtatat agagtatata tacagtatac tatatcgtgt gtatagagta tatataca 418

<210> SEQ ID NO 199
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of chromosome 2 genomic contig;
13591477..13591870

<400> SEQUENCE: 199
ttatatatat tttatatata ttatatatat tttatatata ttatatatat attatatata 60
tattatatat aattatatat aatatatatt atatatatta tatataatta tatataatat 120
atattatata tattatatat ataatatata tataatatat atattttata tatgtattat 180
atatatttta tatatattat atatattata tatatatttt atatatatta tattttatat 240
atataatata acatatataa tatataatta tatattatat atatattata ttatatataa 300
tatatattat atataatata atatataatt atatatatta tatattttat atatttatat 360
aaaaattatt ttatattatt ttatatataa atat 394

<210> SEQ ID NO 200
<211> LENGTH: 1194
<212> TYPE: DNA
<213> ORGANISM: Homo sapiens
<220> FEATURE:
<221> NAME/KEY: misc_binding
<222> LOCATION: (1)..(1194)

<223> OTHER INFORMATION: MAR of chromosome 2 genomic contig;
14996824..14998017

<400> SEQUENCE: 200
taatatttat atatacatat aaaatttata tataatatat aatatttata tatacatata 60
aaatttatat atatatataa tatttatata tacatataaa atttatatat aatatataat 120
atttatatat acatataaaa tttatatata atatataata tttatatata catataaaat 180
ttatatataa taaatattta tatatacata taaaatttat atataattta tatataacat 240
ataatattta tatataaaat ttatatataa catatattta tatataattt atatataaca 300
tataatattt atatataata tatatttatt tatacaattt atatataata tataatactt 360
atatatacat acataattta tatgatatat attatatata taatttatat gatatataat 420
atatctaata tatattatat atattatata tattatatat aatttatata atatatatta 480
tatatataat ttatataata tatatattat atatataatt tatataatat atatattata 540
tatataattt atataatata tattatatat ataatttata taatatatat tatatatata 600
atttatataa tatatattat atataattta tatataacat attttatata catatataat 660
ttatatataa tatatattta catatacata tataattttt atataatata aaatatttct 720
atatacatat ataattttta tataatataa aatatttcta tatacatata taatttttat 780
ataatatata tttctatata catgtctaat ttttatataa tatatatttc tatatacata 840
tataattttt atataatata taatattttt atatacataa tttttatata atatatattt 900
acatatacat atataatttt tatataatat atatttatat atacatatat aatttttaca 960
taatatatat tatatataca tatataattt atatacaaca tataatatat acatatataa 1020
tttatataca acatataata tttatgtata catatataat gtatacacaa tatataatat 1080
ttatatatac atatataatt tatatgtaat atatacatat ataatttata tgtaatatat 1140
atacatgtat aatttatatg tagtatatat acatgtataa tttatatgta gtat 1194

<210> SEQ ID NO 201
<211> LENGTH: 487
<212> TYPE: DNA
<213> ORGANISM: Homo sapiens
<220> FEATURE:
<221> NAME/KEY: misc_binding
<222> LOCATION: (1)..(487)
<223> OTHER INFORMATION: MAR of chromosome 2 genomic contig;
14998429..14998915

<400> SEQUENCE: 201
tagtatacat ttacacatac atgtataatt atatgtaata tataatattt acatatataa 60
ttatagataa tatatattta catatacata tataattata tataatatat aatgtttaca 120
tatacataca taattatata taatatatat ttaaatatac atatacaatt atatataata 180
tatatttaca tatgcatata taattataga taatatatat ttacatatac atatataatt 240
atatataata tataatgttt acatatacat atataattat atataatata tatttaaata 300
tacatataca attatatata atatatattt acatatgcat atataattat agataatata 360
tatttacata tacatatata attatatata atatataata tttacatata catatataat 420
gtatatataa tatataatat ttacatatac atatataatt tatatataat atatattata 480
tatatta 487

<210> SEQ ID NO 202
<211> LENGTH: 421
<212> TYPE: DNA

<213> ORGANISM: Homo sapiens
<220> FEATURE:
<221> NAME/KEY: misc_binding
<222> LOCATION: (1)..(421)
<223> OTHER INFORMATION: MAR of chromosome 2 genomic contig;
16562490..16562910

<400> SEQUENCE: 202
tatatgaata tatatatgaa tatatacgta tatatgaata tatacatgta tgtatatatg 60
aatatatgta tatatatgaa tatatatgta tatatgaata tatgtatata tatgaatata 120
tatgtatata tgtatatata tgaatatata tgtatatatg tatatatatg aatatatatg 180
tatatatgta tatatgtata tatatgaata tatatgtata tatgaatata tatgaatata 240
tatgtatata tatgaatata tatgaatata tgtgtatata tatgaatata tatgtatata 300
tatgaatata tgtatatata tatgaatata tatgtatata tgtatatatg aatatatatg 360
tgtatatgaa tatatatatg aatatatatg tgtatatgaa tatatatgaa tatatatgtg 420
t 421

<210> SEQ ID NO 203
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAR of chromosome 2 genomic contig;
21592301..21592779

<400> SEQUENCE: 203
tatatgtata cgtatataat atattatata ttatatacgt gtacgtatat atgtaatata 60
taatgtatat gtacacgtat ataatatata atatattata tacgtatacg tatacattat 120
atattacata tatacgtata tacgtatata aaatatatgt atatattata tatacgtata 180
taatatatat tatataatat ataatatata cgtatacata taatatatta tatatacata 240
ttatatatta tatatttaaa ttatatatta tatcatatat aatatatatg atataatata 300
taatatacat atattacata atatatatta tatacatata catatataat atataatata 360
ttatatacat atacatatat aatatataat atattatata catatacata tataatatat 420
aatatattat atacatatac atatataata tataatatat tatatataca tattatata 479

<210> SEQ ID NO 204
<211> LENGTH: 870
<212> TYPE: DNA
<213> ORGANISM: Homo sapiens
<220> FEATURE:
<221> NAME/KEY: misc_binding
<222> LOCATION: (1)..(870)
<223> OTHER INFORMATION: MAR of chromosome 2 genomic contig;
22557584..22558453

<400> SEQUENCE: 204
tataatatat aatatacata atatgtatat tttatacaca atataaataa tatacataac 60
atatatgtat attttatata tgtatatttt atatatattt tatatatttt atatatatgt 120
atattttata tataatatat atattgtata taataatata taatatatta tattatatat 180
aatatatata atatatatat aaatatatat tatatataat atgtataata tataatattt 240
tatatataat atgtataata tatattttat atataataat atgtacaata tatattttat 300
atataataat atgtacaata tatattttat atataataat atgtacaata tatattttat 360
gtataatatg tataatatat attttatgta taatatatat tttatgtata atatatattt 420
tacgtatatt ttatatataa tatataatat tttatatata atatataaca ttttatatat 480
aatatataat attatatata ttatatattt tatatataat atatataaat atatatattt 540
tatatataat atattttata tataatatat ataaatatat atattatata taatatattt 600
tatatataat atattttata tataatatat aatatatttt atatattata tataatatat 660
tatatattat atataatata ttatatataa tatataatat ataatatatt atatataata 720
tataatatat aatatattat atataatata taatatataa tatataatat attatatata 780
atatataata tgtaatatat aatattttat atataatata taatataata tataatattt 840
tatatataat atataatata taatatataa 870

<210> SEQ ID NO 205
<211> LENGTH: 1086
<212> TYPE: DNA
<213> ORGANISM: Homo sapiens
<220> FEATURE:
<221> NAME/KEY: misc_binding
<222> LOCATION: (1)..(1086)
<223> OTHER INFORMATION: MAR of chromosome 2 genomic contig; 30591960..30593045

<400> SEQUENCE: 205
gtatatataa tatatattat attatgttat atattatgta gactatgtat taaatatatg 60
tatatattat atataaatat ataatatata tttataattt ataattataa atatatttat 120
aatatatttt tctaaatatt tatatattat atattatatc taatgatata taataaatat 180
atttctaata tattttatat ttataaatat tttatatata ttatatattt tatatatact 240
atatattata tattatatat tttatatata ctatatatta tatagtatat attttatata 300
tactatatat tatatattat atattttata tatactatat attatatatt atatatttta 360
tatatactat atactattta ttatatattt tatatatact atatactatt tattatatat 420
tttatatata ctatatacta tttattatat attttatata tactatatat tatatattat 480
atattttata tataatatat atttattata tattttatat attatatata ttatatatta 540
tatatttata tattatataa tatatattat atatagaata tataatatat attatatata 600
atataatata atatatatta tataaaatat atataatata taaaatatat aatatatgat 660
atatataata tatattctat atttatacat atatatttaa tattatatta atatataatt 720
atatattatc atatgtaata atagatataa tatgtaatat ataaattata attatatatt 780
aatattatat attatttaat atgtatattt acacatatat taattattaa atatatatat 840
ttaatatatt aaatattatg tattaaatat atataatata tttataaata ttttatatat 900
aatatataca tatattaaca tatatgtata tatgtatata ttatatataa cattatatat 960
attatgttac atatactata ttttatatgt tacatatact atatattata tgttacatat 1020
aatatatata acatatatta taatatgtaa catattatat ataacatata atatatagta 1080
tatata 1086

<210> SEQ ID NO 206
<211> LENGTH: 406
<212> TYPE: DNA
<213> ORGANISM: Homo sapiens
<220> FEATURE:
<221> NAME/KEY: misc_binding
<222> LOCATION: (1)..(406)
<223> OTHER INFORMATION: MAR of chromosome 2 genomic contig; 36233909..36234314

<400> SEQUENCE: 206

```
attataaata tatattatag atattagata ttatagatat aatatatata atatatatta     60

tagatattat agatatagat ataatagata ttatagatat tatagatata atatatatta    120

tagatattat agatataata tatattatag atattataga tataatatat attatagata    180

ttatagatat aatatatatt atagatataa tatatattat agatattata gatatagata    240

ttatagatat tatatatatt atagatataa tatatattat agatattata gatatagata    300

ttatagatat aatatatatt atagatatta tagatataat atatattata gatattatag    360

atataatata tattatagat ataagatata ttatagatat tacaga                   406


<210> SEQ ID NO 207
<211> LENGTH: 797
<212> TYPE: DNA
<213> ORGANISM: Homo sapiens
<220> FEATURE:
<221> NAME/KEY: misc_binding
<222> LOCATION: (1)..(797)
<223> OTHER INFORMATION: MAR of chromosome 2 genomic contig;
      36271745..36272541

<400> SEQUENCE: 207

atataaacat atacgtatat acacatatat acaaatacat atatacatat attatatata     60

tgtatatata ttatattata catatattat atatatatta tattatacat atatacatac    120

acacataaac atattacata catatacaaa ttatacacat atacatatat acatatatgt    180

atatacatac attatatata aatatatgta tataaaatgt acattatata tacatatata    240

ttatgtataa ataatatata aaataaacat aatatatatt tatagatatg atatatataa    300

tatatatgta tacatatata catatatgta tatataatgt acattataca tacataaaca    360

tcatatataa atgttatata tataatataa atatatataa tatataatat atactttata    420

tactatatat aatatatata atatgatata acatatacta tatatactat atataatata    480

tactatatat actgtatata atatataata taatatatac tatatatact aaatataata    540

tacataatat aatatatact atatataata tataatatat aatatagtat atatactata    600

tataataatt acatattata tattatacat tatatattat ataattatta tatataatta    660

tatattacat actttgtata taatgtaaat atacattaga atatataatg tatatatatg    720

tacatatata atgtatatat gtatacatta tataaactat atataaacat tatattatat    780

aaacattata tataaac                                                   797


<210> SEQ ID NO 208
<211> LENGTH: 423
<212> TYPE: DNA
<213> ORGANISM: Homo sapiens
<220> FEATURE:
<221> NAME/KEY: misc_binding
<222> LOCATION: (1)..(423)
<223> OTHER INFORMATION: MAR of chromosome 2 genomic contig;
      36498521..36498943

<400> SEQUENCE: 208

tattatatta tatatttaat attatatatt taatatatta tatatttaat attatatatt     60

taatatatta tatatttaat attatatatt taatatatta tatatttaat attatatata    120

taatatatta tatatttaat attatatata taatattata tatataatat tatatattta    180

atattatata tataatatta tatatataat atattatata tttagtatta tgtatttaat    240

atattatata tttagtatta tgtatttaat atattattta tttagtatta tatatttaat    300

atattattta tttagtatta tatatttaat atattatata tttaatatat tatatattta    360
```

ttatatattg tatatttaat atattatata tttattatat attatatata attatatatt 420
taa 423

<210> SEQ ID NO 209
<211> LENGTH: 304
<212> TYPE: DNA
<213> ORGANISM: Homo sapiens
<220> FEATURE:
<221> NAME/KEY: misc_binding
<222> LOCATION: (1)..(304)
<223> OTHER INFORMATION: MAR of chromosome 2 genomic contig;
37179891..37180194

<400> SEQUENCE: 209
gtgtatatat atcatatata ttatatcata tatatgtgta tatatatcat atattatatc 60
atatatatgt gtatatatat catatatata tcatatatgt gtatatatca tatatattat 120
atatcatata tgtgtatata tatcatatat tatatatcat atatatgtgt atatatcata 180
tatattatat atatctcata tgtgtatata tatcatatat aatatatatg tgtatatatc 240
atatatcata tataacatat atatgtgtat atatcatata tataacatat atcatatatg 300
tgta 304

<210> SEQ ID NO 210
<211> LENGTH: 693
<212> TYPE: DNA
<213> ORGANISM: Homo sapiens
<220> FEATURE:
<221> NAME/KEY: misc_binding
<222> LOCATION: (1)..(693)
<223> OTHER INFORMATION: MAR of chromosome 2 genomic contig;
38440448..38441140

<400> SEQUENCE: 210
tatatattct tttatatatt atatataata tatattcttt tatatattat atatagtata 60
tattctttta tatattatat atagtatata ttcttttata tattatatat agtatatatt 120
cttttatata ttatatatag tatatattct tttatatatt atatatagta tatattcttt 180
tatatattat atatagtata tattctttta tatattatat atataatata tattctttta 240
tatatcatat ataatatata ttcttttata tattatatat aatatatatt cttttatata 300
ttatatatca tgtatatata atatacaaaa tatatataga ttttatatat agattattac 360
ataatagaat atattatata ttatatataa tatatacata atatataata ttatatatga 420
tataatatat atcatatata tcatataata tatattatat atcatatatt atatataata 480
atatatagat tatatataat tatatatata atatatataa ttatatatat tatctatata 540
tagataatat atataattat atataatata ttatatagat tatatataat tatattatat 600
acaaaatcta tatataatat atattatatt atatataata tacataacta tataaaaaat 660
ataatatata atatatataa tatataatat ata 693

<210> SEQ ID NO 211
<211> LENGTH: 471
<212> TYPE: DNA
<213> ORGANISM: Homo sapiens
<220> FEATURE:
<221> NAME/KEY: misc_binding
<222> LOCATION: (1)..(471)
<223> OTHER INFORMATION: MAR of chromosome 2 genomic contig;
38887582..38888052

<400> SEQUENCE: 211

-continued

```
aacatatata ctatatatat tatatactat attatatatt atatatataa acatatatac     60

tatatataat atataaacat attatattat acatgatata gataaacata tatattatat    120

ataatataga taaaatatgt tatatataat ataatgtata gacatatatt atatatacat    180

atattctaca tatattatat atatattcta cacatattat attatatata catatattct    240

acatatatta tatatacata tattctacat atattatata tacatatatt ctacatatac    300

atatatacat atattatata tacatatatt atagatatat aatatataaa catatataat    360

attattatat ataatatata taataatatt atataatata taataatatt atatcttata    420

tataaataat atatatattt tatatatata atattatata tatataatat a             471
```

<210> SEQ ID NO 212
<211> LENGTH: 1221
<212> TYPE: DNA
<213> ORGANISM: Homo sapiens
<220> FEATURE:
<221> NAME/KEY: misc_binding
<222> LOCATION: (1)..(1221)
<223> OTHER INFORMATION: MAR of chromosome 2 genomic contig;
43885944..43887164

<400> SEQUENCE: 212

```
catataaaca tatattatat gtaacatata aacatattat atgtaacata taatatataa     60

tatataaaca tatattttat atattatatg ttacatataa tatataatat ataaacatat    120

attatatatt atatgtaaca tataatatat aatatataaa catatatttt atatataata    180

tataaacata ttttatatat aatatataaa catattttat atataatata taaacatata    240

ttttatatat aatatataaa catattttat atataatata taaacatata ttttatataa    300

tatataaaca tataatatat ataatatata aaagtatata atataaatat atataatata    360

aacatatata atataaatat atataaaata taaacatatg taatatataa acatatatta    420

tatataatat ataaacatat attatacgta caatatataa acatatattg tacgtacaat    480

atataaacat atattatacg tacaatatat aaacatatat tatacgtaca atatataaac    540

atatattata cgtacaatat ataaacatat attatacgta caatatataa acatatatta    600

tacgtacaat atataaacat atattatacg tacaatatat aaacatatat tatacgtaca    660

atatataaac atatattata cgtacaatat ataaacatat attatacgta caataaacat    720

atattatacg tacaatatat aaacatatat tatacgtaca atatataaac atatattata    780

cgtacaatat ataaacatat attgtacgta caatatataa acatatatta tatgtataat    840

atataaacat ataatatata atatatatta tatatatgtt tattatatat gtttatatat    900

tatatataac atatattatt atattatata tgtttatata ttatatatta tataatatat    960

atgtttatat attatatatt atataatata tatgtttata tattatatat tatataatat   1020

atatgtttat atattatata ttatataata tatatgttta tatattatat attatataat   1080

atatatgttt atatattata tattatataa tatatatgtt tatatattat atattatata   1140

atatatatgt ttatatatta tatattatat aatatatatg tttatatatt atataaataa   1200

taaacttaca tattttatta a                                             1221
```

<210> SEQ ID NO 213
<211> LENGTH: 543
<212> TYPE: DNA
<213> ORGANISM: Homo sapiens
<220> FEATURE:
<221> NAME/KEY: misc_binding
<222> LOCATION: (1)..(543)
<223> OTHER INFORMATION: MAR of chromosome 2 genomic contig;

45818200..45818742

<400> SEQUENCE: 213
tatgtatata tacatatata tttatacatg tatatatgta tatatacata tatatttata 60
catgtatata tatacatata tatttataca tgtatatata tacatatata tttatacatg 120
tatatatata catatatatt tatacatgta tgtatatata catatatatt tatacatgta 180
tgtatatata catatatatt tatacatgta tgtatatata catatatatt tatacatgta 240
tgtatatata catatatatt tatacatgta tgtatatata catatatatt tatacatgta 300
tgtatatata catatatatt tatacatgta tgtatatata catatatatt tatacatgta 360
tgtatatata catatatatt tatacatgta tgtatatata catatatatt tatacatgta 420
tgtatatata catgtatatt tatacatgta tgtatatata catgtatatt tatacatgta 480
tgtatatata catgtatatt tatacatgta tgtatatata catgtatatt tatacatgta 540
tac 543

<210> SEQ ID NO 214
<211> LENGTH: 463
<212> TYPE: DNA
<213> ORGANISM: Homo sapiens
<220> FEATURE:
<221> NAME/KEY: misc_binding
<222> LOCATION: (1)..(463)
<223> OTHER INFORMATION: MAR of chromosome 2 genomic contig;
47055478..47055940

<400> SEQUENCE: 214
atacatacat atatacatat atacacatat atacatataa tacacacata tttacatata 60
tacacacata tatacatata tacatatata cacatatata catgcataca catatataca 120
tatatacaca catatacaca catatataca tatatacaca tatatacaca tatacacata 180
tatacacaca tatacatata tacacatata tacatatata catatataca cacatataca 240
catatataca tatacacata tatacacata tacatatata cacatatata cacatatata 300
catatataca catatataca tatatacaca tatatacaca catatacaca tatatacata 360
tatacatatg tatacacata tatacatatg tatacacata tatacacata tacatatata 420
catacacata tatacgtata tatgtgtata tatacacata tac 463

<210> SEQ ID NO 215
<211> LENGTH: 2482
<212> TYPE: DNA
<213> ORGANISM: Homo sapiens
<220> FEATURE:
<221> NAME/KEY: misc_binding
<222> LOCATION: (1)..(2482)
<223> OTHER INFORMATION: MAR of chromosome 2 genomic contig;
47492696..47495177

<400> SEQUENCE: 215
aatatatata aaatatatta tattctatgt aatatataga atatataaaa tatattctat 60
atattatata gaatatatat tttataatat atattattta tatattttta tatatttata 120
ttatttatat atttatatat aatttatata atttatacat ataatttata tataatttat 180
ataaattata tatataattt atatataatt tatatataat ttatataaat tatatatata 240
atttatatat aatttatatg atttttatat ataatttata tataatttat ataattttta 300
tatataattt atatataatt tatataattt ttatatataa tttatataat atatatatat 360
aatttatata taatttatat aatttatata tataatttat atataattta tataatttat 420

-continued

```
atatataatt tatatataat ttatataatt tatatatata atttatatat aatttatata    480

atttatatat ataatttata cataatttat ataatttata tatataattt atataattta    540

tatatataat ttatatatat aatttatata atttatatat atgatttata taatttatat    600

atataattta tataatttat atatataaat tatatatata atttttatat aatttatata    660

tttataattt atatatttat ataatttata tatttataat ttatatattt atataattta    720

tatatttata atttatatat ttatataatt tatatataat tattcatata tttatataat    780

ttacatataa ttatttatat attcatatat aatttatata tttatatata atttatatat    840

aattatttac atatttatat atttatatat aatttatata tatttatata taatttataa    900

ataaaatata taatatataa tatataatat tataatagat aaaatatata ctatatatta    960

tatattttac attatattta atattatatg tataatttta tatcatatat aatatatatg   1020

atatatataa ttttatatca tatataatat atatggtata tataatttta tatcatatat   1080

aatatatatg gtatatataa ttttatatca tatataatat atgatatata attttatatc   1140

atataatata tattatatat aattttatat ctacatatta tatattatat atacaatttt   1200

atatctatct ataatatata ttatatatac aattttatat ctatataata tatattatat   1260

atacttttat attatatata aaatgtatat tatatatact tttatattat atataaaatg   1320

tatattatat ataattttat tttatatata aaatgtatat tatatataat tttattttat   1380

atataaaatg tatattatat ataattttat tttatatata aaatgtatat tatatataat   1440

tttattttat atataaaatg tatattatat ataattttat tttatataaa aaatgtatat   1500

tatatataat tttatattat atataatatg tatattatat ataattttat attatatata   1560

atatgtatat tatatataat tttatattat atataatatg tatattatat ataattttat   1620

attatatata atatgtatat tatatataat tttgtattat atataatatg tatattatat   1680

ataattttat attatatata atatgtatat tatatataat tttatattat atataatatg   1740

tatattatat ataattttat attatatata atatgtatat tatatataat tttatattat   1800

atataatatg tatattatat ataattttat attatatata aaatgtatat tatatataat   1860

tttatattat atataatatg tatattatat ataattttat attatatata atatgtatat   1920

tatatataat tttatattat atataaaatg tatattatat ataattttat attatatata   1980

aaatgtatat tatatatatt atatataaaa tgtatattat atatattata tataaaatgt   2040

atattatata tattatatat aaaatgtata ttatatatat tatatataaa atgtatatta   2100

tgtatattat atataatgta tattatgtat attatatata atgtatatta tatataatat   2160

atattatata taatgtatat tatataatat atattatata ttataatata taatatacat   2220

tatatattac atattatata taatatatta tatattatat attacatatt atatataata   2280

tattatatat tatattaaat atatatttta tatattatat attatatatt atataaaata   2340

tatatattat atattatata aaatatatat atattatatt atatattata ttaaatatat   2400

attttatata taatatatat aatatataat atataaaata tatattatat attatatata   2460

aattatatat attatatata aa                                            2482
```

<210> SEQ ID NO 216
<211> LENGTH: 539
<212> TYPE: DNA
<213> ORGANISM: Homo sapiens
<220> FEATURE:
<221> NAME/KEY: misc_binding
<222> LOCATION: (1)..(539)
<223> OTHER INFORMATION: MAR of chromosome 2 genomic contig;
47561069..47561607

<400> SEQUENCE: 216
aacagtaata tatcactaat atataataat atataacagt aatatatcat taatatataa 60
tatatcatta gtatataata ttaatatata ttaatatata atatatcata tacaatatta 120
atatatatta atatataata atatattatt aatgtataat agtaatataa tatattatca 180
atatatatta ctaatatata ataatatatc gttaatatat aatagatcat taatatataa 240
tgttaatata ttatgaatag ataatatatc agtatataat attaatatat taatatatta 300
tatattattt aataatatat aatatattaa taaataatta tatattaata tagcaatata 360
ttaatatatg actgtattat attattaata tataacaata tattatatat tatataataa 420
tttattatat aatatataat aatatattat atattatata acatattaat aatacataat 480
aacattaata atatataata atgttaatat attattatat tatatattaa tatataata 539

<210> SEQ ID NO 217
<211> LENGTH: 336
<212> TYPE: DNA
<213> ORGANISM: Homo sapiens
<220> FEATURE:
<221> NAME/KEY: misc_binding
<222> LOCATION: (1)..(336)
<223> OTHER INFORMATION: MAR of chromosome 2 genomic contig;
52853648..52853983

<400> SEQUENCE: 217
tatatacata aaatatatat attttatata tatacataat atatatatgt atattttatg 60
tatatatcta taatatatat aatataataa aatatacata tatattttat atatatataa 120
tatacatata aaatatacat acataaaata tacatgtata ttttatgtat atataatata 180
tatataaaat atacatgtat attttatata tataatatac atgtataatt aatatacatg 240
tatgttatat atattacatg tatattatat ataatataca tataaatttt aaatttagtg 300
tatattacat gtatattata tataatatat gtatat 336

<210> SEQ ID NO 218
<211> LENGTH: 406
<212> TYPE: DNA
<213> ORGANISM: Homo sapiens
<220> FEATURE:
<221> NAME/KEY: misc_binding
<222> LOCATION: (1)..(406)
<223> OTHER INFORMATION: MAR of chromosome 2 genomic contig;
54866263..54866668

<400> SEQUENCE: 218
tacgtatata aaaatgtata tttacatata taaaataaat attttatata cgtatataaa 60
atatatattt attttatata cgtatataaa atatttattt tatatatgta tataaaatat 120
ttattttata tacatgtata ttaaatatat atttatatat gtatataaaa atatatatta 180
tatacatgta tataaaatat atattatata tgtatataaa aatatatatg tatataaaat 240
atatatatta tatagatata taaaatatat attatataga tatataaaat atatatatta 300
tatagatata taaaatatat atattatata gatatataaa atatatatat tatatagata 360
tataaaatat atatattata tagatatata aaatatatat attata 406

<210> SEQ ID NO 219
<211> LENGTH: 1452
<212> TYPE: DNA
<213> ORGANISM: Homo sapiens
<220> FEATURE:
<221> NAME/KEY: misc_binding
<222> LOCATION: (1)..(1452)
<223> OTHER INFORMATION: MAR of chromosome 2 genomic contig;
55113305..55114756

<400> SEQUENCE: 219
ataatatata atatatattg tatattatat tattatatat tatatattat taaatatata 60
tattatatta tatattatat aatatatatt atatataata atatagaata tataattata 120
tattatatta tatattatat aatatatatt atatataata atatagaata tataattata 180
tattatacta tatattatat aatatatatt atatataata atatagaata tataattata 240
tattatataa tatgtgaata atgtaatata taattatatt atttacatat tatataatat 300
ataattatat tatataatat ataattatat tatttgtata ttatatataa catatacatt 360
atattatata taatataatt atatataatt aattataaat taattatata taattatata 420
atataatata taatatacat aatatataat atataataca taatatacat aatataatat 480
atattatata taatataata tatataatat aatataatat aatgtataat ataattatat 540
attatatata atatataatg ttatataatt atattatatt atataattaa ttatatgtaa 600
ttaatataat ataattatta tatataattt tttatataat ataatatata attatataat 660
ataatataat tatattatat tatataatat atatatatta tataatataa tataattata 720
ttatataatt atataatata atataattat atattatatt atataataaa tataattata 780
taatataata tgattatata atatattatg tatattatat attatatatt gtattatgta 840
tattatatat tatatattat gtatattata tattatgtat attatatatt atgtatatta 900
tatattatat attatattat gtataatata ttatgtatgt tatatataat ataaattata 960
ttatatatta tgtatattat atataaatta tattatatat tatgtatatt atatataata 1020
taaagtatat attatgtata ttatatataa tataaagtat atattatgta tattatatat 1080
aatataaagt atatattatg tatattatat ataatataaa gtatatatta tgtatattat 1140
atataatata aagtatatat tatgtatatt atatataata taaagtatat attatgtata 1200
ttatatataa tataaagtat atattatgta tattatatat aatataaagt atatattatg 1260
tatattatat ataatataaa gtatatatta tgtatattat atataatata aagtatatat 1320
tatgtatatt atatataata taaagtatat attatgtata ttatatataa tataaagtat 1380
atattatgta tattatatat aatataaagt atatattata tgttataaat tatatattgt 1440
tatatattat at 1452

<210> SEQ ID NO 220
<211> LENGTH: 502
<212> TYPE: DNA
<213> ORGANISM: Homo sapiens
<220> FEATURE:
<221> NAME/KEY: misc_binding
<222> LOCATION: (1)..(502)
<223> OTHER INFORMATION: MAR of chromosome 2 genomic contig;
56350637..56351138

<400> SEQUENCE: 220
atatattata gaaatataaa tatatagata tatctatata ttatagaaat ataaatatat 60
agatatatct atatattata gaaatataaa tatatagata tatctatata ttatagaaat 120
ataaatatat agatatacct atatattata gaaatataaa tatatagata tacctatata 180
ttatagaaat ataaatatat agatatacct atatattata gaaatataaa tatatagata 240
tatctatata ttatagaaat ataaatatat agatatatct atatattata gaaatataaa 300
tatatagata tatctatata ttatagaaat ataaatatat agatatatct atatattata 360
gaaatataaa tatatagata tatctatata ttatagaaat ataaatatat agatatatac 420
aacatatatg ttacatatta tatattatat atctatatat ctatataaca ttatatatct 480
atatatctat ataacatata ta 502

<210> SEQ ID NO 221
<211> LENGTH: 794
<212> TYPE: DNA
<213> ORGANISM: Homo sapiens
<220> FEATURE:
<221> NAME/KEY: misc_binding
<222> LOCATION: (1)..(794)
<223> OTHER INFORMATION: MAR of chromosome 2 genomic contig;
57051633..57052426

<400> SEQUENCE: 221
aactatatat actatattat atagttatac tatatatact atattatata gttatataac 60
tattatataa ctgtattata tagttatata actattatat aactgtatta tatagttata 120
taactattat ataactgtat tatatagtta tataactata ttatataact gtgttatata 180
gttatatatt atataactat attatataac tgtattatat agttatatat tatataacta 240
tattatataa ctgtattata tagttatata ttatataact atattatata actgtattat 300
atagttatat attatataac tgtattatat agttataaaa ctatattata taactgtatt 360
atatagttat aaaactacta tataactgta ttatataatt ataaaattat actatataac 420
tgtattatat agttataaaa ctatactata taactgtatt atatagttat aaaactatac 480
tatataactg tattatatag ttataaagct atactatata actgtattat atagttatat 540
aactatacta tataactgta ttatatagtt ataaaactat actatataac tgtattatat 600
agttataaaa ttatattata taactgtatt atatagttat ataactatat tatataactg 660
tattatatag ttatataact atattatata agtgtattat atagttatat aactatatta 720
tataactgta ttatacagtt atataactat attatataac tgtattatat acttatataa 780
ctatattata taac 794

<210> SEQ ID NO 222
<211> LENGTH: 300
<212> TYPE: DNA
<213> ORGANISM: Homo sapiens
<220> FEATURE:
<221> NAME/KEY: misc_binding
<222> LOCATION: (1)..(300)
<223> OTHER INFORMATION: MAR of chromosome 2 genomic contig;
57069272..57069571

<400> SEQUENCE: 222
acacatacat atatgtatat atgcacacac atatatatgt atatatacac atacatatat 60
gtatatatac atatatgtat atacgcacat acatatatgt atatatacac gtacatatat 120
gtctctatat atacacatac acatatgtat atacatatat gtgtatatat acacaatcat 180
atatgtatat acatatatac acatatacac aaacatatat gtatatacat atatgtatat 240
acatatatac acatatacac aaacatatat gtatatacat atatgtatat acatacacaa 300

<210> SEQ ID NO 223
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of chromosome 2 genomic contig;

57235143..57235512

<400> SEQUENCE: 223
tatttttata tataactata tatattttat atataaatta tatatatgat catatatata 60
atcatatata taatcatata tgattatata tgatcatata tatatttata tatataatta 120
tatatactta tatataatta tatatatatt tatatatata attatgtata cttatatata 180
tttatatata taattatata tacaatttat atatataatt atatataatt tatatataat 240
tatatatata aattatatat aagtatatat aattatatat atgtttatat ataattatat 300
atataaatga tatgtataat atataactat atataattat atataaatat atatatagat 360
tttatatata 370

<210> SEQ ID NO 224
<211> LENGTH: 306
<212> TYPE: DNA
<213> ORGANISM: Homo sapiens
<220> FEATURE:
<221> NAME/KEY: misc_binding
<222> LOCATION: (1)..(306)
<223> OTHER INFORMATION: MAR of chromosome 2 genomic contig;
57693125..57693430

<400> SEQUENCE: 224
tacgtatata cacgtataaa tataaatata tacatgtata tacgtatata catgtataaa 60
tataaatata tatatgtata tacgtatata catgtataaa tatatatatg tatatacgta 120
tatacatgta taaatatata tatatgtata tacgtatata catgtataaa tatatataca 180
tgtatatacg tatgttgtgt atacatacaa atctgtacat atatacatat atgttgtgtg 240
tatatataca tctatacatg tgtatgcgta tatatgtata tgtatatata gtatatataa 300
tacatg 306

<210> SEQ ID NO 225
<211> LENGTH: 500
<212> TYPE: DNA
<213> ORGANISM: Homo sapiens
<220> FEATURE:
<221> NAME/KEY: misc_binding
<222> LOCATION: (1)..(500)
<223> OTHER INFORMATION: MAR of chromosome 2 genomic contig;
59810331..59810830

<400> SEQUENCE: 225
tttattatat gtaatatata ttgtatttatt atatatatta tatataatat atattgtatt 60
attatatata ttatatataa tatatattgt attattatat atattatata taatatatat 120
tgtattatta tatatattat atataatata tattgtatat tatatatatt atatattata 180
ttattatata ttatatatat tatattatta tatattatat attatatata ttatattata 240
tattatatat tatattatat atattatatt atatattata tattatatta tatatattat 300
attatatatt atatattata ttatatatat tatattatat atattatata ttatatatta 360
tatatattat atattatata ttatatatat tatatattat atataatata tattatatta 420
ttatataata ttatatatta tatatattat atattatata taatatatat tatattatta 480
tataatatta tatattatat 500

<210> SEQ ID NO 226
<211> LENGTH: 565
<212> TYPE: DNA
<213> ORGANISM: Homo sapiens
<220> FEATURE:

<221> NAME/KEY: misc_binding
<222> LOCATION: (1)..(565)
<223> OTHER INFORMATION: MAR of chromosome 2 genomic contig;
59974589..59975153

<400> SEQUENCE: 226
atatatgtat aatatgtata tatgtatata ttatgtatat gttatatatg taatatatgt 60
atgtatatat tatatatcat atataatata taatgtgtat atatgtatat atgtatgtat 120
acatgtatat actatgtata tattgtatat attatatatg tatatataca tatacatata 180
taatatatac atatattata tacaatatat acatgtatat tatatacgat atatacatat 240
atattatata caatatatac atagtatata aatgtataca tacatacata tatacatatt 300
atatatgtat atatgtatac ataaatgtat atataatata tatacatata taaatgtata 360
catacgtaca tatacgtata tgtatatgca tatatgtata tatgtgcata catatatatg 420
tatatacata tatgtacata tgtacatata cgtatatatg tacatatgta catatacgta 480
tatatgtaca tatgtacata tacgtatata tgtacatatg tacatatacg tatatatgta 540
catatgtaca tatatacata tatat 565

<210> SEQ ID NO 227
<211> LENGTH: 427
<212> TYPE: DNA
<213> ORGANISM: Homo sapiens
<220> FEATURE:
<221> NAME/KEY: misc_binding
<222> LOCATION: (1)..(427)
<223> OTHER INFORMATION: MAR of chromosome 2 genomic contig;
60605573..60605999

<400> SEQUENCE: 227
tatataatgt atataatgga tatagatata gatatagata tatattttat ataatatata 60
ttatatatta tatataatat atgttatata tattatatat tttatataat atatatatta 120
tataaattat atatatataa tatataatat atatattata tatattttat ataatatata 180
tttaatatta tctattatat attttatata atatatattt tatataatat ataatatata 240
atatatattt tacataatat ataatatata atacgtatta tatataatat ataatacgta 300
ttttatataa tatataatac gtattatata taatacgtat tatatattat ataatatata 360
atacgtatta tataatatac gtaattatat tttattataa tacgtattat atattatata 420
atatata 427

<210> SEQ ID NO 228
<211> LENGTH: 1199
<212> TYPE: DNA
<213> ORGANISM: Homo sapiens
<220> FEATURE:
<221> NAME/KEY: misc_binding
<222> LOCATION: (1)..(1199)
<223> OTHER INFORMATION: MAR of chromosome 2 genomic contig;
61229949..61231147

<400> SEQUENCE: 228
gtatacatat ataaagtgta tatataatgt atatacatat atacatatat aaagtatata 60
tataatatat acatatataa agtatatata taatatatac atatataaag tatatataat 120
atatacatat ataaagtata tataatatat acatatataa agtatatata tcatatatac 180
atatataaag tatatatata atatatacat atatacatat ataaagtata tataacatat 240
atacatatat aaagtatata taacatatat acatatataa agtatatata taatatatac 300
atatatacat atataaagta tatataacat atatacatat atacagtata tataacatat 360

```
atacatatat acagtatata taacatatat acatatatac agtatatata acatatatac    420

atatatacag tatatataac atatatacat atatacatga agtatatata acatatatac    480

atatatacat gaagtatata taacatatat acatatatac atgaagtata tataacatat    540

atacatatat acatgaagta tatataacat atatacatat atacatatat aaagtatata    600

taacatatac atatatacat atataaagta taacatatac atatatacat atataaagta    660

tatataatat ataacatata catatataaa gtatatataa tatataacat atacatatat    720

aaagtatata taatatataa catatacata tataaagtat atataatata tacatatata    780

catatataaa gtatatataa tatatatata catatataaa gtatatataa tatatataca    840

tatatacata tataaagtat atataatata tatacatata taaagtatat ataatatata    900

tacatatata catatataaa gtatatataa tatatataca tatatacata tataaagtat    960

atataatata tatacatata tacatatata aagtatatat aatatatata catatataca   1020

tatataaagt atatataata tatatacata tatacatata taaagtatat ataatatata   1080

tacatatata catatataaa gtatatataa tatgtataca tatatacata tataaagtat   1140

atataatatg tatacatata tacatatata aagtatatat ataatatgta tacatatat    1199


<210> SEQ ID NO 229
<211> LENGTH: 454
<212> TYPE: DNA
<213> ORGANISM: Homo sapiens
<220> FEATURE:
<221> NAME/KEY: misc_binding
<222> LOCATION: (1)..(454)
<223> OTHER INFORMATION: MAR of chromosome 2 genomic contig;
      62181058..62181511

<400> SEQUENCE: 229

tatatatcat atattatata tgatatatat tatgtatata atacatatta tatataataa     60

atatttatta tatatgatat atattatgta tataatacat attatatata ataaatatat    120

attatattat atataataaa tatatattat attatatata atatatattt atatataaat    180

atattatata taaatatata ttatatataa aatatttata tattatatat aaatatatat    240

tatatataaa tatttatata ttatatataa atatttatat attatatata aatatttata    300

tattatatat aaaatatatt atatatatta tatatattat atattatata taatatattt    360

aatatataat atataaacat atattatata taatatataa acatatataa atatatttat    420

atataataga taaaaatata tataatatat ataa                                454


<210> SEQ ID NO 230
<211> LENGTH: 658
<212> TYPE: DNA
<213> ORGANISM: Homo sapiens
<220> FEATURE:
<221> NAME/KEY: misc_binding
<222> LOCATION: (1)..(658)
<223> OTHER INFORMATION: MAR of chromosome 2 genomic contig;
      62190919..62191576

<400> SEQUENCE: 230

tatatacaca actatatata taactatata tatacaacta tatatacaac tatatatata     60

actatatata taactatata taactatata tataactata tataactata tatataacta    120

tatatataac tatatataac tatatatata actatatata actatatata actatatata    180

taactatata tataactata tatataacta tatatataac tatatatact atatatataa    240

ctatatatat ataactatat atataactat atatatataa ctatatataa ctatatatat    300
```

ataactatat atataactat atatatataa ctatatatat aactatatat atataactat 360
atatataact atatatatat aactatatat aactatatat atataactat atatataact 420
atatatatat aactatatat ataactatat atatataact atatatataa ctatatatat 480
ataactatat atataactat atatataact atatatataa ctatatatat ataactatat 540
atataactat atatatataa ctatatatat aactatatat ataactatat atataactat 600
atatatataa ctatatatat aactatatat atataactat atatataact atatatat 658

<210> SEQ ID NO 231
<211> LENGTH: 1486
<212> TYPE: DNA
<213> ORGANISM: Homo sapiens
<220> FEATURE:
<221> NAME/KEY: misc_binding
<222> LOCATION: (1)..(1486)
<223> OTHER INFORMATION: MAR of chromosome 2 genomic contig;
62384127..62385612

<400> SEQUENCE: 231
attatatcta atctattata tattatatct aatacatatt atatctaatc tattgtatat 60
tatatctaat atataatata ttatatataa tatattatat attatatatt atatacaata 120
tattatatat tatataatat ataatatatt atatataata tattatatct aatatattac 180
atattatatc taatctatta tagatataat atgtaatata ttatatatta tatctaatag 240
atattagata taatatataa tatattatta atataatata ttagatataa tatataatat 300
aataatatat aatatatatt attggtaata tataatatat aattaataat atatattata 360
tataattatt atgaataata tatcatatat aatatctagt atattatata ttaataacat 420
ataaatatta tattaataat aaataacata ttaatattat attaataata tataatatac 480
taatattata ttaataatat ataatatact aatattatat taataatata taatatacta 540
atattatatt aataatatat aatatactaa tattatatta ataatatata atatactaat 600
attatattaa taatatataa tatactaata tattaagaat atataatata ctaatatatt 660
aagaatatat aatatactaa tattatatta ataatatata tttatattaa taatatatta 720
attattatta attaattatt aataattata taatattgat tatattaata ttatcaattt 780
aataatattg attatatatt atatattata tattatatat tatatattat atattatata 840
ttatatatta ataatatata ttagatataa tataatatat taataatata taagatataa 900
tataatatat taataatata tattagatat aatataatat attaataata tatattagat 960
ataatataat atattaataa tatatattag atataatata atatattaat aatatatatt 1020
agatgtaata taatatatta ataatatata ttagatgtaa tataatatat taataatata 1080
tattagatgt aatataatat attaataata tatattagat gtaatataat atattaataa 1140
tatatattag atgtaatata atatattaat aatatatatt agatgtaata taatatatta 1200
ataatatata ttagatgtaa tataatatat taatatatat tagatgtaat ataatatatt 1260
aataatatat attagatata atataatata ttaataatat attagatata atataatata 1320
ttaataatat ataagatata atataatata ttaataatat ataagatata atataatata 1380
ttaataatat ataagatata atataatata ttaataatat atattagata tataatatat 1440
taataatata tattagatat ctaatatcta ttagatatct aataga 1486

<210> SEQ ID NO 232
<211> LENGTH: 333
<212> TYPE: DNA

<213> ORGANISM: Homo sapiens
<220> FEATURE:
<221> NAME/KEY: misc_binding
<222> LOCATION: (1)..(333)
<223> OTHER INFORMATION: MAR of chromosome 2 genomic contig;
62538649..62538981

<400> SEQUENCE: 232
ttatatatat tatatatata tattttatat atatattata tatatatttt atatatatat 60
tatatatata ttttatatat atattatata tatattttat atatatatta tatatatatt 120
ttatatatat tatatatata ttttatatat attatatata tattttatat atatattata 180
tatatatttt atatatatat tatatatata ttttatatat atattatata tatattttat 240
atatatatta tatatatatt ttatatatat attatatata tattttatat atatattata 300
tatatatttt atatatatat tatatatata ttt 333

<210> SEQ ID NO 233
<211> LENGTH: 480
<212> TYPE: DNA
<213> ORGANISM: Homo sapiens
<220> FEATURE:
<221> NAME/KEY: misc_binding
<222> LOCATION: (1)..(480)
<223> OTHER INFORMATION: MAR of chromosome 2 genomic contig;
63240325..63240804

<400> SEQUENCE: 233
tatatataaa atatatattt tttaaatata aaatatatat atattttaat attaatatat 60
atatatttta atatataata tatatattat atattttata tataaaatat atatattata 120
tattttatat ataaaatata tatattatat attttatata ttaaaatata tattttatat 180
attttaatta ttaaaatata tatattatat attttaaata taaaatatat atattatata 240
ttttaatata taaaatatat atattatata ttttaatata taaaatatat atattttata 300
tttatatata taaatatata tattatatat tttaatatat aaaatatata tattatatat 360
tttaatatat aaaatatata tattatatat tttaatatat aaaatatata tattatatat 420
tttaatatat ataaaatata tatattatat attttatata tattaaatat atattttata 480

<210> SEQ ID NO 234
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of chromosome 2 genomic contig;
63935480..63935781

<400> SEQUENCE: 234
atatatataa atatatatat aattatatat agatatatat aattatatat agatatatat 60
attctatatt ctatatatat ataatatata atatataaat tatatataga atatatatta 120
tatataatat attatatata ttatatataa tatatatatt atatatatta tatataatat 180
atatattata tatattatat ataatttata tatattatat atagaatata tattatatat 240
agaatataga atatatataa tatatataga atacagaata tatatagaat atagaatata 300
ta 302

<210> SEQ ID NO 235
<211> LENGTH: 407
<212> TYPE: DNA
<213> ORGANISM: Homo sapiens
<220> FEATURE:
<221> NAME/KEY: misc_binding
<222> LOCATION: (1)..(407)
<223> OTHER INFORMATION: MAR of chromosome 2 genomic contig;
63935888..63936294

<400> SEQUENCE: 235
tataatatat taatataata tatagacagt atataatata atatacagac agtatataat 60
atacagacag tatataatat ataatattat atataatatt atatataata ttatataata 120
tattatatta tatatattat ataatatatt atattatata taatatatgt aatattatat 180
attatattat acataatata ttatatataa tatattatat ataatattat atatattata 240
tataatatat ataataataa tattataata tataatatat aatagtacag tatatattat 300
atatataatt ctatatataa tatatagaat tctatctatt tataatatat atagaattct 360
atatataata tataatatac agaattctat atatattata tatagaa 407

<210> SEQ ID NO 236
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of chromosome 2 genomic contig;
66958350..66958651

<400> SEQUENCE: 236
tattatatat attgtatata tatgtatatt atatatattg tatatataat gtatattata 60
tatattatat atatatgtat attatatata ttgtatatat atgtatatta tatatattgt 120
atatatgtat atgtatatat gtatgtgtat atatatacac atatacacat atatgtgtat 180
gtatatatat gtgtgtatat acgtatatat acatatatac aatttttgta tatatacata 240
tatacacata tatatgtgta tgtgtatata tatacacata tatgtgtgtg tatatacaca 300
ta 302

<210> SEQ ID NO 237
<211> LENGTH: 651
<212> TYPE: DNA
<213> ORGANISM: Homo sapiens
<220> FEATURE:
<221> NAME/KEY: misc_binding
<222> LOCATION: (1)..(651)
<223> OTHER INFORMATION: MAR of chromosome 2 genomic contig;
68307125..68307775

<400> SEQUENCE: 237
gatattatat attgtatata ttatatatgt atataatata ctattatata ttatatatgt 60
atataatttt attaatatat atattatatt atattatata ttatattata ttatattata 120
tatataatat taatattata tattattata tattatatta tattaatatt atatatatat 180
aatatatata atatatataa tagtattata tataatatat ataatagtat tatatattat 240
atatatataa tactattata tatattatat ataatagtat tatatatatt atatatataa 300
tactattata tataatatat actattatat aatatatata atactattat atatattata 360
tataatacta ttatatataa tatatataat actattatat ataatatata taatactatt 420
atatataata tatataatac tattatatat aatatatata atactattat atataatata 480
tataatacta ttatatataa tatatatatt atatataatt atattaatat ataatagtat 540
catatataat aatagtatat ataatatata atatatatat tatatatatt ataatagtat 600
atataacata taatatagta tatatattat atattatata taaaatattt a 651

<210> SEQ ID NO 238
<211> LENGTH: 367
<212> TYPE: DNA
<213> ORGANISM: Homo sapiens
<220> FEATURE:
<221> NAME/KEY: misc_binding
<222> LOCATION: (1)..(367)
<223> OTHER INFORMATION: MAR of chromosome 2 genomic contig;
68308243..68308609

<400> SEQUENCE: 238
atatatatat atgagtcaac catacacata tatatatata atgtttatat atataatgta 60
tatatataat gtttatatat aatgtatata tataatgttt atatatataa tgtatatata 120
taatgtttat atatataatg tatatatata atgtttatat atataatgtg tatatataat 180
gtttatatat ataatgtgta tatataatgt ttatatataa tgtgtatata taatgtttat 240
atatataatg tgtatatata atgtttatat atataatgtg tatatataat gtttatatat 300
ataatgtgta tatatataat gtttatatat ataatgtgta tatatataat gtttatatat 360
ataatgt 367

<210> SEQ ID NO 239
<211> LENGTH: 499
<212> TYPE: DNA
<213> ORGANISM: Homo sapiens
<220> FEATURE:
<221> NAME/KEY: misc_binding
<222> LOCATION: (1)..(499)
<223> OTHER INFORMATION: MAR of chromosome 2 genomic contig;
410241..410739

<400> SEQUENCE: 239 ataaatatgta tatatattat attatatatt atattacata ttatatatta tattacatat 60
tatatattta tatattacat attatatatt atattttata ttatatatta tatcatatat 120
atgttatgca ttatataata cataatatat tatatatgat ataatatata ttatatatta 180
ttatatataa tataattaat atattatgta ttatataata tatattatgt tataatatat 240
aatatatatt atataattat ataatatatt atgtattata taatatatat tatgttataa 300
tatattatat tatatatatt atatatatat tatatatata atgtatatta tatataatac 360
ataatatatt atatattata tattatttta tataatatat tatataatgt gatatattat 420
ataatatatt atataacata gtatattata taatatatta tataatgtaa tatattatat 480
attatataat atattgtat 499

<210> SEQ ID NO 240
<211> LENGTH: 402
<212> TYPE: DNA
<213> ORGANISM: Homo sapiens
<220> FEATURE:
<221> NAME/KEY: misc_binding
<222> LOCATION: (1)..(402)
<223> OTHER INFORMATION: MAR of chromosome 2 genomic contig;
31531..31932

<400> SEQUENCE: 240
cacattatat atataaacat tatatatata cacattatat atataaacat tatatatata 60
cacattatat atataaacat tatatataca cattatatat ataaacatta tatatacaca 120
ttatatatat aaacattata tatacaaatt atatatataa acattatata tacaaattat 180
atatataaac attatatata tacattatat atataaacat tatatatata cattatatat 240
ataaacatta tatatataca ttatatatat aaacattata tatatacatt atatatataa 300
acattatata tatacattat atatataaac gttatatata tacattatat atataaacat 360
tatatgtata cattatatat ataaacatta tatatatatg tg 402

<210> SEQ ID NO 241
<211> LENGTH: 421
<212> TYPE: DNA
<213> ORGANISM: Homo sapiens
<220> FEATURE:
<221> NAME/KEY: misc_binding
<222> LOCATION: (1)..(421)
<223> OTHER INFORMATION: MAR of chromosome 2 genomic contig;
      32415..32835

<400> SEQUENCE: 241
ataaatattt tatatataat atataatata tatactatat tatatgttat atatactatt 60
ataatatata taatatatat attatatatt atatatacta ttattatata tgatactatt 120
atatattaat ataattatat ataatatata tattatataa tatactatta tatattatat 180
ataatagtat attatataat atatatatta tatataatag tattatatat actattatat 240
attatatata ttatatatat ataaaatata atataatata tataatatat aatattaata 300
ttatatatat aatataatat aatatataat ataatataat atatatatta ataaaattat 360
attaatatat aatatataat agtatattat atacatatat aatatataca atatataata 420
t 421

<210> SEQ ID NO 242
<211> LENGTH: 19
<212> TYPE: DNA
<213> ORGANISM: Artificial Sequence
<220> FEATURE:
<223> OTHER INFORMATION: Drosophila topoisomerase II binding site
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 242
gtnwayattn attnatnnr 19

<210> SEQ ID NO 243
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: “A-box”

<400> SEQUENCE: 243 aataaayaaa 10

<210> SEQ ID NO 244

-continued

```
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: "T-box"

<400> SEQUENCE: 244

ttwtwttwtt                                                          10


<210> SEQ ID NO 245
<211> LENGTH: 18
<212> TYPE: DNA
<213> ORGANISM: Artificial Sequence
<220> FEATURE:
<223> OTHER INFORMATION: consensus Topoisomerase II site for vertebrates
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 245

rnynncnngy ngktnyny                                                 18


<210> SEQ ID NO 246
<211> LENGTH: 15
<212> TYPE: DNA
<213> ORGANISM: Artificial Sequence
<220> FEATURE:
<223> OTHER INFORMATION: consensus Topoisomerase II site for Drosophila
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 246

gtnwayattn atnnr                                                    15
```